(12) United States Patent
Meyer et al.

(10) Patent No.: US 9,617,556 B2
(45) Date of Patent: Apr. 11, 2017

(54) PLANT SEEDS WITH ALTERED STORAGE COMPOUND LEVELS, RELATED CONSTRUCTS AND METHODS INVOLVING GENES ENCODING OXIDOREDUCTASE MOTIF POLYPEPTIDES

(71) Applicant: E I DU PONT DE NEMOURS AND COMPANY, Wilmington, DE (US)

(72) Inventors: Knut Meyer, Wilmington, DE (US); Kevin L Stecca, New Castle, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 555 days.

(21) Appl. No.: 14/082,567

(22) Filed: Nov. 18, 2013

(65) Prior Publication Data

US 2014/0075595 A1 Mar. 13, 2014

Related U.S. Application Data

(63) Continuation of application No. 13/039,779, filed on Mar. 3, 2011, now abandoned.

(60) Provisional application No. 61/309,906, filed on Mar. 3, 2010.

(51) Int. Cl.
  *C12N 15/82* (2006.01)
  *C12N 5/14* (2006.01)
  *C12N 9/02* (2006.01)

(52) U.S. Cl.
  CPC ....... *C12N 15/8251* (2013.01); *C12N 9/0004* (2013.01); *C12N 15/8245* (2013.01); *C12N 15/8247* (2013.01); *C12N 5/14* (2013.01)

(58) Field of Classification Search
  None
  See application file for complete search history.

(56) References Cited

U.S. PATENT DOCUMENTS

| | | |
|---|---|---|
| 2004/0031072 A1 | 2/2004 | LaRosa et al. |
| 2004/0216190 A1 | 10/2004 | Kovalic |
| 2005/0278805 A1 | 12/2005 | Shen et al. |
| 2006/0123505 A1 | 6/2006 | Kikuchi et al. |
| 2007/0061916 A1 | 3/2007 | Kovalic et al. |
| 2009/0070897 A1 | 3/2009 | Goldman et al. |

FOREIGN PATENT DOCUMENTS

| | | |
|---|---|---|
| WO | 97/47731 A2 | 12/1997 |
| WO | 2006/037228 A1 | 4/2006 |
| WO | 2008/157559 A2 | 12/2008 |

OTHER PUBLICATIONS

Lardizabal et al 2008 (Plant Physiology 148: p. 89-96).*
Ekman et al 2008 (Journal of Experimental Botany 59: 15 p. 4247-4257).*
Asa Ekman et al., Carbon partitioning between oil and carbohydrates in developing oat (*Avena sativa* L.) seeds, Journal of Experimental Botany, 2008, pp. 4247-4257, vol. 59, No. 15.
Kathryn Lardizabal et al., Expression of Umbelopis ramanniana DGAT2A in Seed Increases Oil in Soybea, Plant Physiology, Sep. 2008, pp. 89-96, vol. 148.
XP002649997—Database Accession No. Q652K8—Oct. 25, 2004.
XP002649998—Database Accession No. B9HFC2—Mar. 24, 2009.
Database Accession No. AAG56967, Sep. 6, 2000—Need to Get Reference.
International Search Report and Written Opinion—PCT/US2011/027027—mailed Oct. 31, 2011.
European Search Report EP15150126, Date of completion of Search—Mar. 16, 2015.
European Search Report EP15150127, Date of completion of Search—Mar. 9, 2015.

* cited by examiner

*Primary Examiner* — Brent Page
*Assistant Examiner* — Matthew Keogh

(57) ABSTRACT

This invention is in the field of plant molecular biology. More specifically, this invention pertains to isolated nucleic acid fragments encoding ORM proteins in plants and seeds and the use of such fragments to modulate expression of a gene encoding ORM protein activity in a transformed host cell.

24 Claims, 7 Drawing Sheets

FIG. 1A

```
SEQ_ID_NO_26  MVLLHVHHHGLHLHPRISIATSPDYNRLRKSLNDV-LLSMRFGLTRDLPLKRSSFAYYS-
SEQ_ID_NO_28  M-----------------------------------------RFGLTRDLPLKRSSFAYYS-
SEQ_ID_NO_30  MVLF--HHHGLHLHPRISITTSPGYNRLRKSLNDV-LLSMRFGLTRDLRLKRPSFAYYS-
SEQ_ID_NO_32  MRSQTLHR-------LTTTF-------NRSHL----NPIQPSLR-SDSNF----------
SEQ_ID_NO_34  M-AT--------------------------------------------------------
SEQ_ID_NO_36  MRTTA----------PSDFIFT--------QKLHPFNITSTKTSLQRTLP---------YF-
SEQ_ID_NO_38  M-----------------------------------------------------------
SEQ_ID_NO_40  M-----------------------------------------------------------
SEQ_ID_NO_42  M-----------------------------------------------------------
SEQ_ID_NO_44  MLGAVRVPGPIL-PFLPGPTRP---------------------LL--R------------
SEQ_ID_NO_46  MLVAALRVPAPIP-SSLPSPARP--------------------LLRRR------------
SEQ_ID_NO_48  MLGAVVRVPAPILLPLLPGPTRP--------------------LLLRR------------
SEQ_ID_NO_64  M-EATLHNH--FLSRIFSYTLPKPKNPPNDPTHF-IPAMKNPFKPIFI-SPKTITFNSR
SEQ_ID_NO_65  MLVAALRVPAPIP-SSLPSPARP--------------------LLRRR------------
SEQ_ID_NO_66  MLGAVVRVPGPIL-PFLPGPTRP---------------------LL--R------------
SEQ_ID_NO_67  MLGAVVRVPGPIL-PFLPGPTRP---------------------LL--R------------
SEQ_ID_NO_69  MVV--------VSLLPRISIVTSPG------SSLHDV-LLSMRFGLTRHLPLKRS-FSNYSI
                *

SEQ_ID_NO_26  --GSREQQ---PITMATKGDKTSTEVKEKVVEEKKD--NDKKEEVSLPP PEKPEAGDCC
SEQ_ID_NO_28  --GSREQQ---PITMATKGDKTSTEVKEKVVEEKKD--NDKKEEVSLPP PEKPEAGDCC
SEQ_ID_NO_30  --GSRGQQ---PITMATKGDKTSTEVKDKVVEEKKDMDKKEEVSLPP   PEKPEAGDCC
SEQ_ID_NO_32  ----------NLTMADSGSNNKIKSDDGSSAVKDA--TETKKLPEIPP  PEKPLPGDCC
SEQ_ID_NO_34  ----------NKTEPLDSKTHNINKKEE--EKKL---PPPP         PEKPEPGDCC
SEQ_ID_NO_36  LQLNRMAEAARTAHKPAPHPIQPKPD--DKTPNPAKEIPP          PEKPEPGDCC
SEQ_ID_NO_38  AEGARTAHAPAPHPIQPKPD--DKTPNPVKETPP                PEKPEPGDCC
SEQ_ID_NO_40  ----------ASATPCDGGTGKPDAAPA--PTPAPTP---------L   PEKPLPGDCC
SEQ_ID_NO_42  ----------ASATPCDGGTGKPDAAPA--PTPAPTP---------L   PEKPLPGDCC
SEQ_ID_NO_44  ---RRHYLPPETPMASATPSDGGAAKPDAAPA--PVPVPAPAPTPLPL  PEKPLPGDCC
SEQ_ID_NO_46  ---SSHRLPPPPPEAPMASATPSDGAAKPDAAPA--PAPEP-------  PEKPLPGDCC
SEQ_ID_NO_48  ---RRHCLPPEAPMASATPSDGGAAKPDAAPA--PVPVPAPAPTPLPLP PEKPLPGDCC
SEQ_ID_NO_64  SQDPKSCHVTANFVMATENKNEQIESTVMSKQGEEE--SKKKTAPP    PEKPEPGDCC
SEQ_ID_NO_65  ---SSHRLPPPPPAASMADAGGATTNKPAPA--PAPEP----------  PEKPLPGDCC
SEQ_ID_NO_66  ---RRHYLPPETPMASATPCDGGTGKPDAAPA--PTPAPTP-------  PEKPLPGDCC
SEQ_ID_NO_67  ---RRHYLPPETPMASATPCDGGTGKPDAAPA--PTPAPTP------L  PEKPLPGDCC
SEQ_ID_NO_69  TSVSPEQQLKSPVTMATTESKNLVEAS-KEETNKKETEDKKEVGVSVPP PEKPEPGDCC
                                                                ****    ****
                                                              SEQ ID NO:70
```

FIG. 1B

```
             ******  **  *  ***
SEQ_ID_NO_26 GSGCVRCVWDVYYDELEEYNK----LTAFAPGDT-----------KSN.
SEQ_ID_NO_28 GSGCVRCVWDVYYDELEEYNK----LTASAPGDT-----------KSN.
SEQ_ID_NO_30 GSGCVRCVWDVYYDELEEYNK----LTASTPGDT-----------KSN.
SEQ_ID_NO_32 GSGCVRCVWDVYYDELEEYNK----ICKGGSDST-------AGSKVS.
SEQ_ID_NO_34 GSGCVRCVWDVYYEELEEYNK----LYQSHSDS------------KRP.
SEQ_ID_NO_36 GSGCVRCVWDVYYDELEEYNK----RYKQVDPSPK----------PSS.
SEQ_ID_NO_38 GSGCVR---DVYYDELEDTIS----YTNKTIPAPKLLHSLHHRMGGSVMGR.
SEQ_ID_NO_40 GSGCVRCVWDIYFDELDAYDKALAARAA-SSGSGGKDDSADTKPKEGKTTR.
SEQ_ID_NO_42 GSGCVRCVWDIYFDELDAYDKAVAAHAA-SSGSGGKDDSADTKPNEG-AKS.
SEQ_ID_NO_44 GSGCVRCVWDIYFDELDAYDKALAAHAA-SSGSGGKDDSADTKPKEG-AKS.
SEQ_ID_NO_46 GSGCVRCVWDVYYDELDAYNKALAAHSSSAS-SGSKPATSDG-----AKS.
SEQ_ID_NO_48 GSGCVRCVWDIYFDELDAYDKALAAHAAASSGSGAKDDSADTKPSDG-AKS.
SEQ_ID_NO_64 GSGCVRCVWDVYYEELEEYDK----LYKSDSSK------------S
SEQ_ID_NO_65 GSGCVRCVWDVYYDELDAYNKALAAHSSSAS-SGSKPATSDG-----AK-S
SEQ_ID_NO_66 GSGCVRCVWDIYFDELDAYDKALAARAA-SSGSGGKDDSADTKPKEG-AKS-
SEQ_ID_NO_67 GSGCVRCVWDIYFDELDAYDKALAAHAA-SSGSGGKDDSADTKPKEG-AK-S
SEQ_ID_NO_69 GSGCVRCVWDVYYYDELEDYNK----QLS--GET-----------KSI.
             SEQ ID NO:70
```

FIG. 2

Percent Identity

| | 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|---|
| 1 | | 98.1 | 86.9 | 37.4 | 52.1 | 36.4 | 31.5 | 32.6 | 33.0 | 26.8 | 31.0 | 27.8 | 31.7 | 31.3 | 27.0 | 27.0 | 51.8 | 1 | SEQ ID NO 26.pro
| 2 | 0.9 | | 90.7 | 38.3 | 53.4 | 38.3 | 31.5 | 32.6 | 33.0 | 29.0 | 32.7 | 31.8 | 39.3 | 32.7 | 29.0 | 29.0 | 53.3 | 2 | SEQ ID NO 28.pro
| 3 | 7.4 | 5.9 | | 35.7 | 50.7 | 35.6 | 32.6 | 32.6 | 33.0 | 28.5 | 31.9 | 27.8 | 30.3 | 32.2 | 28.7 | 28.7 | 48.2 | 3 | SEQ ID NO 30.pro
| 4 | 106.2 | 88.8 | 100.4 | | 54.8 | 38.3 | 30.3 | 38.2 | 38.6 | 31.3 | 35.7 | 30.4 | 38.3 | 35.7 | 31.3 | 31.3 | 39.1 | 4 | SEQ ID NO 32.pro
| 5 | 72.7 | 65.5 | 69.4 | 69.4 | | 54.8 | 37.0 | 42.5 | 43.8 | 43.8 | 47.9 | 41.1 | 60.3 | 47.9 | 42.5 | 43.8 | 50.7 | 5 | SEQ ID NO 34.pro
| 6 | 103.8 | 89.0 | 100.8 | 94.0 | 66.2 | | 60.7 | 36.0 | 36.4 | 28.8 | 32.8 | 32.2 | 36.4 | 33.0 | 28.8 | 28.8 | 38.2 | 6 | SEQ ID NO 36.pro
| 7 | 98.0 | 98.0 | 87.4 | 113.5 | 95.0 | 29.0 | | 29.2 | 29.5 | 29.2 | 28.1 | 29.2 | 29.2 | 28.1 | 29.2 | 29.2 | 30.3 | 7 | SEQ ID NO 38.pro
| 8 | 97.1 | 97.1 | 101.3 | 89.8 | 93.3 | 101.3 | 150.1 | | 92.0 | 93.3 | 49.4 | 76.4 | 33.7 | 49.4 | 94.4 | 93.3 | 33.7 | 8 | SEQ ID NO 40.pro
| 9 | 97.1 | 97.1 | 101.3 | 83.7 | 93.3 | 101.3 | 155.2 | 7.2 | | 96.6 | 51.1 | 80.7 | 34.1 | 51.1 | 95.5 | 96.6 | 33.0 | 9 | SEQ ID NO 42.pro
| 10 | 115.3 | 100.7 | 119.4 | 116.5 | 97.7 | 142.7 | 155.2 | 4.8 | 2.3 | | 56.0 | 78.9 | 26.8 | 56.5 | 99.2 | 100.0 | 30.9 | 10 | SEQ ID NO 44.pro
| 11 | 124.7 | 101.3 | 124.7 | 104.0 | 75.7 | 104.4 | 114.8 | 54.5 | 47.0 | 49.9 | | 56.0 | 32.8 | 100.0 | 55.2 | 56.0 | 34.5 | 11 | SEQ ID NO 46.pro
| 12 | 115.0 | 103.8 | 118.6 | 129.6 | 96.6 | 151.3 | 156.3 | 16.7 | 12.5 | 11.5 | 48.1 | | 25.6 | 56.5 | 78.7 | 79.5 | 30.9 | 12 | SEQ ID NO 48.pro
| 13 | 130.0 | 109.3 | 124.3 | 79.9 | 39.0 | 118.6 | 104.1 | 93.3 | 93.3 | 144.5 | 124.3 | 149.3 | | 33.0 | 27.0 | 27.0 | 41.8 | 13 | SEQ ID NO 64.pro
| 14 | 123.1 | 99.5 | 123.1 | 106.4 | 73.5 | 106.7 | 112.6 | 52.9 | 47.9 | 50.5 | 0.0 | 48.7 | 121.4 | | 55.7 | 56.5 | 34.5 | 14 | SEQ ID NO 65.pro
| 15 | 115.3 | 100.7 | 119.4 | 116.5 | 97.7 | 137.4 | 155.2 | 3.5 | 3.5 | 0.8 | 51.6 | 12.5 | 144.5 | 52.3 | | 99.2 | 30.9 | 15 | SEQ ID NO 66.pro
| 16 | 113.8 | 99.0 | 117.8 | 119.2 | 95.5 | 146.4 | 152.8 | 3.6 | 2.4 | 0.0 | 50.5 | 11.6 | 140.9 | 49.9 | 0.8 | | 30.9 | 16 | SEQ ID NO 67.pro
| 17 | 41.1 | 41.1 | 48.6 | 81.4 | 61.7 | 96.0 | 101.3 | 95.0 | 95.0 | 104.0 | 99.0 | 109.1 | 114.5 | 97.3 | 104.0 | 102.4 | | 17 | SEQ ID NO 69.pro
| | 1 | 2 | 3 | 4 | 5 | 6 | 7 | 8 | 9 | 10 | 11 | 12 | 13 | 14 | 15 | 16 | 17 | |

FIG. 3A

| | | |
|---|---|---|
| SEQ ID NO 26 | MVLLHVHHGLLHPRISIATSPDYNRLRKSLNDVLLSMRFGLTR-DLPLKRSSFAY-YSGSREQQ------PITMATKGD |
| SEQ ID NO 28 | M----------------------------------------RFGLTR-DLPLKRSSFAY-YSGSREQQ------PITMATKGD |
| SEQ ID NO 30 | MVLF--HHHGLHLHPRISITTSPGYNRLRKSLNDVLLSMRFGLTR-DLRLKRPSFAY-YSGSRGQQ------PITMATKGD |
| SEQ ID NO 32 | MRSQTLHRLTTTFN---------------------------------RSHLNPIQPSLR------------------LTMADSGS |
| SEQ ID NO 34 | MAT-----------------------------------------------SDSNFN------------------------NK |
| SEQ ID NO 36 | MRT-----------------TAPSDF-----IFTQKLHPFN-ITSTKT-SLQRTLPYF------LQLNRMAEAA |
| SEQ ID NO 38 | M--------------------------------------------------------------------------------AEGA |
| SEQ ID NO 40 | M-------------------------------------------------AS-----------------------ATPCDGG |
| SEQ ID NO 42 | M-------------------------------------------------AS-----------------------ATPCDGG |
| SEQ ID NO 44 | MLGAVVRVPGPIL-PFLPGPTRPLL--RR------------------RHYLPPETPMAS-----------ATPCDGG |
| SEQ ID NO 46 | MLVAALRVPAPIP-SSLPSPARPLLRRRS---------------SHRLPPPPPAA-----------SMADAGG |
| SEQ ID NO 48 | MLGAVVRVPAPILLPLLPGPTRPLLLRRR------------------RHCLPPEAPMAS-----------ATPSDGG |
| SEQ ID NO 64 | MEA-TLHNH---FLSRIFSYTLPKPKNPPNDPTHFIFAMKNPF--KPIFISPKTITFNSRSQDPKSCHVTANFVMATENK |
| SEQ ID NO 65 | MLVAALRVPAPIP-SSLPSPARPLLRRRS---------------SHRLPPPPPAA-----------SMADAGG |
| SEQ ID NO 66 | MLGAVVRVPGPIL-PFLPGPTRPLL--RR------------------RHYLPPETPMAS-----------ATPCDGG |
| SEQ ID NO 67 | MLGAVVRVPGPIL-PFLPGPTRPLL--RR------------------RHYLPPETPMAS-----------ATPCDGG |
| SEQ ID NO 69 | MVV------VSLLPRISIVTSPG-------SSLHDVLLSMRFGLTR-HLPLKRSFSNYSITSVSPEQ-QLKSPVTMATTES |
| SEQ ID NO 70 | ---------------------------------------------------------------------------------- |
| SEQ ID NO 102 | MRP------------VATD------FTQKLLPSNLIIATNN-RLQRTSPFF-----------LHPYRMADGA |
| SEQ ID NO 104 | MLGAVLRVSAPIP-SLLPAPTRPLLLRRR------------------SHSLPPETPMAA-----------AAPRDAG |
| SEQ ID NO 105 | MVV------VSL-HRISITTSPG-----SSLHDVLLSMRFGLTRRHLPLKRPFTNYSITSVSPEQ-QLISPVTMATTES |
| SEQ ID NO 106 | MRSPFC-----IPSV-VSARTRV---------CFRF------TCFTMATVSGGGVEGKENL----EKSIEA |
| SEQ ID NO 108 | L------RGPGSPIPPLFPAPGRPLIHLSR-----------R--LPTAPAMA----------------D |
| SEQ ID NO 110 | MVSLH----HIHPRFSTAASSEYNRRRKSFHDVLLSMRFGFTR-DLSLKRSLVNY-YSLSRQQR-HLKSPITMATKSE |
| SEQ ID NO 113 | MKVAFLNYS--LIPSF-FSPSPVLQR------------GLGF------RETTRAAMSGNREPDPDLV--LESTPP |
| SEQ ID NO 116 | MRLGIL--PCPFIRPLLPSPSIA------------------PPSSSLLTFRASPRAMDKQQVLHPKP------ |

FIG. 3B

```
SEQ ID NO 26   KTSTEVKEKVVEEKKD--NDKKEEVSLPPPP-------------EKPEAGDCCGSGCVRCVCWDVYYDEIEEYNK----LTAFAPGDT----
SEQ ID NO 28   KTSTEVKEKVVEEKKD--NDKKEEVSLPPPP-------------EKPEAGDCCGSGCVRCVCWDVYYDEIEEYNK----LTASAPGDT----
SEQ ID NO 30   KTSTEVKDKVVEEKKDMDKDKKEEVSLPPPP-------------EKPEAGDCCGSGCVRCVCWDVYYDEIEEYNK----LTASTPGDT----
SEQ ID NO 32   NNKIKSDDGSSAVKDATETKKLPEI----PPP------------EKPLPGDCCGSGCVRCVCWDVYYDEIEEYNK----ICKGGSDST----
SEQ ID NO 34   TEPLDSKT----HNINKKEEEKL-----PPPPPP----------EEKPEPGDCCGSGCVRCVCWDVYYEEIEEYNK----LYQS-HSDS----
SEQ ID NO 36   RTAHKPAPHPIQPKPD----DKTPNPAKEIPPP-----------EEKPEPGDCCGSGCVRCVCWDVYYDEIEEYNK----RYKQVDPSPK---
SEQ ID NO 38   RTAHAPAPHPIQPKPD----DKTPNPVKETPPP-----------EEKPEPGDCCGSGCVR----DVYYDEIEDTIS---YTNKTIPAPKLLH
SEQ ID NO 40   TGKPDAAPAPTPAPTP----------------------------LPEEKPLPGDCCGSGCVRCVCWDIYFDEIDAYDKALAARAA-SSGSGGKDD
SEQ ID NO 42   TGKPDAAPAPTPAPTP----------------------------LPEEKPLPGDCCGSGCVRCVCWDIYFDEIDAYDKAVAAHAA-SSGSGGKDD
SEQ ID NO 44   TGKPDAAPAPTPAPTP----------------------------LPEEKPLPGDCCGSGCVRCVCWDIYFDEIDAYDKALAAHAA-SSGSGGKDD
SEQ ID NO 46   ATTNKPAPAPAPEP------------------------------EEKPLPGDCCGSGCVRCVCWDIYFDEIDAYNKALAAHSSSAS-SGSKPA
SEQ ID NO 48   AAKPDAAPAPVPVPAPA--------------PTPLPLPEEKPLPGDCCGSGCVRCVCWDIYFDEIDAYDKALAAHAA-ASSGGAKDD
SEQ ID NO 64   NEQIESTV---MSKQGEEESKKKTAPPPPPPEEKPLPGDCCGSGCVRCVCWDVYYEEIEEYDK----LYKS-DSSK----
SEQ ID NO 65   ATTNKPAPAPAPEP------------------------------EEKPLPGDCCGSGCVRCVCWDIYFDEIDAYNKALAAHSSSAS-SGSKPA
SEQ ID NO 66   TGKPDAAPAPTPAPTP----------------------------LPEEKPLPGDCCGSGCVRCVCWDIYFDEIDAYDKALAARAA-SSGSGGKDD
SEQ ID NO 67   TGKPDAAPAPTPAPTP----------------------------LPEEKPLPGDCCGSGCVRCVCWDIYFDEIDAYDKALAAHAA-SSGSGGKDD
SEQ ID NO 69   KNLVEASK---EETNKKETEDKKEVGVSVPPPEEKPEPGDCCGSGCVRCVCWDVYYDEIEDYNK-------QLSGET----
SEQ ID NO 70   ---------------------------------------P----EKPXXGDCCGSGCVRXXXDXYXXEIX
SEQ ID NO 102  ATSNTPAPHQIQPKLDPNAEKKENLPKEIPPPEEKPEPGDCCGSGCVRCVCWDIYYEEIEQYNK----LYKHDDSNPK---
SEQ ID NO 104  ATKPDAAPAPAPVPQF---EETNKKEVEDTKE--ILAPPEEKPLPGDCCGSGCVRCVCWDIYYDEIDAYEKALAAHAASAGGKASPY-
SEQ ID NO 105  QNLVQASK---EETNKKEVEDTKE--ILAPPEEKPLPGDCCGSGCVRCVCWDVYYEEIEDYNK----KLSGET----
SEQ ID NO 106  KAKDEKKKAE-----EEIEKILMEKIGPPEEKPLPGDCCGSGCEICVCWDTYFDQIQEYKK-------------
SEQ ID NO 108  AKKTDAPATPAPEP-----------------------------EEKPLPGDCCGSGCVRCVCWDIYYDEIQDYKEALAAHAAAADPSGDKAC
SEQ ID NO 110  KTSTE------EKDKKEEVSLPPPPPP----------------EEKPLPGDCCGSGCVRCVCWDVYYEEIQEYNK----LSTSLPGQT----
SEQ ID NO 113  KQKQQNHKKEVDGEEKKEEDDAEILRKQLGEPEELGPPEEKPLPGDCCGSGCVRCVCWDIYFDEIELYNS-----------
SEQ ID NO 116  ADLPKNDSKQNDLTLPADQEESQ----LGPPEEKPLPGDCCGSGCVRCVCWDTYFEEIDSYNE----------RKE
```

SEQ ID NO: 117

FIG. 3C

| | | |
|---|---|---|
| SEQ ID NO 26 | ------- | KSN. |
| SEQ ID NO 28 | ------- | KSN. |
| SEQ ID NO 30 | ------- | KSN. |
| SEQ ID NO 32 | ------- | AGSKVS. |
| SEQ ID NO 34 | ------- | KRP. |
| SEQ ID NO 36 | ------- | PSS. |
| SEQ ID NO 38 | SLHHRMGGSVMGR. | |
| SEQ ID NO 40 | SADTKPKEGKTTR. | |
| SEQ ID NO 42 | SADTKPNEG-AKS. | |
| SEQ ID NO 44 | SADTKPKEG-AKS. | |
| SEQ ID NO 46 | TSDG----AKS. | |
| SEQ ID NO 48 | SADTKPSDG-AKS. | |
| SEQ ID NO 64 | ------- | S |
| SEQ ID NO 65 | TSDG----AK-S | |
| SEQ ID NO 66 | SADTKPKEG-AKS | |
| SEQ ID NO 67 | SADTKPKEG-AK-S | |
| SEQ ID NO 69 | ------- | KSI. |
| SEQ ID NO 70 | ------- | P |
| SEQ ID NO 102 | PADXKPSDG--AKS | |
| SEQ ID NO 104 | ------- | KS-V |
| SEQ ID NO 105 | --EKDSILKSISPP | |
| SEQ ID NO 106 | VDEKKTE | |
| SEQ ID NO 108 | ------- | KS-N |
| SEQ ID NO 110 | --RKD-VLDARRAS | |
| SEQ ID NO 113 | AFESRLKKSPPL | |
| SEQ ID NO 116 | | |

FIG.4

SEQUENCE LISTING

<160> NUMBER OF SEQ ID NOS: 121

<210> SEQ ID NO 1
<211> LENGTH: 18491
<212> TYPE: DNA
<213> ORGANISM: Artificial Sequence
<220> FEATURE:
<223> OTHER INFORMATION: pHSbarEND2s activation tagging vector

<400> SEQUENCE: 1

```
catgaatcaa acaaacatac acagcgactt attcacacga gctcaaatta caacggtata      60
tatcctgccg tcgacaacca tggtctagac aggatccccg ggtaccgagc tcgaatttgc     120
aggtcgactg cgtcatccct tacgtcagtg gagatatcac atcaatccac ttgctttgaa     180
gacgtggttg gaacgtcttc tttttccacg atgctcctcg tgggtggggg tccatctttg     240
ggaccactgt cggcagaggc atcttgaacg atagcctttc ctttatcgca atgatggcat     300
ttgtaggtgc caccttcctt ttctactgtc cttttgatga agtgacagat agctgggcaa     360
tggaatccga ggaggtttcc cgatattacc ctttgttgaa aagtctcaat tgcccctttgg    420 tcttctgaga ctgttgcgtc atcccttacg tcagtggaga tatcacatca atccacttgc     480
tttgaagacg tggttggaac gtcttctttt tccacgatgc tcctcgtggg tggggtcca    540 tctttgggac cactgtcggc agaggcatct tgaacgatag cctttccttt atcgcaatga     600
```

```
tggcatttgt aggtgccacc ttccttttct actgtccttt tgatgaagtg acagatagct    660
gggcaatgga atccgaggag gtttcccgat attacccttt gttgaaaagt ctcagttaac    720
ccgcgatcct gcgtcatccc ttacgtcagt ggagatatca catcaatcca cttgctttga    780
agacgtggtt ggaacgtctt ctttttccac gatgctcctc gtgggtgggg gtccatcttt    840
gggaccactg tcggcagagg catcttgaac gatagccttt cctttatcgc aatgatggca    900
tttgtaggtg ccaccttcct tttctactgt ccttttgatg aagtgacaga tagctgggca    960
atggaatccg aggaggtttc cgatattac cctttgttga aaagtctcaa ttgccctttg   1020
gtcttctgag actgttgcgt catccctac gtcagtggag atatcacatc aatccacttg   1080
ctttgaagac gtggttggaa cgtcttcttt ttccacgatg ctcctcgtgg gtggggtcc    1140 atctttggga ccactgtcgg cagaggcatc ttgaacgata gcctttcctt tatcgcaatg   1200
atggcatttg taggtgccac cttccttttc tactgtcctt tgatgaagt gacagatagc    1260 tgggcaatgg aatccgagga ggtttcccga tattaccctt tgttgaaaag tctcagttaa   1320
cccgcaattc actggccgtc gttttacaac gtcgtgactg gaaaaccct ggcgttaccc    1380 aacttaatcg ccttgcagca catccccctt cgccagctg gcgtaatagc gaagaggccc    1440
gcaccgatcg cccttcccaa cagttgcgca gcctgaatgg cgaatggatc gatccgtcga   1500
tcgaccaaag cggccatcgt gcctccccac tcctgcagtt cggggcatg gatgcgcgga    1560 tagccgctgc tggtttcctg gatgccgacg gatttgcact gccggtagaa ctccgcgagg   1620
tcgtccagcc tcaggcagca gctgaaccaa ctcgcgaggg gatcgagccc ctgctgagcc   1680
tcgacatgtt gtcgcaaaat tcgccctgga cccgcccaac gatttgtcgt cactgtcaag   1740
gtttgacctg cacttcattt ggggcccaca tacaccaaaa aaatgctgca taattctcgg   1800
ggcagcaagt cggttacccg gccgccgtgc tggacccggg tgaatggtgc cgtaacttt    1860 cggtagagcg gacggccaat actcaacttc aaggaatctc acccatgcgc gccggcgggg   1920
aaccggagtt cccttcagtg aacgttatta gttcgccgct cggtgtgtcg tagatactag   1980
cccctggggc cttttgaaat ttgaataaga tttatgtaat cagtctttta ggtttgaccg   2040
gttctgccgc tttttttaaa attggatttg taataataaa acgcaattgt tgttattgt    2100 ggcgctctat catagatgtc gctataaacc tattcagcac aatatattgt tttcatttta   2160
atattgtaca tataagtagt agggtacaat cagtaaattg aacggagaat attattcata   2220
aaaatacgat agtaacgggt gatatattca ttagaatgaa ccgaaaccgg cggtaaggat   2280
ctgagctaca catgctcagg ttttttacaa cgtgcacaac agaattgaaa gcaaatatca   2340
tgcgatcata ggcgtctcgc atatctcatt aaagcagggg gtgggcgaag aactccagca   2400
tgagatcccc gcgctggagg atcatccagc cggcgtcccg gaaaacgatt ccgaagccca   2460 accttttcata gaaggcggcg gtggaatcga aatctcgtga tggcaggttg ggcgtcgctt   2520
ggtcggtcat ttcgaacccc agagtccgc tcagaagaac tcgtcaagaa ggcgatagaa    2580
ggcgatgcgc tgcgaatcgg gagcggcgat accgtaaagc acgaggaagc ggtcagccca   2640
ttcgccgcca agctcttcag caatatcacg ggtagccaac gctatgtcct gatagcggtc   2700
cgccacaccc agccggccac agtcgatgaa tccagaaaag cggccatttt ccaccatgat   2760
attcggcaag caggcatcgc catgggtcac gacgagatcc tcgccgtcgg gcatgccccc   2820
caattcactg gccgtcgttt tacaacgtcg tgactgggaa aaccctggcg ttacccaact   2880
taatcgcctt gcagcacatc cccctttcgc cagctggcgt aatagcgaag aggcccgcac   2940
cgatcgccct tcccaacagt tgcgcagcct gaatggcgaa tggcgcctga tgcggtattt   3000
```

```
tctccttacg catctgtgcg gtatttcaca ccgcatatgg tgcactctca gtacaatctg    3060
ctctgatgcc gcatagttaa gccagccccg acacccgcca acacccgctg acgcgccctg    3120
acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga atgtgcgcg gaaccccctat ttgttattt ttctaaatac attcaaatat    3360
gtatccgctc atgagacaat aaccctgata aatgcttcaa taatattgaa aaggaagag    3420
tatgagtatt caacatttcc gtgtcgccct tattcccttt tttgcggcat tttgccttcc    3480
tgttttgct cacccagaaa cgctggtgaa agtaaaagat gctgaagatc agttgggtgc    3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg ggggatcatg taactcgcct    3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt catttttaat ttaaaaggat ctaggtgaag atcctttttg ataatctcat    4380
gaccaaaatc ccttaacgtg agttttcgtt ccactgagcg tcagaccccg tagaaaagat    4440
caaaggatct tcttgagatc ctttttttct gcgcgtaatc tgctgcttgc aaacaaaaaa    4500
accaccgcta ccagcggtgg tttgtttgcc ggatcaagag ctaccaactc tttttccgaa    4560
ggtaactggc ttcagcagag cgcagatacc aaatactgtc cttctagtgt agccgtagtt    4620
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacggggggt tcgtgcacac agcccagctt    4800
ggagcgaacg acctacaccg aactgagata cctacagcgt gagcattgag aaagcgccac    4860
gcttcccgaa gggagaaagg cggacaggta tccggtaagc ggcagggtcg gaacaggaga    4920
gcgcacgagg gagcttccag ggggaaacgc ctggtatctt tatagtcctg tcgggtttcg    4980
ccacctctga cttgagcgtc gatttttgtg atgctcgtca ggggggcgga gcctatggaa    5040
aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
```

```
gctcactcat taggcacccc aggctttaca ctttatgctt ccggctcgta tgttgtgtgg    5400
aattgtgagc ggataacaat ttcacacagg aaacagctat gaccatgatt acgccaagct    5460
ttctaggggg ggggtaccga tctgagatcg gtaacgaaaa cgaacgggta gggatgaaaa    5520
cggtcggtaa cggtcggtaa aatacctcta ccgttttcat tttcatattt aacttgcggg    5580
acggaaacga aaacgggata taccggtaac gaaaacgaac gggataaata cggtaatcga    5640
aaaccgatac gatccggtcg ggttaaagtc gaaatcggac gggaaccggt attttgttc     5700 ggtaaaatca cacatgaaaa catatattca aaacttaaaa acaaatataa aaaattgtaa    5760
acacaagtct taatgatcac tagtggcgcg cctaggagat ctcgagtagg gataacaggg    5820
taatacatag ataaaatcca tataaatctg gagcacacat agtttaatgt agcacataag    5880
tgataagtct tgggctcttg gctaacataa aagccatat aagtctacta gcacacatga     5940
cacaatataa agtttaaaac acatattcat aatcacttgc tcacatctgg atcacttagc    6000
atgctacagc tagtgcaata ttagacactt tccaatattt ctcaaacttt tcactcattg    6060
caacggccat tctcctaatg acaaatttt catgaacaca ccattggtca atcaaatcct     6120
ttatctcaca gaaaccttg taaaataaat ttgcagtgga atattgagta ccagatagga     6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgacatgtac aacaattgag acaaacatac ctgcgaggat cacttgtttt    6360
aagccgtgtt agtgcaggct tataatataa ggcatccctc aacatcaaat aggttgaatt    6420
ccatctagtt gagacatcat atgagatccc tttagattta tccaagtcac attcactagc    6480
acacttcatt agttcttccc actgcaaagg agaagatttt acagcaagaa caatcgcttt    6540
gattttctca attgttcctg caattacagc caagccatcc tttgcaacca agttcagtat    6600
gtgacaagca cacctcacat gaaagaaagc accatcacaa actagatttg aatcagtgtc    6660
ctgcaaatcc tcaattatat cgtgcacagc tacttcattt gcactagcat tatccaaaga    6720
caaggcaaac aatttttttct caatgttcca cttaaccatg attgcagtga aggtttgtga    6780
taacctttgg ccagtgtggc gcccttcaac atgaaaaaag ccaacaattc tttttggag     6840 acaccaatca tcatcaatcc aatggatggt gacacacatg tatgacttat tttgacaaga    6900
tgtccacata tccatagttg tactgaagcg agactgaaca tcttttagtt ttccatacaa    6960
cttttctttt tcttccaaat acaaatccat gatatatttt ctagcagtga cacgggactt    7020
tattggaaag tgagggcgca gagacttaac aaactcaaca aagtactcat gttctacaat    7080
attgaaagga tattcatgca tgattattgc caaatgaagc ttctttaggc taaccacttc    7140
atcgtactta taaggctcaa tgagatttat gtctttgcca tgatcctttt cacttttag     7200 acacaactga cctttaacta aactatgtga tgttctcaag tgatttcgaa atccgcttgt    7260
tccatgatga ccctcagccc tatacttagc cttgcaatta ggaaagttgc aatgtcccca    7320
tacctgaacg tatttctttc catcgacctc cacttcaatt tccttcttgg tgaaatgctg    7380
ccatacatcc gatgtgcact tctttgccct cttctgtggt gcttcttctt cgggttcagg    7440
ttgtggctgt ggttgtggtt ctggttgtgg ttgtggttgt ggttgtggtt catgaacaat    7500
agccatatca tcttgactcg gatctgtagc tgtaccattt gcattactac tgcttacact    7560
ctgaataaaa tgcctctcgg cctcagctgt tgatgatgat ggtgatgtgc ggccacatcc    7620
atgcccacgc gcacgtgcac gtacattctg aatccgacta gaagaggctt cagctttctct   7680 tttcaaccct gttataaaca gattttttcgt attattctac agtcaatatg atgcttccca    7740
```

| | |
|---|---|
| atctacaacc aattagtaat gctaatgcta ttgctactgt tttctaata tataccttga | 7800 |
| gcatatgcag agaatacgga atttgttttg cgagtagaag gcgctcttgt ggtagacatc | 7860 |
| aacttggcca atcttatggc tgagcctgag ggaggattat ttccaaccgg aggcgtcatc | 7920 |
| tgaggaatgg agtcgtagcc ggctagccga agtggagagc agagccctgg acagcaggtg | 7980 |
| ttcagcaatc agcttggtgc tgtactgctg tgacttgtga gcacctggac ggctggacag | 8040 |
| caatcagcag gtgttgcaga gcccctggac agcacacaaa tgacacaaca gcttggtgca | 8100 |
| atggtgctga cgtgctgtac tgctaagtgc tgtgagcctg tgagcagccg tggagacagg | 8160 |
| gagaccgcgc atgccggat gggcgagcgc cgagcagtgg aggtctggag accgctgac | 8220 |
| cgcagatggc ggatggcgga tgggcggacc gcggatgggc gagcagtgga gtggaggtct | 8280 |
| gggcggatgg gcggaccgcg gcggatgg gcgagtcgcg agcagtggag tggagggcgg | 8340 |
| accgtggatg gcggcgtctg cgtccggcgt gccgcgtcac ggccgtcacc gcgtgtggtg | 8400 |
| cctggtgcag cccagcggcc ggccggctgg agacaggga gagtcggaga gagcaggcga | 8460 |
| gagcgagacg cgtcgccggc gtcggcgtgc ggctggcggc gtccggactc cggcgtgggc | 8520 |
| gcgtggcggc gtgtgaatgt gtgatgctgt tactcgtgtg gtgcctggcc gcctgggaga | 8580 |
| gaggcagagc agcgttcgct aggtatttct tacatgggct gggcctcagt ggttatggat | 8640 |
| gggagttgga gctggccata ttgcagtcat cccgaattag aaaatacggt aacgaaacgg | 8700 |
| gatcatcccg attaaaaacg ggatcccggt gaaacggtcg ggaaactagc tctaccgttt | 8760 |
| ccgtttccgt ttaccgtttt gtatatcccg tttccgttcc gttttcgttt tttacctcgg | 8820 |
| gttcgaaatc gatcgggata aaactaacaa aatcggttat acgataacgg tcggtacggg | 8880 |
| attttcccat cctactttca tccctgagat tattgtcgtt tctttcgcag atcggtaccc | 8940 |
| cccccctaga gtcgacatcg atctagtaac atagatgaca ccgcgcgcga taatttatcc | 9000 |
| tagtttgcgc gctatatttt gttttctatc gcgtattaaa tgtataattg cgggactcta | 9060 |
| atcataaaaa cccatctcat aaataacgtc atgcattaca tgttaattat tacatgctta | 9120 |
| acgtaattca acagaaatta tatgataatc atcgcaagac cggcaacagg attcaatctt | 9180 |
| aagaaacttt attgccaaat gtttgaacga tctgcttcga cgcactcctt ctttaggtac | 9240 |
| ggactagatc tcggtgacgg gcaggaccgg acggggcggt accggcaggc tgaagtccag | 9300 |
| ctgccagaaa cccacgtcat gccagttccc gtgcttgaag ccggccgccc gcagcatgcc | 9360 |
| gcgggggca tatccgagcg cctcgtgcat gcgcacgctc gggtcgttgg gcagcccgat | 9420 |
| gacagcgacc acgctcttga agccctgtgc ctccaggac ttcagcaggt gggtgtagag | 9480 |
| cgtggagccc agtcccgtcc gctggtggcg gggggagacg tacacggtcg actcggccgt | 9540 |
| ccagtcgtag gcgttgcgtg ccttccaggg gcccgcgtag gcgatgccgg cgacctcgcc | 9600 |
| gtccacctcg gcgacgagcc agggatagcg ctcccgcaga cggacgaggt cgtccgtcca | 9660 |
| ctcctgcggt tcctgcggct cggtacggaa gttgaccgtg cttgtctcga tgtagtggtt | 9720 |
| gacgatggtg cagaccgccg gcatgtccgc ctcggtggca cggcggatgt cggccgggcg | 9780 |
| tcgttctggg ctcatggatc tggattgaga gtgaatatga gactctaatt ggataccgag | 9840 |
| gggaatttat ggaacgtcag tggagcattt ttgacaagaa atatttgcta gctgatagtg | 9900 |
| accttaggcg acttttgaac gcgcaataat ggtttctgac gtatgtgctt agctcattaa | 9960 |
| actccagaaa cccgcggctg agtggctcct tcaatcgttg cggttctgtc agttccaaac | 10020 |
| gtaaaacggc ttgtcccgcg tcatcggcgg gggtcataac gtgactccct taattctccg | 10080 |

```
ctcatgatcc ccgggtaccg agctcgaatt gcggctgagt ggctccttca atcgttgcgg    10140
ttctgtcagt tccaaacgta aaacggcttg tcccgcgtca tcggcggggg tcataacgtg    10200
actcccttaa ttctccgctc atgatcttga tccctgcgc catcagatcc ttggcggcaa     10260
gaaagccatc cagtttactt tgcagggctt cccaacctta ccagagggcg ccccagctgg    10320
caattccggt tcgcttgctg tatcgatatg gtggatttat cacaaatggg acccgccgcc    10380
gacagaggtg tgatgttagg ccaggacttt gaaaatttgc gcaactatcg tatagtggcc    10440
gacaaattga cgccgagttg acagactgcc tagcatttga gtgaattatg tgaggtaatg    10500
ggctacactg aattggtagc tcaaactgtc agtatttatg tatatgagtg tatattttcg    10560
cataatctca gaccaatctg aagatgaaat gggtatctgg gaatggcgaa atcaaggcat    10620
cgatcgtgaa gtttctcatc taagccccca tttggacgtg aatgtagaca cgtcgaaata    10680
aagatttccg aattagaata atttgtttat tgctttcgcc tataaatacg acggatcgta    10740
atttgtcgtt ttatcaaaat gtactttcat tttataataa cgctgcggac atctacattt    10800
ttgaattgaa aaaaaattgg taattactct ttcttttct ccatattgac catcatactc      10860
attgctgatc catgtagatt tcccggacat gaagccattt acaattgaat atatcctgcc    10920
gccgctgccg ctttgcaccc ggtggagctt gcatgttggt ttctacgcag aactgagccg    10980
gttaggcaga taatttccat tgagaactga gccatgtgca ccttccccc aacacggtga     11040
gcgacggggc aacggagtga tccacatggg acttttaaac atcatccgtc ggatggcgtt    11100
gcgagagaag cagtcgatcc gtgagatcag ccgacgcacc gggcaggcgc gcaacacgat    11160
cgcaaagtat ttgaacgcag gtacaatcga gccgacgttc accgtcaccc tggatgctgt    11220
aggcataggc ttggttatgc cggtactgcc gggcctcttg cgggatatcg tccattccga    11280
cagcatcgcc agtcactatg gcgtgctgct agcgctatat gcgttgatgc aatttctatg    11340
cgcacccgtt ctcggagcac tgtccgaccg ctttggccgc cgcccagtcc tgctcgcttc    11400
gctacttgga gccactatcg actacgcgat catggcgacc acaccgtcc tgtggtccaa     11460
cccctccgct gctatagtgc agtcggcttc tgacgttcag tgcagccgtc ttctgaaaac    11520
gacatgtcgc acaagtccta agttacgcga caggctgccg ccctgccctt ttcctggcgt    11580
tttcttgtcg cgtgttttag tcgcataaag tagaatactt gcgactagaa ccggagacat    11640
tacgccatga acaagagcgc cgccgctggc ctgctgggct atgcccgcgt cagcaccgac    11700
gaccaggact tgaccaacca acgggccgaa ctgcacgcgg ccggctgcac caagctgttt    11760
tccgagaaga tcaccggcac caggcgcgac cgcccggagc tggccaggat gcttgaccac    11820
ctacgccctg gcgacgttgt gacagtgacc aggctagacc gcctggcccg cagcacccgc    11880
gacctactgg acattgccga gcgcatccag gaggccggcg cgggcctgcg tagcctggca    11940
gagccgtggg ccgacaccac cacgccggcc ggccgcatgg tgttgaccgt gttcgccggc    12000
attgccgagt cgagcgttc cctaatcatc gaccgcaccc ggagcgggcg cgaggccgcc     12060
aaggcccgag gcgtgaagtt tggcccccgc cctaccctca ccccggcaca gatcgcgcac    12120
gcccgcgagc tgatcgacca ggaaggccgc accgtgaaag aggcggctgc actgcttggc    12180
gtgcatcgct cgaccctgta ccgcgcactt gagcgcagcg aggaagtgac gcccaccgag    12240
gccaggcggc gcggtgcctt ccgtgaggac gcattgaccg aggccgacgc cctggcggcc    12300
gccgagaatg aacgccaaga ggaacaagca tgaaaccgca ccaggacggc caggacgaac    12360
cgttttcat taccgaagag atcgaggcgg agatgatcgc ggccgggtac gtgttcgagc    12420
cgcccgcgca cgtctcaacc gtgcggctgc atgaaatcct ggccggtttg tctgatgcca    12480
```

```
agctggcggc ctggccggcc agcttggccg ctgaagaaac cgagcgccgc cgtctaaaaa   12540
ggtgatgtgt atttgagtaa aacagcttgc gtcatgcggt cgctgcgtat atgatgcgat   12600
gagtaaataa acaaatacgc aagggaacgc atgaagttat cgctgtactt aaccagaaag   12660
gcgggtcagg caagacgacc atcgcaaccc atctagcccg cgccctgcaa ctcgccgggg   12720
ccgatgttct gttagtcgat tccgatcccc agggcagtgc ccgcgattgg gcggccgtgc   12780
gggaagatca accgctaacc gttgtcggca tcgaccgccc gacgattgac cgcgacgtga   12840
aggccatcgg ccggcgcgac ttcgtagtga tcgacggagc gccccaggcg gcggacttgg   12900
ctgtgtccgc gatcaaggca gccgacttcg tgctgattcc ggtgcagcca gcccttacg    12960 acatatgggc caccgccgac ctggtggagc tggttaagca gcgcattgag gtcacggatg   13020
gaaggctaca agcggccttt gtcgtgtcgc gggcgatcaa aggcacgcgc atcggcggtg   13080
aggttgccga ggcgctggcc gggtacgagc tgcccattct tgagtcccgt atcacgcagc   13140
gcgtgagcta cccaggcact gccgccgccg gcacaaccgt tcttgaatca gaacccgagg   13200
gcgacgctgc ccgcgaggtc caggcgctgg ccgctgaaat taaatcaaaa ctcatttgag   13260
ttaatgaggt aaagagaaaa tgagcaaaag cacaaacacg ctaagtgccg gccgtccgag   13320
cgcacgcagc agcaaggctg caacgttggc cagcctggca gacacgccag ccatgaagcg   13380
ggtcaacttt cagttgccgg cggaggatca caccaagctg aagatgtacg cggtacgcca   13440
aggcaagacc attaccgagc tgctatctga atacatcgcg cagctaccag agtaaatgag   13500
caaatgaata aatgagtaga tgaattttag cggctaaagg aggcggcatg gaaaatcaag   13560
aacaaccagg caccgacgcc gtggaatgcc ccatgtgtgg aggaacgggc ggttggccag   13620
gcgtaagcgg ctgggttgtc tgccggccct gcaatggcac tggaacccc aagcccgagg    13680 aatcggcgtg agcggtcgca aaccatccgg cccggtacaa atcggcgcgg cgctgggtga   13740
tgacctggtg gagaagttga aggccgcgca ggccgcccag cggcaacgca tcgaggcaga   13800
agcacgcccc ggtgaatcgt ggcaagcggc cgctgatcga atccgcaaag aatcccggca   13860
accgccggca gccggtgcgc cgtcgattag gaagccgccc aagggcgacg agcaaccaga   13920
ttttttcgtt ccgatgctct atgacgtggg cacccgcgat agtcgcagca tcatggacgt   13980
ggccgttttc cgtctgtcga agcgtgaccg acgagctggc gaggtgatcc gctacgagct   14040
tccagacggg cacgtagagg tttccgcagg ccggccggc atggcagtg tgtgggatta     14100 cgacctggta ctgatggcgg tttcccatct aaccgaatcc atgaaccgat accgggaagg   14160
gaagggagac aagcccggcc gcgtgttccg tccacacgtt gcggacgtac tcaagttctg   14220
ccggcgagcc gatggcggaa agcagaaaga cgacctggta gaaacctgca ttcggttaaa   14280
caccacgcac gttgccatgc agcgtacgaa gaaggccaag aacggccgcc tggtgacggt   14340
atccgagggt gaagccttga ttagccgcta caagatcgta aagagcgaaa ccgggcggcc   14400
ggagtacatc gagatcgagc tagctgattg gatgtaccgc gagatcacag aaggcaagaa   14460
cccggacgtg ctgacggttc accccgatta cttttgatc gatcccggca tcggccgttt   14520
tctctaccgc ctggcacgcc gcgccgcagg caaggcagaa gccagatggt tgttcaagac   14580
gatctacgaa cgcagtggca gcgccggaga gttcaagaag ttctgtttca ccgtgcgcaa   14640
gctgatcggg tcaaatgacc tgccggagta cgatttgaag gaggaggcgg ggcaggctgg   14700
cccgatccta gtcatgcgct accgcaacct gatcgagggc gaagcatccg ccggttccta   14760
atgtacggag cagatgctag ggcaaattgc cctagcaggg gaaaaaggtc gaaaaggtct   14820
```

```
ctttcctgtg gatagcacgt acattgggaa cccaaagccg tacattggga accggaaccc    14880
gtacattggg aacccaaagc cgtacattgg gaaccggtca cacatgtaag tgactgatat    14940
aaaagagaaa aaaggcgatt tttccgccta aaactcttta aaacttatta aaactcttaa    15000
aacccgcctg gcctgtgcat aactgtctgg ccagcgcaca gccgaagagc tgcaaaaagc    15060
gcctacccct cggtcgctgc gctccctacg ccccgccgct tcgcgtcggc ctatcgcggc    15120
cgctggccgc tcaaaaatgg ctggcctacg gccaggcaat ctaccagggc gcggacaagc    15180
cgcgccgtcg ccactcgacc gccggcgccc acatcaaggc accctgcctc gcgcgtttcg    15240
gtgatgacgg tgaaaacctc tgacacatgc agctcccgga gacggtcaca gcttgtctgt    15300
aagcggatgc cgggagcaga caagcccgtc agggcgcgtc agcgggtgtt ggcgggtgtc    15360
ggggcgcagc catgacccag tcacgtagcg atagcggagt gtatactggc ttaactatgc    15420
ggcatcagag cagattgtac tgagagtgca ccatatgcgg tgtgaaatac cgcacagatg    15480
cgtaaggaga aaataccgca tcaggcgctc ttccgcttcc tcgctcactg actcgctgcg    15540
ctcggtcgtt cggctgcggc gagcggtatc agctcactca aaggcggtaa tacgttatc    15600
cacagaatca ggggataacg caggaaagaa catgtgagca aaaggccagc aaaaggccag    15660
gaaccgtaaa aaggccgcgt tgctggcgtt tttccatagg ctccgccccc ctgacgagca    15720
tcacaaaaat cgacgctcaa gtcagaggtg gcgaaacccg acaggactat aaagatacca    15780
ggcgtttccc cctggaagct ccctcgtgcg ctctcctgtt ccgaccctgc cgcttaccgg    15840
atacctgtcc gcctttctcc cttcgggaag cgtggcgctt tctcatagct cacgctgtag    15900
gtatctcagt tcggtgtagg tcgttcgctc caagctgggc tgtgtgcacg aaccccccgt    15960
tcagcccgac cgctgcgcct tatccggtaa ctatcgtctt gagtccaacc cggtaagaca    16020
cgacttatcg ccactggcag cagccactgg taacaggatt agcagagcga ggtatgtagg    16080
cggtgctaca gagttcttga agtggtggcc taactacggc tacactagaa ggacagtatt    16140
tggtatctgc gctctgctga agccagttac cttcggaaaa agagttggta gctcttgatc    16200
cggcaaacaa accaccgctg gtagcggtgg tttttttgtt tgcaagcagc agattacgcg    16260
cagaaaaaaa ggatctcaag aagatccttt gatcttttct acggggtctg acgctcagtg    16320
gaacgaaaac tcacgttaag ggattttggt catgagatta tcaaaaagga tcttcaccta    16380
gatcctttta aattaaaaat gaagttttaa atcaatctaa agtatatatg agtaaacttg    16440
gtctgacagt taccaatgct taatcagtga ggcacctatc tcagcgatct gtctatttcg    16500
ttcatccata gttgcctgac tccccgtcgt gtagataact acgatacggg agggcttacc    16560
atctggcccc agtgctgcaa tgataccgcg agacccacgc tcaccggctc cagatttatc    16620
agcaataaac cagccagccg gaagggccga gcgcagaagt ggtcctgcaa ctttatccgc    16680
ctccatccag tctattaatt gttgccggga agctagagta agtagttcgc cagttaatag    16740
tttgcgcaac gttgttgcca ttgctacagg catcgtggtg tcacgctcgt cgtttggtat    16800
ggcttcattc agctccggtt cccaacgatc aaggcgagtt acatgatccc ccatgttgtg    16860
caaaaaagcg gttagctcct tcggtcctcc gatcgttgtc agaagtaagt tggccgcagt    16920
gttatcactc atggttatgg cagcactgca taattctctt actgtcatgc catccgtaag    16980
atgcttttct gtgactggtg agtactcaac caagtcattc tgagaatagt gtatgcggcg    17040
accgagttgc tcttgcccgg cgtcaacacg gataataccc gcgccacata gcagaacttt    17100
aaaagtgctc atcattggaa aagacctgca ggggggggg ggaaagccac gttgtgtctc    17160
aaaatctctg atgttacatt gcacaagata aaaatatatc atcatgaaca ataaaactgt    17220
```

```
ctgcttacat aaacagtaat acaaggggtg ttatgagcca tattcaacgg gaaacgtctt    17280
gctcgaggcc gcgattaaat tccaacatgg atgctgattt atatgggtat aaatgggctc    17340
gcgataatgt cgggcaatca ggtgcgacaa tctatcgatt gtatgggaag cccgatgcgc    17400
cagagttgtt tctgaaacat ggcaaaggta gcgttgccaa tgatgttaca gatgagatgg    17460
tcagactaaa ctggctgacg aatttatgc ctcttccgac catcaagcat tttatccgta     17520
ctcctgatga tgcatggtta ctcaccactg cgatccccgg aaaacagca ttccaggtat      17580 tagaagaata tcctgattca ggtgaaaata ttgttgatgc gctggcagtg ttcctgcgcc    17640
ggttgcattc gattcctgtt tgtaattgtc tttttaacag cgatcgcgta tttcgtctcg    17700
ctcaggcgca atcacgaatg aataacggtt tggttgatgc gagtgatttt gatgacgagc    17760
gtaatggctg gcctgttgaa caagtctgga agaaatgca taagcttttg ccattctcac     17820
cggattcagt cgtcactcat ggtgatttct cacttgataa ccttattttt gacgagggga    17880
aattaatagg ttgtattgat gttggacgag tcggaatcgc agaccgatac caggatcttg    17940
ccatcctatg gaactgcctc ggtgagtttt ctccttcatt acagaaacgg cttttttcaaa   18000 aatatggtat tgataatcct gatatgaata aattgcagtt tcatttgatg ctcgatgagt    18060
ttttctaatc agaattggtt aattggttgt aacactggca gagcattacg ctgacttgac    18120 gggacgcgg ctttgttgaa taaatcgaac ttttgctgag ttgaaggatc agatcacgca     18180
tcttcccgac aacgcagacc gttccgtggc aaagcaaaag ttcaaaatca ccaactggtc    18240
cacctacaac aaagctctca tcaaccgtgg ctccctcact ttctggctgg atgatggggc    18300
gattcaggcc tggtatgagt cagcaacacc ttcttcacga ggcagacctc agcgcccccc    18360 ccccctgca ggtcaattcg gtcgatatgg ctattacgaa gaaggctcgt gcgcggagtc     18420
ccgtgaactt cccacgcaa caagtgaacc gcaccgggtt tgccggaggc catttcgtta    18480
aaatgcgcag c                                                                               18491

<210> SEQ ID NO 2
<211> LENGTH: 50
<212> TYPE: DNA
<213> ORGANISM: Artificial Sequence
<220> FEATURE:
<223> OTHER INFORMATION: poly-linker

<400> SEQUENCE: 2
gatcactagt ggcgcgccta ggagatctcg agtagggata acagggtaat                 50

<210> SEQ ID NO 3
<211> LENGTH: 7085
<212> TYPE: DNA
<213> ORGANISM: Artificial Sequence
<220> FEATURE:
<223> OTHER INFORMATION: Plasmid pKR85

<400> SEQUENCE: 3
cgcgccaagc ttttgatcca tgcccttcat ttgccgctta ttaattaatt tggtaacagt    60
ccgtactaat cagttactta tccttccccc atcataatta atcttggtag tctcgaatgc   120
cacaacactg actagtctct tggatcataa gaaaagcca aggaacaaaa gaagacaaaa    180
cacaatgaga gtatcctttg catagcaatg tctaagttca taaaattcaa acaaaaacgc    240
aatcacacac agtggacatc acttatccac tagctgatca ggatcgccgc gtcaagaaaa    300
aaaaactgga ccccaaaagc catgcacaac aaacacgtact cacaaaggtg tcaatcgagc   360
```

```
agcccaaaac attcaccaac tcaacccatc atgagccctc acatttgttg tttctaaccc    420
aacctcaaac tcgtattctc ttccgccacc tcatttttgt ttatttcaac acccgtcaaa    480
ctgcatgcca ccccgtggcc aaatgtccat gcatgttaac aagacctatg actataaata    540
gctgcaatct cggcccaggt tttcatcatc aagaaccagt tcaatatcct agtacaccgt    600
attaaagaat ttaagatata ctgcggccgc aagtatgaac taaaatgcat gtaggtgtaa    660
gagctcatgg agagcatgga atattgtatc cgaccatgta acagtataat aactgagctc    720
catctcactt cttctatgaa taaacaaagg atgttatgat atattaacac tctatctatg    780
caccttattg ttctatgata aatttcctct tattattata aatcatctga atcgtgacgg    840
cttatggaat gcttcaaata gtacaaaaac aaatgtgtac tataagactt tctaaacaat    900 tctaaccttta gcattgtgaa cgagacataa gtgttaagaa gacataacaa ttataatgga    960
agaagtttgt ctccatttat atattatata ttacccactt atgtattata ttaggatgtt   1020
aaggagacat aacaattata aagagagaag tttgtatcca tttatatatt atatactacc   1080
catttatata ttatacttat ccacttattt aatgtcttta taaggtttga tccatgatat   1140
ttctaatatt ttagttgata tgtatatgaa agggtactat ttgaactctc ttactctgta   1200
taaaggttgg atcatcctta aagtgggtct atttaatttt attgcttctt acagataaaa   1260
aaaaaattat gagttggttt gataaaatat tgaaggattt aaaataataa taaataacat   1320
ataatatatg tatataaatt tattataata taacatttat ctataaaaaa gtaaatattg   1380
tcataaatct atacaatcgt ttagccttgc tggacgaatc tcaattattt aaacgagagt   1440
aaacatattt gacttttttgg ttatttaaca aattattatt taacactata tgaaattttt   1500 tttttttatca gcaaagaata aaattaaatt aagaaggaca atggtgtccc aatccttata   1560
caaccaactt ccacaagaaa gtcaagtcag agacaacaaa aaaacaagca aaggaaattt   1620
tttaatttga gttgtcttgt ttgctgcata atttatgcag taaaacacta cacataaccc   1680
ttttagcagt agagcaatgg ttgaccgtgt gcttagcttc ttttatttta tttttttatc   1740
agcaaagaat aaataaaata aaatgagaca cttcagggat gtttcaacaa gcttggatct   1800
cctgcaggat ctggccggcc ggatctcgta cggatccgtc gacggcgcgc cgatcatcc    1860 ggatatagtt cctcctttca gcaaaaaacc cctcaagacc cgtttagagg ccccaagggg   1920
ttatgctagt tattgctcag cggtggcagc agccaactca gcttcctttc gggctttgtt   1980
agcagccgga tcgatccaag ctgtacctca ctattccttt gccctcggac gagtgctggg   2040
gcgtcggttt ccactatcgg cgagtacttc tacacagcca tcggtccaga cggccgcgct   2100
tctgcgggcg atttgtgtac gcccgacagt cccggctccg gatcggacga ttgcgtcgca   2160
tcgaccctgc gcccaagctg catcatcgaa attgccgtca accaagctct gatagagttg   2220
gtcaagacca atgcggagca tatacgcccg gagccgcggc gatcctgcaa gctccggatg   2280
cctccgctcg aagtagcgcg tctgctgctc catacaagcc aaccacgcc tccagaagaa   2340 gatgttggcg acctcgtatt gggaatcccc gaacatcgcc tcgctccagt caatgaccgc   2400
tgttatgcgg ccattgtccg tcaggacatt gttggagccg aaatccgcgt gcacgaggtg   2460
ccggacttcg gggcagtcct cggcccaaag catcagctca tcgagagcct gcgcgacgga   2520
cgcactgacg gtgtcgtcca tcacagtttg ccagtgatac acatggggat cagcaatcgc   2580
gcatatgaaa tcacgccatg tagtgtattg accgattcct tgcggtccga atgggccgaa   2640
cccgctcgtc tggctaagat cggccgcagc gatcgcatcc atagcctccg cgaccggctg   2700
cagaacagcg ggcagttcgg tttcaggcag gtcttgcaac gtgacaccct gtgcacggcg   2760
```

```
ggagatgcaa taggtcaggc tctcgctgaa ttccccaatg tcaagcactt ccggaatcgg    2820
gagcgcggcc gatgcaaagt gccgataaac ataacgatct ttgtagaaac catcggcgca    2880
gctatttacc cgcaggacat atccacgccc tcctacatcg aagctgaaag cacgagattc    2940
ttcgccctcc gagagctgca tcaggtcgga gacgctgtcg aacttttcga tcagaaactt    3000
ctcgacagac gtcgcggtga gttcaggctt ttccatgggt atatctcctt cttaaagtta    3060
aacaaaatta tttctagagg gaaaccgttg tggtctccct atagtgagtc gtattaattt    3120
cgcgggatcg agatcgatcc aattccaatc ccacaaaaat ctgagcttaa cagcacagtt    3180
gctcctctca gagcagaatc gggtattcaa caccctcata tcaactacta cgttgtgtat    3240
aacggtccac atgccggtat atacgatgac tggggttgta caaggcggc aacaaacggc     3300 gttcccggag ttgcacacaa gaaatttgcc actattacag aggcaagagc agcagctgac    3360
gcgtacacaa caagtcagca aacagacagg ttgaacttca tccccaaagg agaagctcaa    3420
ctcaagccca gagctttgc taaggcccta acaagcccac caaagcaaaa agcccactgg     3480
ctcacgctag gaaccaaaag gcccagcagt gatccagccc caaagagat ctcctttgcc     3540 ccggagatta caatgacga tttcctctat ctttacgatc taggaaggaa gttcgaaggt     3600
gaaggtgacg acactatgtt caccactgat aatgagaagg ttagcctctt caatttcaga    3660
aagaatgctg acccacagat ggttagagag gcctacgcag caggtctcat caagacgatc    3720
tacccgagta acaatctcca ggagatcaaa taccttccca agaaggttaa agatgcagtc    3780
aaaagattca ggactaattg catcaagaac acagagaaag acatatttct caagatcaga    3840
agtactattc cagtatggac gattcaaggc ttgcttcata aaccaaggca agtaatagag    3900
attggagtct ctaaaaaggt agttcctact gaatctaagg ccatgcatgg agtctaagat    3960
tcaaatcgag gatctaacag aactcgccgt gaagactggc gaacagttca tacagagtct    4020
tttacgactc aatgacaaga agaaaatctt cgtcaacatg gtggagcacg acactctggt    4080
ctactccaaa aatgtcaaag atacagtctc agaagaccaa agggctattg agacttttca    4140
acaaaggata atttcgggaa acctcctcgg attccattgc ccagctatct gtcacttcat    4200
cgaaaggaca gtagaaaagg aaggtggctc ctacaaatgc catcattgcg ataaaggaaa    4260
ggctatcatt caagatgcct ctgccgacag tggtcccaaa gatggacccc cacccacgag    4320
gagcatcgtg gaaaaagaag acgttccaac cacgtcttca aagcaagtgg attgatgtga    4380
catctccact gacgtaaggg atgacgcaca atcccactat ccttcgcaag acccttcctc    4440
tatataagga agttcatttc atttggagag gacacgctcg agctcatttc tctattactt    4500
cagccataac aaaagaactc ttttctcttc ttattaaacc atgaaaaagc ctgaactcac    4560
cgcgacgtct gtcgagaagt ttctgatcga aaagttcgac agcgtctccg acctgatgca    4620
gctctcggag gcgaagaat ctcgtgcttt cagcttcgat gtaggagggc gtggatatgt     4680
cctgcgggta aatagctgcg ccgatggttt ctacaaagat cgttatgttt atcggcactt    4740
tgcatcggcc gcgctcccga ttccggaagt gcttgacatt ggggaattca gcgagagcct    4800
gacctattgc atctcccgcc gtgcacaggg tgtcacgttg caagacctgc ctgaaaccga    4860
actgcccgct gttctgcagc cggtcgcgga ggccatggat gcgatcgctg cggccgatct    4920
tagccagacg agcgggttcg gcccattcgg accgcaagga atcggtcaat acactacatg    4980
gcgtgatttc atatgcgcga ttgctgatcc ccatgtgtat cactggcaaa ctgtgatgga    5040
cgacaccgtc agtgcgtccg tcgcgcaggc tctcgatgag ctgatgcttt gggccgagga    5100
```

```
ctgccccgaa gtccggcacc tcgtgcacgc ggatttcggc tccaacaatg tcctgacgga    5160
caatggccgc ataacagcgg tcattgactg gagcgaggcg atgttcgggg attcccaata    5220
cgaggtcgcc aacatcttct tctggaggcc gtggttggct tgtatggagc agcagacgcg    5280
ctacttcgag cggaggcatc cggagcttgc aggatcgccg cggctccggg cgtatatgct    5340
ccgcattggt cttgaccaac tctatcagag cttggttgac ggcaatttcg atgatgcagc    5400
ttgggcgcag ggtcgatgcg acgcaatcgt ccgatccgga gccgggactg tcgggcgtac    5460
acaaatcgcc cgcagaagcg cggccgtctg gaccgatggc tgtgtagaag tactcgccga    5520
tagtggaaac cgacgcccca gcactcgtcc gagggcaaag gaatagtgag gtacctaaag    5580
aaggagtgcg tcgaagcaga tcgttcaaac atttggcaat aaagtttctt aagattgaat    5640
cctgttgccg tcttgcgat gattatcata taatttctgt tgaattacgt taagcatgta    5700
ataattaaca tgtaatgcat gacgttattt atgagatggg ttttatgat tagagtcccg    5760 caattataca tttaatacgc gatagaaaac aaaatatagc gcgcaaacta ggataaatta    5820
tcgcgcgcgg tgtcatctat gttactagat cgatgtcgaa tcgatcaacc tgcattaatg    5880
aatcggccaa cgcgcgggga gaggcggttt gcgtattggg cgctcttccg cttcctcgct    5940
cactgactcg ctgcgctcgg tcgttcggct gcggcgagcg gtatcagctc actcaaaggc    6000
ggtaatacgg ttatccacag aatcagggga taacgcagga agaacatgt gagcaaaagg    6060 ccagcaaaag gccaggaacc gtaaaaaggc cgcgttgctg gcgttttttcc ataggctccg    6120 ccccctgac gagcatcaca aaaatcgacg ctcaagtcag aggtggcgaa acccgacagg    6180
actataaaga taccaggcgt ttccccctgg aagctccctc gtgcgctctc ctgttccgac    6240
cctgccgctt accggatacc tgtccgcctt tctcccttcg ggaagcgtgg cgctttctca    6300
atgctcacgc tgtaggtatc tcagttcggt gtaggtcgtt cgctccaagc tgggctgtgt    6360
gcacgaaccc cccgttcagc ccgaccgctg cgccttatcc ggtaactatc gtcttgagtc    6420
caacccggta agacacgact tatcgccact ggcagcagcc actggtaaca ggattagcag    6480
agcgaggtat gtaggcggtg ctacagagtt cttgaagtgg tggcctaact acggctacac    6540
tagaaggaca gtatttggta tctgcgctct gctgaagcca gttaccttcg gaaaaagagt    6600
tggtagctct tgatccggca aacaaaccac cgctggtagc ggtggttttt tgtttgcaa    6660 gcagcagatt acgcgcagaa aaaaaggatc tcaagaagat cctttgatct tttctacggg    6720
gtctgacgct cagtggaacg aaaactcacg ttaagggatt ttggtcatga cattaaccta    6780
taaaaatagg cgtatcacga ggccctttcg tctcgcgcgt ttcggtgatg acggtgaaaa    6840
cctctgacac atgcagctcc cggagacggt cacagcttgt ctgtaagcgg atgccgggag    6900
cagacaagcc cgtcagggcg cgtcagcggg tgttggcggg tgtcggggct ggcttaacta    6960
tgcggcatca gagcagattg tactgagagt gcaccatatg gacatattgt cgttagaacg    7020
cggctacaat taatacataa ccttatgtat catacacata cgatttaggt gacactatag    7080
aacgg                                                                7085
```

<210> SEQ ID NO 4
<211> LENGTH: 5303
<212> TYPE: DNA
<213> ORGANISM: Artificial Sequence
<220> FEATURE:
<223> OTHER INFORMATION: Plasmid pKR278

<400> SEQUENCE: 4

```
agcttggatc tcctgcagga tctggccggc cggatctcgt acggatccgt cgacggcgcg    60
```

```
cccgatcatc cggatatagt tcctcctttc agcaaaaaac ccctcaagac ccgtttagag    120
gccccaaggg gttatgctag ttattgctca gcggtggcag cagccaactc agcttccttt    180
cgggctttgt tagcagccgg atcgatccaa gctgtacctc actattcctt tgccctcgga    240
cgagtgctgg ggcgtcggtt tccactatcg gcgagtactt ctacacagcc atcggtccag    300
acggccgcgc ttctgcgggc gatttgtgta cgcccgacag tcccggctcc ggatcggacg    360
attgcgtcgc atcgaccctg cgcccaagct gcatcatcga aattgccgtc aaccaagctc    420
tgatagagtt ggtcaagacc aatgcggagc atatacgccc ggagccgcgg cgatcctgca    480
agctccggat gcctccgctc gaagtagcgc gtctgctgct ccatacaagc caaccacggc    540
ctccagaaga agatgttggc gacctcgtat tgggaatccc cgaacatcgc ctcgctccag    600
tcaatgaccg ctgttatgcg gccattgtcc gtcaggacta tgttggagcc gaaatccgcg    660
tgcacgaggt gccggacttc ggggcagtcc tcggcccaaa gcatcagctc atcgagagcc    720
tgcgcgacgc acgcactgac ggtgtcgtcc atcacagttt gccagtgata cacatgggga    780
tcagcaatcg cgcatatgaa atcacgccat gtagtgtatt gaccgattcc ttgcggtccg    840
aatgggccga acccgctcgt ctggctaaga tcggccgcag cgatcgcatc catagcctcc    900
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact tctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatcgatc caattccaat cccacaaaaa tctgagctta   1380
acagcacagt tgctcctctc agagcagaat cgggtattca acaccctcat atcaactact   1440
acgttgtgta taacggtcca catgccggta tatacgatga ctggggttgt acaaaggcgg   1500
caacaaacgg cgttcccgga gttgcacaca agaaatttgc cactattaca gaggcaagag   1560
cagcagctga cgcgtacaca acaagtcagc aaacagacag gttgaacttc atccccaaag   1620
gagaagctca actcaagccc aagagctttg ctaaggccct aacaagccca ccaaagcaaa   1680
aagcccactg gctcacgcta ggaaccaaaa ggcccagcag tgatccagcc ccaaaagaga   1740
tctcctttgc cccggagatt acaatggacg atttcctcta tctttacgat ctaggaagga   1800
agttcgaagg tgaaggtgac gacactatgt tcaccactga taatgagaag gttagcctct   1860
tcaatttcag aaagaatgct gacccacaga tggttagaga ggcctacgca gcaggtctca   1920
tcaagacgat ctacccgagt aacaatctcc aggagatcaa ataccttccc aagaaggtta   1980
aagatgcagt caaaagattc aggactaatt gcatcaagaa cacagagaaa gacatatttc   2040
tcaagatcag aagtactatt ccagtatgga cgattcaagg cttgcttcat aaaccaaggc   2100
aagtaataga gattggagtc tctaaaaagg tagttcctac tgaatctaag gccatgcatg   2160
gagtctaaga ttcaaatcga ggatctaaca gaactcgccg tgaagactgg cgaacagttc   2220
atacagagtc ttttacgact caatgacaag aagaaaatct tcgtcaacat ggtggagcac   2280
gacactctgg tctactccaa aaatgtcaaa gatacagtct cagaagacca aagggctatt   2340
gagacttttc aacaaaggat aatttcggga aacctcctcg gattccattg cccagctatc   2400
```

```
tgtcacttca tcgaaaggac agtagaaaag gaaggtggct cctacaaatg ccatcattgc    2460
gataaaggaa aggctatcat tcaagatgcc tctgccgaca gtggtcccaa agatggaccc    2520
ccacccacga ggagcatcgt ggaaaaagaa gacgttccaa ccacgtcttc aaagcaagtg    2580
gattgatgtg acatctccac tgacgtaagg gatgacgcac aatcccacta tccttcgcaa    2640
gacccttcct ctatataagg aagttcattt catttggaga ggacacgctc gagctcattt    2700
ctctattact tcagccataa caaaagaact cttttctctt cttattaaac catgaaaaag    2760
cctgaactca ccgcgacgtc tgtcgagaag tttctgatcg aaaagttcga cagcgtctcc    2820
gacctgatgc agctctcgga gggcgaagaa tctcgtgctt tcagcttcga gtaggaggg     2880 cgtggatatg tcctgcgggt aaatagctgc gccgatggtt tctacaaaga tcgttatgtt    2940
tatcggcact ttgcatcggc cgcgctcccg attccggaag tgcttgacat tggggaattc    3000
agcgagagcc tgacctattg catctcccgc cgtgcacagg gtgtcacgtt gcaagacctg    3060
cctgaaaccg aactgcccgc tgttctgcag ccggtcgcgg aggccatgga tgcgatcgct    3120
gcggccgatc ttagccagac gagcgggttc ggcccattcg gaccgcaagg aatcggtcaa    3180
tacactacat ggcgtgattt catatgcgcg attgctgatc cccatgtgta tcactggcaa    3240
actgtgatgg acgacaccgt cagtgcgtcc gtcgcgcagg ctctcgatga gctgatgctt    3300
tgggccgagg actgccccga agtccggcac ctcgtgcacg cggatttcgg ctccaacaat    3360
gtcctgacgg acaatggccg cataacagcg gtcattgact ggagcgaggc gatgttcggg    3420
gattcccaat acgaggtcgc caacatcttc ttctggaggc cgtggttggc ttgtatggag    3480
cagcagacgc gctacttcga gcggaggcat ccggagcttg caggatcgcc gcggctccgg    3540
gcgtatatgc tccgcattgg tcttgaccaa ctctatcaga gcttggttga cggcaatttc    3600
gatgatgcag cttgggcgca gggtcgatgc gacgcaatcg tccgatccgg agccgggact    3660
gtcgggcgta cacaaatcgc ccgcagaagc gcggccgtct ggaccgatgg ctgtgtagaa    3720
gtactcgccg atagtggaaa ccgacgcccc agcactcgtc cgagggcaaa ggaatagtga    3780
ggtacctaaa gaaggagtgc gtcgaagcag atcgttcaaa catttggcaa taaagtttct    3840
taagattgaa tcctgttgcc ggtcttgcga tgattatcat ataatttctg ttgaattacg    3900
ttaagcatgt aataattaac atgtaatgca tgacgttatt tatgagatgg gtttttatga    3960
ttagagtccc gcaattatac atttaatacg cgatagaaaa caaatatag cgcgcaaact     4020 aggataaatt atcgcgcgcg gtgtcatcta tgttactaga tcgatgtcga atcgatcaac    4080
ctgcattaat gaatcggcca acgcgcgggg agaggcggtt tgcgtattgg gcgctcttcc    4140
gcttcctcgc tcactgactc gctgcgctcg gtcgttcggc tgcggcgagc ggtatcagct    4200
cactcaaagg cggtaatacg gttatccaca gaatcagggg ataacgcagg aaagaacatg    4260
tgagcaaaag gccagcaaaa ggccaggaac cgtaaaaagg ccgcgttgct ggcgtttttc    4320
cataggctcc gccccctga cgagcatcac aaaaatcgac gctcaagtca gaggtggcga    4380
aacccgacag gactataaag ataccaggcg tttccccctg gaagctccct cgtgcgctct    4440
cctgttccga ccctgccgct taccggatac ctgtccgcct ttctcccttc gggaagcgtg    4500
gcgctttctc aatgctcacg ctgtaggtat ctcagttcgg tgtaggtcgt tcgctccaag    4560
ctgggctgtg tgcacgaacc ccccgttcag cccgaccgct gcgccttatc cggtaactat    4620
cgtcttgagt ccaacccggt aagacacgac ttatcgccac tggcagcagc cactggtaac    4680
aggattagca gagcgaggta tgtaggcggt gctacagagt tcttgaagtg gtggcctaac    4740
tacggctaca ctagaaggac agtatttggt atctgcgctc tgctgaagcc agttaccttc    4800
```

| | |
|---|---|
| ggaaaaagag ttggtagctc ttgatccggc aaacaaacca ccgctggtag cggtggtttt | 4860 |
| tttgtttgca agcagcagat tacgcgcaga aaaaaaggat ctcaagaaga tcctttgatc | 4920 |
| ttttctacgg ggtctgacgc tcagtggaac gaaaactcac gttaagggat tttggtcatg | 4980 |
| acattaacct ataaaaatag gcgtatcacg aggccctttc gtctcgcgcg tttcggtgat | 5040 |
| gacggtgaaa acctctgaca catgcagctc ccggagacgg tcacagcttg tctgtaagcg | 5100 |
| gatgccggga gcagacaagc ccgtcaggcg cgtcagcgg gtgttggcgg gtgtcggggc | 5160 |
| tggcttaact atgcggcatc agagcagatt gtactgagag tgcaccatat ggacatattg | 5220 |
| tcgttagaac gcggctacaa ttaatacata accttatgta tcatacacat acgatttagg | 5280 |
| tgacactata gaacggcgcg cca | 5303 |

```
<210> SEQ ID NO 5
<211> LENGTH: 4140
<212> TYPE: DNA
<213> ORGANISM: Artificial Sequence
<220> FEATURE:
<223> OTHER INFORMATION: Plasmid pKR407

<400> SEQUENCE: 5
```

| | |
|---|---|
| ggccgcattt cgcaccaaat caatgaaagt aataatgaaa agtctgaata agaatactta | 60 |
| ggcttagatg cctttgttac ttgtgtaaaa taacttgagt catgtacctt tggcggaaac | 120 |
| agaataaata aaggtgaaa ttccaatgct ctatgtataa gttagtaata cttaatgtgt | 180 |
| tctacggttg tttcaatatc atcaaactct aattgaaact ttagaaccac aaatctcaat | 240 |
| cttttcttaa tgaaatgaaa atcttaatt gtaccatgtt tatgttaaac accttacaat | 300 |
| tggttggaga ggaggaccaa ccgatgggac aacattggga gaaagagatt caatggagat | 360 |
| ttggatagga gaacaacatt ctttttcact tcaatacaag atgagtgcaa cactaaggat | 420 |
| atgtatgaga ctttcagaag ctacgacaac atagatgagt gaggtggtga ttcctagcaa | 480 |
| gaaagacatt agaggaagcc aaaatcgaac aaggaagaca tcaagggcaa gagacaggac | 540 |
| catccatctc aggaaaagga gctttgggat agtccgagaa gttgtacaag aaattttttg | 600 |
| gagggtgagt gatgcattgc tggtgacttt aactcaatca aaattgagaa agaaagaaaa | 660 |
| gggaggggc tcacatgtga atagaaggga acgggagaa ttttacagtt ttgatctaat | 720 |
| gggcatccca gctagtggta acatattcac catgtttaac cttcacgtac gtctagagga | 780 |
| tccccgggc tgcaggaatt cactggccgt cgttttacaa cgtcgtgact gggaaaaccc | 840 |
| tggcgttacc caacttaatc gccttgcagc acatccccct ttcgccagct ggcgtaatag | 900 |
| cgaagaggcc cgcaccgatc gcccttccca acagttgcgc agcctgaatg gcgaatggcg | 960 |
| cctgatgcgg tattttctcc ttacgcatct gtgcggtatt tcacaccgca tatggtgcac | 1020 |
| tctcagtaca atctgctctg atgccgcata gttaagccag ccccgacacc cgccaacacc | 1080 |
| cgctgacgcg ccctgacggg cttgtctgct cccggcatcc gcttacagac aagctgtgac | 1140 |
| cgtctccggg agctgcatgt gtcagaggtt ttcaccgtca tcaccgaaac gcgcgagacg | 1200 |
| aaagggcctc gtgatacgcc tatttttata ggttaatgtc atgataataa tggtttctta | 1260 |
| gacgtcaggt ggcactttc ggggaaatgt gcgcggaacc cctatttgtt tatttttcta | 1320 |
| aatacattca aatatgtatc cgctcatgag acaataaccc tgataaatgc ttcaataata | 1380 |
| ttgaaaaagg aagagtatga gtattcaaca tttccgtgtc gcccttattc ccttttttgc | 1440 |
| ggcattttgc cttcctgttt ttgctcaccc agaaacgctg gtgaaagtaa aagatgctga | 1500 |

```
agatcagttg ggtgcacgag tgggttacat cgaactggat ctcaacagcg gtaagatcct    1560
tgagagtttt cgccccgaag aacgttttcc aatgatgagc acttttaaag ttctgctatg    1620
tggcgcggta ttatcccgta ttgacgccgg gcaagagcaa ctcggtcgcc gcatacacta    1680
ttctcagaat gacttggttg agtactcacc agtcacagaa aagcatctta cggatggcat    1740
gacagtaaga gaattatgca gtgctgccat aaccatgagt gataacactg cggccaactt    1800
acttctgaca acgatcggag gaccgaagga gctaaccgct tttttgcaca catgggggga    1860
tcatgtaact cgccttgatc gttgggaacc ggagctgaat gaagccatac caaacgacga    1920
gcgtgacacc acgatgcctg tagcaatggc aacaacgttg cgcaaactat taactggcga    1980
actacttact ctagcttccc ggcaacaatt aatagactgg atggaggcgg ataaagttgc    2040
aggaccactt ctgcgctcgg cccttccggc tggctggttt attgctgata atctggagc    2100 cggtgagcgt gggtctcgcg gtatcattgc agcactgggg ccagatggta agccctcccg    2160
tatcgtagtt atctacacga cggggagtca ggcaactatg gatgaacgaa atagacagat    2220
cgctgagata ggtgcctcac tgattaagca ttggtaactg tcagaccaag tttactcata    2280
tatactttag attgatttaa aacttcattt ttaatttaaa aggatctagg tgaagatcct    2340
ttttgataat ctcatgacca aaatccctta acgtgagttt tcgttccact gagcgtcaga    2400
ccccgtagaa aagatcaaag gatcttcttg agatcctttt tttctgcgcg taatctgctg    2460
cttgcaaaca aaaaaaccac cgctaccagc ggtggtttgt ttgccggatc aagagctacc    2520
aactcttttt ccgaaggtaa ctggcttcag cagagcgcag ataccaaata ctgtccttct    2580
agtgtagccg tagttaggcc accacttcaa gaactctgta gcaccgccta catacctcgc    2640
tctgctaatc ctgttaccag tggctgctgc cagtggcgat aagtcgtgtc ttaccgggtt    2700
ggactcaaga cgatagttac cggataaggc gcagcggtcg ggctgaacgg ggggttcgtg    2760
cacacagccc agcttggagc gaacgaccta caccgaactg agatacctac agcgtgagct    2820
atgagaaagc gccacgcttc ccgaagggag aaaggcggac aggtatccgg taagcggcag    2880
ggtcggaaca ggagagcgca cgagggagct tccaggggga aacgcctggt atctttatag    2940
tcctgtcggg tttcgccacc tctgacttga gcgtcgattt ttgtgatgct cgtcaggggg    3000
gcggagccta tggaaaaacg ccagcaacgc ggcctttta cggttcctgg ccttttgctg    3060
gccttttgct cacatgttct ttcctgcgtt atcccctgat tctgtggata accgtattac    3120
cgcctttgag tgagctgata ccgctcgccg cagccgaacg accgagcgca gcgagtcagt    3180
gagcgaggaa gcggaagagc gcccaatacg caaaccgcct ctccccgcgc gttggccgat    3240
tcattaatgc agctggcacg acaggtttcc cgactggaaa gcgggcagtg agcgcaacgc    3300
aattaatgtg agttagctca ctcattaggc accccaggct ttacacttta tgcttccggc    3360
tcgtatgttg tgtggaattg tgagcggata acaatttcac acaggaaaca gctatgacca    3420
tgattacgcc aagcttgcat gcctgcaggc tagcctaagt acgtactcaa aatgccaaca    3480
aataaaaaaa aagttgcttt aataatgcca aaacaaatta ataaacact tacaacaccg    3540 gatttttttt aattaaaatg tgccatttag gataaatagt taatatttt aataattatt    3600 taaaaagccg tatctactaa aatgattttt atttggttga aatattaat atgtttaaat    3660 caacacaatc tatcaaaatt aaactaaaaa aaaaataagt gtacgtggtt aacattagta    3720
cagtaatata agaggaaaat gagaaattaa gaaattgaaa gcgagtctaa tttttaaatt    3780
atgaacctgc atatataaaa ggaaagaaag aatccaggaa gaaagaaat gaaccatgc    3840 atggtcccct cgtcatcacg agttctgcc atttgcaata gaaacactga aacacctttc    3900
```

```
tctttgtcac ttaattgaga tgccgaagcc acctcacacc atgaacttca tgaggtgtag    3960
cacccaaggc ttccatagcc atgcatactg aagaatgtct caagctcagc accctacttc    4020
tgtgacgtgt ccctcattca ccttcctctc ttccctataa ataaccacgc ctcaggttct    4080
ccgcttcaca actcaaacat tctctccatt ggtccttaaa cactcatcag tcatcaccgc    4140
```

<210> SEQ ID NO 6
<211> LENGTH: 6747
<212> TYPE: DNA
<213> ORGANISM: Artificial Sequence
<220> FEATURE:
<223> OTHER INFORMATION: Plasmid pKR1468

<400> SEQUENCE: 6

```
gatccgtcga cggcgcgccc gatcatccgg atatagttcc tcctttcagc aaaaaacccc      60
tcaagacccg tttagaggcc ccaaggggtt atgctagtta ttgctcagcg gtggcagcag     120
ccaactcagc ttcctttcgg ctttgttag cagccggatc gatccaagct gtacctcact     180
attcctttgc cctcggacga gtgctgggc gtcggtttcc actatcggcg agtacttcta     240
cacagccatc ggtccagacg gccgcgcttc tgcgggcgat ttgtgtacgc ccgacagtcc     300
cggctccgga tcggacgatt gcgtcgcatc gaccctgcgc ccaagctgca tcatcgaaat     360
tgccgtcaac caagctctga tagagttggt caagaccaat gcggagcata tacgcccgga     420
gccgcggcga tcctgcaagc tccggatgcc tccgctcgaa gtagcgcgtc tgctgctcca     480
tacaagccaa ccacggcctc cagaagaaga tgttggcgac ctcgtattgg gaatccccga     540
acatcgcctc gctccagtca atgaccgctg ttatgcggcc attgtccgtc aggacattgt     600
tggagccgaa atccgcgtgc acgaggtgcc ggacttcggg gcagtcctcg gcccaaagca     660
tcagctcatc gagagcctgc gcgacggacg cactgacggt gtcgtccatc acagtttgcc     720
agtgatacac atggggatca gcaatcgcgc atatgaaatc acgccatgta gtgtattgac     780
cgattccttg cggtccgaat gggccgaacc cgctcgtctg gctaagatcg gccgcagcga     840
tcgcatccat agcctccgcg accggctgca gaacagcggg cagttcggtt tcaggcaggt     900
cttgcaacgt gacaccctgt gcacggcggg agatgcaata ggtcaggctc tcgctgaatt     960
ccccaatgtc aagcacttcc ggaatcggga gcgcggccga tgcaaagtgc cgataaacat    1020
aacgatcttt gtagaaacca tcggcgcagc tatttacccg caggacatat ccacgccctc    1080
ctacatcgaa gctgaaagca cgagattctt cgccctccga gagctgcatc aggtcggaga    1140
cgctgtcgaa cttttcgatc agaaacttct cgacagacgt cgcggtgagt tcaggctttt    1200
ccatgggtat atctccttct taaagttaaa caaaattatt tctagaggga accgttgtg    1260 gtctccctat agtgagtcgt attaatttcg cgggatcgag atcgatccaa ttccaatccc    1320
acaaaaatct gagcttaaca gcacagttgc tcctctcaga gcagaatcgg gtattcaaca    1380
ccctcatatc aactactacg ttgtgtataa cggtccacat gccggtatat acgatgactg    1440
gggttgtaca aaggcggcaa caaacggcgt tcccggagtt gcacacaaga atttgccac    1500 tattacagag gcaagagcag cagctgacgc gtacacaaca agtcagcaaa cagacaggtt    1560
gaacttcatc cccaaaggag aagctcaact caagcccaag agctttgcta aggccctaac    1620
aagcccacca aagcaaaaag cccactggct cacgctagga accaaaaggc ccagcagtga    1680
tccagcccca aaagagatct cctttgcccc ggagattaca atggacgatt tcctctatct    1740
ttacgatcta ggaaggaagt tcgaaggtga aggtgacgac actatgttca ccactgataa    1800
```

```
tgagaaggtt agcctcttca atttcagaaa gaatgctgac ccacagatgg ttagagaggc    1860
ctacgcagca ggtctcatca agacgatcta cccgagtaac aatctccagg agatcaaata    1920
ccttcccaag aaggttaaag atgcagtcaa aagattcagg actaattgca tcaagaacac    1980
agagaaagac atatttctca agatcagaag tactattcca gtatggacga ttcaaggctt    2040
gcttcataaa ccaaggcaag taatagagat tggagtctct aaaaaggtag ttcctactga    2100
atctaaggcc atgcatggag tctaagattc aaatcgagga tctaacagaa ctcgccgtga    2160
agactggcga acagttcata cagagtcttt tacgactcaa tgacaagaag aaaatcttcg    2220
tcaacatggt ggagcacgac actctggtct actccaaaaa tgtcaaagat acagtctcag    2280
aagaccaaag ggctattgag acttttcaac aaaggataat ttcgggaaac ctcctcggat    2340
tccattgccc agctatctgt cacttcatcg aaaggacagt agaaaaggaa ggtggctcct    2400
acaaatgcca tcattgcgat aaaggaaagg ctatcattca agatgcctct gccgacagtg    2460
gtcccaaaga tggacccccca cccacgagga gcatcgtgga aaaagaagac gttccaacca    2520
cgtcttcaaa gcaagtggat tgatgtgaca ctccactga cgtaagggat gacgcacaat    2580
cccactatcc ttcgcaagac ccttcctcta tataaggaag ttcatttcat ttggagagga    2640
cacgctcgag ctcatttctc tattacttca gccataacaa aagaactctt ttctcttctt    2700
attaaaccat gaaaaagcct gaactcaccg cgacgtctgt cgagaagttt ctgatcgaaa    2760
agttcgacag cgtctccgac ctgatgcagc tctcggaggg cgaagaatct cgtgctttca    2820
gcttcgatgt aggagggcgt ggatatgtcc tgcgggtaaa tagctgcgcc gatggtttct    2880
acaaagatcg ttatgtttat cggcactttg catcggccgc gctcccgatt ccggaagtgc    2940
ttgacattgg ggaattcagc gagagcctga cctattgcat ctcccgccgt gcacagggtg    3000
tcacgttgca agacctgcct gaaaccgaac tgcccgctgt tctgcagccg gtcgcggagg    3060
ccatggatgc gatcgctgcg gccgatctta gccagacgag cgggttcggc ccattcggac    3120
cgcaaggaat cggtcaatac actacatggc gtgatttcat atgcgcgatt gctgatcccc    3180
atgtgtatca ctggcaaact gtgatggacg acaccgtcag tgcgtccgtc gcgcaggctc    3240
tcgatgagct gatgctttgg gccgaggact gccccgaagt ccggcacctc gtgcacgcgg    3300
atttcggctc caacaatgtc ctgacggaca atggccgcat aacagcggtc attgactgga    3360
gcgaggcgat gttcggggat tcccaatacg aggtcgccaa catcttcttc tggaggccgt    3420
ggttggcttg tatggagcag cagacgcgct acttcgagcg gaggcatccg gagcttgcag    3480
gatcgccgcg gctccgggcg tatatgctcc gcattggtct tgaccaactc tatcagagct    3540
tggttgacgg caatttcgat gatgcagctt gggcgcaggg tcgatgcgac gcaatcgtcc    3600
gatccggagc cgggactgtc gggcgtacac aaatcgcccg cagaagcgcg gccgtctgga    3660
ccgatggctg tgtagaagta ctcgccgata gtggaaaccg acgccccagc actcgtccga    3720
gggcaaagga atagtgaggt acctaaagaa ggagtgcgtc gaagcagatc gttcaaacat    3780
ttggcaataa agtttcttaa gattgaatcc tgttgccggt cttgcgatga ttatcatata    3840
atttctgttg aattacgtta agcatgtaat aattaacatg taatgcatga cgttatttat    3900
gagatgggtt tttatgatta gagtcccgca attatacatt taatacgcga tagaaaacaa    3960
aatatagcgc gcaaactagg ataaattatc gcgcgcggtg tcatctatgt tactagatcg    4020
atgtcgaatc gatcaacctg cattaatgaa tcggccaacg cgcggggaga ggcggtttgc    4080
gtattgggcg ctcttccgct tcctcgctca ctgactcgct gcgctcggtc gttcggctgc    4140
ggcgagcggt atcagctcac tcaaaggcgg taatacggtt atccacagaa tcaggggata    4200
```

```
acgcaggaaa gaacatgtga gcaaaaggcc agcaaaaggc caggaaccgt aaaaaggccg    4260
cgttgctggc gttttttccat aggctccgcc ccctgacga gcatcacaaa aatcgacgct    4320
caagtcagag gtggcgaaac ccgacaggac tataaagata ccaggcgttt ccccctggaa    4380
gctccctcgt gcgctctcct gttccgaccc tgccgcttac cggatacctg tccgcctttc    4440
tcccttcggg aagcgtggcg ctttctcaat gctcacgctg taggtatctc agttcggtgt    4500
aggtcgttcg ctccaagctg gctgtgtgc acgaacccccc cgttcagccc gaccgctgcg    4560
ccttatccgg taactatcgt cttgagtcca acccggtaag acacgactta tcgccactgg    4620
cagcagccac tggtaacagg attagcagag cgaggtatgt aggcggtgct acagagttct    4680
tgaagtggtg gcctaactac ggctacacta aggacagt atttggtatc tgcgctctgc    4740
tgaagccagt taccttcgga aaagagttg gtagctcttg atccggcaaa caaccaccg    4800 ctggtagcgg tggttttttt gtttgcaagc agcagattac gcgcagaaaa aaaggatctc    4860
aagaagatcc tttgatcttt tctacggggt ctgacgctca gtggaacgaa aactcacgtt    4920
aagggatttt ggtcatgaca ttaacctata aaaataggcg tatcacgagg cccttttcgtc    4980 tcgcgcgttt cggtgatgac ggtgaaaacc tctgacacat gcagctcccg gagacggtca    5040
cagcttgtct gtaagcggat gccgggagca gacaagcccg tcagggcgcg tcagcgggtg    5100
ttggcgggtg tcgggctgg cttaactatg cggcatcaga gcagattgta ctgagagtgc    5160
accatatgga catattgtcg ttagaacgcg gctacaatta atacataacc ttatgtatca    5220
tacacatacg atttaggtga cactatagaa cggcgcgcca agcttgcatg cctgcaggct    5280
agcctaagta cgtactcaaa atgccaacaa ataaaaaaaa agttgcttta ataatgccaa    5340
aacaaattaa taaaacactt acaacaccgg atttttttta attaaaatgt gccatttagg    5400
ataaatagtt aatattttta ataattattt aaaaagccgt atctactaaa atgattttta    5460
tttggttgaa aatattaata tgtttaaatc aacacaatct atcaaaatta aactaaaaaa    5520
aaaataagtg tacgtggtta acattagtac agtaatataa gaggaaaatg agaaattaag    5580
aaattgaaag cgagtctaat ttttaaatta tgaacctgca tatataaaag gaaagaaaga    5640
atccaggaag aaaagaaatg aaaccatgca tggtcccctc gtcatcacga gtttctgcca    5700
tttgcaatag aaacactgaa acacctttct ctttgtcact taattgagat gccgaagcca    5760
cctcacacca tgaacttcat gaggtgtagc acccaaggct tccatagcca tgcatactga    5820
agaatgtctc aagctcagca ccctacttct gtgacgtgtc cctcattcac cttcctctct    5880
tccctataaa taaccacgcc tcaggttctc cgcttcacaa ctcaaacatt ctctccattg    5940
gtccttaaac actcatcagt catcaccgcg gccgcatttc gcaccaaatc aatgaaagta    6000
ataatgaaaa gtctgaataa gaatacttag gcttagatgc ctttgttact tgtgtaaaat    6060
aacttgagtc atgtaccttt ggcggaaaca gaataaataa aaggtgaaat tccaatgctc    6120
tatgtataag ttagtaatac ttaatgtgtt ctacggttgt ttcaatatca tcaaactcta    6180
attgaaactt tagaaccaca aatctcaatc ttttcttaat gaaatgaaaa atcttaattg    6240
taccatgttt atgttaaaca ccttacaatt ggttggagag gaggaccaac cgatgggaca    6300
acattgggag aaagagattc aatggagatt tggataggag aacaacattc ttttcactt    6360 caatacaaga tgagtgcaac actaaggata tgtatgagac tttcagaagc tacgacaaca    6420
tagatgagtg aggtggtgat tcctagcaag aaagacatta gaggaagcca aaatcgaaca    6480
aggaagacat caagggcaag agacaggacc atccatctca ggaaaaggag ctttgggata    6540
```

```
gtccgagaag ttgtacaaga aatttttttgg agggtgagtg atgcattgct ggtgacttta    6600
actcaatcaa aattgagaaa gaaagaaaag gaagggggct cacatgtgaa tagaagggaa    6660
acgggagaat tttacagttt tgatctaatg gcatcccag ctagtggtaa catattcacc     6720
atgtttaacc ttcacgtacg tctagag                                        6747

<210> SEQ ID NO 7
<211> LENGTH: 8462
<212> TYPE: DNA
<213> ORGANISM: Artificial Sequence
<220> FEATURE:
<223> OTHER INFORMATION: Plasmid pKR1475

<400> SEQUENCE: 7
ggccgcattt cgcaccaaat caatgaaagt aataatgaaa agtctgaata agaatactta      60
ggcttagatg cctttgttac ttgtgtaaaa taacttgagt catgtacctt tggcggaaac     120
agaataaata aaaggtgaaa ttccaatgct ctatgtataa gttagtaata cttaatgtgt     180
tctacggttg tttcaatatc atcaaactct aattgaaact ttagaaccac aaatctcaat    240
cttttcttaa tgaaatgaaa aatcttaatt gtaccatgtt tatgttaaac accttacaat    300
tggttggaga ggaggaccaa ccgatgggac aacattggga gaaagagatt caatggagat    360
ttggatagga gaacaacatt cttttttcact tcaatacaag atgagtgcaa cactaaggat    420
atgtatgaga ctttcagaag ctacgacaac atagatgagt gaggtggtga ttcctagcaa    480
gaaagacatt agaggaagcc aaaatcgaac aaggaagaca tcaagggcaa gagacaggac    540
catccatctc aggaaaagga gctttgggat agtccgagaa gttgtacaag aaatttttttg   600 gagggtgagt gatgcattgc tggtgacttt aactcaatca aaattgagaa agaaagaaaa    660 gggaggggggc tcacatgtga atagaaggga acgggagaa ttttacagtt ttgatctaat    720
gggcatccca gctagtggta acatattcac catgtttaac cttcacgtac gtctagagga    780
tccgtcgacg gcgcgcccga tcatccggat atagttcctc cttcagcaa aaaaccctc     840 aagacccgtt tagaggcccc aagggggttat gctagttatt gctcagcggt ggcagcagcc    900
aactcagctt ccttttcgggc tttgttagca gccggatcga tccaagctgt acctcactat    960 tccttttgccc tcggacgagt gctggggcgt cggtttccac tatcggcgag tacttctaca   1020
cagccatcgg tccagacggc cgcgcttctg cgggcgattt tgtgtacgcc gacagtcccg   1080
gctccggatc ggacgattgc gtcgcatcga ccctgcgccc aagctgcatc atcgaaattg   1140
ccgtcaacca agctctgata gagttggtca agaccaatgc ggagcatata cgcccggagc   1200
cgcggcgatc ctgcaagctc cggatgcctc cgctcgaagt agcgcgtctg ctgctccata   1260
caagccaacc acggcctcca gaagaagatg ttggcgacct cgtattggga atcccccgaac  1320 atcgcctcgc tccagtcaat gaccgctgtt atgcggccat tgtccgtcag gacattgttg   1380
gagccgaaat ccgcgtgcac gaggtgccgg acttcggggc agtcctcggc ccaaagcatc   1440
agctcatcga gagcctgcgc gacggacgca ctgacggtgt cgtccatcac agtttgccag   1500
tgatacacat ggggatcagc aatcgcgcat atgaaatcac gccatgtagt gtattgaccg   1560
attccttgcg gtccgaatgg gccgaacccg ctcgtctggc taagatcggc cgcagcgatc   1620
gcatccatag cctccgcgac cggctgcaga acagcgggca gttcggtttc aggcaggtct   1680
tgcaacgtga caccctgtgc acggcgggag atgcaatagg tcaggctctc gctgaattcc   1740
ccaatgtcaa gcacttccgg aatcgggagc gcggccgatg caaagtgccg ataaacataa   1800
cgatctttgt agaaaccatc ggcgcagcta tttacccgca ggacatatcc acgccctcct   1860
```

```
acatcgaagc tgaaagcacg agattcttcg ccctccgaga gctgcatcag gtcggagacg   1920
ctgtcgaact tttcgatcag aaacttctcg acagacgtcg cggtgagttc aggcttttcc   1980
atgggtatat ctccttctta aagttaaaca aaattatttc tagagggaaa ccgttgtggt   2040
ctccctatag tgagtcgtat taatttcgcg ggatcgagat cgatccaatt ccaatcccac   2100
aaaaatctga gcttaacagc acagttgctc ctctcagagc agaatcgggt attcaacacc   2160
ctcatatcaa ctactacgtt gtgtataacg gtccacatgc cggtatatac gatgactggg   2220
gttgtacaaa ggcggcaaca acggcgttc ccggagttgc acacaagaaa tttgccacta   2280
ttacagaggc aagagcagca gctgacgcgt acacaacaag tcagcaaaca gacaggttga   2340
acttcatccc caaggagaa gctcaactca gcccaagag ctttgctaag gccctaacaa   2400
gcccaccaaa gcaaaagcc cactggctca cgctaggaac caaaaggccc agcagtgatc   2460
cagccccaaa agagatctcc tttgccccgg agattacaat ggacgatttc ctctatcttt   2520
acgatctagg aaggaagttc gaaggtgaag gtgacgacac tatgttcacc actgataatg   2580
agaaggttag cctcttcaat ttcagaaaga atgctgaccc acagatggtt agagaggcct   2640
acgcagcagg tctcatcaag acgatctacc cgagtaacaa tctccaggag atcaaatacc   2700
ttcccaagaa ggttaaagat gcagtcaaaa gattcaggac taattgcatc aagaacacag   2760
agaaagacat atttctcaag atcagaagta ctattccagt atggacgatt caaggcttgc   2820
ttcataaacc aaggcaagta atagagattg gagtctctaa aaaggtagtt cctactgaat   2880
ctaaggccat gcatggagtc taagattcaa atcgaggatc taacagaact cgccgtgaag   2940
actggcgaac agttcataca gagtctttta cgactcaatg acaagaagaa aatcttcgtc   3000
aacatggtgg agcacgacac tctggtctac tccaaaaatg tcaaagatac agtctcagaa   3060
gaccaaaggg ctattgagac ttttcaacaa aggataattt cgggaaacct cctcggattc   3120
cattgcccag ctatctgtca cttcatcgaa aggacagtag aaaaggaagg tggctcctac   3180
aaatgccatc attgcgataa aggaaaggct atcattcaag atgcctctgc cgacagtggt   3240
cccaaagatg accccccacc cacgaggagc atcgtggaaa agaagacgt tccaaccacg   3300 tcttcaaagc aagtggattg atgtgacatc tccactgacg taagggatga cgcacaatcc   3360
cactatcctt cgcaagaccc ttcctctata taaggaagtt catttcattt ggagaggaca   3420
cgctcgagct catttctcta ttacttcagc cataacaaaa gaactctttt ctcttcttat   3480
taaaccatga aaaagcctga actcaccgcg acgtctgtcg agaagtttct gatcgaaaag   3540
ttcgacagcg tctccgacct gatgcagctc tcggagggcg aagaatctcg tgctttcagc   3600
ttcgatgtag agggcgtgg atatgtcctg cgggtaaata gctgcgccga tggtttctac   3660
aaagatcgtt atgtttatcg gcactttgca tcggccgcgc tcccgattcc ggaagtgctt   3720
gacattgggg aattcagcga gagcctgacc tattgcatct cccgccgtgc acagggtgtc   3780
acgttgcaag acctgcctga aaccgaactg cccgctgttc tgcagccggt cgcggaggcc   3840
atggatgcga tcgctgcggc cgatcttagc cagacgagcg gttcggccc attcggaccg   3900 caaggaatcg gtcaatacac tacatggcgt gatttcatat gcgcgattgc tgatccccat   3960
gtgtatcact ggcaaactgt gatggacgac accgtcagtg cgtccgtcgc gcaggctctc   4020
gatgagctga tgctttgggc cgaggactgc cccgaagtcc ggcacctcgt gcacgcggat   4080
ttcggctcca acaatgtcct gacgacaat ggccgcataa cagcggtcat tgactggagc   4140
gaggcgatgt tcgggggattc ccaatacgag gtcgccaaca tcttcttctg gaggccgtgg   4200
```

```
ttggcttgta tggagcagca gacgcgctac ttcgagcgga ggcatccgga gcttgcagga    4260
tcgccgcggc tccgggcgta tatgctccgc attggtcttg accaactcta tcagagcttg    4320
gttgacggca atttcgatga tgcagcttgg gcgcagggtc gatgcgacgc aatcgtccga    4380
tccggagccg ggactgtcgg gcgtacacaa atcgcccgca gaagcgcggc cgtctggacc    4440
gatggctgtg tagaagtact cgccgatagt ggaaaccgac gccccagcac tcgtccgagg    4500
gcaaaggaat agtgaggtac ctaaagaagg agtgcgtcga agcagatcgt tcaaacattt    4560
ggcaataaag tttcttaaga ttgaatcctg ttgccggtct tgcgatgatt atcatataat    4620
ttctgttgaa ttacgttaag catgtaataa ttaacatgta atgcatgacg ttatttatga    4680
gatgggtttt tatgattaga gtcccgcaat tatacattta atacgcgata gaaaacaaaa    4740
tatagcgcgc aaactaggat aaattatcgc gcgcggtgtc atctatgtta ctagatcgat    4800
gtcgaatcga tcaacctgca ttaatgaatc ggccaacgcg cggggagagg cggtttgcgt    4860
attgggcgct cttccgcttc ctcgctcact gactcgctgc gctcggtcgt tcggctgcgg    4920
cgagcggtat cagctcactc aaaggcggta atacggttat ccacagaatc aggggataac    4980
gcaggaaaga acatgtgagc aaaaggccag caaaaggcca ggaaccgtaa aaaggccgcg    5040
ttgctggcgt ttttccatag gctccgcccc cctgacgagc atcacaaaaa tcgacgctca    5100
agtcagaggt ggcgaaaccc gacaggacta taaagatacc aggcgtttcc ccctggaagc    5160
tccctcgtgc gctctcctgt tccgaccctg ccgcttaccg gatacctgtc cgcctttctc    5220
ccttcgggaa gcgtggcgct ttctcaatgc tcacgctgta ggtatctcag ttcggtgtag    5280
gtcgttcgct ccaagctggg ctgtgtgcac gaaccccccg ttcagcccga ccgctgcgcc    5340
ttatccggta actatcgtct tgagtccaac ccggtaagac acgacttatc gccactggca    5400
gcagccactg gtaacaggat tagcagagcg aggtatgtag cggtgctac agagttcttg     5460 aagtggtggc ctaactacgg ctacactaga aggacagtat ttggtatctg cgctctgctg    5520
aagccagtta ccttcggaaa aagagttggt agctcttgat ccggcaaaca aaccaccgct    5580
ggtagcggtg gtttttttgt ttgcaagcag cagattacgc gcagaaaaaa aggatctcaa    5640
gaagatcctt tgatctttc tacggggtct gacgctcagt ggaacgaaaa ctcacgttaa    5700
gggattttgg tcatgacatt aacctataaa aataggcgta tcacgaggcc ctttcgtctc    5760
gcgcgtttcg gtgatgacgg tgaaaacctc tgacacatgc agctcccgga gacggtcaca    5820
gcttgtctgt aagcggatgc cgggagcaga caagcccgtc agggcgcgtc agcgggtgtt    5880
ggcgggtgtc ggggctggct taactatgcg gcatcagagc agattgtact gagagtgcac    5940
catatggaca tattgtcgtt agaacgcggc tacaattaat acataacctt atgtatcata    6000
cacatacgat ttaggtgaca ctatagaacg gcgcgccaag cttgcatgcc tgcaggctag    6060
cctaagtacg tactcaaaat gccaacaaat aaaaaaaaag ttgctttaat aatgccaaaa    6120
caaattaata aaacacttac aacaccggat tttttttaat taaaatgtgc catttaggat    6180
aaatagttaa tatttttaat aattatttaa aaagccgtat ctactaaaat gatttttatt    6240
tggttgaaaa tattaatatg tttaaatcaa cacaatctat caaaattaaa ctaaaaaaaa    6300
aataagtgta cgtggttaac attagtacag taatataaga ggaaaatgag aaattaagaa    6360
attgaaagcg agtctaattt ttaaattatg aacctgcata tataaaagga agaaagaat    6420 ccaggaagaa aagaaatgaa accatgcatg gtcccctcgt catcacgagt ttctgccatt    6480
tgcaatagaa acactgaaac accttctctt ttgtcactta attgagatgc cgaagccacc    6540
tcacaccatg aacttcatga ggtgtagcac ccaaggcttc catagccatg catactgaag    6600
```

```
aatgtctcaa gctcagcacc ctacttctgt gacgtgtccc tcattcacct tcctctcttc    6660
cctataaata accacgcctc aggttctccg cttcacaact caaacattct ctccattggt    6720
ccttaaacac tcatcagtca tcaccgcggc catcacaagt ttgtacaaaa aagctgaacg    6780
agaaacgtaa aatgatataa atatcaatat attaaattag attttgcata aaaaacagac    6840
tacataatac tgtaaaacac aacatatcca gtcatattgg cggccgcatt aggcaccccca   6900
ggctttacac tttatgcttc cggctcgtat aatgtgtgga ttttgagtta ggatccgtcg    6960
agattttcag gagctaagga agctaaaatg gagaaaaaaa tcactggata taccaccgtt    7020
gatatatccc aatggcatcg taaagaacat tttgaggcat ttcagtcagt tgctcaatgt    7080
acctataacc agaccgttca gctggatatt acggcctttt taaagaccgt aaagaaaaat    7140
aagcacaagt tttatccggc ctttattcac attcttgccc gcctgatgaa tgctcatccg    7200
gaattccgta tggcaatgaa agacggtgag ctggtgatat gggatagtgt tcacccttgt    7260
tacaccgttt tccatgagca aactgaaacg ttttcatcgc tctggagtga ataccacgac    7320
gatttccggc agtttctaca catatattcg caagatgtgg cgtgttacgg tgaaaacctg    7380
gcctatttcc ctaaagggtt tattgagaat atgttttttcg tctcagccaa tccctgggtg    7440
agtttcacca gttttgattt aaacgtggcc aatatggaca acttcttcgc ccccgttttc    7500
accatgggca aatattatac gcaaggcgac aaggtgctga tgccgctggc gattcaggtt    7560
catcatgccg tttgtgatgg cttccatgtc ggcagaatgc ttaatgaatt acaacagtac    7620
tgcgatgagt ggcagggcgg ggcgtaaacg cgtggatccg gcttactaaa agccagataa    7680
cagtatgcgt atttgcgcgc tgattttttgc ggtataagaa tatatactga tatgtatacc    7740
cgaagtatgt caaaaagagg tatgctatga agcagcgtat tacagtgaca gttgacagcg    7800
acagctatca gttgctcaag gcatatatga tgtcaatatc tccggtctgg taagcacaac    7860
catgcagaat gaagcccgtc gtctgcgtgc cgaacgctgg aaagcggaaa atcaggaagg    7920
gatggctgag gtcgcccggt ttattgaaat gaacggctct tttgctgacg agaacagggg    7980
ctggtgaaat gcagtttaag gtttacacct ataaaagaga gagccgttat cgtctgtttg    8040
tggatgtaca gagtgatatt attgacacgc ccgggcgacg gatggtgatc cccctggcca    8100
gtgcacgtct gctgtcagat aaagtctccc gtgaacttta cccggtggtg catatcgggg    8160
atgaaagctg gcgcatgatg accaccgata tggccagtgt gccggtctcc gttatcgggg    8220
aagaagtggc tgatctcagc caccgcgaaa atgacatcaa aaacgccatt aacctgatgt    8280
tctgggggaat ataaatgtca ggctccctta tacacagcca gtctgcaggt cgaccatagt    8340
gactggatat gttgtgtttt acagcattat gtagtctgtt ttttatgcaa aatctaattt    8400
aatatattga tatttatatc attttacgtt tctcgttcag ctttcttgta caaagtggtg    8460
at                                                                  8462
```

<210> SEQ ID NO 8
<211> LENGTH: 13268
<212> TYPE: DNA
<213> ORGANISM: Artificial Sequence
<220> FEATURE:
<223> OTHER INFORMATION: Plasmid pKR92

<400> SEQUENCE: 8

```
cgcgcctcga gtgggcggat ccccccgggct gcaggaattc actggccgtc gttttacaac     60
gtcgtgactg ggaaaaccct ggcgttaccc aacttaatcg ccttgcagca catccccctt    120
```

```
tcgccagctg gcgtaatagc gaagaggccc gcaccgatcg cccttcccaa cagttgcgca    180
gcctgaatgg cgaatggatc gatccatcgc gatgtacctt ttgttagtca gcctctcgat    240
tgctcatcgt cattacacag taccgaagtt tgatcgatct agtaacatag atgacaccgc    300
gcgcgataat ttatcctagt ttgcgcgcta tattttgttt tctatcgcgt attaaatgta    360
taattgcggg actctaatca taaaaaccca tctcataaat aacgtcatgc attacatgtt    420
aattattaca tgcttaacgt aattcaacag aaattatatg ataatcatcg caagaccggc    480
aacaggattc aatcttaaga aactttattg ccaaatgttt gaacgatctg cttcgacgca    540
ctccttcttt actccaccat ctcgtcctta ttgaaaacgt gggtagcacc aaaacgaatc    600
aagtcgctgg aactgaagtt accaatcacg ctggatgatt tgccagttgg attaatcttg    660
cctttccccg catgaataat attgatgaat gcatgcgtga ggggtagttc gatgttggca    720
atagctgcaa ttgccgcgac atcctccaac gagcataatt cttcagaaaa atagcgatgt    780
tccatgttgt cagggcatgc atgatgcacg ttatgaggtg acggtgctag gcagtattcc    840
ctcaaagttt catagtcagt atcatattca tcattgcatt cctgcaagag agaattgaga    900
cgcaatccac acgctgcggc aaccttccgg cgttcgtggt ctatttgctc ttggacgttg    960
caaacgtaag tgttggatcg atccggggtg ggcgaagaac tccagcatga atccccgcg    1020 ctggaggatc atccagccgg cgtcccggaa aacgattccg aagcccaacc tttcatagaa    1080
ggcggcggtg gaatcgaaat ctcgtgatgg caggttgggc gtcgcttggt cggtcatttc    1140
gaacccagga gtcccgctca gaagaactcg tcaagaaggc gatagaaggc gatgcgctgc    1200
gaatcgggag cggcgatacc gtaaagcacg aggaagcggt cagcccattc gccgccaagc    1260
tcttcagcaa tatcacgggt agccaacgct atgtcctgat agcggtccgc cacacccagc    1320
cggccacagt cgatgaatcc agaaaagcgg ccatttttcca ccatgatatt cggcaagcag    1380
gcatcgccat gggtcacgac gagatcctcg ccgtcgggca tgcgcgcctt gagcctggcg    1440
aacagttcgg ctggcgcgag cccctgatgc tcttcgtcca gatcatcctg atcgacaaga    1500
ccggcttcca tccgagtacg tgctcgctcg atgcgatgtt tcgcttggtg gtcgaatggg    1560
caggtagccg gatcaagcgt atgcagccgc cgcattgcat cagccatgat ggatactttc    1620
tcggcaggag caaggtgaga tgacaggaga tcctgccccg gcacttcgcc caatagcagc    1680
cagtcccttc ccgcttcagt gacaacgtcg agcacagctg cgcaaggaac gcccgtcgtg    1740
gccagccacg atagccgcgc tgcctcgtcc tgcagttcat tcagggcacc ggacaggtcg    1800
gtcttgacaa aaagaaccgg gcgcccctgc gctgacagcc ggaacacggc ggcatcagag    1860
cagccgattg tctgttgtgc ccagtcatag ccgaatagcc tctccaccca agcggccgga    1920
gaacctgcgt gcaatccatc ttgttcaatc atgcgaaacg atccccgcaa gcttggagac    1980
tggtgatttc agcgtgtcct ctccaaatga aatgaacttc cttatataga ggaagggtct    2040
tgcgaaggat agtgggattg tgcgtcatcc cttacgtcag tggagatatc acatcaatcc    2100
acttgctttg aagacgtggt tggaacgtct tcttttttcca cgatgctcct cgtgggtggg    2160
ggtccatctt tgggaccact gtcggcagag gcatcttcaa cgatggcctt tcctttatcg    2220
caatgatggc atttgtagga gccaccttcc ttttccacta tcttcacaat aaagtgacag    2280
atagctgggc aatggaatcc gaggaggttt ccggatatta cccttgttg aaaagtctca    2340 attgcccttt ggtcttctga gactgtatct ttgatatttt tggagtagac aagcgtgtcg    2400
tgctccacca tgttgacgaa gatttttcttc ttgtcattga gtcgtaagag actctgtatg    2460
aactgttcgc cagtctttac ggcgagttct gttaggtcct ctatttgaat ctttgactcc    2520
```

```
atggcctttg attcagtggg aactacctttt ttagagactc caatctctat tacttgcctt    2580
ggtttgtgaa gcaagccttg aatcgtccat actggaatag tacttctgat cttgagaaat    2640
atatctttct ctgtgttctt gatgcagtta gtcctgaatc ttttgactgc atctttaacc    2700
ttcttgggaa ggtatttgat ctcctggaga ttattgctcg ggtagatcgt cttgatgaga    2760
cctgctgcgt aagcctctct aaccatctgt gggttagcat tctttctgaa attgaaaagg    2820
ctaatcttct cattatcagt ggtgaacatg gtatcgtcac cttctccgtc gaacttcctg    2880
actagatcgt agagatagag gaagtcgtcc attgtgatct ctggggcaaa ggagtctgaa    2940
ttaattcgat atggtggatt tatcacaaat gggacccgcc gccgacagag gtgtgatgtt    3000
aggccaggac tttgaaaatt tgcgcaacta tcgtatagtg gccgacaaat tgacgccgag    3060
ttgacagact gcctagcatt tgagtgaatt atgtgaggta atgggctaca ctgaattggt    3120
agctcaaact gtcagtattt atgtatatga gtgtatattt tcgcataatc tcagaccaat    3180
ctgaagatga aatgggtatc tgggaatggc gaaatcaagg catcgatcgt gaagtttctc    3240
atctaagccc ccatttggac gtgaatgtag acacgtcgaa ataaagattt ccgaattaga    3300
ataatttgtt tattgctttc gcctataaat acgacggatc gtaatttgtc gttttatcaa    3360
aatgtacttt cattttataa taacgctgcg gacatctaca tttttgaatt gaaaaaaaat    3420
tggtaattac tctttctttt tctccatatt gaccatcata tcattgctg atccatgtag     3480 atttcccgga catgaagcca tttacaattg aatatatcct gccgccgctg ccgctttgca    3540
cccggtggag cttgcatgtt ggtttctacg cagaactgag ccggttaggc agataatttc    3600
cattgagaac tgagccatgt gcaccttccc cccaacacgg tgagcgacgg ggcaacggag    3660
tgatccacat gggacttta aacatcatcc gtcggatggc gttgcgagag aagcagtcga    3720
tccgtgagat cagccgacgc accgggcagg cgcgcaacac gatcgcaaag tatttgaacg    3780
caggtacaat cgagccgacg ttcacgcgga acgaccaagc aagctagctt taatgcggta    3840
gtttatcaca gttaaattgc taacgcagtc aggcaccgtg tatgaaatct aacaatgcgc    3900
tcatcgtcat cctcggcacc gtcaccctgg atgctgtagg cataggcttg gttatgccgg    3960
tactgccggg cctcttgcgg gatatcgtcc attccgacag catcgccagt cactatggcg    4020
tgctgctagc gctatatgcg ttgatgcaat ttctatgcgc acccgttctc ggagcactgt    4080
ccgaccgctt tggccgccgc ccagtcctgc tcgcttcgct acttggagcc actatcgact    4140
acgcgatcat ggcgaccaca cccgtcctgt ggtccaaccc ctccgctgct atagtgcagt    4200
cggcttctga cgttcagtgc agccgtcttc tgaaaacgac atgtcgcaca agtcctaagt    4260
tacgcgacag gctgccgccc tgcccttttc ctggcgtttt cttgtcgcgt gttttagtcg    4320
cataaagtag aatacttgcg actagaaccg gagacattac gccatgaaca agagcgccgc    4380
cgctggcctg ctgggctatg cccgcgtcag caccgacgac caggacttga ccaaccaacg    4440
ggccgaactg cacgcggccg gctgcaccaa gctgttttcc gagaagatca ccggcaccag    4500
gcgcgaccgc ccggagctgg ccaggatgct tgaccaccta cgccctggcg acgttgtgac    4560
agtgaccagg ctagaccgcc tggcccgcag cacccgcgac ctactggaca ttgccgagcg    4620
catccaggag gccggcgcgg gcctgcgtag cctggcagag ccgtgggccg acaccaccac    4680
gccggccggc cgcatggtgt tgaccgtgtt cgccggcatt gccgagttcg agcgttccct    4740
aatcatcgac cgcacccgga gcgggcgcga ggccgccaag gcccgaggcg tgaagtttgg    4800
cccccgccct accctcaccc cggcacagat cgcgcacgcc cgcgagctga tcgaccagga    4860
```

```
aggccgcacc gtgaaagagg cggctgcact gcttggcgtg catcgctcga ccctgtaccg   4920
cgcacttgag cgcagcgagg aagtgacgcc caccgaggcc aggcggcgcg gtgccttccg   4980
tgaggacgca ttgaccgagg ccgacgccct ggcggccgcc gagaatgaac gccaagagga   5040
acaagcatga aaccgcacca ggacggccag gacgaaccgt ttttcattac cgaagagatc   5100
gaggcggaga tgatcgcggc cgggtacgtg ttcgagccgc ccgcgcacgt ctcaaccgtg   5160
cggctgcatg aaatcctggc cggttttgtct gatgccaagc tggcggcctg gccggccagc   5220
ttggccgctg aagaaaccga gcgccgccgt ctaaaaggt gatgtgtatt tgagtaaaac   5280
agcttgcgtc atgcggtcgc tgcgtatatg atgcgatgag taaataaaca aatacgcaag   5340
ggaacgcatg aagttatcgc tgtacttaac cagaaaggcg ggtcaggcaa gacgaccatc   5400
gcaacccatc tagcccgcgc cctgcaactc gccggggccg atgttctgtt agtcgattcc   5460
gatccccagg gcagtgcccg cgattgggcg gccgtgcggg aagatcaacc gctaaccgtt   5520
gtcggcatcg accgcccgac gattgaccgc gacgtgaagg ccatcggccg gcgcgacttc   5580
gtagtgatcg acggagcgcc ccaggcggcg gacttggctg tgtccgcgat caaggcagcc   5640
gacttcgtgc tgattccggt gcagccaagc ccttacgaca tatgggccac cgccgacctg   5700
gtggagctgg ttaagcagcg cattgaggtc acggatggaa ggctacaagc ggcctttgtc   5760
gtgtcgcggg cgatcaaagg cacgcgcatc ggcggtgagg ttgccgaggc gctggccggg   5820
tacgagctgc ccattcttga gtcccgtatc acgcagcgcg tgagctaccc aggcactgcc   5880
gccgccggca aaccgttct tgaatcagaa cccgagggcg acgctgcccg cgaggtccag   5940
gcgctggccg ctgaaattaa atcaaaactc atttgagtta atgaggtaaa gagaaaatga   6000
gcaaaagcac aaacacgcta agtgccggcc gtccgagcgc acgcagcagc aaggctgcaa   6060
cgttggccaa cctggcagac acgccagcca tgaagcgggt caactttcag ttgccggcgg   6120
aggatcacac caagctgaag atgtacgcgg tacgccaagg caagaccatt accgagctgc   6180
tatctgaata catcgcgcag ctaccagagt aaatgagcaa atgaataaat gagtagatga   6240
attttagcgg ctaaaggagg cggcatggaa aatcaagaac aaccaggcac cgacgccgtg   6300
gaatgcccca tgtgtggagg aacgggcggt tggccaggcg taagcggctg ggttgtctgc   6360
cggccctgca atggcactgg aaccccaag cccgaggaat cggcgtgagc ggtcgcaaac   6420
catccggccc ggtacaaatc ggcgcggcgc tgggtgatga cctggtggag aagttgaagg   6480
ccgcgcaggc cgcccagcgg caacgcatcg aggcagaagc acgccccggt gaatcgtggc   6540
aagcggccgc tgatcgaatc cgcaaagaat cccggcaacc gccggcagcc ggtgcgccgt   6600
cgattaggaa gccgcccaag gcgacgagc aaccagattt tttcgttccg atgctctatg   6660
acgtgggcac ccgcgatagt cgcagcatca tggacgtggc cgttttccgt ctgtcgaagc   6720
gtgaccgacg agctggcgag gtgatccgct acgagcttcc agacgggcac gtagaggttt   6780
ccgcagggcc ggccggcatg gccagtgtgt gggattacga cctggtactg atggcggttt   6840
cccatctaac cgaatccatg aaccgatacc gggaagggaa gggagacaag cccggccgcg   6900
tgttccgtcc acacgttgcg gacgtactca agttctgccg gcgagccgat ggcggaaagc   6960
agaaagacga cctggtagaa acctgcattc ggttaaacac cacgcacgtt gccatgcagc   7020
gtacgaagaa ggccaagaac ggccgcctgg tgacggtatc cgagggtgaa gccttgatta   7080
gccgctacaa gatcgtaaag agcgaaaccg ggcggccgga gtacatcgag atcgagctag   7140
ctgattggat gtaccgcgag atcacagaag gcaagaaccc ggacgtgctg acggttcacc   7200
ccgattactt tttgatcgat cccggcatcg gccgttttct ctaccgcctg gcacgccgcg   7260
```

```
ccgcaggcaa ggcagaagcc agatggttgt tcaagacgat ctacgaacgc agtggcagcg   7320
ccggagagtt caagaagttc tgtttcaccg tgcgcaagct gatcgggtca aatgacctgc   7380
cggagtacga tttgaaggag gaggcggggc aggctggccc gatcctagtc atgcgctacc   7440
gcaacctgat cgagggcgaa gcatccgccg gttcctaatg tacggagcag atgctagggc   7500
aaattgccct agcaggggaa aaaggtcgaa aaggtctctt tcctgtggat agcacgtaca   7560
ttgggaaccc aaagccgtac attgggaacc ggaacccgta cattgggaac ccaaagccgt   7620
acattgggaa ccggtcacac atgtaagtga ctgatataaa agagaaaaaa ggcgattttt   7680
ccgcctaaaa ctctttaaaa cttattaaaa ctcttaaaac ccgcctggcc tgtgcataac   7740
tgtctggcca gcgcacagcc gaagagctgc aaaaagcgcc tacccttcgg tcgctgcgct   7800
ccctacgccc cgccgcttcg cgtcggccta tcgcggccgc tggccgctca aaaatggctg   7860
gcctacggcc aggcaatcta ccagggcgcg acaagccgc gccgtcgcca ctcgaccgcc   7920
ggcgcccaca tcaaggcacc ctgcctcgcg cgtttcggtg atgacggtga aaacctctga   7980
cacatgcagc tcccggagac ggtcacagct tgtctgtaag cggatgccgg gagcagacaa   8040
gcccgtcagg gcgcgtcagc gggtgttggc gggtgtcggg gcgcagccat gacccagtca   8100
cgtagcgata gcggagtgta tactggctta actatgcggc atcagagcag attgtactga   8160
gagtgcacca tatgcggtgt gaaataccgc acagatgcgt aaggagaaaa taccgcatca   8220
ggcgctcttc cgcttcctcg ctcactgact cgctgcgctc ggtcgttcgg ctgcggcgag   8280
cggtatcagc tcactcaaag gcggtaatac ggttatccac agaatcaggg gataacgcag   8340
gaaagaacat gtgagcaaaa ggccagcaaa aggccaggaa ccgtaaaaag gccgcgttgc   8400
tggcgttttt ccataggctc cgcccccctg acgagcatca aaaaatcga cgctcaagtc   8460 agaggtggcg aaacccgaca ggactataaa gataccaggc gtttccccct ggaagctccc   8520
tcgtgcgctc tcctgttccg accctgccgc ttaccggata cctgtccgcc tttctccctt   8580
cgggaagcgt ggcgctttct catagctcac gctgtaggta tctcagttcg gtgtaggtcg   8640
ttcgctccaa gctgggctgt gtgcacgaac cccccgttca gcccgaccgc tgcgccttat   8700
ccggtaacta tcgtcttgag tccaacccgg taagacacga cttatcgcca ctggcagcag   8760
ccactggtaa caggattagc agagcgaggt atgtaggcgg tgctacagag ttcttgaagt   8820
ggtggcctaa ctacgctac actagaagga cagtatttgg tatctgcgct ctgctgaagc   8880
cagttacctt cggaaaaaga gttggtagct cttgatccgg caaacaaacc accgctggta   8940
gcggtggttt ttttgtttgc aagcagcaga ttacgcgcag aaaaaaagga tctcaagaag   9000
atcctttgat cttttctacg gggtctgacg ctcagtggaa cgaaaactca cgttaaggga   9060
ttttggtcat gagattatca aaaaggatct tcacctagat ccttttaaat taaaaatgaa   9120
gttttaaatc aatctaaagt atatatgagt aaacttggtc tgacagttac caatgcttaa   9180
tcagtgaggc acctatctca gcgatctgtc tatttcgttc atccatagtt gcctgactcc   9240
ccgtcgtgta gataactacg atacgggagg gcttaccatc tggccccagt gctgcaatga   9300
taccgcgaga cccacgctca ccggctccag atttatcagc aataaaccag ccagccggaa   9360
gggccgagcg cagaagtggt cctgcaactt tatccgcctc catccagtct attaattgtt   9420
gccgggaagc tagagtaagt agttcgccag ttaatagttt gcgcaacgtt gttgccattg   9480
ctacaggcat cgtggtgtca cgctcgtcgt ttggtatggc ttcattcagc tccgttccc    9540 aacgatcaag gcgagttaca tgatccccca tgttgtgcaa aaaagcggtt agctccttcg   9600
```

```
gtcctccgat cgttgtcaga agtaagttgg ccgcagtgtt atcactcatg gttatggcag    9660
cactgcataa ttctcttact gtcatgccat ccgtaagatg cttttctgtg actggtgagt    9720
actcaaccaa gtcattctga gaatagtgta tgcggcgacc gagttgctct tgcccggcgt    9780
caacacggga taataccgcg ccacatagca gaactttaaa agtgctcatc attggaaaag    9840
acctgcaggg gggggggggc gctgaggtct gcctcgtgaa gaaggtgttg ctgactcata    9900
ccaggcctga atcgcccat catccagcca gaaagtgagg gagccacggt tgatgagagc     9960
tttgttgtag gtggaccagt tggtgatttt gaacttttgc tttgccacgg aacggtctgc   10020
gttgtcggga agatgcgtga tctgatcctt caactcagca aaagttcgat ttattcaaca   10080
aagccgccgt cccgtcaagt cagcgtaatg ctctgccagt gttacaacca attaaccaat   10140
tctgattaga aaaactcatc gagcatcaaa tgaaactgca atttattcat atcaggatta   10200
tcaataccat attttgaaa aagccgtttc tgtaatgaag gagaaaactc accgaggcag    10260
ttccatagga tggcaagatc ctggtatcgg tctgcgattc cgactcgtcc aacatcaata   10320
caacctatta atttccctc gtcaaaaata aggttatcaa gtgagaaatc accatgagtg    10380
acgactgaat ccggtgagaa tggcaaaagc ttatgcattt cttcccagac ttgttcaaca   10440
ggccagccat tacgctcgtc atcaaaatca ctcgcatcaa ccaaaccgtt attcattcgt   10500
gattgcgcct gagcgagacg aaatacgcga tcgctgttaa aaggacaatt acaaacagga   10560
atcgaatgca accggcgcag gaacactgcc agcgcatcaa caatatttc acctgaatca     10620 ggatattctt ctaatacctg gaatgctgtt ttcccgggga tcgcagtggt gagtaaccat   10680
gcatcatcag gagtacggat aaaatgcttg atggtcggaa gaggcataaa ttccgtcagc   10740
cagtttagtc tgaccatctc atctgtaaca tcattggcaa cgctaccttt gccatgtttc   10800
agaaacaact ctggcgcatc gggcttccca tacaatcgat agattgtcgc acctgattgc   10860
ccgacattat cgcgagccca tttataccca tataatcag catccatgtt ggaatttaat     10920
cgcggcctcg agcaagacgt ttcccgttga atatggctca taacacccct tgtattactg   10980
tttatgtaag cagacagttt tattgttcat gatgatatat ttttatcttg tgcaatgtaa   11040
catcagagat tttgagacac aacgtggctt tcccccccc ccctgcaggt caattcggtc      11100
gatatggcta ttacgaagaa ggctcgtgcg cggagtcccg tgaactttcc cacgcaacaa   11160
gtgaaccgca ccgggtttgc cggaggccat ttcgttaaaa tgcgcagcca tggctgcttc   11220
gtccagcatg gcgtaatact gatcctcgtc ttcggctggc ggtatattgc cgatgggctt   11280
caaaagccgc cgtggttgaa ccagtctatc cattccaagg tagcgaactc gaccgcttcg   11340
aagctcctcc atggtccacg ccgatgaatg acctcggcct tgtaaagacc gttgatcgct   11400
tctgcgaggg cgttgtcgtg ctgtcgccga cgcttccgat agatggctcg ataccctgctt  11460 ctgccaaccg ctcggaatag cgaaaggaca cgtattgaac accgcgatcc gagtgatgca   11520
ctaggccgcc atgagcggga cgccgatcat gatgagcctc ctcgagggca tcgaggacaa   11580
agcctgcatg tgctgtccgg ctcgcccgcc atccgacaat gcgacgggcg aagacgtcga   11640
tcacgaaggc cacgtagacg aagccctccc aagtggcgac ataagtacgg acatgcgcaa   11700
aggctttccc ggtttgtcgc tgatggtgca agagacgctg aagcgcgatc cgatgcgcag   11760
gcatctgttc gtcttccgcg gtcgtggcgg tggcctgatc aaggtcactc gccgaagagc   11820
tgcatgattg gctcgaaacc gagcggggga aattgtcgcg cagttctccc gtcgccgagg   11880
cgataaatta catgctcaag cgatgggatg gcattacgtc attcctcgat gacggcccga   11940
tttgcctgac gaacaatgct gccgaacgaa cgctcagagg ctatgtactc ggcaggaagt   12000
```

```
catggctgtt tgccggatcg gatcgttgtg ctgaacgtgc ggcgttcatg gcgacactga   12060
tcatgagcgc caagctcaat aacatcgatc cgcaggcctg gcttgccgac gtccgcgccg   12120
accttgcgga cgctccgatc agcaggcttg agcaacagct gccgtggaac tggacatcca   12180
agacactgag tgctcaggcg gcctgacctg cggccttcac cggatactta ccccattatc   12240
gcagattgcg atgaagcatc agcgtcattc agcaatcttg ccaaagtatg caggctcgcg   12300
agaatcgacg tgcgaaaccg gctggttgcg ccaaagatcc gcttgcggag cggtcgaaca   12360
ttcatgctgg gacttcaaga ggtcgagtag aggaagaacc ggaaaggttg caccggaaaa   12420
tatgcgttcc tttggagagc gcctcatgga cgtgaacaaa tcgcccgac caaggatgcc    12480 acggatacaa aagctcgcga agctcggtcc cgtgggtgtt ctgtcgtctc gttgtacaac   12540
gaaatccatt cccattccgc gctcaagatg gcttcccctc ggcagttcat cagggctaaa   12600
tcaatctagc cgacttgtcc ggtgaaatgg gctgcactcc aacagaaaca atcaaacaaa   12660
catacacagc gacttattca cacgagctca aattacaacg gtatatatcc tgccagtcag   12720
catcatcaca ccaaaagtta ggcccgaata gtttgaaatt agaaagctcg caattgaggt   12780
ctacaggcca aattcgctct tagccgtaca atattactca ccggtgcgat gcccccccatc  12840 gtaggtgaag gtggaaatta atgatccatc ttgagaccac aggcccacaa cagctaccag   12900
tttcctcaag ggtccaccaa aaacgtaagc gcttacgtac atggtcgata agaaaaggca   12960
atttgtagat gttaacatcc aacgtcgctt tcagggatcg atccaatacg caaaccgcct   13020
ctccccgcgc gttggccgat tcattaatgc agctggcacg acaggtttcc cgactggaaa   13080
gcgggcagtg agcgcaacgc aattaatgtg agttagctca ctcattaggc accccaggct   13140
ttacacttta tgcttccggc tcgtatgttg tgtggaattg tgagcggata acaatttcac   13200
acaggaaaca gctatgacca tgattacgcc aagcttgcat gcctgcaggt cgactctaga   13260
ggatctgg                                                          13268
```

<210> SEQ ID NO 9
<211> LENGTH: 16490
<212> TYPE: DNA
<213> ORGANISM: Artificial Sequence
<220> FEATURE:
<223> OTHER INFORMATION: pKR1478

<400> SEQUENCE: 9

```
cgcgccagat cctctagagt cgacctgcag gcatgcaagc ttggcgtaat catggtcata    60
gctgtttcct gtgtgaaatt gttatccgct cacaattcca cacaacatac gagccggaag   120
cataaagtgt aaagcctggg gtgcctaatg agtgagctaa ctcacattaa ttgcgttgcg   180
ctcactgccc gctttccagt cgggaaacct gtcgtgccag ctgcattaat gaatcggcca   240
acgcgcgggg agaggcggtt tgcgtattgg gatcgatccct gaaagcgacg ttggatgtta   300
acatctacaa attgcctttt cttatcgacc atgtacgtaa gcgcttacgt ttttggtgga   360
cccttgagga aactggtagc tgttgtgggc ctgtggtctc aagatggatc attaatttcc   420
accttcacct acgatggggg gcatcgcacc ggtgagtaat attgtacggc taagagcgaa   480
tttggcctgt agacctcaat tgcgagcttt ctaatttcaa actattcggg cctaactttt   540
ggtgtgatga tgctgactgg caggatatat accgttgtaa tttgagctcg tgtgaataag   600
tcgctgtgta tgtttgtttg attgtttctg ttggagtgca gcccattcca ccggacaagt   660
cggctagatt gatttagccc tgatgaactg ccgaggggaa gccatcttga gcgcggaatg   720
```

```
ggaatggatt tcgttgtaca acgagacgac agaacaccca cgggaccgag cttcgcgagc    780
ttttgtatcc gtggcatcct tggtccgggc gatttgttca cgtccatgag gcgctctcca    840
aaggaacgca tattttccgg tgcaacctttt ccggttcttc ctctactcga cctcttgaag   900
tcccagcatg aatgttcgac cgctccgcaa gcggatcttt ggcgcaacca gccggtttcg    960
cacgtcgatt ctcgcgagcc tgcatacttt ggcaagattg ctgaatgacg ctgatgcttc   1020
atcgcaatct gcgataatgg ggtaagtatc cggtgaaggc cgcaggtcag gccgcctgag   1080
cactcagtgt cttggatgtc cagttccacg gcagctgttg ctcaagcctg ctgatcggag   1140
cgtccgcaag gtcggcgcgg acgtcggcaa gccaggcctg cggatcgatg ttattgagct   1200
tggcgctcat gatcagtgtc gccatgaacg ccgcacgttc agcacaacga tccgatccgg   1260
caaacagcca tgacttcctg ccgagtacat agcctctgag cgttcgttcg gcagcattgt   1320
tcgtcaggca atcgggccg tcatcgagga atgacgtaat gccatccat cgcttgagca    1380
tgtaatttat cgcctcggcg acgggagaac tgcgcgacaa tttcccccgc tcggtttcga   1440
gccaatcatg cagctcttcg gcgagtgacc ttgatcaggc caccgccacg accgcggaag   1500
acgaacagat gcctgcgcat cggatcgcgc ttcagcgtct cttgcaccat cagcgacaaa   1560
ccgggaaagc ctttgcgcat gtccgtactt atgtcgccac ttgggagggc ttcgtctacg   1620
tggccttcgt gatcgacgtc ttcgcccgtc gcattgtcgg atggcgggcg agccggacag   1680
cacatgcagg ctttgtcctc gatgcccctcg aggaggctca tcatgatcgg cgtcccgctc   1740
atggcggcct agtgcatcac tcggatcgcg gtgttcaata cgtgtccttt cgctattccg   1800
agcggttggc agaagcaggt atcgagccat ctatcggaag cgtcggcgac agcacgacaa   1860
cgccctcgca gaagcgatca acggtcttta caaggccgag gtcattcatc ggcgtggacc   1920
atggaggagc ttcgaagcgg tcgagttcgc taccttggaa tggatagact ggttcaacca   1980
cggcggcttt tgaagcccat cggcaatata ccgccagccg aagacgagga tcagtattac   2040
gccatgctgg acgaagcagc catggctgcg cattttaacg aaatggcctc cggcaaaccc   2100
ggtgcggttc acttgttgcg tgggaaagtt cacgggactc cgcgcacgag ccttcttcgt   2160
aatagccata tcgaccgaat tgacctgcag ggggggggg gaaagccacg ttgtgtctca    2220
aaatctctga tgttacattg cacaagataa aaatatatca tcatgaacaa taaaactgtc   2280
tgcttacata aacagtaata caaggggtgt tatgagccat attcaacggg aaacgtcttg   2340
ctcgaggccg cgattaaatt ccaacatgga tgctgattta tatgggtata aatgggctcg   2400
cgataatgtc gggcaatcag gtgcgacaat ctatcgattg tatgggaagc ccgatgcgcc   2460
agagttgttt ctgaaacatg gcaaaggtag cgttgccaat gatgttacag atgagatggt   2520
cagactaaac tggctgacgg aatttatgcc tcttccgacc atcaagcatt ttatccgtac   2580
tcctgatgat gcatggttac tcaccactgc gatccccggg aaaacagcat tccaggtatt   2640
agaagaatat cctgattcag gtgaaaaata tgttgatgcg ctggcagtgt tcctgcgccg   2700
gttgcattcg attcctgttt gtaattgtcc ttttaacagc gatcgcgtat tcgtctcgc    2760
tcaggcgcaa tcacgaatga ataacggttt ggttgatgcg agtgattttg atgacgagcg   2820
taatggctgg cctgttgaac aagtctggaa agaaatgcat aagcttttgc cattctcacc   2880
ggattcagtc gtcactcatg gtgatttctc acttgataac cttattttg acgaggggaa    2940
attaataggt tgtattgatg ttggacgagt cggaatcgca gaccgatacc aggatcttgc   3000
catcctatgg aactgcctcg gtgagttttc tccttcatta cagaaacggc ttttttcaaaa   3060
atatggtatt gataatcctg atatgaataa attgcagttt catttgatgc tcgatgagtt   3120
```

```
tttctaatca gaattggtta attggttgta acactggcag agcattacgc tgacttgacg    3180
ggacggcggc tttgttgaat aaatcgaact tttgctgagt tgaaggatca gatcacgcat    3240
cttcccgaca acgcagaccg ttccgtggca aagcaaaagt tcaaaatcac caactggtcc    3300
acctacaaca aagctctcat caaccgtggc tccctcactt tctggctgga tgatggggcg    3360
attcaggcct ggtatgagtc agcaacacct tcttcacgag gcagacctca gcgcccccccc    3420 ccccctgcag gtcttttcca atgatgagca cttttaaagt tctgctatgt ggcgcggtat    3480
tatcccgtgt tgacgccggg caagagcaac tcggtcgccg catacactat tctcagaatg    3540
acttggttga gtactcacca gtcacagaaa agcatcttac ggatggcatg acagtaagag    3600
aattatgcag tgctgccata accatgagtg ataacactgc ggccaactta cttctgacaa    3660
cgatcggagg accgaaggag ctaaccgctt ttttgcacaa catgggggat catgtaactc    3720
gccttgatcg ttgggaaccg gagctgaatg aagccatacc aaacgacgag cgtgacacca    3780
cgatgcctgt agcaatggca acaacgttgc gcaaactatt aactggcgaa ctacttactc    3840
tagcttcccg gcaacaatta atagactgga tggaggcgga taaagttgca ggaccacttc    3900
tgcgctcggc ccttccggct ggctggttta ttgctgataa atctggagcc ggtgagcgtg    3960
ggtctcgcgg tatcattgca gcactggggc cagatggtaa gccctcccgt atcgtagtta    4020
tctacacgac ggggagtcag gcaactatgg atgaacgaaa tagacagatc gctgagatag    4080
gtgcctcact gattaagcat tggtaactgt cagaccaagt ttactcatat atactttaga    4140
ttgatttaaa acttcatttt taatttaaaa ggatctaggt gaagatcctt tttgataatc    4200
tcatgaccaa aatcccttaa cgtgagtttt cgttccactg agcgtcagac cccgtagaaa    4260
agatcaaagg atcttcttga gatcctttt ttctgcgcgt aatctgctgc ttgcaaacaa    4320
aaaaaccacc gctaccagcg gtggtttgtt tgccggatca agagctacca actctttttc    4380
cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccgggttg gactcaagac    4560
gatagttacc ggataaggcg cagcggtcgg gctgaacggg gggttcgtgc acacagccca    4620
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccagggggaa acgcctggta tctttatagt cctgtcgggt    4800
ttcgccacct ctgacttgag cgtcgatttt tgtgatgctc gtcaggggg cggagcctat    4860 ggaaaaacgc cagcaacgcg gcctttttac ggttcctggc cttttgctgg ccttttgctc    4920
acatgttctt tcctgcgtta tcccctgatt ctgtggataa ccgtattacc gcctttgagt    4980
gagctgatac cgctcgccgc agccgaacga ccgagcgcag cgagtcagtg agcgaggaag    5040
cggaagagcg cctgatgcgg tattttctcc ttacgcatct gtgcggtatt tcacaccgca    5100
tatggtgcac tctcagtaca atctgctctg atgccgcata gttaagccag tatacactcc    5160
gctatcgcta cgtgactggg tcatggctgc gccccgacac ccgccaacac ccgctgacgc    5220
gccctgacgg gcttgtctgc tcccggcatc cgcttacaga caagctgtga ccgtctccgg    5280
gagctgcatg tgtcagaggt tttcaccgtc atcaccgaaa cgcgcgaggc agggtgcctt    5340
gatgtgggcg ccggcggtcg agtggcgacg gcgcggcttg tccgcgccct ggtagattgc    5400
ctggccgtag gccagccatt tttgagcggc cagcggccgc gataggccga cgcgaagcgg    5460
```

```
cggggcgtag ggagcgcagc gaccgaaggg taggcgcttt ttgcagctct tcggctgtgc      5520
gctggccaga cagttatgca caggccaggc gggttttaag agtttaata agttttaaag      5580
agttttaggc ggaaaaatcg cctttttct cttttatatc agtcacttac atgtgtgacc      5640
ggttcccaat gtacggcttt gggttcccaa tgtacgggtt ccggttccca atgtacggct      5700
ttgggttccc aatgtacgtg ctatccacag gaaagagacc ttttcgacct ttttcccctg      5760
ctagggcaat tgccctagc atctgctccg tacattagga accggcggat gcttcgccct      5820
cgatcaggtt gcggtagcgc atgactagga tcgggccagc ctgccccgcc tcctccttca      5880
aatcgtactc cggcaggtca tttgacccga tcagcttgcg cacggtgaaa cagaacttct      5940
tgaactctcc ggcgctgcca ctgcgttcgt agatcgtctt gaacaaccat ctggcttctg      6000
ccttgcctgc ggcgcggcgt gccaggcggt agagaaaacg gccgatgccg ggatcgatca      6060
aaaagtaatc ggggtgaacc gtcagcacgt ccgggttctt gccttctgtg atctcgcggt      6120
acatccaatc agctagctcg atctcgatgt actccggccg cccggtttcg ctctttacga      6180
tcttgtagcg gctaatcaag gcttcaccct cggataccgt caccaggcgg ccgttcttgg      6240
ccttcttcgt acgctgcatg gcaacgtgcg tggtgtttaa ccgaatgcag gtttctacca      6300
ggtcgtctt ctgcttccg ccatcggctc gccggcagaa cttgagtacg tccgcaacgt      6360
gtggacggaa cacgcggccg ggcttgtctc ccttcccttc ccggtatcgg ttcatggatt      6420
cggttagatg ggaaaccgcc atcagtacca ggtcgtaatc ccacacactg gccatgccgg      6480
ccggccctgc ggaaacctct acgtgcccgt ctggaagctc gtagcggatc acctcgccag      6540
ctcgtcggtc acgcttcgac agacggaaaa cggccacgtc catgatgctg cgactatcgc      6600
gggtgcccac gtcatagagc atcggaacga aaaatctgg ttgctcgtcg cccttgggcg      6660
gcttcctaat cgacggcgca ccggctgccg gcggttgccg ggattctttg cggattcgat      6720
cagcggccgc ttgccacgat tcaccggggc gtgcttctgc ctcgatgcgt tgccgctggg      6780
cggcctgcgg ggccttcaac ttctccacca ggtcatcacc cagcgccgcg ccgatttgta      6840
ccgggccgga tggtttgcga ccgctcacgc cgattcctcg gcttgggggg ttccagtgcc      6900
attgcagggc cggcagacaa cccagccgct tacgcctggc caaccgcccg ttcctccaca      6960
catgggcat tccacggcgt cggtgcctgg ttgttcttga ttttccatgc cgcctccttt      7020
agccgctaaa attcatctac tcatttattc atttgctcat ttactctggt agctgcgcga      7080
tgtattcaga tagcagctcg gtaatggtct tgccttggcg taccgcgtac atcttcagct      7140
tggtgtgatc ctccgccggc aactgaaagt tgaccgcctt catggctggc gtgtctgcca      7200
ggctggccaa cgttgcagcc ttgctgctgc gtgcgctcgg acggccggca cttagcgtgt      7260
ttgtgctttt gctcattttc tctttacctc attaactcaa atgagttttg atttaatttc      7320
agcggccagc gcctggacct cgcgggcagc gtcgccctcg ggttctgatt caagaacggt      7380
tgtgccggcg gcggcagtgc ctgggtagct cacgcgctgc gtgatacggg actcaagaat      7440
gggcagctcg tacccggcca gcgcctcggc aacctcaccg ccgatgcgcg tgcctttgat      7500
cgcccgcgac acgacaaagg ccgcttgtag ccttccatcc gtgacctcaa tgcgctgctt      7560
aaccagctcc accaggtcgg cggtggccca tatgtcgtaa gggcttggct gcaccggaat      7620
cagcacgaag tcggctgcct tgatcgcgga cacagccaag tccgccgcct ggggcgctcc      7680
gtcgatcact acgaagtcgc gccggccgat ggccttcacg tcgcggtcaa tgtcgggcg      7740
gtcgatgccg acaacggtta gcggttgatc ttccgcacg gccgcccaat cgcgggcact      7800
gccctgggga tcggaatcga ctaacagaac atcggccccg gcgagttgca gggcgcgggc      7860
```

```
tagatgggtt gcgatggtcg tcttgcctga cccgcctttc tggttaagta cagcgataac    7920
ttcatgcgtt cccttgcgta tttgtttatt tactcatcgc atcatatacg cagcgaccgc    7980
atgacgcaag ctgttttact caaatacaca tcaccttttt agacggcggc gctcggtttc    8040
ttcagcggcc aagctggccg gccaggccgc cagcttggca tcagacaaac cggccaggat    8100
ttcatgcagc cgcacggttg agacgtgcgc gggcggctcg aacacgtacc cggccgcgat    8160
catctccgcc tcgatctctt cggtaatgaa aaacggttcg tcctggccgt cctggtgcgg    8220
tttcatgctt gttcctcttg gcgttcattc tcggcggccg ccagggcgtc ggcctcggtc    8280
aatgcgtcct cacggaaggc accgcgccgc ctggcctcgg tgggcgtcac ttcctcgctg    8340
cgctcaagtg cgcggtacag ggtcgagcga tgcacgccaa gcagtgcagc cgcctctttc    8400
acggtgcggc cttcctggtc gatcagctcg cgggcgtgcg cgatctgtgc cggggtgagg    8460
gtagggcggg ggccaaactt cacgcctcgg gccttggcgg cctcgcgccc gctccgggtg    8520
cggtcgatga ttagggaacg ctcgaactcg gcaatgccgg cgaacacggt caacaccatg    8580
cggccggccg gcgtggtggt gtcggcccac ggctctgcca ggctacgcag gcccgcgccg    8640
gcctcctgga tgcgctcggc aatgtccagt aggtcgcggg tgctgcgggc caggcggtct    8700
agcctggtca ctgtcacaac gtcgccaggg cgtaggtggt caagcatcct ggccagctcc    8760
gggcggtcgc gcctggtgcc ggtgatcttc tcggaaaaca gcttggtgca gccggccgcg    8820
tgcagttcgg cccgttggtt ggtcaagtcc tggtcgtcgg tgctgacgcg ggcatagccc    8880
agcaggccag cggcggcgct cttgttcatg gcgtaatgtc tccggttcta gtcgcaagta    8940
ttctacttta tgcgactaaa acacgcgaca agaaaacgcc aggaaaaggg cagggcggca    9000
gcctgtcgcg taacttagga cttgtgcgac atgtcgtttt cagaagacgg ctgcactgaa    9060
cgtcagaagc cgactgcact atagcagcgg aggggttgga ccacaggacg ggtgtggtcg    9120
ccatgatcgc gtagtcgata gtggctccaa gtagcgaagc gagcaggact gggcggcggc    9180
caaagcggtc ggacagtgct ccgagaacgg gtgcgcatag aaattgcatc aacgcatata    9240
gcgctagcag cacgccatag tgactggcga tgctgtcgga atggacgata tcccgcaaga    9300
ggcccggcag taccggcata accaagccta tgcctacagc atccagggtg acggtgccga    9360
ggatgacgat gagcgcattg ttagatttca tacacggtgc ctgactgcgt tagcaattta    9420
actgtgataa actaccgcat taaagctagc ttgcttggtc gttccgcgtg aacgtcggct    9480
cgattgtacc tgcgttcaaa tactttgcga tcgtgttgcg cgcctgcccg gtgcgtcggc    9540
tgatctcacg gatcgactgc ttctctcgca acgccatccg acggatgatg tttaaaagtc    9600
ccatgtggat cactccgttg ccccgtcgct caccgtgttg ggggaaggt gcacatggct    9660 cagttctcaa tggaaattat ctgcctaacc ggctcagttc tgcgtagaaa ccaacatgca    9720
agctccaccg ggtgcaaagc ggcagcggcg gcaggatata ttcaattgta aatggcttca    9780
tgtccgggaa atctacatgg atcagcaatg agtatgatgg tcaatatgga gaaaagaaa    9840 gagtaattac caattttttt tcaattcaaa aatgtagatg tccgcagcgt tattataaaa    9900
tgaaagtaca ttttgataaa acgacaaatt acgatccgtc gtatttatag gcgaaagcaa    9960
taaacaaatt attctaattc ggaaatcttt atttcgacgt gtctacattc acgtccaaat   10020
gggggcttag atgagaaact tcacgatcga tgccttgatt tcgccattcc cagataccca   10080
tttcatcttc agattggtct gagattatgc gaaaatatac actcatatac ataaatactg   10140
acagtttgag ctaccaattc agtgtagccc attacctcac ataattcact caaatgctag   10200
```

```
gcagtctgtc aactcggcgt caatttgtcg gccactatac gatagttgcg caaattttca   10260
aagtcctggc ctaacatcac acctctgtcg gcggcgggtc ccatttgtga taaatccacc   10320
atatcgaatt aattcagact cctttgcccc agagatcaca atggacgact tcctctatct   10380
ctacgatcta gtcaggaagt tcgacggaga aggtgacgat accatgttca ccactgataa   10440
tgagaagatt agccttttca atttcagaaa gaatgctaac ccacagatgg ttagagaggc   10500
ttacgcagca ggtctcatca agacgatcta cccgagcaat aatctccagg agatcaaata   10560
ccttcccaag aaggttaaag atgcagtcaa aagattcagg actaactgca tcaagaacac   10620
agagaaagat atatttctca agatcagaag tactattcca gtatggacga ttcaaggctt   10680
gcttcacaaa ccaaggcaag taatagagat tggagtctct aaaaaggtag ttcccactga   10740
atcaaaggcc atggagtcaa agattcaaat agaggaccta acagaactcg ccgtaaagac   10800
tggcgaacag ttcatacaga gtctcttacg actcaatgac aagaagaaaa tcttcgtcaa   10860
catggtggag cacgacacgc ttgtctactc caaaaatatc aaagatacag tctcagaaga   10920
ccaaagggca attgagactt tcaacaaagg gtaatatcc ggaaacctcc tcggattcca   10980
ttgcccagct atctgtcact ttattgtgaa gatagtggaa aaggaaggtg gctcctacaa   11040
atgccatcat tgcgataaag gaaaggccat cgttgaagat gcctctgccg acagtggtcc   11100
caaagatgga ccccccaccca cgaggagcat cgtggaaaaa gaagacgttc caaccacgtc   11160
ttcaaagcaa gtggattgat gtgatatctc cactgacgta agggatgacg cacaatccca   11220
ctatccttcg caagaccctt cctctatata aggaagttca tttcatttgg agaggacacg   11280
ctgaaatcac cagtctccaa gcttgcgggg atcgtttcgc atgattgaac aagatggatt   11340
gcacgcaggt tctccggccg cttgggtgga gaggctattc ggctatgact gggcacaaca   11400
gacaatcggc tgctctgatg ccgccgtgtt ccggctgtca gcgcaggggc gcccggttct   11460
ttttgtcaag accgacctgt ccggtgccct gaatgaactg caggacgagg cagcgcggct   11520
atcgtggctg gccacgacgg gcgttccttg cgcagctgtg ctcgacgttg tcactgaagc   11580
gggaagggac tggctgctat tgggcgaagt gccggggcag gatctcctgt catctcacct   11640
tgctcctgcc gagaaagtat ccatcatggc tgatgcaatg cggcggctgc atacgcttga   11700
tccggctacc tgcccattcg accaccaagc gaaacatcgc atcgagcgag cacgtactcg   11760
gatggaagcc ggtcttgtcg atcaggatga tctggacgaa gagcatcagg gctcgcgcc   11820
agccgaactg ttcgccaggc tcaaggcgcg catgcccgac ggcgaggatc tcgtcgtgac   11880
ccatggcgat gcctgcttgc cgaatatcat ggtggaaaat ggccgctttt ctggattcat   11940
cgactgtggc cggctgggtg tggcggaccg ctatcaggac atagcgttgg ctacccgtga   12000
tattgctgaa gagcttggcg gcgaatgggc tgaccgcttc ctcgtgcttt acggtatcgc   12060
cgctcccgat tcgcagcgca tcgccttcta tcgccttctt gacgagttct tctgagcggg   12120
actctggggt tcgaaatgac cgaccaagcg acgcccaacc tgccatcacg agatttcgat   12180
tccaccgccg ccttctatga aaggttgggc ttcggaatcg ttttccggga cgccggctgg   12240
atgatcctcc agcgcgggga tctcatgctg gagttcttcg cccaccccgg atcgatccaa   12300
cacttacgtt tgcaacgtcc aagagcaaat agaccacgaa cgccggaagg ttgccgcagc   12360
gtgtggattg cgtctcaatt ctctcttgca ggaatgcaat gatgaatatg atactgacta   12420
tgaaactttg agggaatact gcctagcacc gtcacctcat aacgtgcatc atgcatgccc   12480
tgacaacatg gaacatcgct attttttctga agaattatgc tcgttggagg atgtcgcggc   12540
aattgcagct attgccaaca tcgaactacc cctcacgcat gcattcatca atattattca   12600
```

```
tgcgggaaa  ggcaagatta  atccaactgg  caaatcatcc  agcgtgattg  gtaacttcag   12660
ttccagcgac  ttgattcgtt  ttggtgctac  ccacgttttc  aataaggacg  agatggtgga   12720
gtaaagaagg  agtgcgtcga  agcagatcgt  tcaaacattt  ggcaataaag  tttcttaaga   12780
ttgaatcctg  ttgccggtct  tgcgatgatt  atcatataat  ttctgttgaa  ttacgttaag   12840
catgtaataa  ttaacatgta  atgcatgacg  ttatttatga  gatgggtttt  tatgattaga   12900
gtcccgcaat  tatacattta  atacgcgata  gaaaacaaaa  tatagcgcgc  aaactaggat   12960
aaattatcgc  gcgcggtgtc  atctatgtta  ctagatcgat  caaacttcgg  tactgtgtaa   13020
tgacgatgag  caatcgagag  gctgactaac  aaaaggtaca  tcgcgatgga  tcgatccatt   13080
cgccattcag  gctgcgcaac  tgttgggaag  ggcgatcggt  gcgggcctct  tcgctattac   13140
gccagctggc  gaaaggggga  tgtgctgcaa  ggcgattaag  ttgggtaacg  ccagggtttt   13200
cccagtcacg  acgttgtaaa  acgacggcca  gtgaattcct  gcagcccggg  ggatccgccc   13260
actcgaggcg  cgccaagctt  gcatgcctgc  aggctagcct  aagtacgtac  tcaaaatgcc   13320
aacaaataaa  aaaaagttg  ctttaataat  gccaaaacaa  attaataaaa  cacttacaac   13380
accggatttt  ttttaattaa  aatgtgccat  ttaggataaa  tagttaatat  ttttaataat   13440
tatttaaaaa  gccgtatcta  ctaaaatgat  ttttatttgg  ttgaaaatat  taatatgttt   13500
aaatcaacac  aatctatcaa  aattaaacta  aaaaaaaaat  aagtgtacgt  ggttaacatt   13560
agtacagtaa  tataagagga  aaatgagaaa  ttaagaaatt  gaaagcgagt  ctaattttta   13620
aattatgaac  ctgcatatat  aaaaggaaag  aaagaatcca  ggaagaaaag  aaatgaaacc   13680
atgcatggtc  ccctcgtcat  cacgagtttc  tgccatttgc  aatagaaaca  ctgaaacacc   13740
tttctctttg  tcacttaatt  gagatgccga  agccacctca  caccatgaac  ttcatgaggt   13800
gtagcaccca  aggcttccat  agccatgcat  actgaagaat  gtctcaagct  cagcacccta   13860
cttctgtgac  gtgtccctca  ttcaccttcc  tctcttccct  ataaataacc  acgcctcagg   13920
ttctccgctt  cacaactcaa  acattctctc  cattggtcct  taaacactca  tcagtcatca   13980
ccgcggccat  cacaagtttg  tacaaaaaag  ctgaacgaga  aacgtaaaat  gatataaata   14040
tcaatatatt  aaattagatt  ttgcataaaa  aacagactac  ataatactgt  aaaacacaac   14100
atatccagtc  atattggcgg  ccgcattagg  caccccaggc  tttacacttt  atgcttccgg   14160
ctcgtataat  gtgtggattt  tgagttagga  tccgtcgaga  ttttcaggag  ctaaggaagc   14220
taaaatggag  aaaaaaatca  ctggatatac  caccgttgat  atatcccaat  ggcatcgtaa   14280
agaacatttt  gaggcatttc  agtcagttgc  tcaatgtacc  tataaccaga  ccgttcagct   14340
ggatattacg  gcctttttaa  agaccgtaaa  gaaaaataag  cacaagtttt  atccggcctt   14400
tattcacatt  cttgcccgcc  tgatgaatgc  tcatccggaa  ttccgtatgg  caatgaaaga   14460
cggtgagctg  gtgatatggg  atagtgttca  cccttgttac  accgttttcc  atgagcaaac   14520
tgaaacgttt  tcatcgctct  ggagtgaata  ccacgacgat  ttccggcagt  ttctacacat   14580
atattcgcaa  gatgtggcgt  gttacggtga  aaacctggcc  tatttcccta  aagggtttat   14640
tgagaatatg  ttttcgtct  cagccaatcc  ctgggtgagt  ttcaccagtt  ttgatttaaa   14700
cgtggccaat  atggacaact  tcttcgcccc  cgttttcacc  atgggcaaat  attatacgca   14760
aggcgacaag  gtgctgatgc  cgctggcgat  tcaggttcat  catgccgttt  gtgatggctt   14820
ccatgtcggc  agaatgctta  atgaattaca  acagtactgc  gatgagtggc  agggcggggc   14880
gtaaacgcgt  ggatccggct  tactaaaagc  cagataacag  tatgcgtatt  tgcgcgctga   14940
```

```
tttttgcggt ataagaatat atactgatat gtatacccga agtatgtcaa aaagaggtat   15000
gctatgaagc agcgtattac agtgacagtt gacagcgaca gctatcagtt gctcaaggca   15060
tatatgatgt caatatctcc ggtctggtaa gcacaaccat gcagaatgaa gcccgtcgtc   15120
tgcgtgccga acgctggaaa gcggaaaatc aggaagggag ggctgaggtc gcccggttta   15180
ttgaaatgaa cggctctttt gctgacgaga acagggctg gtgaaatgca gtttaaggtt   15240
tacacctata aaagagagag ccgttatcgt ctgtttgtgg atgtacagag tgatattatt   15300
gacacgcccg ggcgacggat ggtgatcccc ctggccagtg cacgtctgct gtcagataaa   15360
gtctcccgtg aactttaccc ggtggtgcat atcggggatg aaagctggcg catgatgacc   15420
accgatatgg ccagtgtgcc ggtctccgtt atcggggaag aagtggctga tctcagccac   15480
cgcgaaaatg acatcaaaaa cgccattaac ctgatgttct ggggaatata atgtcaggc    15540 tcccttatac acagccagtc tgcaggtcga ccatagtgac tggatatgtt gtgttttaca   15600
gcattatgta gtctgttttt tatgcaaaat ctaatttaat atattgatat ttatatcatt   15660
ttacgtttct cgttcagctt tcttgtacaa agtggtgatg gccgcatttc gcaccaaatc   15720
aatgaaagta ataatgaaaa gtctgaataa gaatacttag gcttagatgc ctttgttact   15780
tgtgtaaaat aacttgagtc atgtaccttt ggcggaaaca gaataaataa aaggtgaaat   15840
tccaatgctc tatgtataag ttagtaatac ttaatgtgtt ctacggttgt ttcaatatca   15900
tcaaactcta attgaaactt tagaaccaca aatctcaatc ttttcttaat gaaatgaaaa   15960
atcttaattg taccatgttt atgttaaaca ccttacaatt ggttggagag gaggaccaac   16020
cgatgggaca acattgggag aaagagattc aatggagatt tggataggag aacaacattc   16080
tttttcactt caatacaaga tgagtgcaac actaaggata tgtatgagac tttcagaagc   16140
tacgacaaca tagatgagtg aggtggtgat tcctagcaag aaagacatta gaggaagcca   16200
aaatcgaaca aggaagacat caagggcaag agacaggacc atccatctca ggaaaaggag   16260
ctttgggata gtccgagaag ttgtacaaga aattttttgg agggtgagtg atgcattgct   16320
ggtgacttta actcaatcaa aattgagaaa gaaagaaaag ggaggggggct cacatgtgaa   16380 tagaagggaa acgggagaat tttacagttt tgatctaatg ggcatcccag ctagtggtaa   16440
catattcacc atgtttaacc ttcacgtacg tctagaggat ccgtcgacgg              16490
```

<210> SEQ ID NO 10
<211> LENGTH: 49
<212> TYPE: DNA
<213> ORGANISM: artificial sequence
<220> FEATURE:
<223> OTHER INFORMATION: Saiff and genomic DNA of lo17849

<400> SEQUENCE: 10

```
gaaggctcta agctgtgttg taggcttctt agcattcatt tctgtttgc                49
```

<210> SEQ ID NO 11
<211> LENGTH: 30
<212> TYPE: DNA
<213> ORGANISM: artificial sequence
<220> FEATURE:
<223> OTHER INFORMATION: primer

<400> SEQUENCE: 11

```
caccatggtt gttgtgtctc ttcttcctcg                                     30
```

<210> SEQ ID NO 12
<211> LENGTH: 23

```
<212> TYPE: DNA
<213> ORGANISM: artificial sequence
<220> FEATURE:
<223> OTHER INFORMATION: primer

<400> SEQUENCE: 12
tcaaattgat ttagtttctc cag                                            23

<210> SEQ ID NO 13
<211> LENGTH: 2988
<212> TYPE: DNA
<213> ORGANISM: artificial sequence
<220> FEATURE:
<223> OTHER INFORMATION: vector

<400> SEQUENCE: 13
aagggtgggc gcgccgaccc agctttcttg tacaaagttg gcattataag aaagcattgc      60
ttatcaattt gttgcaacga acaggtcact atcagtcaaa ataaaatcat tatttgccat     120
ccagctgata tcccctatag tgagtcgtat tacatggtca tagctgtttc ctggcagctc     180
tggcccgtgt ctcaaaatct ctgatgttac attgcacaag ataaaaatat atcatcatga     240
acaataaaac tgtctgctta cataaacagt aatacaaggg gtgttatgag ccatattcaa     300
cgggaaacgt cgaggccgcg attaaattcc aacatggatg ctgatttata tgggtataaa     360
tgggctcgcg ataatgtcgg gcaatcaggt gcgacaatct atcgcttgta tgggaagccc     420
gatgcgccag agttgtttct gaaacatggc aaaggtagcg ttgccaatga tgttacagat     480
gagatggtca gactaaactg gctgacggaa tttatgcctc ttccgaccat caagcatttt     540
atccgtactc ctgatgatgc atggttactc accactgcga tccccggaaa aacagcattc     600
caggtattag aagaatatcc tgattcaggt gaaaatattg ttgatgcgct ggcagtgttc     660
ctgcgccggt tgcattcgat tcctgtttgt aattgtcctt ttaacagcga tcgcgtattt     720
cgtctcgctc aggcgcaatc acgaatgaat aacggtttgg ttgatgcgag tgattttgat     780
gacgagcgta atggctggcc tgttgaacaa gtctggaaag aaatgcataa acttttgcca     840
ttctcaccgg attcagtcgt cactcatggt gatttctcac ttgataacct tatttttgac     900
gaggggaaat taataggttg tattgatgtt ggacgagtcg gaatcgcaga ccgataccag     960
gatcttgcca tcctatggaa ctgcctcggt gagttttctc cttcattaca gaaacggctt    1020
tttcaaaaat atggtattga taatcctgat atgaataaat tgcagtttca tttgatgctc    1080
gatgagtttt tctaatcaga attggttaat tggttgtaac actggcagag cattacgctg    1140
acttgacggg acggcgcaag ctcatgacca aaatccctta acgtgagtta cgcgtcgttc    1200
cactgagcgt cagaccccgt agaaaagatc aaaggatctt cttgagatcc ttttttttctg    1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agcattgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800
```

```
tgctcgtcag ggggggcggag cctatggaaa aacgccagca acgcggcctt tttacggttc    1860 ctggccttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gctagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccgcggat    2280 ttgtcctact caggagagcg ttcaccgaca acaacagat aaaacgaaag gcccagtctt    2340
ccgactgagc ctttcgtttt atttgatgcc tggcagttcc ctactctcgc gttaacgcta    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttta taatgccaac tttgtacaaa aaagcaggct ccgcggccgc ccccttcacc    2580
atggttgttg tgtctcttct tcctcgaatc tcgatcgtta catcaccggg ttctagcctt    2640
cacgatgtgc ttttgagcat gagatttggt ttgacgcgac atctccctct caaacgatct    2700
ttctccaatt attcaatcac ttccgtatct ccagaacaac agctcaaatc tccggtgacc    2760
atggcgacga ccgagagcaa gaatcttgta gaagcttcca aggaggagac aaacaagaag    2820
gagacagaag ataagaagga ggtgggagtt tcggttcctc caccgccaga gaaaccagag    2880
cctggcgatt gttgcggtag cggttgcgtc cgatgcgttt gggatgttta ttacgatgag    2940
ctcgaagatt acaacaagca gctttctgga gaaactaaat caatttga                2988
```

<210> SEQ ID NO 14
<211> LENGTH: 15279
<212> TYPE: DNA
<213> ORGANISM: artificial sequence
<220> FEATURE:
<223> OTHER INFORMATION: vector

<400> SEQUENCE: 14

```
acccagcttt cttgtacaaa gtggtgatgg ccgcatttcg caccaaatca atgaaagtaa    60
taatgaaaag tctgaataag aatacttagg cttagatgcc tttgttactt gtgtaaaata    120
acttgagtca tgtacctttg gcggaaacag aataaataaa aggtgaaatt ccaatgctct    180
atgtataagt tagtaaatact taatgtgttc tacggttgtt tcaatatcat caaactctaa    240
ttgaaacttt agaaccacaa atctcaatct tttcttaatg aaatgaaaaa tcttaattgt    300
accatgttta tgttaaacac cttacaattg gttggagagg aggaccaacc gatgggacaa    360
cattgggaga aagagattca atggagattt ggataggaga acaacattct ttttcacttc    420
aatacaagat gagtgcaaca ctaaggatat gtatgagact ttcagaagct acgacaacat    480
agatgagtga ggtggtgatt cctagcaaga aagacattag aggaagccaa aatcgaacaa    540
ggaagacatc aagggcaaga gacaggacca tccatctcag gaaaggagc tttgggatag    600 tccgagaagt tgtacaagaa attttttgga gggtgagtga tgcattgctg gtgactttaa    660
ctcaatcaaa attgagaaag aaagaaaagg gagggggctc acatgtgaat agaagggaaa    720
cgggagaatt ttacagtttt gatctaatgg gcatcccagc tagtggtaac atattcacca    780
tgtttaacct tcacgtacgt ctagaggatc cgtcgacggc gcgccagatc tctctagagtc    840 gacctgcagg catgcaagct tggcgtaatc atggtcatag ctgtttcctg tgtgaaattg    900
```

```
ttatccgctc acaattccac acaacatacg agccggaagc ataaagtgta aagcctgggg    960
tgcctaatga gtgagctaac tcacattaat tgcgttgcgc tcactgcccg ctttccagtc   1020
gggaaacctg tcgtgccagc tgcattaatg aatcggccaa cgcgcgggga gaggcggttt   1080
gcgtattgga tcgatccctg aaagcgacgt tggatgttaa catctacaaa ttgccttttc   1140
ttatcgacca tgtacgtaag cgcttacgtt tttggtggac ccttgaggaa actggtagct   1200
gttgtgggcc tgtggtctca agatggatca ttaatttcca ccttcaccta cgatgggggg   1260
catcgcaccg gtgagtaata ttgtacggct aagagcgaat ttggcctgta gacctcaatt   1320
gcgagctttc taatttcaaa ctattcgggc ctaacttttg gtgtgatgat gctgactggc   1380
aggatatata ccgttgtaat ttgagctcgt gtgaataagt cgctgtgtat gtttgtttga   1440
ttgtttctgt tggagtgcag cccatttcac cggacaagtc ggctagattg atttagccct   1500
gatgaactgc cgaggggaag ccatcttgag cgcggaatgg gaatggattt cgttgtacaa   1560
cgagacgaca gaacacccac gggaccgagc ttcgcgagct tttgtatccg tggcatcctt   1620
ggtccgggcg atttgttcac gtccatgagg cgctctccaa aggaacgcat attttccggt   1680
gcaacctttc cggttcttcc tctactcgac ctcttgaagt cccagcatga atgttcgacc   1740
gctccgcaag cggatctttg gcgcaaccag ccggtttcgc acgtcgattc tcgcgagcct   1800
gcatactttg gcaagattgc tgaatgacgc tgatgcttca tcgcaatctg cgataatggg   1860
gtaagtatcc ggtgaaggcc gcaggtcagg ccgcctgagc actcagtgtc ttggatgtcc   1920
agttccacgg cagctgttgc tcaagcctgc tgatcggagc gtccgcaagg tcggcgcgga   1980
cgtcggcaag ccaggcctgc ggatcgatgt tattgagctt ggcgctcatg atcagtgtcg   2040
ccatgaacgc cgcacgttca gcacaacgat ccgatccggc aaacagccat gacttcctgc   2100
cgagtacata gcctctgagc gttcgttcgg cagcattgtt cgtcaggcaa atcgggccgt   2160
catcgaggaa tgacgtaatg ccatcccatc gcttgagcat gtaatttatc gcctcggcga   2220
cgggagaact gcgcgacaat ttcccccgct cggtttcgag ccaatcatgc agctcttcgg   2280
cgagtgacct tgatcaggcc accgccacga ccgcggaaga cgaacagatg cctgcgcatc   2340
ggatcgcgct tcagcgtctc ttgcaccatc agcgacaaac cgggaaagcc tttgcgcatg   2400
tccgtactta tgtcgccact tgggagggct tcgtctacgt ggccttcgtg atcgacgtct   2460
tcgcccgtcg cattgtcgga tggcgggcga gccgacagc acatgcaggc tttgtcctcg   2520
atgccctcga ggaggctcat catgatcggc gtcccgctca tggcggccta gtgcatcact   2580
cggatcgcgg tgttcaatac gtgtcctttc gctattccga gcggttggca gaagcaggta   2640
tcgagccatc tatcggaagc gtcggcgaca gcacgacaac gccctcgcag aagcgatcaa   2700
cggtctttac aaggccgagg tcattcatcg gcgtggacca tggaggagct tcgaagcggt   2760
cgagttcgct accttggaat ggatagactg gttcaaccac ggcggctttt gaagcccatc   2820
ggcaatatac cgccagccga agacgaggat cagtattacg ccatgctgga cgaagcagcc   2880
atggctgcgc attttaacga aatggcctcc ggcaaacccg gtgcggttca cttgttgcgt   2940
gggaaagttc acgggactcc gcgcacgagc cttcttcgta atagccatat cgaccgaatt   3000
gacctgcagg ggggggggg aaagccacgt tgtgtctcaa atctctgat gttacattgc    3060
acaagataaa aatatatcat catgaacaat aaaactgtct gcttacataa acagtaatac   3120
aagggggtgtt atgagccata ttcaacggga acgtcttgc tcgaggccgc gattaaattc   3180
caacatggat gctgatttat atgggtataa atgggctcgc gataatgtcg ggcaatcagg   3240
```

```
tgcgacaatc tatcgattgt atgggaagcc cgatgcgcca gagttgtttc tgaaacatgg    3300
caaaggtagc gttgccaatg atgttacaga tgagatggtc agactaaact ggctgacgga    3360
atttatgcct cttccgacca tcaagcattt tatccgtact cctgatgatg catggttact    3420
caccactgcg atccccggga aaacagcatt ccaggtatta aagaatatc ctgattcagg     3480 tgaaaatatt gttgatgcgc tggcagtgtt cctgcgccgg ttgcattcga ttcctgtttg    3540
taattgtcct tttaacagcg atcgcgtatt tcgtctcgct caggcgcaat cacgaatgaa    3600
taacggtttg gttgatgcga gtgattttga tgacgagcgt aatggctggc ctgttgaaca    3660
agtctggaaa gaaatgcata agcttttgcc attctcaccg gattcagtcg tcactcatgg    3720
tgatttctca cttgataacc ttattttga cgaggggaaa ttaataggtt gtattgatgt     3780
tggacgagtc ggaatcgcag accgatacca ggatcttgcc atcctatgga actgcctcgg    3840
tgagttttct ccttcattac agaaacggct ttttcaaaaa tatggtattg ataatcctga    3900
tatgaataaa ttgcagtttc atttgatgct cgatgagttt ttctaatcag aattggttaa    3960
ttggttgtaa cactggcaga gcattacgct gacttgacgg gacggcggct tgttgaata    4020 aatcgaactt tgctgagtt gaaggatcag atcacgcatc ttcccgacaa cgcagaccgt     4080
tccgtggcaa agcaaaagtt caaaatcacc aactggtcca cctacaacaa agctctcatc    4140
aaccgtggct ccctcacttt ctggctggat gatgggcga ttcaggcctg gtatgagtca     4200
gcaacacctt cttcacgagg cagacctcag cgccccccc ccctgcagg tcttttccaa      4260 tgatgagcac ttttaaagtt ctgctatgtg gcgcggtatt atcccgtgtt gacgccgggc    4320
aagagcaact cggtcgccgc atacactatt ctcagaatga cttggttgag tactcaccag    4380
tcacagaaaa gcatcttacg gatggcatga cagtaagaga attatgcagt gctgccataa    4440
ccatgagtga taacactgcg gccaacttac ttctgacaac gatcggagga ccgaaggagc    4500
taaccgcttt tttgcacaac atgggggatc atgtaactcg ccttgatcgt tgggaaccgg    4560
agctgaatga agccatacca aacgacgagc gtgacaccac gatgcctgta gcaatggcaa    4620
caacgttgcg caaactatta actggcgaac tacttactct agcttcccgg caacaattaa    4680
tagactggat ggaggcggat aaagttgcag gaccacttct gcgctcggcc cttccggctg    4740
gctggtttat tgctgataaa tctggagccg gtgagcgtgg gtctcgcggt atcattgcag    4800
cactggggcc agatggtaag ccctcccgta tcgtagttat ctacacgacg gggagtcagg    4860
caactatgga tgaacgaaat agacagatcg ctgagatagg tgcctcactg attaagcatt    4920
ggtaactgtc agaccaagtt tactcatata ctttagat tgatttaaaa cttcattttt       4980
aatttaaaag gatctaggtg aagatccttt ttgataatct catgaccaaa atcccttaac    5040
gtgagttttc gttccactga gcgtcagacc ccgtagaaaa gatcaaagga tcttcttgag    5100
atcctttttt tctgcgcgta atctgctgct tgcaaacaaa aaaccaccg ctaccagcgg     5160 tggtttgttt gccggatcaa gagctaccaa ctctttttcc gaaggtaact ggcttcagca    5220
gagcgcagat accaaatact gtccttctag tgtagccgta gttaggccac cacttcaaga    5280
actctgtagc accgcctaca tacctcgctc tgctaatcct gttaccagtg gctgctgcca    5340
gtggcgataa gtcgtgtctt accgggttgg actcaagacg atagttaccg gataaggcgc    5400
agcggtcggg ctgaacgggg ggttcgtgca cacagcccag cttggagcga acgacctaca    5460
ccgaactgag atacctacag cgtgagctat gagaaagcgc cacgcttccc gaagggagaa    5520
aggcggacag gtatccggta agcggcaggg tcggaacagg agagcgcacg agggagcttc    5580
cagggggaaa cgcctggtat ctttatagtc ctgtcgggtt tcgccacctc tgacttgagc    5640
```

```
gtcgattttt gtgatgctcg tcagggggc ggagcctatg gaaaaacgcc agcaacgcgg     5700
ccttttacg gttcctggcc ttttgctggc cttttgctca catgttcttt cctgcgttat      5760
cccctgattc tgtggataac cgtattaccg cctttgagtg agctgatacc gctcgccgca     5820
gccgaacgac cgagcgcagc gagtcagtga gcgaggaagc ggaagagcgc ctgatgcggt     5880
attttctcct tacgcatctg tgcggtattt cacaccgcat atggtgcact ctcagtacaa     5940
tctgctctga tgccgcatag ttaagccagt atacactccg ctatcgctac gtgactgggt     6000
catggctgcg ccccgacacc cgccaacacc cgctgacgcg ccctgacggg cttgtctgct     6060
cccggcatcc gcttacagac aagctgtgac cgtctccggg agctgcatgt gtcagaggtt     6120
ttcaccgtca tcaccgaaac gcgcgaggca gggtgccttg atgtgggcgc cggcggtcga     6180
gtggcgacgg cgcggcttgt ccgcgccctg gtagattgcc tggccgtagg ccagccattt     6240
ttgagcggcc agcggccgcg ataggccgac gcgaagcggc ggggcgtagg gagcgcagcg     6300
accgaagggt aggcgctttt tgcagctctt cggctgtgcg ctggccagac agttatgcac     6360
aggccaggcg ggttttaaga gttttaataa gttttaaaga gtttaggcg gaaaaatcgc      6420
cttttttctc ttttatatca gtcacttaca tgtgtgaccg gttcccaatg tacggctttg     6480
ggttcccaat gtacgggttc cggttcccaa tgtacggctt tgggttccca atgtacgtgc     6540
tatccacagg aaagagacct tttcgacctt ttcccctgc tagggcaatt tgccctagca      6600
tctgctccgt acattaggaa ccggcggatg cttcgccctc gatcaggttg cggtagcgca     6660
tgactaggat cgggccagcc tgccccgcct cctccttcaa atcgtactcc ggcaggtcat     6720
ttgacccgat cagcttgcgc acggtgaaac agaacttctt gaactctccg gcgctgccac     6780
tgcgttcgta gatcgtcttg aacaaccatc tggcttctgc cttgcctgcg gcgcggcgtg     6840
ccaggcggta gagaaaacgg ccgatgccgg gatcgatcaa aaagtaatcg gggtgaaccg     6900
tcagcacgtc cgggttcttg ccttctgtga tctcgcggta catccaatca gctagctcga     6960
tctcgatgta ctccggccgc ccggtttcgc tctttacgat cttgtagcgg ctaatcaagg     7020
cttcaccctc ggataccgtc accaggcggc cgttcttggc cttcttcgta cgctgcatgg     7080
caacgtgcgt ggtgtttaac cgaatgcagg tttctaccag gtcgtctttc tgctttccgc     7140
catcggctcg ccggcagaac ttgagtacgt ccgcaacgtg tggacggaac acgcggccgg     7200
gcttgtctcc cttcccttcc cggtatcggt tcatggattc ggttagatgg gaaaccgcca     7260
tcagtaccag gtcgtaatcc cacacactgg ccatgccggc cggccctgcg gaaacctcta     7320
cgtgcccgtc tggaagctcg tagcggatca cctcgccagc tcgtcggtca cgcttcgaca     7380
gacggaaaac ggccacgtcc atgatgctgc gactatcgcg ggtgcccacg tcatagagca     7440
tcggaacgaa aaaatctggt tgctcgtcgc ccttgggcgg cttcctaatc gacggcgcac     7500
cggctgccgg cggttgccgg gattctttgc ggattcgatc agcggccgct tgccacgatt     7560
caccggggcg tgcttctgcc tcgatgcgtt gccgctgggc ggcctgcgcg ccttcaact      7620
tctccaccag gtcatcaccc agcgccgcgc cgatttgtac cgggccggat ggtttgcgac     7680
cgctcacgcc gattcctcgg gcttgggggt tccagtgcca ttgcagggcc ggcagacaac     7740
ccagccgctt acgcctggcc aaccgccgt tcctccacac atgggcatt ccacggcgtc       7800
ggtgcctggt tgttcttgat tttccatgcc gcctccttta gccgctaaaa ttcatctact     7860
catttattca tttgctcatt tactctggta gctgcgcgat gtattcagat agcagctcgg     7920
taatggtctt gccttggcgt accgcgtaca tcttcagctt ggtgtgatcc tccgccggca     7980
```

```
actgaaagtt gacccgcttc atggctggcg tgtctgccag gctggccaac gttgcagcct    8040
tgctgctgcg tgcgctcgga cggccggcac ttagcgtgtt tgtgcttttg ctcattttct    8100
ctttacctca ttaactcaaa tgagttttga tttaatttca gcggccagcg cctggacctc    8160 gcggcagcg tcgccctcgg gttctgattc aagaacggtt gtgccggcgg cggcagtgcc     8220
tgggtagctc acgcgctgcg tgatacggga ctcaagaatg ggcagctcgt acccggccag    8280
cgcctcggca acctcaccgc cgatgcgcgt gcctttgatc gcccgcgaca cgacaaaggc    8340
cgcttgtagc cttccatccg tgacctcaat gcgctgctta accagctcca ccaggtcggc    8400
ggtggcccat atgtcgtaag ggcttggctg caccggaatc agcacgaagt cggctgcctt    8460
gatcgcggac acagccaagt ccgccgcctg gggcgctccg tcgatcacta cgaagtcgcg    8520
ccggccgatg gccttcacgt cgcggtcaat cgtcggcgg tcgatgccga caacggttag     8580
cggttgatct tcccgcacgg ccgcccaatc gcgggcactg ccctggggat cggaatcgac    8640
taacagaaca tcggcccgg cgagttgcag ggcgcgggct agatgggttg cgatggtcgt     8700
cttgcctgac ccgcctttct ggttaagtac agcgataact tcatgcgttc ccttgcgtat    8760
ttgtttattt actcatcgca tcatatacgc agcgaccgca tgacgcaagc tgttttactc    8820
aaatacacat caccttttta gacggcggcg ctcggtttct tcagcggcca agctggccgg    8880
ccaggccgcc agcttggcat cagacaaacc ggccaggatt tcatgcagcc gcacggttga    8940
gacgtgcgcg ggcggctcga acacgtaccc ggccgcgatc atctccgcct cgatctcttc    9000
ggtaatgaaa acggttcgt cctggccgtc ctggtgcggt ttcatgcttg ttcctcttgg     9060
cgttcattct cggcggccgc cagggcgtcg gcctcggtca atgcgtcctc acggaaggca    9120
ccgcgccgcc tggcctcggt gggcgtcact tcctcgctgc gctcaagtgc gcggtacagg    9180
gtcgagcgat gcacgccaag cagtgcagcc gcctcttca cggtgcggcc ttcctggtcg     9240
atcagctcgc gggcgtgcgc gatctgtgcc ggggtgaggg tagggcgggg gccaaacttc    9300
acgcctcggg ccttggcggc ctcgcgcccg ctccgggtgc ggtcgatgat tagggaacgc    9360
tcgaactcgg caatgccggc gaacacggtc aacaccatgc ggccggccgg cgtggtggtg    9420
tcggcccacg gctctgccag gctacgcagg cccgcgccgg cctcctggat gcgctcggca    9480
atgtccagta ggtcgcgggt gctgcgggcc aggcggtcta gcctggtcac tgtcacaacg    9540
tcgccagggc gtaggtggtc aagcatcctg gccagctccg ggcggtcgcg cctggtgccg    9600
gtgatcttct cggaaaacag cttggtgcag ccggccgcgt gcagttcggc ccgttggttg    9660
gtcaagtcct ggtcgtcggt gctgacgcgg gcatagccca gcaggccagc ggcggcgctc    9720
ttgttcatgg cgtaatgtct ccggttctag tcgcaagtat tctactttat gcgactaaaa    9780
cacgcgacaa gaaaacgcca ggaaaagggc agggcggcag cctgtcgcgt aacttaggac    9840
ttgtgcgaca tgtcgttttc agaagacggc tgcactgaac gtcagaagcc gactgcacta    9900
tagcagcgga ggggttggac cacaggacgg gtgtggtcgc catgatcgcg tagtcgatag    9960
tggctccaag tagcgaagcg agcaggactg ggcggcggcc aaagcggtcg acagtgctc     10020 cgagaacggg tgcgcataga aattgcatca acgcatatag cgctagcagc acgccatagt    10080
gactggcgat gctgtcggaa tggacgatat cccgcaagag gcccggcagt accggcataa    10140
ccaagcctat gcctacagca tccagggtga cggtgccgag gatgacgatg agcgcattgt    10200
tagatttcat acacggtgcc tgactgcgtt agcaatttaa ctgtgataaa ctaccgcatt    10260
aaagctagct tgcttggtcg ttccgcgtga acgtcggctc gattgtacct gcgttcaaat    10320
actttgcgat cgtgttgcgc gcctgcccgg tgcgtcggct gatctcacgg atcgactgct    10380
```

```
tctctcgcaa cgccatccga cggatgatgt ttaaaagtcc catgtggatc actccgttgc    10440
cccgtcgctc accgtgttgg ggggaaggtg cacatggctc agttctcaat ggaaattatc    10500
tgcctaaccg gctcagttct gcgtagaaac caacatgcaa gctccaccgg gtgcaaagcg    10560
gcagcggcgg caggatatat tcaattgtaa atggcttcat gtccgggaaa tctacatgga    10620
tcagcaatga gtatgatggt caatatggag aaaagaaag agtaattacc aattttttt     10680 caattcaaaa atgtagatgt ccgcagcgtt attataaaat gaaagtacat tttgataaaa    10740
cgacaaatta cgatccgtcg tatttatagg cgaaagcaat aaacaaatta ttctaattcg    10800 gaaatctta tttcgacgtg tctacattca cgtccaaatg ggggcttaga tgagaaactt    10860
cacgatcgat gccttgattt cgccattccc agatacccat ttcatcttca gattggtctg    10920
agattatgcg aaaatataca ctcatataca taaatactga cagtttgagc taccaattca    10980
gtgtagccca ttacctcaca taattcactc aaatgctagg cagtctgtca actcggcgtc    11040
aatttgtcgg ccactatacg atagttcgc aaattttcaa agtcctggcc taacatcaca    11100
cctctgtcgg cggcgggtcc catttgtgat aaatccacca tatcgaatta attcagactc    11160
ctttgcccca gagatcacaa tggacgactt cctctatctc tacgatctag tcaggaagtt    11220
cgacggagaa ggtgacgata ccatgttcac cactgataat gagaagatta gccttttcaa    11280
tttcagaaag aatgctaacc cacagatggt tagagaggct tacgcagcag gtctcatcaa    11340
gacgatctac ccgagcaata atctccagga gatcaaatac cttcccaaga aggttaaaga    11400
tgcagtcaaa agattcagga ctaactgcat caagaacaca gagaaagata tatttctcaa    11460
gatcagaagt actattccag tatggacgat tcaaggcttg cttcacaaac caaggcaagt    11520
aatagagatt ggagtctcta aaaaggtagt tcccactgaa tcaaaggcca tggagtcaaa    11580
gattcaaata gaggacctaa cagaactcgc cgtaaagact ggcgaacagt tcatacagag    11640
tctcttacga ctcaatgaca agaagaaaat cttcgtcaac atggtggagc acgacacgct    11700
tgtctactcc aaaaatatca aagatacagt ctcagaagac caaagggcaa ttgagacttt    11760
tcaacaaagg gtaatatccg gaaacctcct cggattccat tgcccagcta tctgtcactt    11820
tattgtgaag atagtggaaa aggaaggtgg ctcctacaaa tgccatcatt gcgataaagg    11880
aaaggccatc gttgaagatg cctctgccga cagtggtccc aaagatggac ccccacccac    11940
gaggagcatc gtggaaaaag aagacgttcc aaccacgtct tcaaagcaag tggattgatg    12000
tgatatctcc actgacgtaa gggatgacgc acaatcccac tatccttcgc aagacccttc    12060
ctctatataa ggaagttcat ttcatttgga gaggacacgc tgaaatcacc agtctccaag    12120
cttgcgggga tcgtttcgca tgattgaaca agatggattg cacgcaggtt ctccggccgc    12180
ttgggtggag aggctattcg gctatgactg ggcacaacag acaatcggct gctctgatgc    12240
cgccgtgttc cggctgtcag cgcaggggcg cccggttctt tttgtcaaga ccgacctgtc    12300
cggtgccctg aatgaactgc aggacgaggc agcgcggcta tcgtggctgg ccacgacggg    12360
cgttccttgc gcagctgtgc tcgacgttgt cactgaagcg ggaagggact ggctgctatt    12420
gggcgaagtg ccggggcagg atctcctgtc atctcacctt gctcctgccg agaaagtatc    12480
catcatggct gatgcaatgc ggcggctgca tacgcttgat ccggctacct gcccattcga    12540
ccaccaagcg aaacatcgca tcgagcgagc acgtactcgg atggaagccg gtcttgtcga    12600
tcaggatgat ctggacgaag agcatcaggg gctcgcgcca gccgaactgt tcgccaggct    12660
caaggcgcgc atgcccgacg gcgaggatct cgtcgtgacc catggcgatg cctgcttgcc    12720
```

```
gaatatcatg gtggaaaatg gccgcttttc tggattcatc gactgtggcc ggctgggtgt   12780
ggcggaccgc tatcaggaca tagcgttggc tacccgtgat attgctgaag agcttggcgg   12840
cgaatgggct gaccgcttcc tcgtgcttta cggtatcgcc gctcccgatt cgcagcgcat   12900
cgccttctat cgccttcttg acgagttctt ctgagcggga ctctgggptt cgaaatgacc   12960
```
(Note: line 12960 reading: cgccttctat cgccttcttg acgagttctt ctgagcggga ctctgggntt cgaaatgacc)



```
gaatatcatg gtggaaaatg ccgcttttc tggattcatc gactgtggcc ggctgggtgt   12780
ggcggaccgc tatcaggaca tagcgttggc tacccgtgat attgctgaag agcttggcgg   12840
cgaatgggct gaccgcttcc tcgtgcttta cggtatcgcc gctcccgatt cgcagcgcat   12900
cgccttctat cgccttcttg acgagttctt ctgagcggga ctctgggtt cgaaatgacc    12960
gaccaagcga cgcccaacct gccatcacga gatttcgatt ccaccgccgc cttctatgaa   13020
aggttgggct tcggaatcgt tttccgggac gccggctgga tgatcctcca gcgcgggat    13080
ctcatgctgg agttcttcgc ccaccccgga tcgatccaac acttacgttt gcaacgtcca   13140
agagcaaata gaccacgaac gccggaaggt tgccgcagcg tgtggattgc gtctcaattc   13200
tctcttgcag gaatgcaatg atgaatatga tactgactat gaaactttga gggaatactg   13260
cctagcaccg tcacctcata acgtgcatca tgcatgccct gacaacatgg aacatcgcta   13320
tttttctgaa gaattatgct cgttggagga tgtcgcggca attgcagcta ttgccaacat   13380
cgaactaccc ctcacgcatg cattcatcaa tattattcat gcggggaaag gcaagattaa   13440
tccaactggc aaatcatcca gcgtgattgg taacttcagt tccagcgact tgattcgttt   13500
tggtgctacc cacgttttca ataaggacga gatggtggag taagaagga gtgcgtcgaa    13560
gcagatcgtt caaacatttg gcaataaagt ttcttaagat tgaatcctgt tgccggtctt   13620
gcgatgatta tcatataatt tctgttgaat tacgttaagc atgtaataat taacatgtaa   13680
tgcatgacgt tatttatgag atgggttttt atgattagag tcccgcaatt atacatttaa   13740
tacgcgatag aaaacaaaat atagcgcgca aactaggata aattatcgcg cgcggtgtca   13800
tctatgttac tagatcgatc aaacttcggt actgtgtaat gacgatgagc aatcgagagg   13860
ctgactaaca aaaggtacat cgcgatggat cgatccattc gccattcagg ctgcgcaact   13920
gttgggaagg gcgatcggtg cgggcctctt cgctattacg ccagctggcg aaaggggggat  13980
gtgctgcaag gcgattaagt tgggtaacgc cagggttttc ccagtcacga cgttgtaaaa   14040
cgacggccag tgaattcctg cagcccgggg gatccgccca ctcgaggcgc gccaagcttg   14100
catgcctgca ggctagccta agtacgtact caaaatgcca acaaataaaa aaaaagttgc   14160
tttaataatg ccaaaacaaa ttaataaaac acttacaaca ccggattttt tttaattaaa   14220
atgtgccatt taggataaat agttaatatt tttaataatt atttaaaaag ccgtatctac   14280
taaaatgatt tttatttggt tgaaaatatt aatatgttta aatcaacaca atctatcaaa   14340
attaaactaa aaaaaaaata agtgtacgtg gttaacatta gtacagtaat ataagaggaa   14400
aatgagaaat taagaaattg aaagcgagtc taattttaa attatgaacc tgcatatata   14460
aaaggaaaga aagaatccag gaagaaaaga aatgaaacca tgcatggtcc cctcgtcatc   14520
acgagtttct gccatttgca atagaaacac tgaaacacct ttctctttgt cacttaattg   14580
agatgccgaa gccacctcac accatgaact tcatgaggtg tagcacccaa ggcttccata   14640
gccatgcata ctgaagaatg tctcaagctc agcaccctac ttctgtgacg tgtccctcat   14700
tcaccttcct ctcttcccta taaataacca cgcctcaggt tctccgcttc acaactcaaa   14760
cattctctcc attggtcctt aaacactcat cagtcatcac cgcggccatc acaagtttgt   14820
acaaaaaagc aggctccgcg gccgccccct tcaccatggt tgttgtgtct cttcttcctc   14880
gaatctcgat cgttacatca ccgggttcta gccttcacga tgtgcttttg agcatgagat   14940
ttggttttgac gcgacatctc cctctcaaac gatctttctc caattattca atcacttccg   15000
tatctccaga acaacagctc aaatctccgg tgaccatggc gacgaccgag agcaagaatc   15060
ttgtagaagc ttccaaggag gagacaaaca agaaggagac agaagataag aaggaggtgg   15120
```

-continued

```
gagtttcggt tcctccaccg ccagagaaac cagagcctgg cgattgttgc ggtagcggtt    15180
gcgtccgatg cgtttgggat gtttattacg atgagctcga agattacaac aagcagcttt    15240
ctggagaaac taaatcaatt tgaaagggtg ggcgcgccg                            15279
```

<210> SEQ ID NO 15
<211> LENGTH: 17273
<212> TYPE: DNA
<213> ORGANISM: artificial sequence
<220> FEATURE:
<223> OTHER INFORMATION: vector

<400> SEQUENCE: 15

```
cgcgccagat cctctagagt cgacctgcag gcatgcaagc ttggcgtaat catggtcata      60
gctgtttcct gtgtgaaatt gttatccgct cacaattcca cacaacatac gagccggaag     120
cataaagtgt aaagcctggg gtgcctaatg agtgagctaa ctcacattaa ttgcgttgcg     180
ctcactgccc gctttccagt cgggaaacct gtcgtgccag ctgcattaat gaatcggcca     240
acgcgcgggg agaggcggtt tgcgtattgg atcgatccct gaaagcgacg ttggatgtta     300
acatctacaa attgcctttt cttatcgacc atgtacgtaa gcgcttacgt ttttggtgga     360
cccttgagga aactggtagc tgttgtgggc ctgtggtctc aagatggatc attaatttcc     420
accttcacct cgatgggggg gcatcgcacc ggtgagtaat attgtacggc taagagcgaa     480
tttggcctgt agacctcaat tgcgagcttt ctaatttcaa actattcggg cctaactttt     540
ggtgtgatga tgctgactgg caggatatat accgttgtaa tttgagctcg tgtgaataag     600
tcgctgtgta tgtttgtttg attgtttctg ttggagtgca gcccatttca ccggacaagt     660
cggctagatt gatttagccc tgatgaactg ccgaggggaa gccatcttga gcgcggaatg     720
ggaatggatt tcgttgtaca acgagacgac agaacaccca cgggaccgag cttcgcgagc     780
ttttgtatcc gtggcatcct tggtccgggc gatttgttca cgtccatgag gcgctctcca     840
aaggaacgca tattttccgg tgcaaccttt ccggttcttc ctctactcga cctcttgaag     900
tcccagcatg aatgttcgac cgctccgcaa gcggatcttt ggcgcaacca gccggtttcg     960
cacgtcgatt ctcgcgagcc tgcatacttt ggcaagattg ctgaatgacg ctgatgcttc    1020
atcgcaatct gcgataatgg ggtaagtatc cggtgaaggc cgcaggtcag gccgcctgag    1080
cactcagtgt cttggatgtc cagttccacg gcagctgttg ctcaagcctg ctgatcggag    1140
cgtccgcaag gtcggcgcgg acgtcggcaa gccaggcctg cggatcgatg ttattgagct    1200
tggcgctcat gatcagtgtc gccatgaacg ccgcacgttc agcacaacga tccgatccgg    1260
caaacagcca tgacttcctg ccgagtacat agcctctgag cgttcgttcg gcagcattgt    1320
tcgtcaggca aatcgggccg tcatcgagga atgacgtaat gccatccat cgcttgagca    1380 tgtaatttat cgcctcggcg acgggagaac tgcgcgacaa tttcccccgc tcggtttcga    1440
gccaatcatg cagctcttcg gcgagtgacc ttgatcaggc caccgccacg accgcggaag    1500
acgaacagat gcctgcgcat cggatcgcgc ttcagcgtct cttgcaccat cagcgacaaa    1560 ccggaaagc ctttgcgcat gtccgtactt atgtcgccac ttgggagggc ttcgtctacg    1620
tggccttcgt gatcgacgtc ttcgcccgtc gcattgtcgg atggcgggcg agccggacag    1680
cacatgcagg ctttgtcctc gatgccctcg aggaggctca tcatgatcgg cgtcccgctc    1740
atggcggcct agtgcatcac tcggatcgcg gtgttcaata cgtgtccttt cgctattccg    1800
agcggttggc agaagcaggt atcgagccat ctatcggaag cgtcggcgac agcacgacaa    1860
```

```
cgccctcgca gaagcgatca acggtcttta caaggccgag gtcattcatc ggcgtggacc   1920
atggaggagc ttcgaagcgg tcgagttcgc taccttggaa tggatagact ggttcaacca   1980
cggcggcttt tgaagcccat cggcaatata ccgccagccg aagacgagga tcagtattac   2040
gccatgctgg acgaagcagc catgctgcgc cattttaacg aaatggcctc cggcaaaccc   2100
ggtgcggttc acttgttgcg tgggaaagtt cacgggactc cgcgcacgag ccttcttcgt   2160
aatagccata tcgaccgaat tgacctgcag gggggggggg gaaagccacg ttgtgtctca   2220
aaatctctga tgttacattg cacaagataa aaatatatca tcatgaacaa taaaactgtc   2280
tgcttacata aacagtaata caaggggtgt tatgagccat attcaacggg aaacgtcttg   2340
ctcgaggccg cgattaaatt ccaacatgga tgctgattta tatgggtata aatgggctcg   2400
cgataatgtc gggcaatcag gtgcgacaat ctatcgattg tatgggaagc ccgatgcgcc   2460
agagttgttt ctgaaacatg gcaaaggtag cgttgccaat gatgttacag atgagatggt   2520
cagactaaac tggctgacgg aatttatgcc tcttccgacc atcaagcatt ttatccgtac   2580
tcctgatgat gcatggttac tcaccactgc gatccccggg aaaacagcat tccaggtatt   2640
agaagaatat cctgattcag gtgaaaatat tgttgatgcg ctggcagtgt tcctgcgccg   2700
gttgcattcg attcctgttt gtaattgtcc ttttaacagc gatcgcgtat ttcgtctcgc   2760
tcaggcgcaa tcacgaatga ataacggttt ggttgatgcg agtgattttg atgacgagcg   2820
taatggctgg cctgttgaac aagtctggaa agaaatgcat aagcttttgc cattctcacc   2880
ggattcagtc gtcactcatg gtgatttctc acttgataac cttatttttg acgaggggaa   2940
attaataggt tgtattgatg ttggacgagt cggaatcgca gaccgatacc aggatcttgc   3000
catcctatgg aactgcctcg gtgagttttc tccttcatta cagaaacggc ttttttcaaaa   3060 atatggtatt gataatcctg atatgaataa attgcagttt catttgatgc tcgatgagtt   3120
tttctaatca gaattggtta attggttgta acactggcag agcattacgc tgacttgacg   3180
ggacggcggc tttgttgaat aaatcgaact tttgctgagt tgaaggatca gatcacgcat   3240
cttcccgaca acgcagaccg ttccgtggca aagcaaaagt tcaaaatcac caactggtcc   3300
acctacaaca aagctctcat caaccgtggc tccctcactt tctggctgga tgatggggcg   3360
attcaggcct ggtatgagtc agcaacacct tcttcacgag gcagacctca gcgcccccgc   3420
ccccctgcag gtcttttcca atgatgagca cttttaaagt tctgctatgt ggcgcggtat   3480
tatcccgtgt tgacgccggg caagagcaac tcggtcgccg catacactat tctcagaatg   3540
acttggttga gtactcacca gtcacagaaa agcatcttac ggatggcatg acagtaagag   3600
aattatgcag tgctgccata accatgagtg ataacactgc ggccaactta cttctgacaa   3660
cgatcggagg accgaaggag ctaaccgctt ttttgcacaa catgggggat catgtaactc   3720
gccttgatcg ttgggaaccg gagctgaatg aagccatacc aaacgacgag cgtgacacca   3780
cgatgcctgt agcaatggca acaacgttgc gcaaactatt aactggcgaa ctacttactc   3840
tagcttcccg gcaacaatta atagactgga tggaggcgga taaagttgca ggaccacttc   3900
tgcgctcggc ccttccggct ggctggttta ttgctgataa atctggagcc ggtgagcgtg   3960
ggtctcgcgg tatcattgca gcactggggc cagatggtaa gccctcccgt atcgtagtta   4020
tctacacgac ggggagtcag gcaactatgg atgaacgaaa tagacagatc gctgagatag   4080
gtgcctcact gattaagcat tggtaactgt cagaccaagt ttactcatat atactttaga   4140
ttgatttaaa acttcatttt taatttaaaa ggatctaggt gaagatcctt tttgataatc   4200
tcatgaccaa aatcccttaa cgtgagtttt cgttccactg agcgtcagac cccgtagaaa   4260
```

```
agatcaaagg atcttcttga gatccttttt ttctgcgcgt aatctgctgc ttgcaaacaa    4320
aaaaaccacc gctaccagcg gtggtttgtt tgccggatca agagctacca actctttttc    4380
cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccggggtg gactcaagac    4560
gatagttacc ggataaggcg cagcggtcgg gctgaacggg gggttcgtgc acacagccca    4620
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccaggggaaa cgcctggta tctttatagt cctgtcgggt    4800
ttcgccacct ctgacttgag cgtcgatttt tgtgatgctc gtcagggggg cggagcctat    4860
ggaaaaacgc cagcaacgcg gcctttttac ggttcctggc cttttgctgg ccttttgctc    4920
acatgttctt tcctgcgtta tcccctgatt ctgtggataa ccgtattacc gcctttgagt    4980
gagctgatac cgctcgccgc agccgaacga ccgagcgcag cgagtcagtg agcgaggaag    5040
cggaagagcg cctgatgcgg tattttctcc ttacgcatct gtgcggtatt tcacaccgca    5100
tatggtgcac tctcagtaca atctgctctg atgccgcata gttaagccag tatacactcc    5160
gctatcgcta cgtgactggg tcatggctgc gccccgacac ccgccaacac ccgctgacgc    5220
gccctgacgg gcttgtctgc tcccggcatc cgcttacaga caagctgtga ccgtctccgg    5280
gagctgcatg tgtcagaggt tttcaccgtc atcaccgaaa cgcgcgaggc agggtgcctt    5340
gatgtgggcg ccggcggtcg agtggcgacg gcgcggcttg tccgcgccct ggtagattgc    5400
ctggccgtag gccagccatt tttgagcggc agcggccgc gataggccga cgcgaagcgg    5460
cggggcgtag ggagcgcagc gaccgaaggg taggcgcttt ttgcagctct tcggctgtgc    5520
gctggccaga cagttatgca caggccaggc gggttttaag agttttaata agttttaaag    5580
agttttaggc ggaaaaatcg cctttttttct cttttatatc agtcacttac atgtgtgacc    5640
ggttcccaat gtacggcttt gggttcccaa tgtacgggtt ccggttccca atgtacggct    5700
ttgggttccc aatgtacgtg ctatccacag gaaagagacc ttttcgacct ttttcccctg    5760
ctagggcaat tgccctagc atctgctccg tacattagga accggcggat gcttcgccct    5820
cgatcaggtt gcggtagcgc atgactagga tcgggccagc ctgccccgcc tcctccttca    5880
aatcgtactc cggcaggtca tttgacccga tcagcttgcg cacggtgaaa cagaacttct    5940
tgaactctcc ggcgctgcca ctgcgttcgt agatcgtctt gaacaaccat ctggcttctg    6000
ccttgcctgc ggcgcggcgt gccaggcggt agagaaaacg gccgatgccg ggatcgatca    6060 aaagtaatc ggggtgaacc gtcagcacgt ccgggttctt gccttctgtg atctcgcggt    6120
acatccaatc agctagctcg atctcgatgt actccggccg cccggtttcg ctctttacga    6180
tcttgtagcg gctaatcaag gcttcaccct cggataccgt caccaggcgg ccgttcttgg    6240
ccttcttcgt acgctgcatg gcaacgtgcg tggtgtttaa ccgaatgcag gtttctacca    6300
ggtcgtcttt ctgctttccg ccatcggctc gccggcagaa cttgagtacg tccgcaacgt    6360
gtggacggaa cacgcggccg ggcttgtctc ccttcccttc ccgtatcgg ttcatggatt    6420 cggttagatg ggaaaccgcc atcagtacca ggtcgtaatc ccacacactg gccatgccgg    6480
ccggccctgc ggaaacctct acgtgcccgt ctggaagctc gtagcggatc acctcgccag    6540
ctcgtcggtc acgcttcgac agacggaaaa cggccacgtc catgatgctg cgactatcgc    6600
```

-continued

```
gggtgcccac gtcatagagc atcggaacga aaaaatctgg ttgctcgtcg cccttgggcg   6660
gcttcctaat cgacggcgca ccggctgccg gcggttgccg ggattctttg cggattcgat   6720
cagcggccgc ttgccacgat tcaccggggc gtgcttctgc ctcgatgcgt tgccgctggg   6780
cggcctgcgc ggccttcaac ttctccacca ggtcatcacc cagcgccgcg ccgatttgta   6840
ccgggccgga tggtttgcga ccgctcacgc cgattcctcg ggcttggggg ttccagtgcc   6900
attgcagggc cggcagacaa cccagccgct tacgcctggc caaccgcccg ttcctccaca   6960 catgggcat tccacggcgt cggtgcctgg ttgttcttga ttttccatgc cgcctccttt    7020
agccgctaaa attcatctac tcatttattc atttgctcat ttactctggt agctgcgcga   7080
tgtattcaga tagcagctcg gtaatggtct tgccttggcg taccgcgtac atcttcagct   7140
tggtgtgatc ctccgccggc aactgaaagt tgacccgctt catggctggc gtgtctgcca   7200
ggctggccaa cgttgcagcc ttgctgctgc gtgcgctcgg acggccggca cttagcgtgt   7260
ttgtgctttt gctcattttc tctttacctc attaactcaa atgagttttg atttaatttc   7320
agcggccagc gcctggacct cgcgggcagc gtcgccctcg ggttctgatt caagaacggt   7380
tgtgccggcg gcggcagtgc ctgggtagct cacgcgctgc gtgatacggg actcaagaat   7440
gggcagctcg tacccggcca gcgcctcggc aacctcaccg ccgatgcgcg tgcctttgat   7500
cgcccgcgac acgacaaagg ccgcttgtag ccttccatcc gtgacctcaa tgcgctgctt   7560
aaccagctcc accaggtcgg cggtggccca tatgtcgtaa gggcttggct gcaccggaat   7620
cagcacgaag tcggctgcct tgatcgcgga cacagccaag tccgccgcct ggggcgctcc   7680
gtcgatcact acgaagtcgc gccggccgat ggccttcacg tcgcggtcaa tcgtcgggcg   7740
gtcgatgccg acaacggtta gcggttgatc ttcccgcacg ccgcccaat cgcgggcact    7800 gccctgggga tcggaatcga ctaacagaac atcggcccg gcgagttgca gggcgcgggc    7860
tagatgggtt gcgatggtcg tcttgcctga cccgcctttc tggttaagta cagcgataac   7920
ttcatgcgtt cccttgcgta tttgtttatt tactcatcgc atcatatacg cagcgaccgc   7980
atgacgcaag ctgttttact caaatacaca tcaccttttt agacggcggc gctcggtttc   8040
ttcagcggcc aagctggccg gccaggccgc cagcttggca tcagacaaac cggccaggat   8100
ttcatgcagc cgcacggttg agacgtgcgc gggcggctcg aacacgtacc cggccgcgat   8160
catctccgcc tcgatctctt cggtaatgaa aaacggttcg tcctggccgt cctggtgcgg   8220
tttcatgctt gttcctcttg gcgttcattc tcggcggccg ccagggcgtc ggcctcggtc   8280
aatgcgtcct cacggaaggc accgcgccgc ctggcctcgg tgggcgtcac ttcctcgctg   8340
cgctcaagtg cgcggtacag ggtcgagcga tgcacgccaa gcagtgcagc cgcctctttc   8400
acggtgcggc cttcctggtc gatcagctcg cgggcgtgcg cgatctgtgc cggggtgagg   8460
gtagggcggg ggccaaactt cacgcctcgg gccttggcgg cctcgcgccc gctccgggtg   8520
cggtcgatga ttagggaacg ctcgaactcg gcaatgccgg cgaacacggt caacaccatg   8580
cggccggccg gcgtggtggt gtcggcccac ggctctgcca ggctacgcag gcccgcgccg   8640
gcctcctgga tgcgctcggc aatgtccagt aggtcgcggg tgctgcgggc caggcggtct   8700
agcctggtca ctgtcacaac gtcgccaggg cgtaggtggt caagcatcct ggccagctcc   8760
gggcggtcgc gcctggtgcc ggtgatcttc tcggaaaaca gcttggtgca gccggccgcg   8820
tgcagttcgg cccgttggtt ggtcaagtcc tggtcgtcgg tgctgacgcg ggcatagccc   8880
agcaggccag cggcggcgct cttgttcatg gcgtaatgtc tccggttcta gtcgcaagta   8940
ttctacttta tgcgactaaa acacgcgaca agaaaacgcc aggaaaaggg cagggcggca   9000
```

```
gcctgtcgcg taacttagga cttgtgcgac atgtcgtttt cagaagacgg ctgcactgaa   9060
cgtcagaagc cgactgcact atagcagcgg aggggttgga ccacaggacg ggtgtggtcg   9120
ccatgatcgc gtagtcgata gtggctccaa gtagcgaagc gagcaggact gggcggcggc   9180
caaagcggtc ggacagtgct ccgagaacgg gtgcgcatag aaattgcatc aacgcatata   9240
gcgctagcag cacgccatag tgactggcga tgctgtcgga atggacgata tcccgcaaga   9300
ggcccggcag taccggcata accaagccta tgcctacagc atccagggtg acggtgccga   9360
ggatgacgat gagcgcattg ttagatttca tacacggtgc ctgactgcgt tagcaattta   9420
actgtgataa actaccgcat taaagctagc ttgcttggtc gttccgcgtg aacgtcggct   9480
cgattgtacc tgcgttcaaa tactttgcga tcgtgttgcg cgcctgcccg gtgcgtcggc   9540
tgatctcacg gatcgactgc ttctctcgca acgccatccg acggatgatg tttaaaagtc   9600
ccatgtggat cactccgttg ccccgtcgct caccgtgttg gggggaaggt gcacatggct   9660
cagttctcaa tggaaattat ctgcctaacc ggctcagttc tgcgtagaaa ccaacatgca   9720
agctccaccg ggtgcaaagc ggcagcggcg gcaggatata ttcaattgta aatggcttca   9780
tgtccgggaa atctcatgg atcagcaatg agtatgatgg tcaatatgga gaaaagaaa   9840
gagtaattac caattttttt tcaattcaaa aatgtagatg tccgcagcgt tattataaaa   9900
tgaaagtaca ttttgataaa acgacaaatt acgatccgtc gtatttatag gcgaaagcaa   9960
taaacaaatt attctaattc ggaaatcttt atttcgacgt gtctacattc acgtccaaat  10020
gggggcttag atgagaaact tcacgatcga tgccttgatt tcgccattcc cagatacccca 10080
tttcatcttc agattggtct gagattatgc gaaaatatac actcatatac ataaatactg  10140
acagtttgag ctaccaattc agtgtagccc attacctcac ataattcact caaatgctag  10200
gcagtctgtc aactcggcgt caatttgtcg gccactatac gatagttgcg caaattttca  10260
aagtcctggc ctaacatcac acctctgtcg gcggcgggtc ccatttgtga taaatccacc  10320
atatcgaatt aattcagact cctttgcccc agagatcaca atggacgact tcctctatct  10380
ctacgatcta gtcaggaagt tcgacggaga aggtgacgat accatgttca ccactgataa  10440
tgagaagatt agccttttca atttcagaaa gaatgctaac ccacagatgg ttagagaggc  10500
ttacgcagca ggtctcatca agacgatcta cccgagcaat aatctccagg agatcaaata  10560
ccttcccaag aaggttaaag atgcagtcaa aagattcagg actaactgca tcaagaacac  10620
agagaaagat atatttctca agatcagaag tactattcca gtatggacga ttcaaggctt  10680
gcttcacaaa ccaaggcaag taatagagat tggagtctct aaaaaggtag ttcccactga  10740
atcaaaggcc atggagtcaa agattcaaat agaggaccta acagaactcg ccgtaaagac  10800
tggcgaacag ttcatacaga gtctcttacg actcaatgac aagaagaaaa tcttcgtcaa  10860
catggtggag cacgacacgc ttgtctactc caaaaatatc aaagatacag tctcagaaga  10920
ccaaagggca attgagactt ttcaacaaag ggtaatatcc ggaaacctcc tcggattcca  10980
ttgcccagct atctgtcact ttattgtgaa gatagtggaa aaggaaggtg ctcctacaa   11040
atgccatcat tgcgataaag gaaaggccat cgttgaagat gcctctgccg acagtggtcc  11100
caaagatgga cccccaccca cgaggagcat cgtggaaaaa gaagacgttc caaccacgtc  11160
ttcaaagcaa gtggattgat gtgatatctc cactgacgta agggatgacg cacaatccca  11220
ctatccttcg caagaccctt cctctatata aggaagttca tttcatttgg agaggacacg  11280
ctgaaatcac cagtctccaa gcttgcgggg atcgtttcgc atgattgaac aagatggatt  11340
```

```
gcacgcaggt tctccggccg cttgggtgga gaggctattc ggctatgact gggcacaaca    11400
gacaatcggc tgctctgatg ccgccgtgtt ccggctgtca gcgcaggggc gcccggttct    11460
ttttgtcaag accgacctgt ccggtgccct gaatgaactg caggacgagg cagcgcggct    11520
atcgtggctg gccacgacgg gcgttccttg cgcagctgtg ctcgacgttg tcactgaagc    11580
gggaagggac tggctgctat tgggcgaagt gccggggcag gatctcctgt catctcacct    11640
tgctcctgcc gagaaagtat ccatcatggc tgatgcaatg cggcggctgc atacgcttga    11700
tccggctacc tgcccattcg accaccaagc gaaacatcgc atcgagcgag cacgtactcg    11760
gatggaagcc ggtcttgtcg atcaggatga tctggacgaa gagcatcagg ggctcgcgcc    11820
agccgaactg ttcgccaggc tcaaggcgcg catgcccgac ggcgaggatc tcgtcgtgac    11880
ccatggcgat gcctgcttgc cgaatatcat ggtggaaaat ggccgctttt ctggattcat    11940
cgactgtggc cggctgggtg tggcggaccg ctatcaggac atagcgttgg ctacccgtga    12000
tattgctgaa gagcttggcg gcgaatgggc tgaccgcttc ctcgtgcttt acggtatcgc    12060
cgctcccgat tcgcagcgca tcgccttcta tcgccttctt gacgagttct tctgagcggg    12120
actctggggt tcgaaatgac cgaccaagcg acgcccaacc tgccatcacg agatttcgat    12180
tccaccgccg ccttctatga aaggttgggc ttcggaatcg ttttccggga cgccggctgg    12240
atgatcctcc agcgcgggga tctcatgctg gagttcttcg cccaccccgg atcgatccaa    12300
cacttacgtt tgcaacgtcc aagagcaaat agaccacgaa cgccggaagg ttgccgcagc    12360
gtgtggattg cgtctcaatt ctctcttgca ggaatgcaat gatgaatatg atactgacta    12420
tgaaactttg agggaatact gcctagcacc gtcacctcat aacgtgcatc atgcatgccc    12480
tgacaacatg gaacatcgct attttttctga agaattatgc tcgttggagg atgtcgcggc    12540
aattgcagct attgccaaca tcgaactacc cctcacgcat gcattcatca atattattca    12600
tgcggggaaa ggcaagatta atccaactgg caaatcatcc agcgtgattg gtaacttcag    12660
ttccagcgac ttgattcgtt ttggtgctac ccacgttttc aataaggacg agatggtgga    12720
gtaaagaagg agtgcgtcga agcagatcgt tcaaacattt ggcaataaag tttcttaaga    12780
ttgaatcctg ttgccggtct tgcgatgatt atcatataat ttctgttgaa ttacgttaag    12840
catgtaataa ttaacatgta atgcatgacg ttatttatga gatgggtttt tatgattaga    12900
gtcccgcaat tatacattta atacgcgata gaaaacaaaa tatagcgcgc aaactaggat    12960
aaattatcgc gcgcggtgtc atctatgtta ctagatcgat caaacttcgg tactgtgtaa    13020
tgacgatgag caatcgagag gctgactaac aaaaggtaca tcgcgatgga tcgatccatt    13080
cgccattcag gctgcgcaac tgttgggaag ggcgatcggt gcgggcctct tcgctattac    13140
gccagctggc gaaaggggga tgtgctgcaa ggcgattaag ttgggtaacg ccagggtttt    13200
cccagtcacg acgttgtaaa acgacggcca gtgaattcct gcagcccggg ggatccgccc    13260
actcgaggcg cgccaagctt gcatgcctgc aggctagcct aagtacgtac tcaaaatgcc    13320
aacaaataaa aaaaagttg ctttaataat gccaaaacaa attaataaaa cacttacaac    13380
accggatttt ttttaattaa aatgtgccat ttaggataaa tagttaatat ttttaataat    13440
tatttaaaaa gccgtatcta ctaaaatgat ttttatttgg ttgaaaatat taatatgttt    13500
aaatcaacac aatctatcaa aattaaacta aaaaaaaaat aagtgtacgt ggttaacatt    13560
agtacagtaa tataagagga aaatgagaaa ttaagaaatt gaaagcgagt ctaattttta    13620
aattatgaac ctgcatatat aaaaggaaag aaagaatcca ggaagaaaag aaatgaaacc    13680
atgcatggtc ccctcgtcat cacgagtttc tgccatttgc aatagaaaca ctgaaacacc    13740
```

```
tttctctttg tcacttaatt gagatgccga agccacctca caccatgaac ttcatgaggt  13800
gtagcaccca aggcttccat agccatgcat actgaagaat gtctcaagct cagcacccta  13860
cttctgtgac gtgtccctca ttcaccttcc tctcttccct ataaataacc acgcctcagg  13920
ttctccgctt cacaactcaa acattctctc cattggtcct taaacactca tcagtcatca  13980
ccgcggccct agacgcccat cacaagtttg tacaaaaaag ctgaacgaga acgtaaaat   14040
gatataaata tcaatatatt aaattagatt ttgcataaaa aacagactac ataatactgt  14100
aaaacacaac atatccagtc atattggcgg ccgcattagg caccccaggc tttacacttt  14160
atgcttccgg ctcgtataat gtgtggattt tgagttagga tccgtcgaga ttttcaggag  14220
ctaaggaagc taaatggag aaaaaaatca ctggatatac caccgttgat atatcccaat   14280
ggcatcgtaa agaacatttt gaggcatttc agtcagttgc tcaatgtacc tataaccaga  14340
ccgttcagct ggatattacg gcctttttaa agaccgtaaa gaaaaataag cacaagtttt  14400
atccggcctt tattcacatt cttgcccgcc tgatgaatgc tcatccggaa ttccgtatgg  14460
caatgaaaga cggtgagctg gtgatatggg atagtgttca cccttgttac accgttttcc  14520
atgagcaaac tgaaacgttt tcatcgctct ggagtgaata ccacgacgat ttccggcagt  14580
ttctacacat atattcgcaa gatgtggcgt gttacggtga aaacctggcc tatttcccta  14640
aagggtttat tgagaatatg ttttcgtct cagccaatcc ctgggtgagt ttcaccagtt    14700
ttgatttaaa cgtggccaat atggacaact tcttcgcccc cgttttcacc atgggcaaat  14760
attatacgca aggcgacaag gtgctgatgc cgctggcgat tcaggttcat catgccgttt  14820
gtgatggctt ccatgtcggc agaatgctta atgaattaca acagtactgc gatgagtggc  14880
agggcgggc gtaaacgcgt ggatccggct tactaaaagc cagataacag tatgcgtatt   14940
tgcgcgctga tttttgcggt ataagaatat atactgatat gtatacccga agtatgtcaa  15000
aaagaggtat gctatgaagc agcgtattac agtgacagtt gacagcgaca gctatcagtt  15060
gctcaaggca tatatgatgt caatatctcc ggtctggtaa gcacaaccat gcagaatgaa  15120
gcccgtcgtc tgcgtgccga acgctggaaa gcggaaaatc aggaagggat ggctgaggtc  15180
gcccggttta ttgaaatgaa cggctctttt gctgacgaga cagggggctg gtgaaatgca  15240
gtttaaggtt tacacctata aaagagagag ccgttatcgt ctgtttgtgg atgtacagag  15300
tgatattatt gacacgcccg ggcgacggat ggtgatcccc ctggccagtg cacgtctgct  15360
gtcagataaa gtctcccgtg aactttaccc ggtggtgcat atcggggatg aaagctggcg  15420
catgatgacc accgatatgg ccagtgtgcc ggtctccgtt atcggggaag aagtggctga  15480
tctcagccac cgcgaaaatg acatcaaaaa cgccattaac ctgatgttct ggggaatata  15540
aatgtcaggc tcccttatac acagccagtc tgcaggtcga ccatagtgac tggatatgtt  15600
gtgttttaca gcattatgta gtctgttttt tatgcaaaat ctaatttaat atattgatat  15660
ttatatcatt ttacgtttct cgttcagctt tcttgtacaa agtggtgatg ataaccaagt  15720
ttaacgtgag tttatatatt cacagttcca tttacagatc ttatgctgat tgcagcatat  15780
aacatagtcg caacttaact ttatccctgc ttacgtaaag aaacatacat attgtttgtg  15840
gcttcgtagt ggaacatatg caattatgta atctttatat tatgagcctt tacttacaaa  15900
gattacttga gatttatgta cgtgtgctat tttcactttt caaacatgaa tttcctacgt  15960
ttacaatcat ttaatgtaaa agggatgata taatgtattt acgtacatgt gaacaaccaa  16020
gcatgttatt ttttccttt ttgttgcaac ttacaatcaa gtaatgatta tggttatgat    16080
```

```
tatgatattg gtgtgtgtct tttgccttat atatatattt atccctttcg tttaactttg    16140
caatataatt attactgatc actatatttt ggtttgaaat ggcgcaggtt gtaatgatcg    16200
atcatcacca ctttgtacaa gaaagctgaa cgagaaacgt aaaatgatat aaatatcaat    16260
atattaaatt agattttgca taaaaaacag actacaataa gctgtaaaac acaacatatc    16320
cagtcactat ggtcgacctg cagactggct gtgtataagg gagcctgaca tttatattcc    16380
ccagaacatc aggttaatgg cgttttttgat gtcattttcg cggtggctga gatcagccac    16440
ttcttccccg ataacggaga ccggcacact ggccatatcg gtggtcatca tgcgccagct    16500
ttcatccccg atatgcacca ccgggtaaag ttcacgggag actttatctg acagcagacg    16560
tgcactggcc aggggggatca ccatccgtcg cccgggcgtg tcaataatat cactctgtac    16620
atccacaaac agacgataac ggctctctct tttataggtg taaaccttaa actgcatttc    16680
accagcccct gttctcgtca gcaaaagagc cgttcatttc aataaaccgg gcgacctcag    16740
ccatcccttc ctgatttttcc gctttccagc gttcggcacg cagacgacgg gcttcattct    16800
gcatggttgt gcttaccaga ccggagatat tgacatcata tatgccttga gcaactgata    16860
gctgtcgctg tcaactgtca ctgtaatacg ctgcttcata gcatacctct ttttgacata    16920
cttcgggtat acatatcagt atatattctt ataccgcaaa aatcagcgcg caaatacgca    16980
tactgttatc tggcttttag taagccggat cctaactcaa aatccacaca ttatacgagc    17040
cggaagcata aagtgtaaag cctggggtgc ctaatgcggc cgccaatatg actggatatg    17100
ttgtgtttta cagtattatg tagtctgttt tttatgcaaa atctaattta atatattgat    17160
atttatatca ttttacgttt ctcgttcagc ttttttgtac aaacttgtga tgggcgtcta    17220
gcgaactaga ggatcccccgg gtaccgaggt acgtctagag gatccgtcga cgg         17273
```

```
<210> SEQ ID NO 16
<211> LENGTH: 38
<212> TYPE: DNA
<213> ORGANISM: artificial sequence
<220> FEATURE:
<223> OTHER INFORMATION: primer

<400> SEQUENCE: 16
cctagggtta accaagttta acgtgagttt atatattc                            38

<210> SEQ ID NO 17
<211> LENGTH: 38
<212> TYPE: DNA
<213> ORGANISM: artificial sequence
<220> FEATURE:
<223> OTHER INFORMATION: primer

<400> SEQUENCE: 17
actagttcgc gatcattaca acctgcgcca tttcaaac                            38

<210> SEQ ID NO 18
<211> LENGTH: 506
<212> TYPE: DNA
<213> ORGANISM: artificial sequence
<220> FEATURE:
<223> OTHER INFORMATION: PCR product & intron

<400> SEQUENCE: 18
cctagggtta accaagttta acgtgagttt atatattcac agttccattt acagatctta    60
tgctgattgc agcatataac atagtcgcaa cttaacttta tccctgctta cgtaaagaaa    120
catacatatt gtttgtggct tcgtagtgga acatatgcaa ttatgtaatc tttatattat    180
```

```
gagcctttac ttacaaagat tacttgagat ttatgtacgt gtgctatttt cacttttcaa    240
acatgaattt cctacgttta caatcattta atgtaaaagg gatgatataa tgtatttacg    300
tacatgtgaa caaccaagca tgttattttt tcctttttg ttgcaactta caatcaagta     360
atgattatgg ttatgattat gatattggtg tgtgtcttt gccttatata tatatttatc    420
cctttcgttt aactttgcaa tataattatt actgatcact atattttggt ttgaaatggc    480
gcaggttgta atgatcgcga actagt                                        506
```

<210> SEQ ID NO 19  
<211> LENGTH: 1724  
<212> TYPE: DNA  
<213> ORGANISM: artificial sequence  
<220> FEATURE:  
<223> OTHER INFORMATION: synthetic DNA fragment

<400> SEQUENCE: 19

```
ctagacgccc atcacaagtt tgtacaaaaa agctgaacga gaaacgtaaa atgatataaa     60
tatcaatata ttaaattaga ttttgcataa aaaacagact acataatact gtaaaacaca    120
acatatccag tcatattggc ggccgcatta ggcaccccag gctttacact ttatgcttcc    180
ggctcgtata atgtgtggat tttgagttag gatccgtcga gattttcagg agctaaggaa    240
gctaaaatgg agaaaaaaat cactggatat accaccgttg atatatccca atggcatcgt    300
aaagaacatt ttgaggcatt tcagtcagtt gctcaatgta cctataacca gaccgttcag    360
ctggatatta cggcctttt aaagaccgta aagaaaaata agcacaagtt ttatccggcc     420
tttattcaca ttcttgcccg cctgatgaat gctcatccgg aattccgtat ggcaatgaaa    480
gacggtgagc tggtgatatg ggatagtgtt cacccttgtt acaccgtttt ccatgagcaa    540
actgaaacgt tttcatcgct ctggagtgaa taccacgacg atttccggca gtttctacac    600
atatattcgc aagatgtggc gtgttacggt gaaaacctgg cctatttccc taaagggttt    660
attgagaata tgttttttcgt ctcagccaat ccctgggtga gtttcaccag ttttgattta    720
aacgtggcca atatggacaa cttcttcgcc cccgtttca ccatgggcaa atattatacg     780
caaggcgaca aggtgctgat gccgctggcg attcaggttc atcatgccgt tgtgatggc     840 ttccatgtcg gcagaatgct taatgaatta caacagtact gcgatgagtg cagggcggg     900 gcgtaaacgc gtggatccgg cttactaaaa gccagataac agtatgcgta tttgcgcgct    960 gattttgcg gtataagaat atatactgat atgtatacccc gaagtatgtc aaaaagaggt    1020
atgctatgaa gcagcgtatt acagtgacag ttgacagcga cagctatcag ttgctcaagg    1080
catatatgat gtcaatatct ccggtctggt aagcacaacc atgcagaatg aagcccgtcg    1140
tctgcgtgcc gaacgctgga aagcggaaaa tcaggaaggg atggctgagg tcgcccggtt    1200
tattgaaatg aacggctctt tgctgacga gaacaggggc tggtgaaatg cagtttaagg    1260
tttacaccta taaagagag agccgttatc gtctgtttgt ggatgtacag agtgatatta    1320
ttgacacgcc cgggcgacgg atggtgatcc ccctggccag tgcacgtctg ctgtcagata    1380
aagtctcccg tgaactttac ccggtggtgc atatcgggga tgaaagctgg cgcatgatga    1440
ccaccgatat ggccagtgtg ccggtctccg ttatcgggga agaagtggct gatctcagcc    1500
accgcgaaaa tgacatcaaa aacgccatta acctgatgtt ctggggaata taaatgtcag    1560
gctcccttat acacagccag tctgcaggtc gaccatagtg actggatatg ttgtgtttta    1620
cagcattatg tagtctgttt tttatgcaaa atctaattta atatattgat atttatatca    1680
```

```
ttttacgttt ctcgttcagc tttcttgtac aaagtggtga tgat              1724
```

<210> SEQ ID NO 20
<211> LENGTH: 4934
<212> TYPE: DNA
<213> ORGANISM: artificial sequence
<220> FEATURE:
<223> OTHER INFORMATION: plasmid

<400> SEQUENCE: 20

```
ctagaggatc ccgggtacc gagctcgaat tcgtaatcat ggtcatagct gtttcctgtg    60
tgaaattgtt atccgctcac aattccacac aacatacgag ccggaagcat aaagtgtaaa  120
gcctggggtg cctaatgagt gagctaactc acattaattg cgttgcgctc actgcccgct  180
ttccagtcgg gaaacctgtc gtgccagctg cattaatgaa tcggccaacg cgcgggaga   240
ggcggtttgc gtattgggcg ctagcggagt gtatactggc ttactatgtt ggcactgatg  300
agggtgtcag tgaagtgctt catgtggcag gagaaaaaag gctgcaccgg tgcgtcagca  360
gaatatgtga tacaggatat attccgcttc ctcgctcact gactcgctac gctcggtcgt  420
tcgactgcgg cgagcggaaa tggcttacga cggggcgga gatttcctgg aagatgccag  480
gaagatactt aacaggaag tgagagggcc gcggcaaagc cgttttttcca taggctccgc  540
ccccctgaca agcatcacga aatctgacgc tcaaatcagt ggtggcgaaa cccgacagga  600
ctataaagat accaggcgtt tcccctggc ggctccctcg tgcgctctcc tgttcctgcc  660
tttcggttta ccggtgtcat tccgctgtta tggccgcgtt tgtctcattc cacgcctgac  720
actcagttcc gggtaggcag ttcgctccaa gctggactgt atgcacgaac ccccgttca   780
gtccgaccgc tgcgccttat ccggtaacta tcgtcttgag tccaacccgg aaagacatgc  840
aaaagcacca ctggcagcag ccactggtaa ttgatttaga ggagttagtc ttgaagtcat  900
gcgccggtta aggctaaact gaaaggacaa gttttggtga ctgcgctcct ccaagccagt  960
tacctcggtt caaagagttg gtagctcaga gaaccttcga aaaaccgccc tgcaaggcgg 1020
ttttttcgtt ttcagagcaa gagattacgc gcagaccaaa acgatctcaa gaagatcatc 1080
ttattaaggg gtctgacgct cagtggaacg aaaactcacg ttaagggatt ttggtcatga 1140
gattatcaaa aaggatcttc acctagatcc tttttaaatta aaaatgaagt tttaaatcaa 1200
tctaaagtat atatgagtaa acttggtctg acagttacca atgcttaatc agtgaggcac 1260
ctatctcagc gatctgtcta tttcgttcat ccatagttgc ctgactcccc gtcgtgtaga 1320
taactacgat acgggagggc ttaccatctg gccccagtgc tgcaatgata ccgcgagacc 1380
cacgctcacc ggctccagat ttatcagcaa taaaccagcc agccggaagg gccgagcgca 1440
gaagtggtcc tgcaacttta tccgcctcca tccagtctat taattgttgc cgggaagcta 1500
gagtaagtag ttcgccagtt aatagtttgc gcaacgttgt tgccattgct acaggcatcg 1560
tggtgtcacg ctcgtcgttt ggtatggctt cattcagctc cggttcccaa cgatcaaggc 1620
gagttacatg atccccccatg ttgtgcaaaa aagcggttag ctccttcggt cctccgatcg 1680
ttgtcagaag taagttggcc gcagtgttat cactcatggt tatggcagca ctgcataatt 1740
ctcttactgt catgccatcc gtaagatgct tttctgtgac tggtgagtac tcaaccaagt 1800
cattctgaga atagtgtatg cggcgaccga gttgctcttg cccggcgtca atacgggata 1860
ataccgcgcc acatagcaga actttaaaag tgctcatcat tggaaaacgt tcttcggggc 1920
gaaaactctc aaggatctta ccgctgttga gatccagttc gatgtaaccc actcgtgcac 1980
ccaactgatc ttcagcatct tttactttca ccagcgtttc tgggtgagca aaaacaggaa 2040
```

```
ggcaaaatgc cgcaaaaaag ggaataaggg cgacacggaa atgttgaata ctcatactct   2100
tcctttttca atattattga agcatttatc agggttattg tctcatgagc ggatacatat   2160
ttgaatgtat ttagaaaaat aaacaaatag gggttccgcg cacatttccc cgaaaagtgc   2220
cacctgacgt ctaagaaacc attattatca tgacattaac ctataaaaat aggcgtatca   2280
cgaggccctt tcgtctcgcg cgtttcggtg atgacggtga aaacctctga cacatgcagc   2340
tcccggagac ggtcacagct tgtctgtaag cggatgccgg gagcagacaa gcccgtcagg   2400
gcgcgtcagc gggtgttggc gggtgtcggg gctggcttaa ctatgcggca tcagagcaga   2460
ttgtactgag agtgcaccat atgcggtgtg aaataccgca cagatgcgta aggagaaaat   2520
accgcatcag gcgccattcg ccattcaggc tgcgcaactg ttgggaaggg cgatcggtgc   2580
gggcctcttc gctattacgc cagctggcga aggggggatg tgctgcaagg cgattaagtt   2640
gggtaacgcc agggttttcc cagtcacgac gttgtaaaac gacggccagt gccaagcttg   2700
catgcctgca ggtcgactct agacgcccat cacaagtttg tacaaaaaag ctgaacgaga   2760
aacgtaaaat gatataaata tcaatatatt aaattagatt ttgcataaaa aacagactac   2820
ataatactgt aaaacacaac atatccagtc atattggcgg ccgcattagg caccccaggc   2880
tttacacttt atgcttccgg ctcgtataat gtgtggattt tgagttagga tccgtcgaga   2940
ttttcaggag ctaaggaagc taaaatggag aaaaaaatca ctggatatac caccgttgat   3000
atatcccaat ggcatcgtaa agaacatttt gaggcatttc agtcagttgc tcaatgtacc   3060
tataaccaga ccgttcagct ggatattacg gcctttttaa agaccgtaaa gaaaaataag   3120
cacaagtttt atccggcctt tattcacatt cttgcccgcc tgatgaatgc tcatccggaa   3180
ttccgtatgg caatgaaaga cggtgagctg gtgatatggg atagtgttca cccttgttac   3240
accgttttcc atgagcaaac tgaaacgttt tcatcgctct ggagtgaata ccacgacgat   3300
ttccggcagt ttctacacat atattcgcaa gatgtggcgt gttacggtga aaacctggcc   3360
tatttcccta aagggtttat tgagaatatg ttttttcgtct cagccaatcc ctgggtgagt   3420
ttcaccagtt ttgatttaaa cgtggccaat atggacaact tcttcgcccc cgttttcacc   3480
atgggcaaat attatacgca aggcgacaag gtgctgatgc cgctggcgat tcaggttcat   3540
catgccgttt gtgatggctt ccatgtcggc agaatgctta atgaattaca acagtactgc   3600
gatgagtggc agggcggggc gtaaacgcgt ggatccggct tactaaaagc cagataacag   3660
tatgcgtatt tgcgcgctga ttttgcggt ataagaatat atactgatat gtatacccga   3720
agtatgtcaa aaagaggtat gctatgaagc agcgtattac agtgacagtt gacagcgaca   3780
gctatcagtt gctcaaggca tatatgatgt caatatctcc ggtctggtaa gcacaaccat   3840
gcagaatgaa gcccgtcgtc tgcgtgccga acgctggaaa gcggaaaatc aggaagggat   3900
ggctgaggtc gcccggttta ttgaaatgaa cggctctttt gctgacgaga caggggctg    3960 gtgaaatgca gtttaaggtt tacacctata aagagagag ccgttatcgt ctgtttgtgg    4020
atgtacagag tgatattatt gacacgcccg gcgacggat ggtgatcccc ctggccagtg    4080
cacgtctgct gtcagataaa gtctcccgtg aactttaccc ggtggtgcat atcggggatg   4140
aaagctggcg catgatgacc accgatatgg ccagtgtgcc ggtctccgtt atcggggaag   4200
aagtggctga tctcagccac cgcgaaaatg acatcaaaaa cgccattaac ctgatgttct   4260
ggggaatata aatgtcaggc tcccttatac acagccagtc tgcaggtcga ccatagtgac   4320
tggatatgtt gtgttttaca gcattatgta gtctgttttt tatgcaaaat ctaatttaat   4380
```

```
atattgatat ttatatcatt ttacgtttct cgttcagctt tcttgtacaa agtggtgatg    4440
ataaccaagt ttaacgtgag tttatatatt cacagttcca tttacagatc ttatgctgat    4500
tgcagcatat aacatagtcg caacttaact ttatccctgc ttacgtaaag aaacatacat    4560
attgtttgtg gcttcgtagt ggaacatatg caattatgta atctttatat tatgagcctt    4620
tacttacaaa gattacttga gatttatgta cgtgtgctat tttcactttt caaacatgaa    4680
tttcctacgt ttacaatcat ttaatgtaaa agggatgata taatgtattt acgtacatgt    4740
gaacaaccaa gcatgttatt ttttcctttt ttgttgcaac ttacaatcaa gtaatgatta    4800
tggttatgat tatgatattg gtgtgtgtct tttgccttat atatatattt atccctttcg    4860
tttaactttg caatataatt attactgatc actatatttt ggtttgaaat ggcgcaggtt    4920
gtaatgatcg cgaa                                                      4934

<210> SEQ ID NO 21
<211> LENGTH: 1021
<212> TYPE: DNA
<213> ORGANISM: artificial sequence
<220> FEATURE:
<223> OTHER INFORMATION: synthetic DNA fragment

<400> SEQUENCE: 21
ctagacgccc atcacaagtt tgtacaaaaa agctgaacga gaaacgtaaa atgatataaa      60
tatcaatata ttaaattaga ttttgcataa aaaacagact acataatact gtaaaacaca     120
acatatccag tcatattggc ggccgcatta ggcaccccag gctttacact ttatgcttcc     180
ggctcgtata atgtgtggat tttgagttag gatccggctt actaaaagcc agataacagt     240
atgcgtattt gcgcgctgat ttttgcggta taagaatata tactgatatg tatacccgaa     300
gtatgtcaaa aagaggtatg ctatgaagca gcgtattaca gtgacagttg acagcgacag     360
ctatcagttg ctcaaggcat atatgatgtc aatatctccg gtctggtaag cacaaccatg     420
cagaatgaag cccgtcgtct gcgtgccgaa cgctggaaag cggaaaatca ggaagggatg     480
gctgaggtcg cccggtttat tgaaatgaac ggctcttttg ctgacgagaa caggggctgg     540
tgaaatgcag tttaaggttt acacctataa aagagagagc cgttatcgtc tgtttgtgga     600
tgtacagagt gatattattg cacgcccgg gcgacggatg gtgatccccc tggccagtgc      660
acgtctgctg tcagataaag tctcccgtga actttacccg gtggtgcata tcggggatga     720
aagctggcgc atgatgacca ccgatatggc cagtgtgccg gtctccgtta tcggggaaga     780
agtggctgat ctcagccacc gcgaaaatga catcaaaaac gccattaacc tgatgttctg     840
gggaatataa atgtcaggct cccttataca cagccagtct gcaggtcgac catagtgact     900
ggatatgttg tgttttacag cattatgtag tctgtttttt atgcaaaatc taatttaata     960
tattgatatt tatatcattt tacgtttctc gttcagcttt cttgtacaaa gtggtgatga    1020
t                                                                   1021

<210> SEQ ID NO 22
<211> LENGTH: 5955
<212> TYPE: DNA
<213> ORGANISM: artificial sequence
<220> FEATURE:
<223> OTHER INFORMATION: plasmid

<400> SEQUENCE: 22
atcatcacca ctttgtacaa gaaagctgaa cgagaaacgt aaaatgatat aaatatcaat      60
atattaaatt agattttgca taaaaaacag actacataat gctgtaaaac acaacatatc     120
```

```
cagtcactat ggtcgacctg cagactggct gtgtataagg gagcctgaca tttatattcc    180
ccagaacatc aggttaatgg cgttttttgat gtcattttcg cggtggctga gatcagccac   240
```


```
cagtcactat ggtcgacctg cagactggct gtgtataagg gagcctgaca tttatattcc    180
ccagaacatc aggttaatgg cgtttttgat gtcattttcg cggtggctga gatcagccac    240 ttcttcccg ataacggaga ccggcacact ggccatatcg gtggtcatca tgcgccagct     300 ttcatcccg atatgcacca ccgggtaaag ttcacgggag actttatctg acagcagacg     360
tgcactggcc aggggatca ccatccgtcg cccgggcgtg tcaataatat cactctgtac     420
atccacaaac agacgataac ggctctctct tttataggtg taaaccttaa actgcatttc    480
accagcccct gttctcgtca gcaaaagagc cgttcatttc aataaaccgg gcgacctcag    540
ccatcccttc ctgattttcc gctttccagc gttcggcacg cagacgacgg gcttcattct    600
gcatggttgt gcttaccaga ccggagatat tgacatcata tatgccttga gcaactgata   660
gctgtcgctg tcaactgtca ctgtaatacg ctgcttcata gcatacctct ttttgacata    720
cttcgggtat acatatcagt atatattctt ataccgcaaa aatcagcgcg caaatacgca    780
tactgttatc tggcttttag taagccggat cctaactcaa aatccacaca ttatacgagc    840
cggaagcata agtgtaaag cctggggtgc ctaatgcggc cgccaatatg actggatatg     900
ttgtgtttta cagtattatg tagtctgttt tttatgcaaa atctaattta atatattgat   960
atttatatca ttttacgttt ctcgttcagc ttttttgtac aaacttgtga tgggcgtcta    1020
gcgaactaga ggatccccgg gtaccgagct cgaattcgta atcatggtca tagctgtttc    1080
ctgtgtgaaa ttgttatccg ctcacaattc cacacaacat acgagccgga agcataaagt    1140
gtaaagcctg gggtgcctaa tgagtgagct aactcacatt aattgcgttg cgctcactgc    1200
ccgctttcca gtcgggaaac ctgtcgtgcc agctgcatta atgaatcggc caacgcgcgg    1260
ggagaggcgg tttgcgtatt gggcgctagc ggagtgtata ctggcttact atgttggcac    1320
tgatgagggt gtcagtgaag tgcttcatgt ggcaggagaa aaaaggctgc accggtgcgt    1380
cagcagaata tgtgatacag gatatattcc gcttcctcgc tcactgactc gctacgctcg    1440
gtcgttcgac tgcggcgagc ggaaatggct tacgaacggg gcggagattt cctggaagat    1500
gccaggaaga tacttaacag ggaagtgaga gggccgcggc aaagccgttt ttccataggc    1560
tccgcccccc tgacaagcat cacgaaatct gacgctcaaa tcagtggtgg cgaaacccga    1620
caggactata aagataccag gcgtttcccc ctggcggctc cctcgtgcgc tctcctgttc    1680
ctgcctttcg gtttaccggt gtcattccgc tgttatggcc gcgtttgtct cattccacgc    1740
ctgacactca gttccgggta ggcagttcgc tccaagctgg actgtatgca cgaacccccc    1800
gttcagtccg accgctgcgc cttatccggt aactatcgtc ttgagtccaa cccggaaaga    1860
catgcaaaag caccactggc agcagccact ggtaattgat ttagaggagt tagtcttgaa    1920
gtcatgcgcc ggttaaggct aaactgaaag acaagttttt ggtgactgcg ctcctccaag    1980
ccagttacct cggttcaaag agttggtagc tcagagaacc ttcgaaaaac cgccctgcaa    2040
ggcggttttt tcgttttcag agcaagagat tacgcgcaga ccaaaacgat ctcaagaaga    2100
tcatcttatt aaggggtctg acgctcagtg aacgaaaac tcacgttaag ggattttggt     2160
catgagatta tcaaaaagga tcttcaccta gatccttta aattaaaaat gaagttttaa     2220
atcaatctaa agtatatatg agtaaacttg gtctgacagt taccaatgct taatcagtga    2280
ggcacctatc tcagcgatct gtctatttcg ttcatccata gttgcctgac tccccgtcgt    2340
gtagataact acgatacggg agggcttacc atctggcccc agtgctgcaa tgataccgcg    2400
agacccacgc tcaccggctc cagatttatc agcaataaac cagccagccg gaagggccga    2460
```

```
gcgcagaagt ggtcctgcaa ctttatccgc ctccatccag tctattaatt gttgccggga    2520
agctagagta agtagttcgc cagttaatag tttgcgcaac gttgttgcca ttgctacagg    2580
catcgtggtg tcacgctcgt cgtttggtat ggcttcattc agctccggtt cccaacgatc    2640
aaggcgagtt acatgatccc ccatgttgtg caaaaaagcg gttagctcct tcggtcctcc    2700
gatcgttgtc agaagtaagt tggccgcagt gttatcactc atggttatgg cagcactgca    2760
taattctctt actgtcatgc catccgtaag atgcttttct gtgactggtg agtactcaac    2820
caagtcattc tgagaatagt gtatgcggcg accgagttgc tcttgcccgg cgtcaatacg    2880
ggataatacc gcgccacata gcagaacttt aaaagtgctc atcattggaa aacgttcttc    2940
ggggcgaaaa ctctcaagga tcttaccgct gttgagatcc agttcgatgt aacccactcg    3000
tgcacccaac tgatcttcag catcttttac tttcaccagc gtttctgggt gagcaaaaac    3060
aggaaggcaa aatgccgcaa aaaagggaat aagggcgaca cggaaatgtt gaatactcat    3120
actcttcctt tttcaatatt attgaagcat ttatcagggt tattgtctca tgagcggata    3180
catatttgaa tgtatttaga aaaataaaca ataggggcc gcgcacat ttccccgaaa    3240 agtgccacct gacgtctaag aaaccattat tatcatgaca ttaacctata aaaataggcg    3300
tatcacgagg ccctttcgtc tcgcgcgttt cggtgatgac ggtgaaaacc tctgacacat    3360
gcagctcccg gagacggtca cagcttgtct gtaagcggat gccgggagca gacaagcccg    3420
tcagggcgcg tcagcgggtg ttggcgggtg tcggggctgg cttaactatg cggcatcaga    3480
gcagattgta ctgagagtgc accatatgcg gtgtgaaata ccgcacagat gcgtaaggag    3540
aaaataccgc atcaggcgcc attcgccatt caggctgcgc aactgttggg aagggcgatc    3600
ggtgcgggcc tcttcgctat tacgccagct ggcgaaaggg ggatgtgctg caaggcgatt    3660
aagttgggta acgccagggt tttcccagtc acgacgttgt aaaacgacgg ccagtgccaa    3720
gcttgcatgc ctgcaggtcg actctagacg cccatcacaa gtttgtacaa aaaagctgaa    3780
cgagaaacgt aaaatgatat aaatatcaat atattaaatt agattttgca taaaaaacag    3840
actacataat actgtaaaac acaacatatc cagtcatatt ggcggccgca ttaggcaccc    3900
caggctttac actttatgct tccggctcgt ataatgtgtg gattttgagt taggatccgt    3960
cgagattttc aggagctaag gaagctaaaa tggagaaaaa aatcactgga tataccaccg    4020
ttgatatatc ccaatggcat cgtaaagaac attttgaggc atttcagtca gttgctcaat    4080
gtacctataa ccagaccgtt cagctggata ttacggcctt tttaaagacc gtaaagaaaa    4140
ataagcacaa gttttatccg gcctttattc acattcttgc ccgcctgatg aatgctcatc    4200
cggaattccg tatggcaatg aaagacggtg agctggtgat atgggatagt gttcacccut    4260
gttacaccgt tttccatgag caaactgaaa cgttttcatc gctctggagt gaataccacg    4320
acgatttccg gcagtttcta cacatatatt cgcaagatgt ggcgtgttac ggtgaaaacc    4380
tggcctattt ccctaaaggg tttattgaga atatgttttt cgtctcagcc aatccctggg    4440
tgagtttcac cagttttgat ttaaacgtgg ccaatatgga aacttcttc gccccgtttt    4500 tcaccatggg caaatattat acgcaaggcg acaaggtgct gatgccgctg gcgattcagg    4560
ttcatcatgc cgtttgtgat ggcttccatg tcggcagaat gcttaatgaa ttacaacagt    4620
actgcgatga gtggcagggc ggggcgtaaa cgcgtggatc cggcttacta aaagccagat    4680
aacagtatgc gtatttgcgc gctgattttt gcggtataag aatatatact gatatgtata    4740
cccgaagtat gtcaaaaaga ggtatgctat gaagcagcgt attacagtga cagttgacag    4800
cgacagctat cagttgctca aggcatatat gatgtcaata tctccggtct ggtaagcaca    4860
```

```
accatgcaga atgaagcccg tcgtctgcgt gccgaacgct ggaaagcgga aaatcaggaa    4920
gggatggctg aggtcgcccg gtttattgaa atgaacggct cttttgctga cgagaacagg    4980
ggctggtgaa atgcagttta aggtttacac ctataaaaga gagagccgtt atcgtctgtt    5040
tgtggatgta cagagtgata ttattgacac gcccgggcga cggatggtga tcccctggc     5100 cagtgcacgt ctgctgtcag ataaagtctc ccgtgaactt acccggtgg tgcatatcgg      5160 ggatgaaagc tggcgcatga tgaccaccga tatggccagt gtgccggtct ccgttatcgg    5220
ggaagaagtg gctgatctca gccaccgcga aaatgacatc aaaaacgcca ttaacctgat    5280 gttctggga atataaatgt caggctccct tatacacagc cagtctgcag gtcgaccata     5340
gtgactggat atgttgtgtt ttacagcatt atgtagtctg ttttttatgc aaaatctaat    5400
ttaatatatt gatatttata tcattttacg tttctcgttc agctttcttg tacaaagtgg    5460
tgatgataac caagtttaac gtgagtttat atattcacag ttccatttac agatcttatg    5520
ctgattgcag catataacat agtcgcaact taactttatc cctgcttacg taagaaaca     5580 tacatattgt ttgtggcttc gtagtggaac atatgcaatt atgtaatctt tatattatga    5640
gcctttactt acaaagatta cttgagattt atgtacgtgt gctattttca cttttcaaac    5700
atgaatttcc tacgtttaca atcatttaat gtaaaggga tgatataatg tatttacgta    5760
catgtgaaca accaagcatg ttatttttc ctttttgtt gcaacttaca atcaagtaat       5820
gattatggtt atgattatga tattggtgtg tgtcttttgc cttatatata tatttatccc    5880
tttcgtttaa ctttgcaata taattattac tgatcactat attttggttt gaaatggcgc    5940
aggttgtaat gatcg                                                      5955
```

<210> SEQ ID NO 23
<211> LENGTH: 9245
<212> TYPE: DNA
<213> ORGANISM: artificial sequence
<220> FEATURE:
<223> OTHER INFORMATION: vector
<400> SEQUENCE: 23

```
gtacgtctag aggatccgtc gacggcgcgc ccgatcatcc ggatatagtt cctcctttca      60
gcaaaaaacc cctcaagacc cgtttagagg ccccaagggg ttatgctagt tattgctcag     120
cggtggcagc agccaactca gcttcctttc gggctttgtt agcagccgga tcgatccaag    180
ctgtacctca ctattccttt gccctcggac gagtgctggg gcgtcggttt ccactatcgg    240
cgagtacttc tacacagcca tcggtccaga cggccgcgct tctgcgggcg atttgtgtac    300
gcccgacagt cccggctccg gatcggacga ttgcgtcgca tcgaccctgc gcccaagctg    360
catcatcgaa attgccgtca accaagctct gatagagttg gtcaagacca atgcggagca    420
tatacgcccg gagccgcggc gatcctgcaa gctccggatg cctccgctcg aagtagcgcg    480
tctgctgctc catacaagcc aaccacggcc tccagaagaa gatgttggcg acctcgtatt    540
gggaatcccc gaacatcgcc tcgctccagt caatgaccgc tgttatgcgg ccattgtccg    600
tcaggacatt gttggagccg aaatccgcgt gcacgaggtg ccggacttcg ggcagtcct     660 cggcccaaag catcagctca tcgagagcct gcgcgacgga cgcactgacg gtgtcgtcca    720
tcacagtttg ccagtgatac acatgggat cagcaatcgc gcatatgaaa tcacgccatg     780
tagtgtattg accgattcct tgcggtccga atgggccgaa cccgctcgtc tggctaagat    840
cggccgcagc gatcgcatcc atagcctccg cgaccggctg cagaacagcg ggcagttcgg    900
```

```
tttcaggcag gtcttgcaac gtgacaccct gtgcacggcg ggagatgcaa taggtcaggc    960
tctcgctgaa ttccccaatg tcaagcactt ccggaatcgg gagcgcggcc gatgcaaagt   1020
gccgataaac ataacgatct tgtagaaac catcggcgca gctatttacc cgcaggacat    1080
atccacgccc tcctacatcg aagctgaaag cacgagattc ttcgccctcc gagagctgca   1140
tcaggtcgga gacgctgtcg aacttttcga tcagaaactt ctcgacagac gtcgcggtga   1200
gttcaggctt ttccatgggt atatctcctt cttaaagtta aacaaaatta tttctagagg   1260
gaaaccgttg tggtctccct atagtgagtc gtattaattt cgcgggatcg agatcgatcc   1320
aattccaatc ccacaaaaat ctgagcttaa cagcacagtt gctcctctca gagcagaatc   1380
gggtattcaa caccctcata tcaactacta cgttgtgtat aacggtccac atgccggtat   1440
atacgatgac tggggttgta caaggcggc aacaaacggc gttcccggag ttgcacacaa    1500
gaaatttgcc actattacag aggcaagagc agcagctgac gcgtacacaa caagtcagca   1560
aacagacagg ttgaacttca tccccaaagg agaagctcaa ctcaagccca agagctttgc   1620
taaggcccta acaagcccac caaagcaaaa agccccactgg ctcacgctag gaaccaaaag  1680
gcccagcagt gatccagccc caaaagagat ctccttttgcc ccggagatta caatggacga   1740
tttcctctat ctttacgatc taggaaggaa gttcgaaggt gaaggtgacg acactatgtt   1800
caccactgat aatgagaagg ttagcctctt caatttcaga aagaatgctg acccacagat   1860
ggttagagag gcctacgcag caggtctcat caagacgatc tacccgagta caatctcca    1920
ggagatcaaa taccttccca agaaggttaa agatgcagtc aaaagattca ggactaattg   1980
catcaagaac acagagaaag acatatttct caagatcaga agtactattc cagtatggac   2040
gattcaaggc ttgcttcata aaccaaggca agtaatagag attggagtct ctaaaaaggt   2100
agttcctact gaatctaagg ccatgcatgg agtctaagat tcaaatcgag gatctaacag   2160
aactcgccgt gaagactggc gaacagttca tacagagtct tttacgactc aatgacaaga   2220
agaaaatctt cgtcaacatg gtggagcacg acactctggt ctactccaaa aatgtcaaag   2280
atacagtctc agaagaccaa agggctattg agacttttca acaaggata atttcgggaa    2340
acctcctcgg attccattgc ccagctatct gtcacttcat cgaaggaca gtagaaaagg    2400
aaggtggctc ctacaaatgc catcattgcg ataaaggaaa ggctatcatt caagatgcct   2460
ctgccgacag tggtcccaaa gatggacccc cacccacgag gagcatcgtg gaaaaagaag   2520
acgttccaac cacgtcttca aagcaagtgg attgatgtga catctccact gacgtaaggg   2580
atgacgcaca atcccactat ccttcgcaag acccttcctc tatataagga agttcatttc   2640
atttggagag gacacgctcg agctcatttc tctattactt cagccataac aaaagaactc   2700
tttttctcttc ttattaaacc atgaaaaagc ctgaactcac cgcgacgtct gtcgagaagt   2760
ttctgatcga aaagttcgac agcgtctccg acctgatgca gctctcggag gcgaagaat   2820
ctcgtgcttt cagcttcgat gtaggagggc gtggatatgt cctgcgggta aatagctgcg   2880
ccgatggttt ctacaaagat cgttatgttt atcggcactt tgcatcggcc gcgctcccga   2940
ttccggaagt gcttgacatt ggggaattca gcgagagcct gacctattgc atctcccgcc   3000
gtgcacaggg tgtcacgttg caagacctgc ctgaaaccga actgcccgct gttctgcagc   3060
cggtcgcgga ggccatggat gcgatcgctg cggccgatct tagccagacg agcgggttcg   3120
gcccattcgg accgcaagga atcggtcaat acactacatg gcgtgatttc atatgcgcga   3180
ttgctgatcc ccatgtgtat cactggcaaa ctgtgatgga cgacaccgtc agtgcgtccg   3240
tcgcgcaggc tctcgatgag ctgatgcttt gggccgagga ctgccccgaa gtccggcacc   3300
```

```
tcgtgcacgc ggatttcggc tccaacaatg tcctgacgga caatggccgc ataacagcgg      3360
tcattgactg gagcgaggcg atgttcgggg attcccaata cgaggtcgcc aacatcttct      3420
tctggaggcc gtggttggct tgtatggagc agcagacgcg ctacttcgag cggaggcatc      3480
cggagcttgc aggatcgccg cggctccggg cgtatatgct ccgcattggt cttgaccaac      3540
tctatcagag cttggttgac ggcaatttcg atgatgcagc ttgggcgcag ggtcgatgcg      3600
acgcaatcgt ccgatccgga gccgggactg tcgggcgtac acaaatcgcc cgcagaagcg      3660
cggccgtctg gaccgatggc tgtgtagaag tactcgccga tagtggaaac cgacgcccca      3720
gcactcgtcc gagggcaaag gaatagtgag gtacctaaag aaggagtgcg tcgaagcaga      3780
tcgttcaaac atttggcaat aaagtttctt aagattgaat cctgttgccg gtcttgcgat      3840
gattatcata taatttctgt tgaattacgt taagcatgta ataattaaca tgtaatgcat      3900
gacgttattt atgagatggg tttttatgat tagagtcccg caattataca tttaatacgc      3960
gatagaaaac aaaatatagc gcgcaaacta ggataaatta tcgcgcgcgg tgtcatctat      4020
gttactagat cgatgtcgaa tcgatcaacc tgcattaatg aatcggccaa cgcgcgggga      4080
gaggcggttt gcgtattggg cgctcttccg cttcctcgct cactgactcg ctgcgctcgg      4140
tcgttcggct gcggcgagcg gtatcagctc actcaaaggc ggtaatacgg ttatccacag      4200
aatcagggga taacgcagga aagaacatgt gagcaaaagg ccagcaaaag gccaggaacc      4260
gtaaaaaggc cgcgttgctg gcgttttttcc ataggctccg ccccccctgac gagcatcaca      4320 aaaatcgacg ctcaagtcag aggtggcgaa acccgacagg actataaaga taccaggcgt      4380
ttccccctgg aagctccctc gtgcgctctc ctgttccgac cctgccgctt accggatacc      4440
tgtccgcctt tctcccttcg ggaagcgtgg cgctttctca atgctcacgc tgtaggtatc      4500
tcagttcggt gtaggtcgtt cgctccaagc tgggctgtgt gcacgaaccc cccgttcagc      4560
ccgaccgctg cgccttatcc ggtaactatc gtcttgagtc aacccggta agacacgact      4620 tatcgccact ggcagcagcc actggtaaca ggattagcag agcgaggtat gtaggcggtg      4680
ctacagagtt cttgaagtgg tggcctaact acggctacac tagaaggaca gtatttggta      4740
tctgcgctct gctgaagcca gttaccttcg gaaaaagagt tggtagctct tgatccggca      4800
aacaaaccac cgctggtagc ggtggttttt ttgtttgcaa gcagcagatt acgcgcagaa      4860
aaaaaggatc tcaagaagat cctttgatct tttctacggg gtctgacgct cagtggaacg      4920
aaaactcacg ttaagggatt ttggtcatga cattaaccta aaaaatagg cgtatcacga      4980 ggccctttcg tctcgcgcgt ttcggtgatg acggtgaaaa cctctgacac atgcagctcc      5040
cggagacggt cacagcttgt ctgtaagcgg atgccgggag cagacaagcc cgtcagggcg      5100
cgtcagcggg tgttggcggg tgtcggggct ggcttaacta tgcggcatca gagcagattg      5160
tactgagagt gcaccatatg gacatattgt cgttagaacg cggctacaat taatacataa      5220
ccttatgtat catacacata cgatttaggt gacactatag aacggcgcgc caagcttgca      5280
tgcctgcagg ctagcctaag tacgtactca aaatgccaac aaataaaaaa aagttgctt      5340 taataatgcc aaaacaaatt aataaaacac ttcaacacc ggattttttt taattaaaat      5400
gtgccattta ggataaatag ttaatatttt taataattat ttaaaagcc gtatctacta      5460 aaatgatttt tatttggttg aaaatattaa tatgtttaaa tcaacacaat ctatcaaaat      5520
taaactaaaa aaaaaataag tgtacgtggt taacattagt acagtaatat aagaggaaaa      5580
tgagaaatta agaaattgaa agcgagtcta attttttaaat tatgaacctg catatataaa      5640
```

```
aggaaagaaa gaatccagga agaaaagaaa tgaaaccatg catggtcccc tcgtcatcac   5700
gagtttctgc catttgcaat agaaacactg aaacaccttt ctctttgtca cttaattgag   5760
atgccgaagc cacctcacac catgaacttc atgaggtgta gcacccaagg cttccatagc   5820
catgcatact gaagaatgtc tcaagctcag caccctactt ctgtgacgtg tccctcattc   5880
accttcctct cttccctata ataaccacg cctcaggttc tccgcttcac aactcaaaca   5940
ttctctccat tggtccttaa acactcatca gtcatcaccg cggccctaga cgcccatcac   6000
aagtttgtac aaaaaagctg aacgagaaac gtaaaatgat ataaatatca atatattaaa   6060
ttagattttg cataaaaaac agactacata atactgtaaa acacaacata tccagtcata   6120
ttggcggccg cattaggcac cccaggcttt acactttatg cttccggctc gtataatgtg   6180
tggattttga gttaggatcc gtcgagattt caggagcta aggaagctaa aatggagaaa   6240
aaaatcactg gatataccac cgttgatata tcccaatggc atcgtaaaga acattttgag   6300
gcatttcagt cagttgctca atgtacctat aaccagaccg ttcagctgga tattacggcc   6360
tttttaaaga ccgtaaagaa aaataagcac aagttttatc cggcctttat tcacattctt   6420
gcccgcctga tgaatgctca tccggaattc cgtatggcaa tgaaagacgg tgagctggtg   6480
atatgggata gtgttcaccc ttgttacacc gttttccatg agcaaactga aacgttttca   6540
tcgctctgga gtgaatacca cgacgatttc cggcagtttc tacacatata ttcgcaagat   6600
gtggcgtgtt acggtgaaaa cctggcctat ttccctaaag ggtttattga atatgttt   6660
ttcgtctcag ccaatccctg ggtgagtttc accagttttg atttaaacgt ggccaatatg   6720
gacaacttct tcgcccccgt tttcaccatg gcaaatatt atacgcaagg cgacaaggtg   6780
ctgatgccgc tggcgattca ggttcatcat gccgtttgtg atggcttcca tgtcggcaga   6840
atgcttaatg aattacaaca gtactgcgat gagtggcagg gcggggcgta aacgcgtgga   6900
tccggcttac taaaagccag ataacagtat gcgtatttgc gcgctgattt ttgcggtata   6960
agaatatata ctgatatgta tacccgaagt atgtcaaaaa gaggtatgct atgaagcagc   7020
gtattacagt gacagttgac agcgacagct atcagttgct caaggcatat atgatgtcaa   7080
tatctccggt ctggtaagca caaccatgca gaatgaagcc cgtcgtctgc gtgccgaacg   7140
ctggaaagcg gaaaatcagg aagggatggc tgaggtcgcc cggtttattg aaatgaacgg   7200
ctcttttgct gacgagaaca ggggctggtg aaatgcagtt taaggtttac acctataaaa   7260
gagagagccg ttatcgtctg tttgtggatg tacagagtga tattattgac acgcccgggc   7320
gacggatggt gatcccctg gccagtgcac gtctgctgtc agataaagtc tcccgtgaac   7380
tttacccggt ggtgcatatc ggggatgaaa gctggcgcat gatgaccacc gatatggcca   7440
gtgtgccggt ctccgttatc ggggaagaag tggctgatct cagccaccgc gaaaatgaca   7500
tcaaaaacgc cattaacctg atgttctggg aatataaat gtcaggctcc cttatacaca   7560
gccagtctgc aggtcgacca tagtgactgg atatgttgtg ttttacagca ttatgtagtc   7620
tgttttttat gcaaaatcta atttaatata ttgatattta tatcatttta cgtttctcgt   7680
tcagctttct tgtacaaagt ggtgatgata accaagttta acgtgagttt atatattcac   7740
agttccattt acagatctta tgctgattgc agcatataac atagtcgcaa cttaacttta   7800
tccctgctta cgtaaagaaa catacatatt gtttgtggct tcgtagtgga acatatgcaa   7860
ttatgtaatc tttatattat gagcctttac ttacaaagat tacttgagat ttatgtacgt   7920
gtgctatttt cactttcaa acatgaattt cctacgttta caatcattta atgtaaaagg   7980
gatgatataa tgtatttacg tacatgtgaa caaccaagca tgttattttt tcctttttg    8040
```

```
ttgcaactta caatcaagta atgattatgg ttatgattat gatattggtg tgtgtctttt    8100
gccttatata tatatttatc cctttcgttt aactttgcaa tataattatt actgatcact    8160
atattttggt ttgaaatggc gcaggttgta atgatcgatc atcaccactt tgtacaagaa    8220
agctgaacga gaaacgtaaa atgatataaa tatcaatata ttaaattaga ttttgcataa    8280
aaaacagact acataatgct gtaaaacaca acatatccag tcactatggt cgacctgcag    8340
actggctgtg tataagggag cctgacattt atattcccca gaacatcagg ttaatggcgt    8400
ttttgatgtc attttcgcgg tggctgagat cagccacttc ttccccgata acggagaccg    8460
gcacactggc catatcggtg gtcatcatgc gccagctttc atccccgata tgcaccaccg    8520
ggtaaagttc acgggagact ttatctgaca gcagacgtgc actggccagg gggatcacca    8580
tccgtcgccc gggcgtgtca ataatatcac tctgtacatc cacaaacaga cgataacggc    8640
tctctctttt ataggtgtaa accttaaact gcatttcacc agcccctgtt ctcgtcagca    8700
aaagagccgt tcatttcaat aaaccgggcg acctcagcca tcccttcctg attttccgct    8760
ttccagcgtt cggcacgcag acgacgggct tcattctgca tggttgtgct taccagaccg    8820
gagatattga catcatatat gccttgagca actgatagct gtcgctgtca actgtcactg    8880
taatacgctg cttcatagca tacctctttt tgacatactt cgggtataca tatcagtata    8940
tattcttata ccgcaaaaat cagcgcgcaa atacgcatac tgttatctgg cttttagtaa    9000
gccggatcct aactcaaaat ccacacatta tacgagccgg aagcataaag tgtaaagcct    9060
ggggtgccta atgcggccgc caatatgact ggatatgttg tgttttacag tattatgtag    9120
tctgtttttt atgcaaaatc taatttaata tattgatatt tatatcattt tacgtttctc    9180
gttcagcttt tttgtacaaa cttgtgatgg gcgtctagcg aactagagga tccccgggta    9240
ccgag                                                                9245

<210> SEQ ID NO 24
<211> LENGTH: 15500
<212> TYPE: DNA
<213> ORGANISM: artificial sequence
<220> FEATURE:
<223> OTHER INFORMATION: vector

<400> SEQUENCE: 24
ccgcggccgc ccccttcacc atggttgttg tgtctcttct tcctcgaatc tcgatcgtta      60
catcaccggg ttctagcctt cacgatgtgc ttttgagcat gagatttggt ttgacgcgac     120
atctccctct caaacgatct ttctccaatt attcaatcac ttccgtatct ccagaacaac     180
agctcaaatc tccggtgacc atggcgacga ccgagagcaa gaatcttgta gaagcttcca     240
aggaggagac aaacaagaag gagacagaag ataagaagga ggtgggagtt tcggttcctc     300
caccgccaga gaaaccagag cctggcgatt gttgcggtag cggttgcgtc cgatgcgttt     360 gggatgtttta ttacgatgag ctcgaagatt acaacaagca gctttctgga gaaactaaat     420
caatttgaaa gggtgggcgc gccgacccag ctttcttgta caaagtggtg tgagtttata     480
tattcacagt tccatttaca gatcttatgc tgattgcagc atataacata gtcgcaactt     540
aactttatcc ctgcttacgt aaagaaacat acatattgtt tgtggcttcg tagtggaaca     600
tatgcaatta tgtaatcttt atattatgag cctttactta caaagattac ttgagattta     660
tgtacgtgtg ctatttcac ttttcaaaca tgaattcct acgttacaa tcatttaatg     720 taaaagggat gatataatgt atttacgtac atgtgaacaa ccaagcatgt tattttttcc     780
```

```
ttttttgttg caacttacaa tcaagtaatg attatggtta tgattatgat attggtgtgt   840
gtcttttgcc ttatatatat atttatccct ttcgtttaac tttgcaatat aattattact   900
gatcactata ttttggtttg aaatggcgca gaccactttg tacaagaaag ctgggtcggc   960
gcgcccaccc tttcaaattg atttagtttc tccagaaagc tgcttgttgt aatcttcgag  1020
ctcatcgtaa taaacatccc aaacgcatcg gacgcaaccg ctaccgcaac aatcgccagg  1080
ctctggtttc tctggcggtg gaggaaccga aactcccacc tccttcttat cttctgtctc  1140
cttcttgttt gtctcctcct tggaagcttc tacaagattc ttgctctcgg tcgtcgccat  1200
ggtcaccgga gatttgagct gttgttctgg agatacggaa gtgattgaat aattggagaa  1260
agatcgtttg agagggagat gtcgcgtcaa accaaatctc atgctcaaaa gcacatcgtg  1320
aaggctagaa cccggtgatg taacgatcga gattcgagga agaagagaca caacaaccat  1380
ggtgaagggg gcggccgcgg agcctgcttt tttgtacaaa cttgtgatgg gcgtctagcg  1440
aactagagga tccccgggta ccgaggtacg tctagaggat ccgtcgacgg cgcgccagat  1500
cctctagagt cgacctgcag gcatgcaagc ttggcgtaat catggtcata gctgtttcct  1560
gtgtgaaatt gttatccgct cacaattcca cacaacatac gagccggaag cataaagtgt  1620
aaagcctggg gtgcctaatg agtgagctaa ctcacattaa ttgcgttgcg ctcactgccc  1680
gctttccagt cgggaaacct gtcgtgccag ctgcattaat gaatcggcca acgcgcgggg  1740
agaggcggtt tgcgtattgg atcgatccct gaaagcgacg ttggatgtta acatctacaa  1800
attgcctttt cttatcgacc atgtacgtaa gcgcttacgt ttttggtgga cccttgagga  1860
aactggtagc tgttgtgggc ctgtggtctc aagatggatc attaatttcc accttcacct  1920
acgatggggg gcatcgcacc ggtgagtaat attgtacggc taagagcgaa tttggcctgt  1980
agacctcaat tgcgagcttt ctaatttcaa actattcggg cctaacttt ggtgtgatga  2040
tgctgactgg caggatatat accgttgtaa tttgagctcg tgtgaataag tcgctgtgta  2100
tgtttgtttg attgtttctg ttggagtgca gcccatttca ccggacaagt cggctagatt  2160
gatttagccc tgatgaactg ccgaggggaa gccatcttga gcgcggaatg ggaatggatt  2220
tcgttgtaca acgagacgac agaacaccca cgggaccgag cttcgcgagc ttttgtatcc  2280
gtggcatcct tggtccgggc gatttgttca cgtccatgag gcgctctcca aaggaacgca  2340
tattttccgg tgcaaccttt ccggttcttc ctctactcga cctcttgaag tcccagcatg  2400
aatgttcgac cgctccgcaa gcggatcttt ggcgcaacca gccggtttcg cacgtcgatt  2460
ctcgcgagcc tgcatacttt ggcaagattg ctgaatgacg ctgatgcttc atcgcaatct  2520
gcgataatgg ggtaagtatc cggtgaaggc cgcaggtcag gccgcctgag cactcagtgt  2580
cttggatgtc cagttccacg gcagctgttg ctcaagcctg ctgatcggag cgtccgcaag  2640
gtcggcgcgg acgtcggcaa gccaggcctg cggatcgatg ttattgagct ggcgctcat   2700
gatcagtgtc gccatgaacg ccgcacgttc agcacaacga tccgatccgg caaacagcca  2760
tgacttcctg ccgagtacat agcctctgag cgttcgttcg gcagcattgt tcgtcaggca  2820
aatcgggccg tcatcgagga atgacgtaat gccatccat cgcttgagca tgtaatttat   2880
cgcctcggcg acgggagaac tgcgcgacaa tttcccccgc tcggtttcga gccaatcatg  2940
cagctcttcg gcgagtgacc ttgatcaggc caccgccacg accgcggaag acgaacagat  3000
gcctgcgcat cggatcgcgc ttcagcgtct cttgcaccat cagcgacaaa ccgggaaagc  3060
ctttgcgcat gtccgtactt atgtcgcgcac ttggagggc ttcgtctacg tggccttcgt  3120
gatcgacgtc ttcgcccgtc gcattgtcgg atggcgggcg agccggacag cacatgcagg  3180
```

```
ctttgtcctc gatgccctcg aggaggctca tcatgatcgg cgtcccgctc atggcggcct   3240
agtgcatcac tcggatcgcg gtgttcaata cgtgtccttt cgctattccg agcggttggc   3300
agaagcaggt atcgagccat ctatcggaag cgtcggcgac agcacgacaa cgccctcgca   3360
gaagcgatca acggtcttta caaggccgag gtcattcatc ggcgtggacc atggaggagc   3420
ttcgaagcgg tcgagttcgc taccttggaa tggatagact ggttcaacca cggcggcttt   3480
tgaagcccat cggcaatata ccgccagccg aagacgagga tcagtattac gccatgctgg   3540
acgaagcagc catggctgcg cattttaacg aaatggcctc cggcaaaccc ggtgcggttc   3600
acttgttgcg tgggaaagtt cacgggactc cgcgcacgag ccttcttcgt aatagccata   3660
tcgaccgaat tgacctgcag gggggggggg gaaagccacg ttgtgtctca aaatctctga   3720
tgttacattg cacaagataa aaatatatca tcatgaacaa taaaactgtc tgcttacata   3780
aacagtaata caaggggtgt tatgagccat attcaacggg aaacgtcttg ctcgaggccg   3840
cgattaaatt ccaacatgga tgctgattta tgggtata aatgggctcg cgataatgtc   3900
gggcaatcag gtgcgacaat ctatcgattg tatgggaagc ccgatgcgcc agagttgttt   3960
ctgaaacatg gcaaaggtag cgttgccaat gatgttacag atgagatggt cagactaaac   4020
tggctgacgg aatttatgcc tcttccgacc atcaagcatt ttatccgtac tcctgatgat   4080
gcatggttac tcaccactgc gatccccggg aaaacagcat tccaggtatt agaagaatat   4140
cctgattcag gtgaaaatat tgttgatgcg ctggcagtgt tcctgcgccg gttgcattcg   4200
attcctgttt gtaattgtcc ttttaacagc gatcgcgtat ttcgtctcgc tcaggcgcaa   4260
tcacgaatga ataacggttt ggttgatgcg agtgattttg atgacgagcg taatggctgg   4320
cctgttgaac aagtctggaa agaaatgcat aagcttttgc cattctcacc ggattcagtc   4380
gtcactcatg gtgatttctc acttgataac cttatttttg acgaggggaa attaataggt   4440
tgtattgatg ttggacgagt cggaatcgca gaccgatacc aggatcttgc catcctatgg   4500
aactgcctcg gtgagttttc tccttcatta cagaaacggc ttttttcaaaa atatggtatt   4560
gataatcctg atatgaataa attgcagttt catttgatgc tcgatgagtt tttctaatca   4620
gaattggtta attggttgta acactggcag agcattacgc tgacttgacg ggacggcggc   4680
tttgttgaat aaatcgaact tttgctgagt tgaaggatca gatcacgcat cttcccgaca   4740
acgcagaccg ttccgtggca aagcaaaagt tcaaaatcac caactggtcc acctacaaca   4800
aagctctcat caaccgtggc tccctcactt tctggctgga tgatggggcg attcaggcct   4860
ggtatgagtc agcaacacct tcttcacgag gcagacctca gcgccccccc ccccctgcag   4920
gtcttttcca atgatgagca cttttaaagt tctgctatgt ggcgcggtat tatcccgtgt   4980
tgacgccggg caagagcaac tcggtcgccg catacactat tctcagaatg acttggttga   5040
gtactcacca gtcacagaaa agcatcttac ggatggcatg acagtaagag aattatgcag   5100
tgctgccata accatgagtg ataacactgc ggccaactta cttctgacaa cgatcggagg   5160
accgaaggag ctaaccgctt ttttgcacaa catgggggat catgtaactc gccttgatcg   5220
ttgggaaccg gagctgaatg aagccatacc aaacgacgag cgtgacacca cgatgcctgt   5280
agcaatggca acaacgttgc gcaaactatt aactggcgaa ctacttactc tagcttcccg   5340
gcaacaatta atagactgga tggaggcgga taaagttgca ggaccacttc tgcgctcggc   5400
ccttccggct ggctggttta ttgctgataa atctggagcc ggtgagcgtg gtctcgcgcg   5460
tatcattgca gcactggggc cagatggtaa gccctcccgt atcgtagtta tctacacgac   5520
```

```
ggggagtcag gcaactatgg atgaacgaaa tagacagatc gctgagatag gtgcctcact    5580
gattaagcat tggtaactgt cagaccaagt ttactcatat atactttaga ttgatttaaa    5640
acttcatttt taatttaaaa ggatctaggt gaagatcctt tttgataatc tcatgaccaa    5700
aatcccttaa cgtgagtttt cgttccactg agcgtcagac cccgtagaaa agatcaaagg    5760
atcttcttga tccttttttt tctgcgcgt aatctgctgc ttgcaaacaa aaaaaccacc    5820
gctaccagcg gtggtttgtt tgccggatca agagctacca actcttttc cgaaggtaac    5880
tggcttcagc agagcgcaga taccaaatac tgtccttcta gtgtagccgt agttaggcca    5940
ccacttcaag aactctgtag caccgcctac atacctcgct ctgctaatcc tgttaccagt    6000
ggctgctgcc agtggcgata gtcgtgtct taccgggttg gactcaagac gatagttacc    6060
ggataaggcg cagcggtcgg gctgaacggg gggttcgtgc acacagccca gcttggagcg    6120
aacgacctac accgaactga gatacctaca gcgtgagcta tgagaaagcg ccacgcttcc    6180
cgaagggaga aaggcggaca ggtatccggt aagcggcagg gtcggaacag gagagcgcac    6240
gagggagctt ccagggggaa acgcctggta tctttatagt cctgtcgggt ttcgccacct    6300
ctgacttgag cgtcgatttt tgtgatgctc gtcagggggg cggagcctat ggaaaaacgc    6360
cagcaacgcg gcctttttac ggttcctggc cttttgctgg ccttttgctc acatgttctt    6420
tcctgcgtta tcccctgatt ctgtggataa ccgtattacc gcctttgagt gagctgatac    6480
cgctcgccgc agccgaacga ccgagcgcag cgagtcagtg agcgaggaag cggaagagcg    6540
cctgatgcgg tattttctcc ttacgcatct gtgcggtatt tcacaccgca tatggtgcac    6600
tctcagtaca atctgctctg atgccgcata gttaagccag tatacactcc gctatcgcta    6660
cgtgactggg tcatggctgc gccccgacac ccgccaacac ccgctgacgc gccctgacgg    6720
gcttgtctgc tcccggcatc cgcttacaga caagctgtga ccgtctccgg agctgcatg    6780
tgtcagaggt tttcaccgtc atcaccgaaa cgcgcgaggc agggtgcctt gatgtgggcg    6840
ccggcggtcg agtggcgacg gcgcggcttg tccgcgccct ggtagattgc ctggccgtag    6900
gccagccatt tttgagcggc cagcggccgc gataggccga cgcgaagcgg cggggcgtag    6960
ggagcgcagc gaccgaaggg taggcgcttt ttgcagctct tcggctgtgc gctggccaga    7020
cagttatgca caggccaggc gggttttaag agttttaata agttttaaag agtttaggc    7080
ggaaaaatcg cctttttctc ttttatatc agtcacttac atgtgtgacc ggttcccaat    7140
gtacggcttt gggttcccaa tgtacgggtt ccggttccca atgtacggct ttgggttccc    7200
aatgtacgtg ctatccacag gaaagagacc ttttcgacct ttttcccctg ctagggcaat    7260
ttgccctagc atctgctccg tacattagga accggcggat gcttcgccct cgatcaggtt    7320
gcggtagcgc atgactagga tcgggccagc ctgccccgcc tcctccttca aatcgtactc    7380
cggcaggtca tttgacccga tcagcttgcg cacggtgaaa cagaacttct tgaactctcc    7440
ggcgctgcca ctgcgttcgt agatcgtctt gaacaaccat ctggcttctg ccttgcctgc    7500
ggcgcggcgt gccaggcggt agagaaaacg gccgatgccg ggatcgatca aaagtaatc    7560
ggggtgaacc gtcagcacgt ccgggttctt gccttctgtg atctcgcggt acatccaatc    7620
agctagctcg atctcgatgt actccggccg cccggtttcg ctctttacga tcttgtagcg    7680
gctaatcaag gcttcacccc tcggataccgt caccaggcgg ccgttcttgg ccttcttcgt    7740
acgctgcatg gcaacgtgcg tggtgtttaa ccgaatgcag gtttctacca ggtcgtcttt    7800
ctgctttccg ccatcggctc gccggcagaa cttgagtacg tccgcaacgt gtggacggaa    7860
cacgcggccg gcttgtctc ccttcccttc ccggtatcgg ttcatggatt cggttagatg    7920
```

```
ggaaaccgcc atcagtacca ggtcgtaatc ccacacactg gccatgccgg ccggccctgc    7980
ggaaacctct acgtgcccgt ctggaagctc gtagcggatc acctcgccag ctcgtcggtc    8040
acgcttcgac agacggaaaa cggccacgtc catgatgctg cgactatcgc gggtgcccac    8100
gtcatagagc atcggaacga aaaaatctgg ttgctcgtcg cccttgggcg gcttcctaat    8160
cgacggcgca ccggctgccg gcggttgccg ggattctttg cggattcgat cagcggccgc    8220
ttgccacgat tcaccggggc gtgcttctgc ctcgatgcgt tgccgctggg cggcctgcgc    8280
ggccttcaac ttctccacca ggtcatcacc cagcgccgcg ccgatttgta ccgggccgga    8340
tggtttgcga ccgctcacgc cgattcctcg ggcttggggg ttccagtgcc attgcagggc    8400
cggcagacaa cccagccgct tacgcctggc caaccgcccg ttcctccaca catggggcat    8460
tccacggcgt cggtgcctgg ttgttcttga ttttccatgc cgcctccttt agccgctaaa    8520
attcatctac tcatttattc atttgctcat ttactctggt agctgcgcga tgtattcaga    8580
tagcagctcg gtaatggtct tgccttggcg taccgcgtac atcttcagct tggtgtgatc    8640
ctccgccggc aactgaaagt tgacccgctt catggctggc gtgtctgcca ggctggccaa    8700
cgttgcagcc ttgctgctgc gtgcgctcgg acggccggca cttagcgtgt ttgtgctttt    8760
gctcattttc tctttacctc attaactcaa atgagttttg atttaatttc agcggccagc    8820
gcctggacct cgcgggcagc gtcgccctcg ggttctgatt caagaacggt tgtgccggcg    8880
gcggcagtgc ctgggtagct cacgcgctgc gtgatacggg actcaagaat gggcagctcg    8940
tacccggcca gcgcctcggc aacctcaccg ccgatgcgcg tgcctttgat cgcccgcgac    9000
acgacaaagg ccgcttgtag ccttccatcc gtgacctcaa tgcgctgctt aaccagctcc    9060
accaggtcgg cggtggccca tatgtcgtaa gggcttggct gcaccggaat cagcacgaag    9120
tcggctgcct tgatcgcgga cacagccaag tccgccgcct ggggcgctcc gtcgatcact    9180
acgaagtcgc gccggccgat ggccttcacg tcgcggtcaa tcgtcgggcg gtcgatgccg    9240
acaacggtta gcggttgatc ttcccgcacg gccgcccaat cgcgggcact gccctgggga    9300
tcggaatcga ctaacagaac atcggccccg gcgagttgca gggcgcgggc tagatgggtt    9360
gcgatggtcg tcttgcctga cccgcctttc tggttaagta cagcgataac ttcatgcgtt    9420
cccttgcgta tttgtttatt tactcatcgc atcatatacg cagcgaccgc atgacgcaag    9480
ctgttttact caaatacaca tcaccttttt agacggcggc gctcggtttc ttcagcggcc    9540
aagctggccg gccaggccgc cagcttggca tcagacaaac cggccaggat tcatgcagc    9600 cgcacggttg agacgtgcgc gggcggctcg aacacgtacc cggccgcgat catctccgcc    9660
tcgatctctt cggtaatgaa aaacggttcg tcctggccgt cctggtgcgg tttcatgctt    9720
gttcctcttg gcgttcattc tcggcggccg ccagggcgtc ggcctcggtc aatgcgtcct    9780
cacggaaggc accgcgccgc ctggcctcgg tgggcgtcac ttcctcgctg cgctcaagtg    9840
cgcggtacag ggtcgagcga tgcacgccaa gcagtgcagc cgcctctttc acggtgcggc    9900
cttcctggtc gatcagctcg cgggcgtgcg cgatctgtgc cggggtgagg gtagggcggg    9960
ggccaaactt cacgcctcgg gccttggcgg cctcgcgccc gctccgggtg cggtcgatga   10020
ttagggaacg ctcgaactcg gcaatgccgg cgaacacggt caacaccatg cggccggccg   10080
gcgtggtggt gtcggcccac ggctctgcca ggctacgcag gcccgcgccg gcctcctgga   10140
tgcgctcgga aatgtccagt aggtcgcggg tgctgcgggc caggcggtct agcctggtca   10200
ctgtcacaac gtcgccaggg cgtaggtggt caagcatcct ggccagctcc gggcggtcgc   10260
```

```
gcctggtgcc ggtgatcttc tcggaaaaca gcttggtgca gccggccgcg tgcagttcgg    10320
cccgttggtt ggtcaagtcc tggtcgtcgg tgctgacgcg ggcatagccc agcaggccag    10380
cggcggcgct cttgttcatg gcgtaatgtc tccggttcta gtcgcaagta ttctacttta    10440
tgcgactaaa acacgcgaca agaaaacgcc aggaaaaggg cagggcggca gcctgtcgcg    10500
taacttagga cttgtgcgac atgtcgtttt cagaagacgg ctgcactgaa cgtcagaagc    10560
cgactgcact atagcagcgg aggggttgga ccacaggacg ggtgtggtcg ccatgatcgc    10620
gtagtcgata gtggctccaa gtagcgaagc gagcaggact gggcggcggc caaagcggtc    10680
ggacagtgct ccgagaacgg gtgcgcatag aaattgcatc aacgcatata gcgctagcag    10740
cacgccatag tgactggcga tgctgtcgga atggacgata tcccgcaaga ggcccggcag    10800
taccggcata accaagccta tgcctacagc atccagggtg acggtgccga ggatgacgat    10860
gagcgcattg ttagatttca tacacggtgc ctgactgcgt tagcaattta actgtgataa    10920
actaccgcat taaagctagc ttgcttggtc gttccgcgtg aacgtcggct cgattgtacc    10980
tgcgttcaaa tactttgcga tcgtgttgcg cgcctgcccg gtgcgtcggc tgatctcacg    11040
gatcgactgc ttctctcgca acgccatccg acggatgatg tttaaaagtc ccatgtggat    11100
cactccgttg ccccgtcgct caccgtgttg ggggaaggt gcacatggct cagttctcaa    11160
tggaaattat ctgcctaacc ggctcagttc tgcgtagaaa ccaacatgca agctccaccg    11220
ggtgcaaagc ggcagcggcg gcaggatata ttcaattgta aatggcttca tgtccgggaa    11280
atctacatgg atcagcaatg agtatgatgg tcaatatgga gaaaagaaa gagtaattac    11340
caattttttt tcaattcaaa aatgtagatg tccgcagcgt tattataaaa tgaaagtaca    11400
ttttgataaa acgacaaatt acgatccgtc gtatttatag gcgaaagcaa taaacaaatt    11460
attctaattc ggaaatcttt atttcgacgt gtctacattc acgtccaaat gggggcttag    11520
atgagaaact tcacgatcga tgccttgatt tcgccattcc cagatacccca tttcatcttc    11580
agattggtct gagattatgc gaaaatatac actcatatac ataaatactg acagtttgag    11640
ctaccaattc agtgtagccc attacctcac ataattcact caaatgctag gcagtctgtc    11700
aactcggcgt caatttgtcg gccactatac gatagttgcg caaattttca aagtcctggc    11760
ctaacatcac acctctgtcg gcggcgggtc ccatttgtga taaatccacc atatcgaatt    11820
aattcagact cctttgcccc agagatcaca atggacgact tcctctatct ctacgatcta    11880
gtcaggaagt tcgacggaga aggtgacgat accatgttca ccactgataa tgagaagatt    11940
agccttttca atttcagaaa gaatgctaac ccacagatgg ttagagaggc ttacgcagca    12000
ggtctcatca agacgatcta cccgagcaat aatctccagg agatcaaata ccttcccaag    12060
aaggttaaag atgcagtcaa aagattcagg actaactgca tcaagaacac agagaaagat    12120
atatttctca agatcagaag tactattcca gtatggacga ttcaaggctt gcttcacaaa    12180
ccaaggcaag taatagagat tggagtctct aaaaaggtag ttcccactga atcaaaggcc    12240
atggagtcaa agattcaaat agaggaccta acagaactcg ccgtaaagac tggcgaacag    12300
ttcatacaga gtctcttacg actcaatgac aagaagaaaa tcttcgtcaa catggtggag    12360
cacgacacgc ttgtctactc caaaaatatc aaagatacag tctcagaaga ccaaagggca    12420
attgagactt tcaacaaag ggtaatatcc ggaaacctcc tcggattcca ttgcccagct    12480
atctgtcact ttattgtgaa gatagtggaa aaggaaggtg gctcctacaa atgccatcat    12540
tgcgataaag gaaaggccat cgttgaagat gcctctgccg acagtggtcc caaagatgga    12600
cccccaccca cgaggagcat cgtggaaaaa gaagacgttc caaccacgtc ttcaaagcaa    12660
```

```
gtggattgat gtgatatctc cactgacgta agggatgacg cacaatccca ctatccttcg   12720
caagacccct cctctatata aggaagttca tttcatttgg agaggacacg ctgaaatcac   12780
cagtctccaa gcttgcgggg atcgtttcgc atgattgaac aagatggatt gcacgcaggt   12840
tctccggccg cttgggtgga gaggctattc ggctatgact gggcacaaca gacaatcggc   12900
tgctctgatg ccgccgtgtt ccggctgtca gcgcaggggc gcccggttct ttttgtcaag   12960
accgacctgt ccggtgccct gaatgaactg caggacgagg cagcgcggct atcgtggctg   13020
gccacgacgg gcgttccttg cgcagctgtg ctcgacgttg tcactgaagc gggaagggac   13080
tggctgctat tgggcgaagt gccggggcag gatctcctgt catctcacct tgctcctgcc   13140
gagaaagtat ccatcatggc tgatgcaatg cggcggctgc atacgcttga tccggctacc   13200
tgcccattcg accaccaagc gaaacatcgc atcgagcgag cacgtactcg gatgaagcc    13260 ggtcttgtcg atcaggatga tctggacgaa gagcatcagg gctcgcgcc agccgaactg    13320 ttcgccaggc tcaaggcgcg catgcccgac ggcgaggatc tcgtcgtgac ccatggcgat   13380
gcctgcttgc cgaatatcat ggtggaaaat ggccgctttt ctggattcat cgactgtggc   13440
cggctgggtg tggcggaccg ctatcaggac atagcgttgg ctacccgtga tattgctgaa   13500
gagcttggcg gcgaatgggc tgaccgcttc ctcgtgcttt acggtatcgc cgctcccgat   13560
tcgcagcgca tcgccttcta tcgccttctt gacgagttct tctgagcggg actctggggt   13620
tcgaaatgac cgaccaagcg acgcccaacc tgccatcacg agatttcgat tccaccgccg   13680
ccttctatga aaggttgggc ttcggaatcg ttttccggga cgccggctgg atgatcctcc   13740
agcgcgggga tctcatgctg gagttcttcg cccaccccgg atcgatccaa cacttacgtt   13800
tgcaacgtcc aagagcaaat agaccacgaa cgccggaagg ttgccgcagc gtgtggattg   13860
cgtctcaatt ctctcttgca ggaatgcaat gatgaatatg atactgacta tgaaactttg   13920
agggaatact gcctagcacc gtcacctcat aacgtgcatc atgcatgccc tgacaacatg   13980
gaacatcgct attttctga agaattatgc tcgttggagg atgtcgcggc aattgcagct    14040
attgccaaca tcgaactacc cctcacgcat gcattcatca atattattca tgcggggaaa   14100
ggcaagatta atccaactgg caaatcatcc agcgtgattg gtaacttcag ttccagcgac   14160
ttgattcgtt ttggtgctac ccacgttttc aataaggacg agatggtgga gtaaagaagg   14220
agtgcgtcga agcagatcgt tcaaacattt ggcaataaag tttcttaaga ttgaatcctg   14280
ttgccggtct tgcgatgatt atcatataat ttctgttgaa ttacgttaag catgtaataa   14340
ttaacatgta atgcatgacg ttatttatga gatgggtttt tatgattaga gtcccgcaat   14400
tatacattta atacgcgata gaaaacaaaa tatagcgcgc aaactaggat aaattatcgc   14460
gcgcggtgtc atctatgtta ctagatcgat caaacttcgg tactgtgtaa tgacgatgag   14520
caatcgagag gctgactaac aaaaggtaca tcgcgatgga tcgatccatt cgccattcag   14580
gctgcgcaac tgttgggaag ggcgatcggt gcgggcctct tcgctattac gccagctggc   14640
gaaaggggga tgtgctgcaa ggcgattaag ttgggtaacg ccagggtttt cccagtcacg   14700
acgttgtaaa acgacggcca gtgaattcct gcagcccggg ggatccgccc actcgaggcg   14760
cgccaagctt gcatgcctgc aggctagcct aagtacgtac tcaaaatgcc aacaaataaa   14820 aaaaagttg ctttaataat gccaaaacaa attaataaaa cacttacaac accggatttt    14880
ttttaattaa aatgtgccat ttaggataaa tagttaatat tttaataat tatttaaaaa    14940 gccgtatcta ctaaaatgat ttttatttgg ttgaaaatat taatatgttt aaatcaacac   15000
```

```
aatctatcaa aattaaacta aaaaaaaaat aagtgtacgt ggttaacatt agtacagtaa    15060
tataagagga aaatgagaaa ttaagaaatt gaaagcgagt ctaattttta aattatgaac    15120
ctgcatatat aaaaggaaag aaagaatcca ggaagaaaag aaatgaaacc atgcatggtc    15180
ccctcgtcat cacgagtttc tgccatttgc aatagaaaca ctgaaacacc tttctctttg    15240
tcacttaatt gagatgccga agccacctca caccatgaac ttcatgaggt gtagcaccca    15300
aggcttccat agccatgcat actgaagaat gtctcaagct cagcaccta cttctgtgac     15360 gtgtccctca ttcaccttcc tctcttccct ataaataacc acgcctcagg ttctccgctt    15420
cacaactcaa acattctctc cattggtcct taaacactca tcagtcatca ccgcacaagt    15480
ttgtacaaaa aagcaggcta                                                15500

<210> SEQ ID NO 25
<211> LENGTH: 585
<212> TYPE: DNA
<213> ORGANISM: Brassica napus

<400> SEQUENCE: 25
gatattcgta tggttttgtt gcatgtccat caccacggtc ttcatctcca tcccagaatc      60
tcgatcgcca catcgcccga ttacaatcgc ctccggaaaa gccttaacga tgtgcttttg     120
agcatgagat ttggactaac gcgagatctc cctctgaaac gatcatcatt cgcctattat     180
tccggatctc gagaacaaca gcccatcacc atggcgacca agggcgacaa gacttcgacg     240
gaggtgaaag aaaaggtagt ggaggagaag aaggataatg ataagaagga ggaggtatcg     300
ctcccaccgc cgccggagaa accagaggct ggcgattgtt gcggtagcgg ttgcgtccga     360
tgcgtttggg atgtgtatta cgatgaactc gaagaataca acaagcttac tgctttcgct     420
cctggagata ctaaatccaa ttgattgaat tgctttgttc tctattgttg ttagattcgc     480
tcctggagat actaaatcca attgattgaa ttgctttgtt ctctattgtt gttagaaaaa     540
gttaaacaat cgctttgttc gaataaaaag tactgatcga ccata                    585

<210> SEQ ID NO 26
<211> LENGTH: 144
<212> TYPE: PRT
<213> ORGANISM: Brassica napus

<400> SEQUENCE: 26

Met Val Leu Leu His Val His His Gly Leu His Leu His Pro Arg
1               5                   10                  15

Ile Ser Ile Ala Thr Ser Pro Asp Tyr Asn Arg Leu Arg Lys Ser Leu
            20                  25                  30

Asn Asp Val Leu Leu Ser Met Arg Phe Gly Leu Thr Arg Asp Leu Pro
        35                  40                  45

Leu Lys Arg Ser Ser Phe Ala Tyr Tyr Ser Gly Ser Arg Glu Gln Gln
    50                  55                  60

Pro Ile Thr Met Ala Thr Lys Gly Asp Lys Thr Ser Thr Glu Val Lys
65                  70                  75                  80

Glu Lys Val Val Glu Glu Lys Lys Asp Asn Asp Lys Lys Glu Glu Val
                85                  90                  95

Ser Leu Pro Pro Pro Glu Lys Pro Glu Ala Gly Asp Cys Cys Gly
                100                 105                 110

Ser Gly Cys Val Arg Cys Val Trp Asp Val Tyr Tyr Asp Glu Leu Glu
            115                 120                 125

Glu Tyr Asn Lys Leu Thr Ala Phe Ala Pro Gly Asp Thr Lys Ser Asn
```

<210> SEQ ID NO 27
<211> LENGTH: 552
<212> TYPE: DNA
<213> ORGANISM: Brassica napus

<400> SEQUENCE: 27

```
ggattcaaaa aagtcttcga ttttcccgaa gggttttgtt gcatgttcat caccacggtc      60
ttcatctcca tcccagaatc tcgatcgcca catcgcccga ttacaatcgc ctccggaaaa     120
gccttaacga tgtgcttttg agcatgagat ttggactaac gcgagatctc cctctgaaac     180
gatcatcatt cgcctattat tccggatctc gagaacaaca gcccatcacc atggcgacca     240
agggcgacaa gacttcgacg gaggtgaaag aaaaggtagt ggaggagaag aaggataatg     300
ataagaagga ggaggtatcg ctcccaccgc cgccggagaa accagaggct ggcgattgtt     360
gcggtagcgg ttgcgtccga tgcgtttggg atgtgtatta cgatgagctc gaagaataca     420
acaagcttac tgcttccgct cctggagata ctaaatccaa ttgattgaat tgctttgttc     480
tctattgttg ttagaaaaag ttaaacaatc gctttgttcg aataaaaagt actgatcgac     540
cattttaaac ga                                                        552
```

<210> SEQ ID NO 28
<211> LENGTH: 106
<212> TYPE: PRT
<213> ORGANISM: Brassica napus

<400> SEQUENCE: 28

```
Met Arg Phe Gly Leu Thr Arg Asp Leu Pro Leu Lys Arg Ser Ser Phe
1               5                   10                  15

Ala Tyr Tyr Ser Gly Ser Arg Glu Gln Gln Pro Ile Thr Met Ala Thr
            20                  25                  30

Lys Gly Asp Lys Thr Ser Thr Glu Val Lys Glu Lys Val Val Glu Glu
        35                  40                  45

Lys Lys Asp Asn Asp Lys Lys Glu Glu Val Ser Leu Pro Pro Pro Pro
    50                  55                  60

Glu Lys Pro Glu Ala Gly Asp Cys Cys Gly Ser Gly Cys Val Arg Cys
65                  70                  75                  80

Val Trp Asp Val Tyr Tyr Asp Glu Leu Glu Glu Tyr Asn Lys Leu Thr
                85                  90                  95

Ala Ser Ala Pro Gly Asp Thr Lys Ser Asn
            100                 105
```

<210> SEQ ID NO 29
<211> LENGTH: 600
<212> TYPE: DNA
<213> ORGANISM: Brassica napus

<400> SEQUENCE: 29

```
gagcaaaaga agtcttcgat atattcgtat ggttttgttc catcaccacg gtcttcatct      60
ccatcccaga atctcgatca ccacatcgcc cggttacaat cgactccgga aaagccttaa     120
cgatgtgctt ctgagcatga gatttggact aacacgagat ctccgtctga aacgaccatc     180
attcgcatac tattccggat ctcgaggaca acagcccatc accatggcga ccaagggcga     240
caagacttcg acagaggtga agataaggt agtggaggag aagaaggata tggataagga     300
taagaaggaa gaggtatcgc tcccaccgcc gccggagaaa ccagaggctg gcgattgttg     360
```

```
cggtagcggt tgcgtccgat gcgtttggga tgtgtattac gatgagctcg aagaatacaa    420
caagcttact gcttccactc ctggagatac taaatccaat tgattgaatt gggattgctt    480
tgttctgatt gttaccctat tgttgctaga aaaagttaaa caattgcttt gttctataat    540
aaagactggt caagaactga tcgaccaata ttaaacgatt tcaatctttt tttcactgtg    600
```

<210> SEQ ID NO 30
<211> LENGTH: 144
<212> TYPE: PRT
<213> ORGANISM: Brassica napus

<400> SEQUENCE: 30

```
Met Val Leu Phe His His His Gly Leu His Leu His Pro Arg Ile Ser
1               5                   10                  15

Ile Thr Thr Ser Pro Gly Tyr Asn Arg Leu Arg Lys Ser Leu Asn Asp
            20                  25                  30

Val Leu Leu Ser Met Arg Phe Gly Leu Thr Arg Asp Leu Arg Leu Lys
        35                  40                  45

Arg Pro Ser Phe Ala Tyr Tyr Ser Gly Ser Arg Gly Gln Gln Pro Ile
    50                  55                  60

Thr Met Ala Thr Lys Gly Asp Lys Thr Ser Thr Glu Val Lys Asp Lys
65                  70                  75                  80

Val Val Glu Glu Lys Lys Asp Met Asp Lys Asp Lys Lys Glu Glu Val
                85                  90                  95

Ser Leu Pro Pro Pro Glu Lys Pro Glu Ala Gly Asp Cys Cys Gly
            100                 105                 110

Ser Gly Cys Val Arg Cys Val Trp Asp Val Tyr Tyr Asp Glu Leu Glu
        115                 120                 125

Glu Tyr Asn Lys Leu Thr Ala Ser Thr Pro Gly Asp Thr Lys Ser Asn
    130                 135                 140
```

<210> SEQ ID NO 31
<211> LENGTH: 619
<212> TYPE: DNA
<213> ORGANISM: Helianthus annuus

<400> SEQUENCE: 31

```
aagctggagc tccaccgcgg tggcggccgc tctagaacta gtggatcccc cgggctgcag    60
gaattcggca cgagctccga cgccatggca ccgttaaccg tcactcgcct atgagatcac   120
agactctgca ccgactcacc accactttta accgatctca tctcaatcca attcaacctt   180
ctctcagatc tgattcaaat ttcaacctca ccatggctga ttcaggttct aataataaaa   240
tcaagtcaga tgacggttcg agcgccgtta aggacgcaac ggagacgaaa aagctgccgg   300
agatccctcc gccgccggag aaaccgttgc cgggagactg ttgtggcagc ggttgtgttc   360
ggtgcgtttg ggacgtgtat acgacgagc ttgaagagta taataagatt tgtaaaggag   420
gatctgattc tacagctgga tctaaggttt cgtaaacgtt ttgtagaaat gtttgattga   480
ttgattgtta tagatcaatt tgattattga ttgttataga tctatttgat gttcaaataa   540
acgaattagt tcgatatctg tgttgtgagt ttcttgtcat gatgtgtctt tgtttacata   600
taatcgatcg aatatgatt                                                619
```

<210> SEQ ID NO 32
<211> LENGTH: 114
<212> TYPE: PRT
<213> ORGANISM: Helianthus annuus -continued

<400> SEQUENCE: 32

Met Arg Ser Gln Thr Leu His Arg Leu Thr Thr Thr Phe Asn Arg Ser
1               5                   10                  15

His Leu Asn Pro Ile Gln Pro Ser Leu Arg Ser Asp Ser Asn Phe Asn
            20                  25                  30

Leu Thr Met Ala Asp Ser Gly Ser Asn Asn Lys Ile Lys Ser Asp Asp
        35                  40                  45

Gly Ser Ser Ala Val Lys Asp Ala Thr Glu Thr Lys Lys Leu Pro Glu
    50                  55                  60

Ile Pro Pro Pro Glu Lys Pro Leu Pro Gly Asp Cys Cys Gly Ser
65              70                  75                  80

Gly Cys Val Arg Cys Val Trp Asp Val Tyr Tyr Asp Glu Leu Glu Glu
            85                  90                  95

Tyr Asn Lys Ile Cys Lys Gly Gly Ser Asp Ser Thr Ala Gly Ser Lys
            100                 105                 110

Val Ser

<210> SEQ ID NO 33
<211> LENGTH: 219
<212> TYPE: DNA
<213> ORGANISM: Castor canadensis

<400> SEQUENCE: 33
atggccacca acaaaactga acctctagat tcaaaaacac acaatataaa taagaaagaa      60
gaagaaaaga aattgccgcc gccgccgccg ccggagaagc cggagcctgg ggattgttgt     120
ggaagcggat gtgttaggtg cgtatgggat gtgtattatg aagagcttga agaatataat     180
aagctttatc aatcccattc tgattctaag cgcccttga                            219

<210> SEQ ID NO 34
<211> LENGTH: 72
<212> TYPE: PRT
<213> ORGANISM: Castor canadensis

<400> SEQUENCE: 34

Met Ala Thr Asn Lys Thr Glu Pro Leu Asp Ser Lys Thr His Asn Ile
1               5                   10                  15

Asn Lys Lys Glu Glu Glu Lys Lys Leu Pro Pro Pro Pro Pro Pro Glu
            20                  25                  30

Lys Pro Glu Pro Gly Asp Cys Cys Gly Ser Gly Cys Val Arg Cys Val
        35                  40                  45

Trp Asp Val Tyr Tyr Glu Glu Leu Glu Glu Tyr Asn Lys Leu Tyr Gln
    50                  55                  60

Ser His Ser Asp Ser Lys Arg Pro
65              70

<210> SEQ ID NO 35
<211> LENGTH: 771
<212> TYPE: DNA
<213> ORGANISM: Glycine max

<400> SEQUENCE: 35
cggcagggtt acaatcttat cttcgtattg gacttcaatt gatcccaaag aaaaatatag      60
agagagagag aatgtggtgg cggcggcgcc cgagaccatg agaactacag caccttccga     120
tttcattttc acccaaaagc ttcacccttt caacatcacc tccaccaaaa cctccctcca     180
acgaacccta ccctatttc tccaactcaa tcgcatggcc gaggctgcac gaaccgcgca     240

-continued

```
taaacccgcg ccgcacccga tccaacccaa acccgacgat aaaacccga atccggcgaa    300 ggagattccg ccgccgccgg agaagccgga gcccggcgat tgctgcggca gcgggtgcgt    360
ccgatgcgtc tgggatgtgt actacgacga actcgaagaa tacaataagc gatacaaaca    420
ggtcgatccc agcccaaac cttcttcgta atcttcaaca tcgcttggat tagctttatt    480
aatttattta tattacatcc taatttaaa aagctttggg tatttcttga tttcgtgaat    540
tgtccctttt tatcaaaaag gatcgaaatg ttgtatgtgg aattatacat gtagaataaa    600 ctgattttt taaaaaaat gccagggcta aaatgtacga tttatataat cccgaagatt    660
aattcggaga tttacttctc agatcgcata attcccaagt tttttggtaa tagtacgctg    720
tgttttttct ttcatgactt tgtttatgta ttttttataa ccatttgat a              771
```

<210> SEQ ID NO 36
<211> LENGTH: 117
<212> TYPE: PRT
<213> ORGANISM: Glycine max

<400> SEQUENCE: 36

```
Met Arg Thr Thr Ala Pro Ser Asp Phe Ile Phe Thr Gln Lys Leu His
1               5                   10                  15

Pro Phe Asn Ile Thr Ser Thr Lys Thr Ser Leu Gln Arg Thr Leu Pro
            20                  25                  30

Tyr Phe Leu Gln Leu Asn Arg Met Ala Glu Ala Ala Arg Thr Ala His
        35                  40                  45

Lys Pro Ala Pro His Pro Ile Gln Pro Lys Pro Asp Asp Lys Thr Pro
    50                  55                  60

Asn Pro Ala Lys Glu Ile Pro Pro Pro Glu Lys Pro Glu Pro Gly
65                  70                  75                  80

Asp Cys Cys Gly Ser Gly Cys Val Arg Cys Val Trp Asp Val Tyr Tyr
                85                  90                  95

Asp Glu Leu Glu Glu Tyr Asn Lys Arg Tyr Lys Gln Val Asp Pro Ser
            100                 105                 110

Pro Lys Pro Ser Ser
        115
```

<210> SEQ ID NO 37
<211> LENGTH: 664
<212> TYPE: DNA
<213> ORGANISM: Glycine max

<400> SEQUENCE: 37

```
ggacttcaaa ttcaattgat ccgtttccca acccaaagaa agagagagaa tgtggtggtg    60
gcggcggcgg cgtagatctt gagaacatct ccttcttccg atttcatttt cacccaaaag   120
cttctcgctt tcaacatcac cctcaccaaa acccctcttc aacgagccct actcttcttc   180
tttctccatc ccaatcgaat ggccgagggt gcacgaaccg cgcatgcacc cgccccgcac   240
ccgatccaac ccaaacccga cgataaaacc ccgaatccgg tgaaggagac tccgccgccg   300
ccggagaaac cggagcccgg cgattgctgc ggcagcggat gcgtccggga cgtttactac   360
gacgaactcg aagatacaat aagctataca aacaagacga tcccagcccc aaagcttctt   420
catagtcttc atcatcgcat gggtggaagt gttatgggtc gatgattgtt gggttattgt   480
cgtcgtcaat acaccaggta tgttgttact gggtgagtgt gttaagtgat tcgtaaggca   540
aattttaaca tatagatcaa cttgaattat atggatgaag ttgattcgta agttgataat   600
```

```
aaactaacgg atcatgttga tttgtattga ttacagattt tgattttta aaaatttctt    660 aaaa                                                                664
```

<210> SEQ ID NO 38
<211> LENGTH: 88
<212> TYPE: PRT
<213> ORGANISM: Glycine max

<400> SEQUENCE: 38

```
Met Ala Glu Gly Ala Arg Thr Ala His Ala Pro Ala Pro His Pro Ile
1               5                   10                  15

Gln Pro Lys Pro Asp Asp Lys Thr Pro Asn Pro Val Lys Glu Thr Pro
            20                  25                  30

Pro Pro Pro Glu Lys Pro Glu Pro Gly Asp Cys Cys Gly Ser Gly Cys
        35                  40                  45

Val Arg Asp Val Tyr Tyr Asp Glu Leu Glu Asp Thr Ile Ser Tyr Thr
    50                  55                  60

Asn Lys Thr Ile Pro Ala Pro Lys Leu Leu His Ser Leu His His Arg
65                  70                  75                  80

Met Gly Gly Ser Val Met Gly Arg
                85
```

<210> SEQ ID NO 39
<211> LENGTH: 689
<212> TYPE: DNA
<213> ORGANISM: Zea mays

<400> SEQUENCE: 39

```
ggggctgtat gctgggcgcc gtcgtccgtg tcccgggccc gatcctacct ttcctgcccg    60
ggccgacgcg cccctctcct ccgccgccgc cactacctcc cgcccgaaac gcccatggcc   120
tcggccaccc cttgcgatgg cggcaccggg aagcccgacg ccgcgccggc tcccacgccc   180
gcgccaacgc cgctgccgcc cgagaagcct ctcccgggcg actgctgcgg cagcggctgc   240
gttcgctgcg tctgggacat atatttcgac gagctcgacg cgtacgacaa ggccctcgcc   300
gcgcgcgcgg cctcctcagg ctccggcggc aaggacgact ctgctgatac caagcccaaa   360
gaaggcaaga caacaaggtg aaagaaacca agcgtgagg ccaacctgtt gcagttggaa    420
acattgaacc tgtccccggc gacgcattgc cctttccacc gccgcggagc ctcgctcatg   480
ccgtcgtctc taaaactggc cgactctggc cagattcctg caaagcgcgg accaccagga   540
cacctcagtc ttcgaactga atgtcagtc ctaatcccag ttgctactga agaaaagaa    600 agtgaaggga atctcctca ccagtgtcta gcacaccgat aatggaatcc tcaccgaacc    660
tactctctgg gaggattcca gccgaatgc                                     689
```

<210> SEQ ID NO 40
<211> LENGTH: 88
<212> TYPE: PRT
<213> ORGANISM: Zea mays

<400> SEQUENCE: 40

```
Met Ala Ser Ala Thr Pro Cys Asp Gly Gly Thr Gly Lys Pro Asp Ala
1               5                   10                  15

Ala Pro Ala Pro Thr Pro Ala Pro Thr Pro Leu Pro Pro Glu Lys Pro
            20                  25                  30

Leu Pro Gly Asp Cys Cys Gly Ser Gly Cys Val Arg Cys Val Trp Asp
        35                  40                  45
```

```
Ile Tyr Phe Asp Glu Leu Asp Ala Tyr Asp Lys Ala Leu Ala Ala Arg
 50                  55                  60

Ala Ala Ser Ser Gly Ser Gly Gly Lys Asp Asp Ser Ala Asp Thr Lys
 65                  70                  75                  80

Pro Lys Glu Gly Lys Thr Thr Arg
                 85
```

<210> SEQ ID NO 41
<211> LENGTH: 503
<212> TYPE: DNA
<213> ORGANISM: Zea mays

<400> SEQUENCE: 41

```
gaggcgccgt cgtccgtgtc ccgggcccga tcctgccttt cctgcccggg ccgacgcgcc      60
ctttcctccg ccgccgccac tacctcccgg cccgagacgc ccatggcctc ggccacccct     120
tgccgatggcg gcaccgggaa gcccgacgcc gcgccggctc ccacgcccgc gccaacgccg     180
ctgccgcccg agaagcctct cccgggcgac tgctgcggca gggctgcgt ccgctgcgtc      240
tgggacatat atttcgacga gctcgacgcc tacgacaagg ccgtcgccgc ccacgcggcc     300
tcctcaggct ccggcggcaa ggacgactcc gctgatacca gcccaacga aggtgccaag      360
tcctgaagtg cgcctctcat gtgtaatgac ctcttctgct ctgaactgaa tttagattac     420
tggcgttcac atacgccact accaattctt agcactcgaa acattacagt accgttgtgc     480
ctgctgtctt aatatgctta gac                                             503
```

<210> SEQ ID NO 42
<211> LENGTH: 87
<212> TYPE: PRT
<213> ORGANISM: Zea mays

<400> SEQUENCE: 42

```
Met Ala Ser Ala Thr Pro Cys Asp Gly Gly Thr Gly Lys Pro Asp Ala
 1               5                  10                  15

Ala Pro Ala Pro Thr Pro Ala Pro Thr Pro Leu Pro Pro Glu Lys Pro
                 20                  25                  30

Leu Pro Gly Asp Cys Cys Gly Ser Gly Cys Val Arg Cys Val Trp Asp
             35                  40                  45

Ile Tyr Phe Asp Glu Leu Asp Ala Tyr Asp Lys Ala Val Ala Ala His
 50                  55                  60

Ala Ala Ser Ser Gly Ser Gly Gly Lys Asp Asp Ser Ala Asp Thr Lys
 65                  70                  75                  80

Pro Asn Glu Gly Ala Lys Ser
                 85
```

<210> SEQ ID NO 43
<211> LENGTH: 674
<212> TYPE: DNA
<213> ORGANISM: Zea mays

<400> SEQUENCE: 43

```
cttgtggcag ttggattctc ctgcgtccca atcacgcagc ctcttggcct ccgcgaccgt      60
ccctcccct ccccttttga cgagcgaggg gctgtatgct gggcgccgtc gtccgtgtcc     120
cgggcccgat cctacctttc tgcccgggc cgacgcgccc tctcctccgc cgccgccact     180
acctcccgcc cgagacgccc atggcctcgg ccacccttg cgatggcggc accgggaagc     240
ccgacgccgc gccggctccc acgcccgcgc caacgccgct gccgcccgag aagcctctcc     300
```

-continued

| | |
|---|---|
| cgggcgactg ctgcggcagc ggctgcgttc gctgcgtctg ggacatatat ttcgacgagc | 360 |
| tcgacgcgta cgacaaggcc ctcgccgcgc acgcggcctc ctcaggctcc ggcggcaagg | 420 |
| acgactctgc tgataccaag cccaagaag gtgccaaatc ctgaagtgcg cctctcatgt | 480 |
| gtaatgacct cttctgctct gaactgaatt agattgctgg cgtctcacca gattcacata | 540 |
| cgctggtacc aattcttagc actcgagaca ttacaatact cttgtgcctg ctgtgttata | 600 |
| tgctagatta agatgcttta tcaattcagc ctccttattg tgtaacagga ggaagttatg | 660 |
| aaacaaaaaa aaaa | 674 |

<210> SEQ ID NO 44
<211> LENGTH: 122
<212> TYPE: PRT
<213> ORGANISM: Zea mays

<400> SEQUENCE: 44

```
Met Leu Gly Ala Val Val Arg Val Pro Gly Pro Ile Leu Pro Phe Leu
1               5                   10                  15
Pro Gly Pro Thr Arg Pro Leu Leu Arg Arg Arg His Tyr Leu Pro Pro
            20                  25                  30
Glu Thr Pro Met Ala Ser Ala Thr Pro Cys Asp Gly Thr Gly Lys
        35                  40                  45
Pro Asp Ala Ala Pro Ala Pro Thr Pro Ala Pro Thr Pro Leu Pro Pro
    50                  55                  60
Glu Lys Pro Leu Pro Gly Asp Cys Cys Gly Ser Gly Cys Val Arg Cys
65                  70                  75                  80
Val Trp Asp Ile Tyr Phe Asp Glu Leu Asp Ala Tyr Asp Lys Ala Leu
                85                  90                  95
Ala Ala His Ala Ala Ser Ser Gly Ser Gly Gly Lys Asp Asp Ser Ala
            100                 105                 110
Asp Thr Lys Pro Lys Glu Gly Ala Lys Ser
        115                 120
```

<210> SEQ ID NO 45
<211> LENGTH: 653
<212> TYPE: DNA
<213> ORGANISM: Oryza sativa

<400> SEQUENCE: 45

| | |
|---|---|
| cccttctctt ccgcatgctg gtcgccgccc tccgcgtccc ggcgccgatc ccctcgtcgc | 60 |
| tccctcgcc ggcgcgccct ctcctccgcc gccgcagcag ccaccgcctg cccctcccc | 120 |
| cgccccccgc cgcgtcaatg ccgacgccg gcggcgccac acgaacaag cccgctccgg | 180 |
| cccccggccc ggagccgccc gagaagccgc tcccggcga ctgctgcggc agcggctgcg | 240 |
| tccgctgcgt ctgggacgtc tactacgacg agctcgacgc ctacaataag gctctcgccg | 300 |
| cccactcctc gtcggcatcc tccggcagca agcccgctac cagcgacggc gccaaatcat | 360 |
| gaggcgaatc aggattcagg agttctgagg acgacttgca gtatgcgtcc cttcctctct | 420 |
| tttcattttt tttccccttc cccaaatcgg ggtcttggtg tggtactcct accagctagt | 480 |
| agtattaaaa ttactcgttt gattatagtg aaacatttgt gttatctcat tgtgtatgct | 540 |
| gcaatttgta ctagagtgga atggttgttg ttccaacgaa aaattccctg attacataca | 600 |
| gagaattgtt catggatagt tcttgtgtaa caaacattag catttggca gaa | 653 |

<210> SEQ ID NO 46
<211> LENGTH: 115

```
<212> TYPE: PRT
<213> ORGANISM: Oryza sativa

<400> SEQUENCE: 46

Met Leu Val Ala Ala Leu Arg Val Pro Ala Pro Ile Pro Ser Ser Leu
1               5                   10                  15

Pro Ser Pro Ala Arg Pro Leu Leu Arg Arg Ser Ser His Arg Leu
            20                  25                  30

Pro Pro Pro Pro Pro Pro Ala Ala Ser Met Ala Asp Ala Gly Gly Ala
            35                  40                  45

Thr Thr Asn Lys Pro Ala Pro Ala Pro Ala Pro Glu Pro Pro Glu Lys
        50                  55                  60

Pro Leu Pro Gly Asp Cys Cys Gly Ser Gly Cys Val Arg Cys Val Trp
65                  70                  75                  80

Asp Val Tyr Tyr Asp Glu Leu Asp Ala Tyr Asn Lys Ala Leu Ala Ala
                85                  90                  95

His Ser Ser Ser Ala Ser Ser Gly Ser Lys Pro Ala Thr Ser Asp Gly
            100                 105                 110

Ala Lys Ser
        115

<210> SEQ ID NO 47
<211> LENGTH: 399
<212> TYPE: DNA
<213> ORGANISM: Sorghum bicolor

<400> SEQUENCE: 47
atgctgggcg ccgtcgtccg tgtcccggcg ccgatcctgc tgcctctcct ccccggaccg     60
acgcgccctc tcctcctccg ccgccgccgc cactgcctcc cgcccgaggc gcccatggcc    120
tcggccaccc ctagcgacgg cggcgccgcg aagcccgatg ccgcgcccgc gcccgtgccc    180
gtgcccgcgc ccgcgccaac gccgctgccg ctgccgcccg agaagcctct cccgggcgac    240
tgctgcggca gcggctgcgt gcgctgcgtc tgggacatat atttcgacga gctcgacgcg    300
tacgacaagg cgctcgccgc ccacgcggcc gcctcctcag gctccggcgc caaggacgac    360
tccgccgata ccaagcccag cgacggcgcc aagtcctga                          399

<210> SEQ ID NO 48
<211> LENGTH: 132
<212> TYPE: PRT
<213> ORGANISM: Sorghum bicolor

<400> SEQUENCE: 48

Met Leu Gly Ala Val Val Arg Val Pro Ala Pro Ile Leu Leu Pro Leu
1               5                   10                  15

Leu Pro Gly Pro Thr Arg Pro Leu Leu Leu Arg Arg Arg Arg His Cys
            20                  25                  30

Leu Pro Pro Glu Ala Pro Met Ala Ser Ala Thr Pro Ser Asp Gly Gly
            35                  40                  45

Ala Ala Lys Pro Asp Ala Ala Pro Ala Pro Val Pro Val Pro Ala Pro
        50                  55                  60

Ala Pro Thr Pro Leu Pro Leu Pro Glu Lys Pro Leu Pro Gly Asp
65                  70                  75                  80

Cys Cys Gly Ser Gly Cys Val Arg Cys Val Trp Asp Ile Tyr Phe Asp
                85                  90                  95

Glu Leu Asp Ala Tyr Asp Lys Ala Leu Ala Ala His Ala Ala Ser
            100                 105                 110
```

```
Ser Gly Ser Gly Ala Lys Asp Asp Ser Ala Asp Thr Lys Pro Ser Asp
        115                 120                 125

Gly Ala Lys Ser
    130

<210> SEQ ID NO 49
<211> LENGTH: 34
<212> TYPE: DNA
<213> ORGANISM: artificial sequence
<220> FEATURE:
<223> OTHER INFORMATION: linker

<400> SEQUENCE: 49
ggcgcgccaa gcttggatcc gtcgacggcg cgcc                                34

<210> SEQ ID NO 50
<211> LENGTH: 4974
<212> TYPE: DNA
<213> ORGANISM: artificial sequence
<220> FEATURE:
<223> OTHER INFORMATION: vector
<220> FEATURE:
<221> NAME/KEY: unsure
<222> LOCATION: (3951)..(3951)
<223> OTHER INFORMATION: n=a,c,g,or t

<400> SEQUENCE: 50
ggccgccgac tcgacgatga gcgagatgac cagctccggc cgcgacacaa gtgtgagagt      60
actaaataaa tgctttggtt gtacgaaatc attacactaa ataaaataat caaagcttat     120
atatgccttc cgctaaggcc gaatgcaaag aaattggttc tttctcgtta tcttttgcca     180
cttttactag tacgtattaa ttactactta atcatctttg tttacggctc attatatccg     240
tcgacggcgc gcccgatcat ccggatatag ttcctccttt cagcaaaaaa cccctcaaga     300
cccgtttaga ggccccaagg ggttatgcta gttattgctc agcggtggca gcagccaact     360
cagcttcctt tcgggctttg ttagcagccg gatcgatcca agctgtacct cactattcct     420
ttgccctcgg acgagtgctg gggcgtcggt ttccactatc ggcgagtact tctacacagc     480
catcggtcca gacggccgcg cttctgcggg cgatttgtgt acgcccgaca gtcccggctc     540
cggatcggac gattgcgtcg catcgaccct gcgcccaagc tgcatcatcg aaattgccgt     600
caaccaagct ctgatagagt tggtcaagac caatgcggag catatacgcc cggagccgcg     660
gcgatcctgc aagctccgga tgcctccgct cgaagtagcg cgtctgctgc tccatacaag     720
ccaaccacgg cctccagaag aagatgttgg cgacctcgta ttgggaatcc ccgaacatcg     780
cctcgctcca gtcaatgacc gctgttatgc ggccattgtc cgtcaggaca ttgttggagc     840
cgaaatccgc gtgcacgagg tgccggactt cggggcagtc ctcggcccaa agcatcagct     900
catcgagagc ctgcgcgacg gacgcactga cggtgtcgtc catcacagtt gccagtgat      960 acacatgggg atcagcaatc gcgcatatga atcacgccat gtagtgtat tgaccgattc     1020 cttgcggtcc gaatgggccg aacccgctcg tctggctaag atcggccgca gcgatcgcat    1080
ccatagcctc cgcgaccggc tgcagaacag cgggcagttc ggtttcaggc aggtcttgca    1140
acgtgacacc ctgtgcacgg cgggagatgc aataggtcag gctctcgctg aattccccaa    1200
tgtcaagcac ttccggaatc gggagcgcgg ccgatgcaaa gtgccgataa acataacgat    1260
ctttgtagaa accatcggcg cagctattta cccgcaggac atatccacgc cctcctacat    1320
cgaagctgaa agcacgagat tcttcgccct ccgagagctg catcaggtcg agacgctgt    1380
```

```
cgaactttc  gatcagaaac  ttctcgacag  acgtcgcggt  gagttcaggc  ttttccatgg    1440
gtatatctcc  ttcttaaagt  taaacaaaat  tatttctaga  gggaaaccgt  tgtggtctcc    1500
ctatagtgag  tcgtattaat  ttcgcgggat  cgagatctga  tcaacctgca  ttaatgaatc    1560
ggccaacgcg  cggggagagg  cggtttgcgt  attgggcgct  cttccgcttc  ctcgctcact    1620
gactcgctgc  gctcggtcgt  tcggctgcgg  cgagcggtat  cagctcactc  aaaggcggta    1680
atacggttat  ccacagaatc  aggggataac  gcaggaaaga  acatgtgagc  aaaaggccag    1740
caaaaggcca  ggaaccgtaa  aaaggccgcg  ttgctggcgt  ttttccatag  gctccgcccc    1800
cctgacgagc  atcacaaaaa  tcgacgctca  agtcagaggt  ggcgaaaccc  gacaggacta    1860
taaagatacc  aggcgtttcc  ccctggaagc  tccctcgtgc  gctctcctgt  tccgaccctg    1920
ccgcttaccg  gatacctgtc  cgcctttctc  ccttcgggaa  gcgtggcgct  ttctcaatgc    1980
tcacgctgta  ggtatctcag  ttcggtgtag  gtcgttcgct  ccaagctggg  ctgtgtgcac    2040 gaacccccg   ttcagcccga  ccgctgcgcc  ttatccggta  actatcgtct  tgagtccaac    2100
ccggtaagac  acgacttatc  gccactggca  gcagccactg  gtaacaggat  tagcagagcg    2160
aggtatgtag  gcggtgctac  agagttcttg  aagtggtggc  ctaactacgg  ctacactaga    2220
aggacagtat  ttggtatctg  cgctctgctg  aagccagtta  ccttcggaaa  aagagttggt    2280
agctcttgat  ccggcaaaca  aaccaccgct  ggtagcggtg  gtttttttgt  ttgcaagcag    2340
cagattacgc  gcagaaaaaa  aggatctcaa  gaagatcctt  tgatctttc   tacggggtct    2400 gacgctcagt  ggaacgaaaa  ctcacgttaa  gggattttgg  tcatgacatt  aacctataaa    2460
aataggcgta  tcacgaggcc  ctttcgtctc  gcgcgtttcg  gtgatgacgg  tgaaaacctc    2520
tgacacatgc  agctcccgga  gacggtcaca  gcttgtctgt  aagcggatgc  cgggagcaga    2580
caagcccgtc  agggcgcgtc  agcgggtgtt  ggcgggtgtc  ggggctggct  taactatgcg    2640
gcatcagagc  agattgtact  gagagtgcac  catatggaca  tattgtcgtt  agaacgcggc    2700
tacaattaat  acataacctt  atgtatcata  cacatacgat  ttaggtgaca  ctatagaacg    2760
gcgcgccaag  cttggatcct  cgaagagaag  ggttaataac  acattttta   acatttttaa    2820 cacaaatttt  agttatttaa  aaatttatta  aaaaatttaa  aataagaaga  ggaactcttt    2880
aaataaatct  aacttacaaa  atttatgatt  tttaataagt  tttcaccaat  aaaaaatgtc    2940
ataaaaatat  gttaaaaagt  atattatcaa  tattctcttt  atgataaata  aaagaaaaa    3000 aaaaataaaa  gttaagtgaa  aatgagattg  aagtgacttt  aggtgtgtat  aaatatatca    3060
accccgccaa  caatttattt  aatccaaata  tattgaagta  tattattcca  tagcctttat    3120
ttatttatat  atttattata  taaaagcttt  atttgttcta  ggttgttcat  gaaatatttt    3180
tttggtttta  tctccgttgt  aagaaaatca  tgtgctttgt  gtcgccactc  actattgcag    3240 cttttttcatg  cattggtcag  attgacggtt  gattgtattt  ttgttttta   tggttttgtg    3300 ttatgactta  agtcttcatc  tctttatctc  ttcatcaggt  ttgatggtta  cctaatatgg    3360
tccatgggta  catgcatggt  taaattaggt  ggccaacttt  gttgtgaacg  atagaatttt    3420
ttttatatta  agtaaactat  ttttatatta  tgaaataata  ataaaaaaaa  tattttatca    3480
ttattaacaa  aatcatatta  gttaatttgt  taactctata  ataaagaaa   tactgtaaca    3540 ttcacattac  atggtaacat  cttccaccc   tttcatttgt  ttttgtttg   atgactttt    3600 ttcttgttta  aatttatttc  ccttcttta   aatttggaat  acattatcat  catatataaa    3660
ctaaaatact  aaaacagga   ttacacaaat  gataaataat  aacacaaata  tttataaatc    3720
tagctgcaat  atatttaaac  tagctatatc  gatattgtaa  aataaaacta  gctgcattga    3780
```

-continued

```
tactgataaa aaaatatcat gtgctttctg gactgatgat gcagtatact tttgacattg     3840
cctttatttt attttcaga aaagcttcct tagttctggg ttcttcatta tttgtttccc      3900
atctccattg tgaattgaat catttgcttc gtgtcacaaa tacaatttag ntaggtacat     3960
gcattggtca gattcacggt ttattatgtc atgacttaag ttcatggtag tacattacct    4020
gccacgcatg cattatattg gttagatttg ataggcaaat ttggttgtca acaatataaa    4080
tataaataat gttttatat tacgaaataa cagtgatcaa acaaacagt tttatcttta      4140 ttaacaagat tttgtttttg tttgatgacg ttttttaatg tttacgcttt ccccttctt     4200 ttgaatttag aacactttat catcataaaa tcaaatacta aaaaattac atatttcata     4260 aataataaca caaatatttt taaaaaatct gaataataa tgaacaatat tacatattat     4320
cacgaaaatt cattaataaa aatattatat aaataaaatg taatagtagt tatatgtagg    4380
aaaaaagtac tgcacgcata atatatacaa aaagattaaa atgaactatt ataaataata    4440
acactaaatt aatggtgaat catatcaaaa taatgaaaaa gtaaataaaa tttgtaatta    4500
acttctatat gtattacaca cacaaataat aaataatagt aaaaaaatt atgataaata    4560 tttaccatct cataagatat ttaaaataat gataaaaata tagattattt tttatgcaac    4620
tagctagcca aaagagaac acgggtatat ataaaaagag tacctttaaa ttctactgta     4680
cttcctttat tcctgacgtt tttatatcaa gtggacatac gtgaagattt taattatcag    4740
tctaaatatt tcattagcac ttaatacttt tctgttttat tcctatccta taagtagtcc    4800
cgattctccc aacattgctt attcacacaa ctaactaaga aagtcttcca tagcccccca    4860
agcggccgga gctggtcatc tcgctcatcg tcgagtcggc ggccggagct ggtcatctcg    4920
ctcatcgtcg agtcggcggc cgccgactcg acgatgagcg agatgaccag ctcc          4974
```

<210> SEQ ID NO 51
<211> LENGTH: 80
<212> TYPE: DNA
<213> ORGANISM: artificial sequence
<220> FEATURE:
<223> OTHER INFORMATION: EagI ELVISLIVES sequence

<400> SEQUENCE: 51

```
cggccggagc tggtcatctc gctcatcgtc gagtcggcgg ccgccgactc gacgatgagc     60
gagatgacca gctccggccg                                                 80
```

<210> SEQ ID NO 52
<211> LENGTH: 118
<212> TYPE: DNA
<213> ORGANISM: artificial sequence
<220> FEATURE:
<223> OTHER INFORMATION: 2XELVISLIVES

<400> SEQUENCE: 52

```
cggccggagc tggtcatctc gctcatcgtc gagtcggcgg ccggagctgg tcatctcgct     60
catcgtcgag tcggcggccg ccgactcgac gatgagcgag atgaccagct ccggccgc      118
```

<210> SEQ ID NO 53
<211> LENGTH: 92
<212> TYPE: DNA
<213> ORGANISM: artificial sequence
<220> FEATURE:
<223> OTHER INFORMATION: primer

<400> SEQUENCE: 53

```
gaattccggc cggagctggt catctcgctc atcgtcgagt cggcggccgc cgactcgacg    60
atgagcgaga tgaccagctc cggccggaat tc                                 92

<210> SEQ ID NO 54
<211> LENGTH: 15
<212> TYPE: DNA
<213> ORGANISM: artificial sequence
<220> FEATURE:
<223> OTHER INFORMATION: primer

<400> SEQUENCE: 54
gaattccggc cggag                                                    15

<210> SEQ ID NO 55
<211> LENGTH: 29
<212> TYPE: DNA
<213> ORGANISM: artificial sequence
<220> FEATURE:
<223> OTHER INFORMATION: primer

<400> SEQUENCE: 55
gcggccgcat gtataattcc acatacaac                                     29

<210> SEQ ID NO 56
<211> LENGTH: 29
<212> TYPE: DNA
<213> ORGANISM: artificial sequence
<220> FEATURE:
<223> OTHER INFORMATION: primer

<400> SEQUENCE: 56
gcggccgcat gtataattcc acatacaac                                     29

<210> SEQ ID NO 57
<211> LENGTH: 26
<212> TYPE: DNA
<213> ORGANISM: artificial sequence
<220> FEATURE:
<223> OTHER INFORMATION: primer

<400> SEQUENCE: 57
tctagaccac atacaacatt tcgatc                                        26

<210> SEQ ID NO 58
<211> LENGTH: 26
<212> TYPE: DNA
<213> ORGANISM: artificial sequence
<220> FEATURE:
<223> OTHER INFORMATION: primer

<400> SEQUENCE: 58
tctagaccac atacaacatt tcgatc                                        26

<210> SEQ ID NO 59
<211> LENGTH: 3402
<212> TYPE: DNA
<213> ORGANISM: artificial sequence
<220> FEATURE:
<223> OTHER INFORMATION: plasmid

<400> SEQUENCE: 59
gcggccgctc aatcgcatgg ccgaggctgc acgaaccgcg cataaacccg cgccgcaccc    60
gatccaaccc aaacccgacg ataaaacccc gaatccggcg aaggagattc cgccgccgcc   120
ggagaagccg gagcccggcg attgctgcgg cagcgggtgc gtccgatgcg tctgggatgt   180
```

```
gtactacgac gaactcgaag aatacaataa gcgatacaaa caggtcgatc ccagccccaa    240
accttcttcg taatcttcaa catcgcttgg attagcttta ttaatttatt tatattacat    300 cctaattttta aaaagctttg ggtatttctt gatttcgtga attgtccctt tttatcaaaa    360
aggatcgaaa tgttgtatgt ggaattatac atgcggccgc aatcactagt gcggccgcct    420
gcaggtcgac catatgggag agctcccaac gcgttggatg catagcttga gtattctata    480
gtgtcaccta aatagcttgg cgtaatcatg gtcatagctg tttcctgtgt gaaattgtta    540
tccgctcaca attccacaca acatacgagc cggaagcata aagtgtaaag cctggggtgc    600
ctaatgagtg agctaactca cattaattgc gttgcgctca ctgcccgctt tccagtcggg    660
aaacctgtcg tgccagctgc attaatgaat cggccaacgc gcgggagag gcggtttgcg    720 tattgggcgc tcttccgctt cctcgctcac tgactcgctg cgctcggtcg ttcggctgcg    780
gcgagcggta tcagctcact caaaggcggt aatacggtta tccacagaat caggggataa    840
cgcaggaaag aacatgtgag caaaaggcca gcaaaaggcc aggaaccgta aaaaggccgc    900
gttgctggcg ttttttccata ggctccgccc ccctgacgag catcacaaaa atcgacgctc    960
aagtcagagg tggcgaaacc cgacaggact ataaagatac caggcgtttc ccctggaag   1020 ctccctcgtg cgctctcctg ttccgaccct gccgcttacc ggatacctgt ccgcctttct   1080
cccttcggga agcgtggcgc tttctcatag ctcacgctgt aggtatctca gttcggtgta   1140
ggtcgttcgc tccaagctgg gctgtgtgca cgaacccccc gttcagcccg accgctgcgc   1200
cttatccggt aactatcgtc ttgagtccaa cccggtaaga cacgacttat cgccactggc   1260
agcagccact ggtaacagga ttagcagagc gaggtatgta ggcggtgcta cagagttctt   1320
gaagtggtgg cctaactacg gctacactag aagaacagta tttggtatct gcgctctgct   1380
gaagccagtt accttcggaa aaagagttgg tagctcttga tccggcaaac aaaccaccgc   1440
tggtagcggt ggtttttttg tttgcaagca gcagattacg cgcagaaaaa aaggatctca   1500
agaagatcct ttgatctttt ctacggggtc tgacgctcag tggaacgaaa actcacgtta   1560
agggattttg gtcatgagat tatcaaaaag gatcttcacc tagatccttt taaattaaaa   1620
atgaagtttt aaatcaatct aaagtatata tgagtaaact tggtctgaca gttaccaatg   1680
cttaatcagt gaggcaccta tctcagcgat ctgtctattt cgttcatcca tagttgcctg   1740
actccccgtc gtgtagataa ctacgatacg ggagggctta ccatctggcc ccagtgctgc   1800
aatgataccg cgagacccac gctcaccggc tccagattta tcagcaataa accagccagc   1860
cggaagggcc gagcgcagaa gtggtcctgc aactttatcc gcctccatcc agtctattaa   1920
ttgttgccgg gaagctagag taagtagttc gccagttaat agtttgcgca acgttgttgc   1980
cattgctaca ggcatcgtgg tgtcacgctc gtcgtttggt atggcttcat tcagctccgg   2040
ttcccaacga tcaaggcgag ttacatgatc ccccatgttg tgcaaaaaag cggttagctc   2100
cttcggtcct ccgatcgttg tcagaagtaa gttggccgca gtgttatcac tcatggttat   2160
ggcagcactg cataattctc ttactgtcat gccatccgta agatgctttt ctgtgactgg   2220
tgagtactca accaagtcat tctgagaata gtgtatgcgg cgaccgagtt gctcttgccc   2280
ggcgtcaata cgggataata ccgcgccaca tagcagaact ttaaaagtgc tcatcattgg   2340
aaaacgttct cggggcgaa aactctcaag gatcttaccg ctgttgagat ccagttcgat   2400
gtaacccact cgtgcaccca actgatcttc agcatctttt actttcacca gcgtttctgg   2460
gtgagcaaaa acaggaaggc aaaatgccgc aaaaaaggga taagggcga cacggaaatg   2520
```

| | |
|---|---|
| ttgaatactc atactcttcc tttttcaata ttattgaagc atttatcagg gttattgtct | 2580 |
| catgagcgga tacatatttg aatgtattta gaaaaataaa caaatagggg ttccgcgcac | 2640 |
| atttccccga aaagtgccac ctgatgcggt gtgaaatacc gcacagatgc gtaaggagaa | 2700 |
| aataccgcat caggaaattg taagcgttaa tattttgtta aaattcgcgt taaattttg | 2760 |
| ttaaatcagc tcattttta accaataggc cgaaatcggc aaaatccctt ataaatcaaa | 2820 |
| agaatagacc gagatagggt tgagtgttgt tccagtttgg aacaagagtc cactattaaa | 2880 |
| gaacgtggac tccaacgtca aagggcgaaa aaccgtctat cagggcgatg gcccactacg | 2940 |
| tgaaccatca ccctaatcaa gttttttggg gtcgaggtgc cgtaaagcac taaatcggaa | 3000 |
| ccctaaaggg agcccccgat ttagagcttg acggggaaag ccggcgaacg tggcgagaaa | 3060 |
| ggaagggaag aaagcgaaag gagcgggcgc tagggcgctg gcaagtgtag cggtcacgct | 3120 |
| gcgcgtaacc accacacccg ccgcgcttaa tgcgccgcta cagggcgcgt ccattcgcca | 3180 |
| ttcaggctgc gcaactgttg ggaagggcga tcggtgcggg cctcttcgct attacgccag | 3240 |
| ctggcgaaag gggatgtgc tgcaaggcga ttaagttggg taacgccagg gttttcccag | 3300 |
| tcacgacgtt gtaaaacgac ggccagtgaa ttgtaatacg actcactata gggcgaattg | 3360 |
| ggcccgacgt cgcatgctcc cggccgccat ggccgcggga tt | 3402 |

<210> SEQ ID NO 60
<211> LENGTH: 3204
<212> TYPE: DNA
<213> ORGANISM: artificial sequence
<220> FEATURE:
<223> OTHER INFORMATION: plasmid

<400> SEQUENCE: 60

| | |
|---|---|
| aatcactagt gcggccgcct gcaggtcgac catatgggag agctcccaac gcgttggatg | 60 |
| catagcttga gtattctata gtgtcaccta aatagcttgg cgtaatcatg gtcatagctg | 120 |
| tttcctgtgt gaaattgtta tccgctcaca attccacaca acatacgagc cggaagcata | 180 |
| aagtgtaaag cctggggtgc ctaatgagtg agctaactca cattaattgc gttgcgctca | 240 |
| ctgcccgctt tccagtcggg aaacctgtcg tgccagctgc attaatgaat cggccaacgc | 300 |
| gcggggagag gcggtttgcg tattgggcgc tcttccgctt cctcgctcac tgactcgctg | 360 |
| cgctcggtcg ttcggctgcg gcgagcggta tcagctcact caaaggcggt aatacggtta | 420 |
| tccacagaat caggggataa cgcaggaaag aacatgtgag caaaaggcca gcaaaaggcc | 480 |
| aggaaccgta aaaaggccgc gttgctggcg tttttccata ggctccgccc ccctgacgag | 540 |
| catcacaaaa atcgacgctc aagtcagagg tggcgaaacc cgacaggact ataaagatac | 600 |
| caggcgtttc ccctggaag ctccctcgtg cgctctcctg ttccgaccct gccgcttacc | 660 |
| ggatacctgt ccgcctttct cccttcggga agcgtggcgc tttctcatag ctcacgctgt | 720 |
| aggtatctca gttcggtgta ggtcgttcgc tccaagctgg gctgtgtgca cgaaccccc | 780 |
| gttcagcccg accgctgcgc cttatccggt aactatcgtc ttgagtccaa cccggtaaga | 840 |
| cacgacttat cgccactggc agcagccact ggtaacagga ttagcagagc gaggtatgta | 900 |
| ggcggtgcta cagagttctt gaagtggtgg cctaactacg gctacactag aagaacagta | 960 |
| tttggtatct gcgctctgct gaagccagtt accttcggaa aaagagttgg tagctcttga | 1020 |
| tccggcaaac aaaccaccgc tggtagcggt ggtttttttg tttgcaagca gcagattacg | 1080 |
| cgcagaaaaa aaggatctca agaagatcct ttgatctttt ctacgggtc tgacgctcag | 1140 |
| tggaacgaaa actcacgtta agggattttg gtcatgagat tatcaaaaag gatcttcacc | 1200 |

| | | | |
|---|---|---|---|
| tagatccttt | taaattaaaa atgaagtttt aaatcaatct aaagtatata | tgagtaaact | 1260 |
| tggtctgaca | gttaccaatg cttaatcagt gaggcaccta tctcagcgat | ctgtctattt | 1320 |
| cgttcatcca | tagttgcctg actccccgtc gtgtagataa ctacgatacg | ggagggctta | 1380 |
| ccatctggcc | ccagtgctgc aatgataccg cgagacccac gctcaccggc | tccagattta | 1440 |
| tcagcaataa | accagccagc cggaagggcc gagcgcagaa gtggtcctgc | aactttatcc | 1500 |
| gcctccatcc | agtctattaa ttgttgccgg gaagctagag taagtagttc | gccagttaat | 1560 |
| agtttgcgca | acgttgttgc cattgctaca ggcatcgtgg tgtcacgctc | gtcgtttggt | 1620 |
| atggcttcat | tcagctccgg ttcccaacga tcaaggcgag ttacatgatc | ccccatgttg | 1680 |
| tgcaaaaaag | cggttagctc cttcggtcct ccgatcgttg tcagaagtaa | gttggccgca | 1740 |
| gtgttatcac | tcatggttat ggcagcactg cataattctc ttactgtcat | gccatccgta | 1800 |
| agatgctttt | ctgtgactgg tgagtactca accaagtcat tctgagaata | gtgtatgcgg | 1860 |
| cgaccgagtt | gctcttgccc ggcgtcaata cgggataata ccgcgccaca | tagcagaact | 1920 |
| ttaaaagtgc | tcatcattgg aaaacgttct tcggggcgaa aactctcaag | gatcttaccg | 1980 |
| ctgttgagat | ccagttcgat gtaacccact cgtgcaccca actgatcttc | agcatctttt | 2040 |
| actttcacca | gcgtttctgg gtgagcaaaa acaggaaggc aaaatgccgc | aaaaagggga | 2100 |
| ataagggcga | cacggaaatg ttgaatactc atactcttcc ttttcaata | ttattgaagc | 2160 |
| atttatcagg | gttattgtct catgagcgga tacatatttg aatgtattta | gaaaaataaa | 2220 |
| caaataggg | ttccgcgcac atttccccga aaagtgccac ctgatgcggt | gtgaaatacc | 2280 |
| gcacagatgc | gtaaggagaa aataccgcat caggaaattg taagcgttaa | tattttgtta | 2340 |
| aaattcgcgt | taaattttg ttaaatcagc tcattttta accaataggc | cgaaatcggc | 2400 |
| aaaatccctt | ataaatcaaa agaatagacc gagatagggt tgagtgttgt | tccagtttgg | 2460 |
| aacaagagtc | cactattaaa gaacgtggac tccaacgtca aagggcgaaa | aaccgtctat | 2520 |
| cagggcgatg | gcccactacg tgaaccatca ccctaatcaa gttttttggg | gtcgaggtgc | 2580 |
| cgtaaagcac | taaatcggaa ccctaaaggg agccccccgat ttagagcttg | acggggaaag | 2640 |
| ccggcgaacg | tggcgagaaa ggaagggaag aaagcgaaag gagcgggcgc | tagggcgctg | 2700 |
| gcaagtgtag | cggtcacgct gcgcgtaacc accacacccg ccgcgcttaa | tgcgccgcta | 2760 |
| cagggcgcgt | ccattcgcca ttcaggctgc gcaactgttg gaagggcga | tcggtgcggg | 2820 |
| cctcttcgct | attacgccag ctggcgaaag ggggatgtgc tgcaaggcga | ttaagttggg | 2880 |
| taacgccagg | gttttcccag tcacgacgtt gtaaaacgac ggccagtgaa | ttgtaatacg | 2940 |
| actcactata | gggcgaattg ggcccgacgt cgcatgctcc cggccgccat | ggccgcggga | 3000 |
| ttggatccac | tcgaagaata caataagcga tacaaacagg tcgatcccag | ccccaaacct | 3060 |
| tcttcgtaat | cttcaacatc gcttggatta gctttattaa tttatttata | ttacatccta | 3120 |
| attttaaaaa | gctttgggta tttcttgatt tcgtgaattg tccctttta | tcaaaaagga | 3180 |
| tcgaaatgtt | gtatgtggtc taga | | 3204 |

<210> SEQ ID NO 61
<211> LENGTH: 3790
<212> TYPE: DNA
<213> ORGANISM: artificial sequence
<220> FEATURE:
<223> OTHER INFORMATION: plasmid

<400> SEQUENCE: 61

```
gatccactcg aagaatacaa taagcgatac aaacaggtcg atcccagccc caaaccttct      60
tcgtaatctt caacatcgct tggattagct ttattaattt atttatatta catcctaatt     120
ttaaaaagct ttgggtattt cttgatttcg tgaattgtcc cttttttatca aaaaggatcg    180
aaatgttgta tgtggtctag aaatcactag tgcggccgcc tgcaggtcga ccatatggga     240
gagctcccaa cgcgttggat gcatagcttg agtattctat agtgtcacct aaatagcttg     300
gcgtaatcat ggtcatagct gtttcctgtg tgaaattgtt atccgctcac aattccacac     360
aacatacgag ccggaagcat aaagtgtaaa gcctggggtg cctaatgagt gagctaactc     420
acattaattg cgttgcgctc actgcccgct ttccagtcgg gaaacctgtc gtgccagctg     480
cattaatgaa tcggccaacg cgcggggaga ggcggtttgc gtattgggcg ctcttccgct     540
tcctcgctca ctgactcgct gcgctcggtc gttcggctgc ggcgagcggt atcagctcac     600
tcaaaggcgg taatacggtt atccacagaa tcagggata acgcaggaaa gaacatgtga     660
gcaaaaggcc agcaaaaggc caggaaccgt aaaaaggccg cgttgctggc gtttttccat     720
aggctccgcc cccctgacga gcatcacaaa aatcgacgct caagtcagag gtggcgaaac     780
ccgacaggac tataaagata ccaggcgttt ccccctggaa gctccctcgt gcgctctcct     840
gttccgaccc tgccgcttac cggatacctg tccgcctttc tcccttcggg aagcgtggcg     900
ctttctcata gctcacgctg taggtatctc agttcggtgt aggtcgttcg ctccaagctg     960
ggctgtgtgc acgaaccccc cgttcagccc gaccgctgcg ccttatccgg taactatcgt    1020
cttgagtcca acccggtaag acacgactta tcgccactgg cagcagccac tggtaacagg    1080
attagcagag cgaggtatgt aggcggtgct acagagttct tgaagtggtg cctaactac     1140
ggctacacta agaacagt atttggtatc tgcgctctgc tgaagccagt taccttcgga      1200
aaaagagttg gtagctcttg atccggcaaa caaaccaccg ctggtagcgg tggttttttt    1260
gtttgcaagc agcagattac gcgcagaaaa aaggatctc aagaagatcc tttgatcttt    1320
tctacggggt ctgacgctca gtggaacgaa aactcacgtt aagggatttt ggtcatgaga    1380
ttatcaaaaa ggatcttcac ctagatcctt ttaaattaaa aatgaagttt taaatcaatc    1440
taaagtatat atgagtaaac ttggtctgac agttaccaat gcttaatcag tgaggcacct    1500
atctcagcga tctgtctatt tcgttcatcc atagttgcct gactccccgt cgtgtagata    1560
actacgatac gggagggctt accatctggc cccagtgctg caatgatacc gcgagaccca    1620
cgctcaccgg ctccagattt atcagcaata aaccagccag ccggaagggc cgagcgcaga    1680
agtggtcctg caactttatc cgcctccatc cagtctatta attgttgccg ggaagctaga    1740
gtaagtagtt cgccagttaa tagtttgcgc aacgttgttg ccattgctac aggcatcgtg    1800
gtgtcacgct cgtcgtttgg tatggcttca ttcagctccg gttcccaacg atcaaggcga    1860
gttacatgat cccccatgtt gtgcaaaaaa gcggttagct ccttcggtcc tccgatcgtt    1920
gtcagaagta agttggccgc agtgttatca ctcatggtta tggcagcact gcataattct    1980
cttactgtca tgccatccgt aagatgcttt tctgtgactg gtgagtactc aaccaagtca    2040
ttctgagaat agtgtatgcg gcgaccgagt tgctcttgcc cggcgtcaat acgggataat    2100
accgcgccac atagcagaac tttaaaagtg ctcatcattg gaaaacgttc ttcggggcga    2160
aaactctcaa ggatcttacc gctgttgaga tccagttcga tgtaacccac tcgtgcaccc    2220
aactgatctt cagcatcttt tactttcacc agcgtttctg ggtgagcaaa aacaggaagg    2280
caaaatgccg caaaaaaggg aataagggcg acacggaaat gttgaatact catactcttc    2340
ctttttcaat attattgaag catttatcag ggttattgtc tcatgagcgg atacatattt    2400
```

```
gaatgtattt agaaaaataa acaaataggg gttccgcgca catttccccg aaaagtgcca    2460
cctgatgcgg tgtgaaatac cgcacagatg cgtaaggaga aaataccgca tcaggaaatt    2520
gtaagcgtta atattttgtt aaaattcgcg ttaaattttt gttaaatcag ctcattttt    2580 aaccaatagg ccgaaatcgg caaaatccct tataaatcaa agaatagac cgagataggg    2640 ttgagtgttg ttccagtttg gaacaagagt ccactattaa agaacgtgga ctccaacgtc    2700
aaagggcgaa aaaccgtcta tcagggcgat ggcccactac gtgaaccatc accctaatca    2760
agttttttgg ggtcgaggtg ccgtaaagca ctaaatcgga accctaaagg gagcccccga    2820
tttagagctt gacggggaaa gccggcgaac gtggcgagaa aggaagggaa gaaagcgaaa    2880
ggagcgggcg ctagggcgct ggcaagtgta gcggtcacgc tgcgcgtaac caccacaccc    2940
gccgcgctta atgcgccgct acagggcgcg tccattcgcc attcaggctg cgcaactgtt    3000
gggaagggcg atcggtgcgg gcctcttcgc tattacgcca gctggcgaaa ggggatgtg    3060 ctgcaaggcg attaagttgg gtaacgccag ggttttccca gtcacgacgt tgtaaaacga    3120
cggccagtga attgtaatac gactcactat agggcgaatt gggcccgacg tcgcatgctc    3180
ccggccgcca tggccgcggg attggatcca acgcaattaa tgtgagttag ctcactcatt    3240
aggcacccca ggctttacac tttatgcttc cggctcgtat gttgtgtgga attgtgagcg    3300
gataacaatt tcacacagga aacagctatg accatgatta cgccaagcta tttaggtgac    3360
actatagaat actcaagcta tgcatccaac gcgttgggag ctctcccata tggtcgacct    3420
gcaggcggcc gcactagtga ttgcggccgc atgtataatt ccacatacaa catttcgatc    3480 cttttttgata aaagggaca attcacgaaa tcaagaaata cccaaagctt tttaaaatta    3540
ggatgtaata taaataaatt aataaagcta atccaagcga tgttgaagat tacgaagaag    3600
gtttggggct gggatcgacc tgtttgtatc gcttattgta ttcttcgagt tcgtcgtagt    3660
acacatccca gacgcatcgg acgcacccgc tgccgcagca atcgccgggc tccggcttct    3720
ccggcggcgg cggaatctcc ttcgccggat tcggggtttt atcgtcgggt ttgggttgga    3780
tcgggtgcgg                                                          3790
```

<210> SEQ ID NO 62
<211> LENGTH: 8113
<212> TYPE: DNA
<213> ORGANISM: artificial sequence
<220> FEATURE:
<223> OTHER INFORMATION: vector
<220> FEATURE:
<221> NAME/KEY: unsure
<222> LOCATION: (6642)..(6642)
<223> OTHER INFORMATION: n = a, c, g, or t

<400> SEQUENCE: 62

```
ggccgcgaca caagtgtgag agtactaaat aaatgctttg gttgtacgaa atcattacac      60
taaataaaat aatcaaagct tatatatgcc ttccgctaag gccgaatgca aagaaattgg     120
ttctttctcg ttatcttttg ccactttac tagtacgtat taattactac ttaatcatct     180
ttgtttacgg ctcattatat ccgtcgacgg cgcgcccgat catccggata tagttcctcc     240
tttcagcaaa aaacccctca agacccgttt agaggcccca aggggttatg ctagttattg     300
ctcagcggtg gcagcagcca actcagcttc ctttcgggct ttgttagcag ccggatcgat     360
ccaagctgta cctcactatt cctttgccct cggacgagtg ctggggcgtc ggtttccact     420
atcggcgagt acttctacac agccatcggt ccagacggcc gcgcttctgc gggcgatttg     480
```

```
tgtacgcccg acagtcccgg ctccggatcg gacgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc cgcgtcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct    1020
aagatcggcc gcagcgatcg catccatagc ctccgcgacc ggctgcagaa cagcgggcag    1080
ttcggtttca ggcaggtctt gcaacgtgac accctgtgca cggcgggaga tgcaataggt    1140
caggctctcg ctgaattccc caatgtcaag cacttccgga atcgggagcg cggccgatgc    1200
aaagtgccga taaacataac gatctttgta gaaaccatcg gcgcagctat ttacccgcag    1260
gacatatcca cgccctccta catcgaagct gaaagcacga gattcttcgc cctccgagag    1320
ctgcatcagg tcgagacgc tgtcgaactt ttcgatcaga aacttctcga cagacgtcgc    1380
ggtgagttca ggcttttcca tgggtatatc tccttcttaa agttaaacaa aattatttct    1440
agagggaaac cgttgtggtc tccctatagt gagtcgtatt aatttcgcgg gatcgagatc    1500
gatccaattc caatcccaca aaaatctgag cttaacagca cagttgctcc tctcagagca    1560
gaatcgggta ttcaacaccc tcatatcaac tactacgttg tgtataacgg tccacatgcc    1620
ggtatatacg atgactgggg ttgtacaaag gcggcaacaa acggcgttcc cggagttgca    1680
cacaagaaat ttgccactat tacagaggca agagcagcag ctgacgcgta cacaacaagt    1740
cagcaaacag acaggttgaa cttcatcccc aaaggagaag ctcaactcaa gcccaagagc    1800
tttgctaagg ccctaacaag cccaccaaag caaaaagccc actggctcac gctaggaacc    1860
aaaaggccca gcagtgatcc agccccaaaa gagatctcct ttgccccgga gattacaatg    1920
gacgatttcc tctatcttta cgatctagga aggaagttcg aaggtgaagg tgacgacact    1980
atgttcacca ctgataatga aaggttagc ctcttcaatt tcagaaagaa tgctgaccca    2040
cagatggtta gagaggccta cgcagcaggt ctcatcaaga cgatctaccc gagtaacaat    2100
ctccaggaga tcaaataccct tcccaagaag gttaaagatg cagtcaaaag attcaggact    2160
aattgcatca gaacacaga gaaagacata tttctcaaga tcagaagtac tattccagta    2220
tggacgattc aaggcttgct tcataaacca aggcaagtaa tagagattgg agtctctaaa    2280
aaggtagttc ctactgaatc taaggccatg catggagtct aagattcaaa tcgaggatct    2340
aacagaactc gccgtgaaga ctggcgaaca gttcatacag agtcttttac gactcaatga    2400
caagaagaaa atcttcgtca acatggtgga gcacgacact ctggtctact ccaaaaatgt    2460
caaagataca gtctcagaag accaaagggc tattgagact tttcaacaaa ggataatttc    2520
gggaaacctc ctcggattcc attgcccagc tatctgtcac ttcatcgaaa ggacagtaga    2580
aaaggaaggt ggctcctaca aatgccatca ttgcgataaa ggaaaggcta tcattcaaga    2640
tgcctctgcc gacagtggtc ccaaagatgg acccccaccc acgaggagca tcgtggaaaa    2700
agaagacgtt ccaaccacgt cttcaaagca agtggattga tgtgacatct ccactgacgt    2760
aagggatgac gcacaatccc actatccttc gcaagaccct tcctctatat aaggaagttc    2820
atttcatttg gagaggacac gctcgagctc atttctctat tacttcagcc ataacaaaag    2880
```

```
aactctttc  tcttcttatt  aaaccatgaa  aaagcctgaa  ctcaccgcga  cgtctgtcga   2940
gaagtttctg  atcgaaaagt  tcgacagcgt  ctccgacctg  atgcagctct  cggagggcga   3000
agaatctcgt  gctttcagct  tcgatgtagg  agggcgtgga  tatgtcctgc  gggtaaatag   3060
ctgcgccgat  ggtttctaca  aagatcgtta  tgtttatcgg  cactttgcat  cggccgcgct   3120
cccgattccg  gaagtgcttg  acattgggga  attcagcgag  agcctgacct  attgcatctc   3180
ccgccgtgca  cagggtgtca  cgttgcaaga  cctgcctgaa  accgaactgc  cgctgttct    3240 gcagccggtc  gcggaggcca  tggatgcgat  cgctgcggcc  gatcttagcc  agacgagcgg   3300
gttcggccca  ttcggaccgc  aaggaatcgg  tcaatacact  acatggcgtg  atttcatatg   3360
cgcgattgct  gatccccatg  tgtatcactg  gcaaactgtg  atggacgaca  ccgtcagtgc   3420
gtccgtcgcg  caggctctcg  atgagctgat  gctttgggcc  gaggactgcc  ccgaagtccg   3480
gcacctcgtg  cacgcggatt  tcggctccaa  caatgtcctg  acggacaatg  gccgcataac   3540
agcggtcatt  gactggagcg  aggcgatgtt  cggggattcc  caatacgagg  tcgccaacat   3600
cttcttctgg  aggccgtggt  tggcttgtat  ggagcagcag  acgcgctact  tcgagcggag   3660
gcatccggag  cttgcaggat  cgccgcggct  ccgggcgtat  atgctccgca  ttggtcttga   3720
ccaactctat  cagagcttgg  ttgacggcaa  tttcgatgat  gcagcttggg  cgcagggtcg   3780
atgcgacgca  atcgtccgat  ccggagccgg  gactgtcggg  cgtacacaaa  tcgcccgcag   3840
aagcgcggcc  gtctggaccg  atggctgtgt  agaagtactc  gccgatagtg  gaaaccgacg   3900
ccccagcact  cgtccgaggg  caaaggaata  gtgaggtacc  taaagaagga  gtgcgtcgaa   3960
gcagatcgtt  caaacatttg  gcaataaagt  ttcttaagat  tgaatcctgt  tgccggtctt   4020
gcgatgatta  tcatataatt  tctgttgaat  tacgttaagc  atgtaataat  taacatgtaa   4080
tgcatgacgt  tatttatgag  atgggttttt  atgattagag  tcccgcaatt  atacatttaa   4140
tacgcgatag  aaaacaaaat  atagcgcgca  aactaggata  aattatcgcg  cgcggtgtca   4200
tctatgttac  tagatcgatg  tcgaatctga  tcaacctgca  ttaatgaatc  ggccaacgcg   4260
cggggagagg  cggtttgcgt  attgggcgct  cttccgcttc  ctcgctcact  gactcgctgc   4320
gctcggtcgt  tcggctgcgg  cgagcggtat  cagctcactc  aaaggcggta  atacggttat   4380
ccacagaatc  aggggataac  gcaggaaaga  acatgtgagc  aaaaggccag  caaaaggcca   4440
ggaaccgtaa  aaaggccgcg  ttgctggcgt  ttttccatag  gctccgcccc  cctgacgagc   4500
atcacaaaaa  tcgacgctca  agtcagaggt  ggcgaaaccc  gacaggacta  taaagatacc   4560
aggcgtttcc  ccctggaagc  tccctcgtgc  gctctcctgt  tccgaccctg  ccgcttaccg   4620
gatacctgtc  cgcctttctc  ccttcgggaa  gcgtggcgct  ttctcaatgc  tcacgctgta   4680
ggtatctcag  ttcggtgtag  gtcgttcgct  ccaagctggg  ctgtgtgcac  gaaccccccg   4740
ttcagcccga  ccgctgcgcc  ttatccggta  actatcgtct  tgagtccaac  ccggtaagac   4800
acgacttatc  gccactggca  gcagccactg  gtaacaggat  tagcagagcg  aggtatgtag   4860
gcggtgctac  agagttcttg  aagtggtggc  ctaactacgg  ctacactaga  aggacagtat   4920
ttggtatctg  cgctctgctg  aagccagtta  ccttcggaaa  aagagttggt  agctcttgat   4980
ccggcaaaca  aaccaccgct  ggtagcggtg  gtttttttgt  ttgcaagcag  cagattacgc   5040
gcagaaaaaa  aggatctcaa  gaagatcctt  tgatcttttc  tacgggtct   gacgctcagt   5100 ggaacgaaaa  ctcacgttaa  gggattttgg  tcatgacatt  aacctataaa  aataggcgta   5160
tcacgaggcc  ctttcgtctc  gcgcgtttcg  gtgatgacgg  tgaaaacctc  tgacacatgc   5220
```

```
agctcccgga gacggtcaca gcttgtctgt aagcggatgc cgggagcaga caagcccgtc    5280
agggcgcgtc agcgggtgtt ggcgggtgtc ggggctggct taactatgcg gcatcagagc    5340
agattgtact gagagtgcac catatggaca tattgtcgtt agaacgcggc tacaattaat    5400
acataacctt atgtatcata cacatacgat ttaggtgaca ctatagaacg gcgcgccaag    5460
cttggatcct cgaagagaag ggttaataac acactttttt aacatttttta acacaaattt    5520 tagttattta aaaatttatt aaaaaattta aaataagaag aggaactctt taaataaatc    5580
taacttacaa aatttatgat ttttaataag ttttcaccaa taaaaaatgt cataaaaata    5640
tgttaaaaag tatattatca atattctctt tatgataaat aaaaagaaaa aaaaaataaa    5700
agttaagtga aaatgagatt gaagtgactt taggtgtgta taaatatatc aaccccgcca    5760
acaatttatt taatccaaat atattgaagt atattattcc atagccttta tttatttata    5820
tatttattat ataaaagctt tatttgttct aggttgttca tgaaatattt ttttggtttt    5880
atctccgttg taagaaaatc atgtgctttg tgtcgccact cactattgca gcttttcat     5940 gcattggtca gattgacggt tgattgtatt tttgtttttt atggttttgt gttatgactt    6000
aagtcttcat ctctttatct cttcatcagg tttgatggtt acctaatatg gtccatgggt    6060
acatgcatgg ttaaattagg tggccaactt tgttgtgaac gatagaattt tttttatatt    6120
aagtaaacta ttttttatatt atgaaataat aataaaaaaa atattttatc attattaaca    6180
aaatcatatt agttaatttg ttaactctat aataaaagaa atactgtaac attcacatta    6240
catggtaaca tcttttccacc ctttcatttg tttttttgttt gatgactttt tttcttgttt    6300
aaatttattt cccttcttttt aaatttggaa tacattatca tcatatataa actaaaatac    6360
taaaaacagg attacacaaa tgataaaataa taacacaaat atttataaat ctagctgcaa    6420
tatatttaaa ctagctatat cgatattgta aaataaaact agctgcattg atactgataa    6480
aaaaatatca tgtgctttct ggactgatga tgcagtatac ttttgacatt gcctttattt    6540 tattttttcag aaaagctttc ttagttctgg gttcttcatt atttgtttcc catctccatt    6600
gtgaattgaa tcatttgctt cgtgtcacaa atacaattta gntaggtaca tgcattggtc    6660
agattcacgg tttattatgt catgacttaa gttcatggta gtacattacc tgccacgcat    6720
gcattatatt ggttagattt gataggcaaa tttggttgtc aacaatataa atataaataa    6780 tgttttttata ttacgaaata acagtgatca aaacaaacag ttttatcttt attaacaaga    6840
ttttgttttt gtttgatgac gttttttaat gtttacgctt tccccccttct tttgaattta    6900 gaacactttta tcatcataaa atcaaatact aaaaaaatta catatttcat aaataataac    6960
acaaatattt ttaaaaaatc tgaaataata atgaacaata ttacatatta tcacgaaaat    7020
tcattaataa aaatattata taaataaat gtaaatagtag ttatatgtag gaaaaaagta    7080
ctgcacgcat aatatataca aaaagattaa aatgaactat tataaataat aacactaaat    7140
taatggtgaa tcatatcaaa ataatgaaaa agtaaataaa atttgtaatt aacttctata    7200
tgtattacac acacaaataa taaataatag taaaaaaaat tatgataaat atttaccatc    7260
tcataagata tttaaaataa tgataaaaat atagattatt ttttatgcaa ctagctagcc    7320
aaaaagagaa cacggtata tataaaaaga gtacctttaa attctactgt acttccttta    7380
ttcctgacgt ttttatatca agtggacata cgtgaagatt ttaattatca gtctaaatat    7440
ttcattagca cttaatactt ttctgttta ttcctatcct ataagtagtc ccgattctcc     7500
caacattgct tattcacaca actaactaag aaagtcttcc atagccccc aagcggccgc     7560 atgtataatt ccacatacaa catttcgatc ctttttgata aaaagggaca attcacgaaa    7620
```

| | | |
|---|---|---|
| tcaagaaata | cccaaagctt tttaaaatta ggatgtaata taaataaatt aataaagcta | 7680 |
| atccaagcga | tgttgaagat tacgaagaag gtttggggct gggatcgacc tgtttgtatc | 7740 |
| gcttattgta | ttcttcgagt tcgtcgtagt acacatccca gacgcatcgg acgcacccgc | 7800 |
| tgccgcagca | atcgccgggc tccggcttct ccggcggcgg cggaatctcc ttcgccggat | 7860 |
| tcggggtttt | atcgtcgggt ttgggttgga tcgggtgcgg gatccactcg aagaatacaa | 7920 |
| taagcgatac | aaacaggtcg atcccagccc caaaccttct tcgtaatctt caacatcgct | 7980 |
| tggattagct | ttattaattt atttatatta catcctaatt ttaaaaagct ttgggtattt | 8040 |
| cttgatttcg | tgaattgtcc cttttatca aaaaggatcg aaatgttgta tgtggtctag | 8100 |
| aaatcactag | tgc | 8113 |

<210> SEQ ID NO 63
<211> LENGTH: 5267
<212> TYPE: DNA
<213> ORGANISM: artificial sequence
<220> FEATURE:
<223> OTHER INFORMATION: vector

<400> SEQUENCE: 63

| | | |
|---|---|---|
| atctgatcaa | cctgcattaa tgaatcggcc aacgcgcggg gagaggcggt ttgcgtattg | 60 |
| ggcgctcttc | cgcttcctcg ctcactgact cgctgcgctc ggtcgttcgg ctgcggcgag | 120 |
| cggtatcagc | tcactcaaag gcggtaatac ggttatccac agaatcaggg gataacgcag | 180 |
| gaaagaacat | gtgagcaaaa ggccagcaaa aggccaggaa ccgtaaaaag gccgcgttgc | 240 |
| tggcgttttt | ccataggctc cgcccccctg acgagcatca caaaaatcga cgctcaagtc | 300 |
| agaggtggcg | aaacccgaca ggactataaa gataccaggc gtttccccct ggaagctccc | 360 |
| tcgtgcgctc | tcctgttccg accctgccgc ttaccggata cctgtccgcc tttctccctt | 420 |
| cgggaagcgt | ggcgctttct caatgctcac gctgtaggta tctcagttcg gtgtaggtcg | 480 |
| ttcgctccaa | gctgggctgt gtgcacgaac cccccgttca gcccgaccgc tgcgccttat | 540 |
| ccggtaacta | tcgtcttgag tccaacccgg taagacacga cttatcgcca ctggcagcag | 600 |
| ccactggtaa | caggattagc agagcgaggt atgtaggcgg tgctacagag ttcttgaagt | 660 |
| ggtggcctaa | ctacggctac actagaagga cagtatttgg tatctgcgct ctgctgaagc | 720 |
| cagttacctt | cggaaaaaga gttggtagct cttgatccgg caaacaaacc accgctggta | 780 |
| gcggtggttt | ttttgtttgc aagcagcaga ttacgcgcag aaaaaaagga tctcaagaag | 840 |
| atcctttgat | cttttctacg gggtctgacg ctcagtggaa cgaaaactca cgttaaggga | 900 |
| ttttggtcat | gacattaacc tataaaaata ggcgtatcac gaggccctt cgtctcgcgc | 960 |
| gtttcggtga | tgacggtgaa aacctctgac acatgcagct cccggagacg tcacagctt | 1020 |
| gtctgtaagc | ggatgccggg agcagacaag cccgtcaggg cgcgtcagcg ggtgttggcg | 1080 |
| ggtgtcgggg | ctggcttaac tatgcggcat cagagcagat tgtactgaga gtgcaccata | 1140 |
| tggacatatt | gtcgttagaa cgcggctaca attaatacat aaccttatgt atcatacaca | 1200 |
| tacgatttag | gtgacactat agaacggcgc gccaagcttg gatccgtcga cggcgcgccc | 1260 |
| gatcatccgg | atatagttcc tcctttcagc aaaaaacccc tcaagacccg tttagaggcc | 1320 |
| ccaaggggtt | atgctagtta ttgctcagcg gtggcagcag ccaactcagc ttcctttcgg | 1380 |
| gctttgttag | cagccggatc gatccaagct gtacctcact attcctttgc cctcggacga | 1440 |
| gtgctggggc | gtcggtttcc actatcggcg agtacttcta cacagccatc ggtccagacg | 1500 |

```
gccgcgcttc tgcgggcgat tgtgtacgc ccgacagtcc cggctccgga tcggacgatt      1560
gcgtcgcatc gaccctgcgc ccaagctgca tcatcgaaat tgccgtcaac caagctctga      1620
tagagttggt caagaccaat gcggagcata tacgcccgga gccgcggcga tcctgcaagc      1680
tccggatgcc tccgctcgaa gtagcgcgtc tgctgctcca tacaagccaa ccacggcctc      1740
cagaagaaga tgttggcgac ctcgtattgg gaatccccga acatcgcctc gctccagtca      1800
atgaccgctg ttatgcggcc attgtccgtc aggacattgt tggagccgaa atccgcgtgc      1860
acgaggtgcc ggacttcggg gcagtcctcg gcccaaagca tcagctcatc gagagcctgc      1920
gcgacggacg cactgacggt gtcgtccatc acagtttgcc agtgatacac atggggatca      1980
gcaatcgcgc atatgaaatc acgccatgta gtgtattgac cgattccttg cggtccgaat      2040
gggccgaacc cgctcgtctg gctaagatcg gccgcagcga tcgcatccat agcctccgcg      2100
accggctgca gaacagcggg cagttcggtt tcaggcaggt cttgcaacgt gacaccctgt      2160
gcacggcggg agatgcaata ggtcaggctc tcgctgaatt ccccaatgtc aagcacttcc      2220
ggaatcggga gcgcggccga tgcaaagtgc cgataaacat aacgatcttt gtagaaacca      2280
tcggcgcagc tatttacccg caggacatat ccacgccctc ctacatcgaa gctgaaagca      2340
cgagattctt cgccctccga gagctgcatc aggtcggaga cgctgtcgaa cttttcgatc      2400
agaaacttct cgacagacgt cgcggtgagt tcaggctttt ccatgggtat atctccttct      2460
taaagttaaa caaaattatt tctagaggga accgttgtg gtctccctat agtgagtcgt      2520
attaatttcg cgggatcgag atcgatccaa ttccaatccc acaaaaatct gagcttaaca      2580
gcacagttgc tcctctcaga gcagaatcgg gtattcaaca ccctcatatc aactactacg      2640
ttgtgtataa cggtccacat gccggtatat acgatgactg gggttgtaca aaggcggcaa      2700
caaacggcgt tccggagtt gcacacaaga aatttgccac tattacagag gcaagagcag      2760
cagctgacgc gtacacaaca agtcagcaaa cagacaggtt gaacttcatc cccaaaggag      2820
aagctcaact caagcccaag agctttgcta aggccctaac aagcccacca aagcaaaaag      2880
cccactggct cacgctagga accaaaaggc ccagcagtga tccagcccca aaagagatct      2940
cctttgcccc ggagattaca atggacgatt tcctctatct ttacgatcta ggaaggaagt      3000
tcgaaggtga aggtgacgac actatgttca ccactgataa tgagaaggtt agcctcttca      3060
atttcagaaa gaatgctgac ccacagatgg ttagagaggc ctacgcagca ggtctcatca      3120
agacgatcta cccgagtaac aatctccagg agatcaaata ccttcccaag aaggttaaag      3180
atgcagtcaa aagattcagg actaattgca tcaagaacac agagaaagac atatttctca      3240
agatcagaag tactattcca gtatggacga ttcaaggctt gcttcataaa ccaaggcaag      3300
taatagagat tggagtctct aaaaaggtag ttcctactga atctaaggcc atgcatggag      3360
tctaagattc aaatcgagga tctaacagaa ctcgccgtga agactggcga acagttcata      3420
cagagtcttt tacgactcaa tgacaagaag aaaatcttcg tcaacatggt ggagcacgac      3480
actctggtct actccaaaaa tgtcaaagat acagtctcag aagaccaaag ggctattgag      3540
acttttcaac aaaggataat ttcgggaaac ctcctcggat tccattgccc agctatctgt      3600
cacttcatcg aaaggacagt agaaaaggaa ggtggctcct acaaatgcca tcattgcgat      3660
aaaggaaagg ctatcattca agatgcctct gccgacagtg gtcccaaaga tggacccca       3720
cccacgagga gcatcgtgga aaaagaagac gttccaacca cgtcttcaaa gcaagtggat      3780
tgatgtgaca tctccactga cgtaagggat gacgcacaat cccactatcc ttcgcaagac      3840
ccttcctcta tataaggaag ttcatttcat ttggagagga cacgctcgag ctcatttctc      3900
```

```
tattacttca gccataacaa aagaactctt ttctcttctt attaaaccat gaaaaagcct    3960
gaactcaccg cgacgtctgt cgagaagttt ctgatcgaaa agttcgacag cgtctccgac    4020
ctgatgcagc tctcggaggg cgaagaatct cgtgctttca gcttcgatgt aggagggcgt    4080
ggatatgtcc tgcgggtaaa tagctgcgcc gatggtttct acaaagatcg ttatgtttat    4140
cggcactttg catcggccgc gctcccgatt ccggaagtgc ttgacattgg ggaattcagc    4200
gagagcctga cctattgcat ctcccgccgt gcacagggtg tcacgttgca agacctgcct    4260
gaaaccgaac tgcccgctgt tctgcagccg gtcgcggagg ccatggatgc gatcgctgcg    4320
gccgatctta gccagacgag cgggttcggc ccattcggac cgcaaggaat cggtcaatac    4380
actacatggc gtgatttcat atgcgcgatt gctgatcccc atgtgtatca ctggcaaact    4440
gtgatggacg acaccgtcag tgcgtccgtc gcgcaggctc tcgatgagct gatgctttgg    4500
gccgaggact gccccgaagt ccggcacctc gtgcacgcgg atttcggctc caacaatgtc    4560
ctgacggaca atggccgcat aacagcggtc attgactgga gcgaggcgat gttcggggat    4620
tcccaatacg aggtcgccaa catcttcttc tggaggccgt ggttggcttg tatggagcag    4680
cagacgcgct acttcgagcg gaggcatccg gagcttgcag atcgccgcg gctccgggcg    4740
tatatgctcc gcattggtct tgaccaactc tatcagagct tggttgacgg caatttcgat    4800
gatgcagctt gggcgcaggg tcgatgcgac gcaatcgtcc gatccggagc cgggactgtc    4860
gggcgtacac aaatcgcccg cagaagcgcg gccgtctgga ccgatggctg tgtagaagta    4920
ctcgccgata gtggaaaccg acgccccagc actcgtccga gggcaaagga atagtgaggt    4980
acctaaagaa ggagtgcgtc gaagcagatc gttcaaacat ttggcaataa agtttcttaa    5040
gattgaatcc tgttgccggt cttgcgatga ttatcatata atttctgttg aattacgtta    5100
agcatgtaat aattaacatg taatgcatga cgttatttat gagatgggtt tttatgatta    5160
gagtcccgca attatacatt taatacgcga tagaaaacaa aatatagcgc gcaaactagg    5220
ataaattatc gcgcgcggtg tcatctatgt tactagatcg atgtcga                 5267
```

<210> SEQ ID NO 64
<211> LENGTH: 142
<212> TYPE: PRT
<213> ORGANISM: Populus trichocarpa

<400> SEQUENCE: 64

```
Met Glu Ala Thr Leu His Asn His Phe Leu Ser Arg Ile Phe Ser Tyr
1               5                   10                  15

Thr Leu Pro Lys Pro Lys Asn Pro Asn Asp Pro Thr His Phe Ile
            20                  25                  30

Phe Ala Met Lys Asn Pro Phe Lys Pro Ile Phe Ile Ser Pro Lys Thr
        35                  40                  45

Ile Thr Phe Asn Ser Arg Ser Gln Asp Pro Lys Ser Cys His Val Thr
    50                  55                  60

Ala Asn Phe Val Met Ala Thr Glu Asn Lys Asn Glu Gln Ile Glu Ser
65                  70                  75                  80

Thr Val Met Ser Lys Gln Gly Glu Glu Glu Ser Lys Lys Lys Thr Ala
                85                  90                  95

Pro Pro Pro Pro Pro Pro Glu Lys Pro Glu Pro Gly Asp Cys Cys
            100                 105                 110

Gly Ser Gly Cys Val Arg Cys Val Trp Asp Val Tyr Tyr Glu Glu Leu
        115                 120                 125
```

```
Glu Glu Tyr Asp Lys Leu Tyr Lys Ser Asp Ser Ser Lys Ser
    130                 135                 140
```

<210> SEQ ID NO 65
<211> LENGTH: 115
<212> TYPE: PRT
<213> ORGANISM: Oryza sativa

<400> SEQUENCE: 65

```
Met Leu Val Ala Ala Leu Arg Val Pro Ala Pro Ile Pro Ser Ser Leu
1               5                   10                  15

Pro Ser Pro Ala Arg Pro Leu Leu Arg Arg Arg Ser Ser His Arg Leu
            20                  25                  30

Pro Pro Pro Pro Pro Ala Ala Ser Met Ala Asp Ala Gly Gly Ala
        35                  40                  45

Thr Thr Asn Lys Pro Ala Pro Ala Pro Ala Pro Glu Pro Pro Glu Lys
    50                  55                  60

Pro Leu Pro Gly Asp Cys Cys Gly Ser Gly Cys Val Arg Cys Val Trp
65                  70                  75                  80

Asp Val Tyr Tyr Asp Glu Leu Asp Ala Tyr Asn Lys Ala Leu Ala Ala
                85                  90                  95

His Ser Ser Ser Ala Ser Ser Gly Ser Lys Pro Ala Thr Ser Asp Gly
            100                 105                 110

Ala Lys Ser
        115
```

<210> SEQ ID NO 66
<211> LENGTH: 122
<212> TYPE: PRT
<213> ORGANISM: Zea mays

<400> SEQUENCE: 66

```
Met Leu Gly Ala Val Val Arg Val Pro Gly Pro Ile Leu Pro Phe Leu
1               5                   10                  15

Pro Gly Pro Thr Arg Pro Leu Leu Arg Arg Arg His Tyr Leu Pro Pro
            20                  25                  30

Glu Thr Pro Met Ala Ser Ala Thr Pro Cys Asp Gly Gly Thr Gly Lys
        35                  40                  45

Pro Asp Ala Ala Pro Ala Pro Thr Pro Ala Pro Thr Pro Leu Pro Pro
    50                  55                  60

Glu Lys Pro Leu Pro Gly Asp Cys Cys Gly Ser Gly Cys Val Arg Cys
65                  70                  75                  80

Val Trp Asp Ile Tyr Phe Asp Glu Leu Asp Ala Tyr Asp Lys Ala Leu
                85                  90                  95

Ala Ala Arg Ala Ala Ser Ser Gly Ser Gly Gly Lys Asp Asp Ser Ala
            100                 105                 110

Asp Thr Lys Pro Lys Glu Gly Ala Lys Ser
        115                 120
```

<210> SEQ ID NO 67
<211> LENGTH: 122
<212> TYPE: PRT
<213> ORGANISM: Zea mays

<400> SEQUENCE: 67

```
Met Leu Gly Ala Val Val Arg Val Pro Gly Pro Ile Leu Pro Phe Leu
1               5                   10                  15

Pro Gly Pro Thr Arg Pro Leu Leu Arg Arg Arg His Tyr Leu Pro Pro
```

```
            20                  25                  30
Glu Thr Pro Met Ala Ser Ala Thr Pro Cys Asp Gly Thr Gly Lys
             35                  40                  45

Pro Asp Ala Ala Pro Ala Pro Thr Pro Ala Pro Thr Pro Leu Pro Pro
 50                  55                  60

Glu Lys Pro Leu Pro Gly Asp Cys Cys Gly Ser Gly Cys Val Arg Cys
 65                  70                  75                  80

Val Trp Asp Ile Tyr Phe Asp Glu Leu Asp Ala Tyr Asp Lys Ala Leu
                 85                  90                  95

Ala Ala His Ala Ala Ser Ser Gly Ser Gly Gly Lys Asp Asp Ser Ala
                100                 105                 110

Asp Thr Lys Pro Lys Glu Gly Ala Lys Ser
                115                 120
```

<210> SEQ ID NO 68
<211> LENGTH: 597
<212> TYPE: DNA
<213> ORGANISM: Arabidopsis thaliana

<400> SEQUENCE: 68

```
acgaaaaaag gaaatagaaa aaaaaagaag agaacaaatc tttttgatct gtgcgtatgg      60
ttgttgtgtc tcttcttcct cgaatctcga tcgttacatc accgggttct agccttcacg     120
atgtgctttt gagcatgaga tttggtttga cgcgacatct ccctctcaaa cgatctttct     180
ccaattattc aatcacttcc gtatctccag aacaacagct caaatctccg gtgaccatgg     240
cgacgaccga gagcaagaat cttgtagaag cttccaagga ggagacaaac aagaaggaga     300
cagaagataa gaaggaggtg ggagtttcgg ttcctccacc gccagagaaa ccagagcctg     360
gcgattgttg cggtagcggt tgcgtccgat gcgtttggga tgtttattac gatgagctcg     420
aagattacaa caagcagctt tctggagaaa ctaaatcaat ttgactgatt tttcctcgca     480
ttgttaatgg agaaattaaa catttgtctt tgtcgatttg atgatacagt gcttttgttg     540
aacaacattt tggatctctc tatgaacttg agctgattta cttgtgaata aagaaa        597
```

<210> SEQ ID NO 69
<211> LENGTH: 135
<212> TYPE: PRT
<213> ORGANISM: Arabidopsis thaliana

<400> SEQUENCE: 69

```
Met Val Val Val Ser Leu Leu Pro Arg Ile Ser Ile Val Thr Ser Pro
  1               5                  10                  15

Gly Ser Ser Leu His Asp Val Leu Leu Ser Met Arg Phe Gly Leu Thr
             20                  25                  30

Arg His Leu Pro Leu Lys Arg Ser Phe Ser Asn Tyr Ser Ile Thr Ser
             35                  40                  45

Val Ser Pro Glu Gln Gln Leu Lys Ser Pro Val Thr Met Ala Thr Thr
         50                  55                  60

Glu Ser Lys Asn Leu Val Glu Ala Ser Lys Glu Glu Thr Asn Lys Lys
 65                  70                  75                  80

Glu Thr Glu Asp Lys Lys Glu Val Gly Val Ser Val Pro Pro Pro
                 85                  90                  95

Glu Lys Pro Glu Pro Gly Asp Cys Cys Gly Ser Gly Cys Val Arg Cys
                100                 105                 110

Val Trp Asp Val Tyr Tyr Asp Glu Leu Glu Asp Tyr Asn Lys Gln Leu
                115                 120                 125
```

Ser Gly Glu Thr Lys Ser Ile
    130             135

<210> SEQ ID NO 70
<211> LENGTH: 27
<212> TYPE: PRT
<213> ORGANISM: Artificial sequence
<220> FEATURE:
<223> OTHER INFORMATION: misc_feature
<220> FEATURE:
<221> NAME/KEY: misc_feature
<222> LOCATION: (5)..(5)
<223> OTHER INFORMATION: X=EorL
<220> FEATURE:
<221> NAME/KEY: misc_feature
<222> LOCATION: (6)..(6)
<223> OTHER INFORMATION: X=A or P
<220> FEATURE:
<221> NAME/KEY: misc_feature
<222> LOCATION: (17)..(17)
<223> OTHER INFORMATION: X=any amino acid
<220> FEATURE:
<221> NAME/KEY: misc_feature
<222> LOCATION: (18)..(18)
<223> OTHER INFORMATION: X=any amino acid
<220> FEATURE:
<221> NAME/KEY: misc_feature
<222> LOCATION: (19)..(19)
<223> OTHER INFORMATION: X=any amino acid
<220> FEATURE:
<221> NAME/KEY: misc_feature
<222> LOCATION: (21)..(21)
<223> OTHER INFORMATION: X=V or I
<220> FEATURE:
<221> NAME/KEY: misc_feature
<222> LOCATION: (23)..(23)
<223> OTHER INFORMATION: X=Y or F
<220> FEATURE:
<221> NAME/KEY: misc_feature
<222> LOCATION: (24)..(24)
<223> OTHER INFORMATION: X=D or E
<220> FEATURE:
<221> NAME/KEY: misc_feature
<222> LOCATION: (27)..(27)
<223> OTHER INFORMATION: X=D or E

<400> SEQUENCE: 70

Pro Glu Lys Pro Xaa Xaa Gly Asp Cys Cys Gly Ser Gly Cys Val Arg
1               5                   10                  15

Xaa Xaa Xaa Asp Xaa Tyr Xaa Xaa Glu Leu Xaa
            20                  25

<210> SEQ ID NO 71
<211> LENGTH: 30
<212> TYPE: DNA
<213> ORGANISM: artificial sequence
<220> FEATURE:
<223> OTHER INFORMATION: primer

<400> SEQUENCE: 71
gcggccgcgt tgttgtgtct cttcttcctc                                      30

<210> SEQ ID NO 72
<211> LENGTH: 30
<212> TYPE: DNA
<213> ORGANISM: artificial sequence
<220> FEATURE:
<223> OTHER INFORMATION: primer

<400> SEQUENCE: 72
ggatccctac aagattcttg ctctcggtcg                                      30

<210> SEQ ID NO 73
<211> LENGTH: 30
<212> TYPE: DNA
<213> ORGANISM: artificial sequence
<220> FEATURE:
<223> OTHER INFORMATION: ggatccttccaaggaggagacaaacaagaa

<400> SEQUENCE: 73
ggatccttcc aaggaggaga caaacaagaa                                    30

<210> SEQ ID NO 74
<211> LENGTH: 30
<212> TYPE: DNA
<213> ORGANISM: artificial sequence
<220> FEATURE:
<223> OTHER INFORMATION: primer

<400> SEQUENCE: 74
gctgcagtta gtttctccag aaagctgctt                                    30

<210> SEQ ID NO 75
<211> LENGTH: 38
<212> TYPE: DNA
<213> ORGANISM: artificial sequence
<220> FEATURE:
<223> OTHER INFORMATION: primer

<400> SEQUENCE: 75
gaattcgcgg ccgcgttgtt gtgtctcttc ttcctcga                           38

<210> SEQ ID NO 76
<211> LENGTH: 30
<212> TYPE: DNA
<213> ORGANISM: artificial sequence
<220> FEATURE:
<223> OTHER INFORMATION: primer

<400> SEQUENCE: 76
ctgcagctac aagattcttg ctctcggtcg                                    30

<210> SEQ ID NO 77
<211> LENGTH: 3239
<212> TYPE: DNA
<213> ORGANISM: artificial sequence
<220> FEATURE:
<223> OTHER INFORMATION: plasmid

<400> SEQUENCE: 77
taatcactag tgaattcgcg gccgcctgca ggtcgaccat atgggagagc tcccaacgcg    60
ttggatgcat agcttgagta ttctatagtg tcacctaaat agcttggcgt aatcatggtc   120
atagctgttt cctgtgtgaa attgttatcc gctcacaatt ccacacaaca tacgagccgg   180
aagcataaag tgtaaagcct ggggtgccta atgagtgagc taactcacat taattgcgtt   240
gcgctcactg cccgctttcc agtcgggaaa cctgtcgtgc cagctgcatt aatgaatcgg   300
ccaacgcgcg gggagaggcg gtttgcgtat tgggcgctct tccgcttcct cgctcactga   360
ctcgctgcgc tcggtcgttc ggctgcggcg agcggtatca gctcactcaa aggcggtaat   420
acggttatcc acagaatcag gggataacgc aggaaagaac atgtgagcaa aaggccagca   480
aaaggccagg aaccgtaaaa aggccgcgtt gctggcgttt ttccataggc tccgcccccc   540
tgacgagcat cacaaaaatc gacgctcaag tcagaggtgg cgaaacccga caggactata   600

```
aagataccag gcgtttcccc ctggaagctc cctcgtgcgc tctcctgttc cgaccctgcc      660
gcttaccgga tacctgtccg cctttctccc ttcgggaagc gtggcgcttt ctcatagctc      720
acgctgtagg tatctcagtt cggtgtaggt cgttcgctcc aagctgggct gtgtgcacga      780
accccccgtt cagcccgacc gctgcgcctt atccggtaac tatcgtcttg agtccaaccc      840
ggtaagacac gacttatcgc cactggcagc agccactggt aacaggatta gcagagcgag      900
gtatgtaggc ggtgctacag agttcttgaa gtggtggcct aactacggct acactagaag      960
aacagtattt ggtatctgcg ctctgctgaa gccagttacc ttcggaaaaa gagttggtag     1020
ctcttgatcc ggcaaacaaa ccaccgctgg tagcggtggt ttttttgttt gcaagcagca     1080
gattacgcgc agaaaaaaag gatctcaaga agatcctttg atcttttcta cggggtctga     1140
cgctcagtgg aacgaaaact cacgttaagg gattttggtc atgagattat caaaaaggat     1200
cttcacctag atccttttaa attaaaaatg aagttttaaa tcaatctaaa gtatatatga     1260
gtaaacttgg tctgacagtt accaatgctt aatcagtgag gcacctatct cagcgatctg     1320
tctatttcgt tcatccatag ttgcctgact ccccgtcgtg tagataacta cgatacggga     1380
gggcttacca tctggcccca gtgctgcaat gataccgcga gacccacgct caccggctcc     1440
agatttatca gcaataaacc agccagccgg aagggccgag cgcagaagtg gtcctgcaac     1500
tttatccgcc tccatccagt ctattaattg ttgccgggaa gctagagtaa gtagttcgcc     1560
agttaatagt ttgcgcaacg ttgttgccat tgctacaggc atcgtggtgt cacgctcgtc     1620
gtttggtatg gcttcattca gctccggttc ccaacgatca aggcgagtta catgatcccc     1680
catgttgtgc aaaaaagcgg ttagctcctt cggtcctccg atcgttgtca gaagtaagtt     1740
ggccgcagtg ttatcactca tggttatggc agcactgcat aattctctta ctgtcatgcc     1800
atccgtaaga tgcttttctg tgactggtga gtactcaacc aagtcattct gagaatagtg     1860
tatgcggcga ccgagttgct cttgcccggc gtcaatacgg gataataccg cgccacatag     1920
cagaacttta aaagtgctca tcattggaaa acgttcttcg gggcgaaaac tctcaaggat     1980
cttaccgctg ttgagatcca gttcgatgta acccactcgt gcacccaact gatcttcagc     2040
atcttttact ttcaccagcg tttctgggtg agcaaaaaca ggaaggcaaa atgccgcaaa     2100
aaagggaata agggcgacac ggaaatgttg aatactcata ctcttccttt ttcaatatta     2160
ttgaagcatt tatcagggtt attgtctcat gagcggatac atatttgaat gtatttagaa     2220
aaataaacaa ataggggttc cgcgcacatt tccccgaaaa gtgccacctg atgcggtgtg     2280
aaataccgca cagatgcgta aggagaaaat accgcatcag gaaattgtaa gcgttaatat     2340
tttgttaaaa ttcgcgttaa attttttgtta aatcagctca ttttttaacc aataggccga     2400
aatcggcaaa atcccttata aatcaaaaga tagaccgag ataggggttga gtgttgttcc     2460 agtttggaac aagagtccac tattaaagaa cgtggactcc aacgtcaaag ggcgaaaaac     2520
cgtctatcag ggcgatggcc cactacgtga accatcaccc taatcaagtt ttttggggtc     2580
gaggtgccgt aaagcactaa atcggaaccc taaagggagc ccccgattta gagcttgacg     2640
gggaaagccg gcgaacgtgg cgagaaagga agggaagaaa gcgaaaggag cgggcgctag     2700
ggcgctggca agtgtagcgg tcacgctgcg cgtaaccacc acaccccgccg cgcttaatgc     2760 gccgctacag ggcgcgtcca ttcgccattc aggctgcgca actgttggga agggcgatcg     2820
gtgcgggcct cttcgctatt acgccagctg gcgaaagggg gatgtgctgc aaggcgatta     2880
agttgggtaa cgccagggtt ttcccagtca cgacgttgta aaacgacggc cagtgaattg     2940
taatacgact cactataggg cgaattgggc ccgacgtcgc atgctcccgg ccgccatggc     3000
```

```
ggccgcggga attcgatgcg gccgcgttgt tgtgtctctt cttcctcgaa tctcgatcgt   3060
tacatcaccg ggttctagcc ttcacgatgt gcttttgagc atgagatttg gtttgacgcg   3120
acatctccct ctcaaacgat ctttctccaa ttattcaatc acttccgtat ctccagaaca   3180
acagctcaaa tctccggtga ccatggcgac gaccgagagc aagaatcttg tagggatcc    3239
```

<210> SEQ ID NO 78
<211> LENGTH: 3213
<212> TYPE: DNA
<213> ORGANISM: artificial sequence
<220> FEATURE:
<223> OTHER INFORMATION: plasmid

<400> SEQUENCE: 78

```
taatcactag tgaattcgcg gccgcctgca ggtcgaccat atgggagagc tcccaacgcg     60
ttggatgcat agcttgagta ttctatagtg tcacctaaat agcttggcgt aatcatggtc    120
atagctgttt cctgtgtgaa attgttatcc gctcacaatt ccacacaaca tacgagccgg    180
aagcataaag tgtaaagcct ggggtgccta atgagtgagc taactcacat taattgcgtt    240
gcgctcactg cccgctttcc agtcgggaaa cctgtcgtgc cagctgcatt aatgaatcgg    300
ccaacgcgcg gggagaggcg gtttgcgtat tgggcgctct tccgcttcct cgctcactga    360
ctcgctgcgc tcggtcgttc ggctgcggcg agcggtatca gctcactcaa aggcggtaat    420
acggttatcc acagaatcag gggataacgc aggaaagaac atgtgagcaa aaggccagca    480
aaaggccagg aaccgtaaaa aggccgcgtt gctggcgttt ttccataggc tccgcccccc    540
tgacgagcat cacaaaaatc gacgctcaag tcagaggtgg cgaaacccga caggactata    600
aagataccag gcgtttcccc ctggaagctc cctcgtgcgc tctcctgttc cgaccctgcc    660
gcttaccgga tacctgtccg cctttctccc ttcgggaagc gtggcgcttt ctcatagctc    720
acgctgtagg tatctcagtt cggtgtaggt cgttcgctcc aagctgggct gtgtgcacga    780
accccccgtt cagcccgacc gctgcgcctt atccggtaac tatcgtcttg agtccaaccc    840
ggtaagacac gacttatcgc cactggcagc agccactggt aacaggatta gcagagcgag    900
gtatgtaggc ggtgctacag agttcttgaa gtggtggcct aactacggct acactagaag    960
aacagtattt ggtatctgcg ctctgctgaa gccagttacc ttcggaaaaa gagttggtag   1020
ctcttgatcc ggcaaacaaa ccaccgctgg tagcggtggt ttttttgttt gcaagcagca   1080
gattacgcgc agaaaaaaag gatctcaaga agatcctttg atcttttcta cggggtctga   1140
cgctcagtgg aacgaaaact cacgttaagg gattttggtc atgagattat caaaaaggat   1200
cttcacctag atccttttaa attaaaaatg aagttttaaa tcaatctaaa gtatatatga   1260
gtaaacttgg tctgacagtt accaatgctt aatcagtgag gcacctatct cagcgatctg   1320
tctatttcgt tcatccatag ttgcctgact ccccgtcgtg tagataacta cgatacggga   1380
gggcttacca tctggcccca gtgctgcaat gataccgcga acccacgct caccggctcc    1440 agatttatca gcaataaacc agccagccgg aagggccgag cgcagaagtg gtcctgcaac   1500
tttatccgcc tccatccagt ctattaattg ttgccgggaa gctagagtaa gtagttcgcc   1560
agttaatagt ttgcgcaacg ttgttgccat tgctacaggc atcgtggtgt cacgctcgtc   1620
gtttggtatg gcttcattca gctccggttc ccaacgatca aggcgagtta catgatcccc   1680
catgttgtgc aaaaaagcgg ttagctcctt cggtcctccg atcgttgtca gaagtaagtt   1740
ggccgcagtg ttatcactca tggttatggc agcactgcat aattctctta ctgtcatgcc   1800
```

```
atccgtaaga tgcttttctg tgactggtga gtactcaacc aagtcattct gagaatagtg    1860
tatgcggcga ccgagttgct cttgcccggc gtcaataccg gataataccg cgccacatag    1920
cagaacttta aaagtgctca tcattggaaa acgttcttcg gggcgaaaac tctcaaggat    1980
cttaccgctg ttgagatcca gttcgatgta acccactcgt gcacccaact gatcttcagc    2040
atcttttact ttcaccagcg tttctgggtg agcaaaaaca ggaaggcaaa atgccgcaaa    2100
aaagggaata agggcgacac ggaaatgttg aatactcata ctcttccttt ttcaatatta    2160
ttgaagcatt tatcagggtt attgtctcat gagcggatac atatttgaat gtatttagaa    2220
aaataaacaa ataggggttc cgcgcacatt tccccgaaaa gtgccacctg atgcggtgtg    2280
aaataccgca cagatgcgta aggagaaaat accgcatcag gaaattgtaa gcgttaatat    2340
tttgttaaaa ttcgcgttaa attttttgtta aatcagctca ttttttaacc aataggccga    2400
aatcggcaaa atcccttata atcaaaaga atagaccgag atagggttga gtgttgttcc    2460
agtttggaac aagagtccac tattaaagaa cgtggactcc aacgtcaaag ggcgaaaaac    2520
cgtctatcag ggcgatggcc cactacgtga accatcaccc taatcaagtt ttttggggtc    2580
gaggtgccgt aaagcactaa atcggaaccc taaagggagc ccccgattta gagcttgacg    2640
gggaaagccg gcgaacgtgg cgagaaagga agggaagaaa gcgaaaggag cgggcgctag    2700
ggcgctggca agtgtagcgg tcacgctgcg cgtaaccacc acacccgccg cgcttaatgc    2760
gccgctacag ggcgcgtcca ttcgccattc aggctgcgca actgttggga agggcgatcg    2820
gtgcgggcct cttcgctatt acgccagctg gcgaaagggg gatgtgctgc aaggcgatta    2880
agttgggtaa cgccagggtt ttcccagtca cgacgttgta aaacgacggc cagtgaattg    2940
taatacgact cactataggg cgaattgggc ccgacgtcgc atgctcccgg ccgccatggc    3000
ggccgcggga attcgatgga tccttccaag gaggagacaa acaagaagga gacagaagat    3060
aagaaggagg tgggagtttc ggttcctcca ccgccagaga aaccagagcc tggcgattgt    3120
tgcggtagcg gttgcgtccg atgcgtttgg gatgttattt acgatgagct cgaagattac    3180
aacaagcagc tttctggaga aactaactgc agc                                 3213
```

<210> SEQ ID NO 79
<211> LENGTH: 3245
<212> TYPE: DNA
<213> ORGANISM: artificial sequence
<220> FEATURE:
<223> OTHER INFORMATION: plasmid

<400> SEQUENCE: 79

```
taatcactag tgaattcgcg gccgcctgca ggtcgaccat atgggagagc tcccaacgcg     60
ttggatgcat agcttgagta ttctatagtg tcacctaaat agcttggcgt aatcatggtc    120
atagctgttt cctgtgtgaa attgttatcc gctcacaatt ccacacaaca tacgagccgg    180
aagcataaag tgtaaagcct ggggtgccta atgagtgagc taactcacat taattgcgtt    240
gcgctcactg cccgctttcc agtcgggaaa cctgtcgtgc cagctgcatt aatgaatcgg    300
ccaacgcgcg gggagaggcg gtttgcgtat tgggcgctct tccgcttcct cgctcactga    360
ctcgctgcgc tcggtcgttc ggctgcggcg agcggtatca gctcactcaa aggcggtaat    420
acggttatcc acagaatcag gggataacgc aggaaagaac atgtgagcaa aaggccagca    480
aaaggccagg aaccgtaaaa aggccgcgtt gctggcgttt ttccataggc tccgcccccc    540
tgacgagcat cacaaaaatc gacgctcaag tcagaggtgg cgaaacccga caggactata    600
aagataccag gcgtttcccc ctggaagctc cctcgtgcgc tctcctgttc cgaccctgcc    660
```

```
gcttaccgga tacctgtccg cctttctccc ttcgggaagc gtggcgcttt ctcatagctc    720
acgctgtagg tatctcagtt cggtgtaggt cgttcgctcc aagctgggct gtgtgcacga    780
acccccgtt cagcccgacc gctgcgcctt atccggtaac tatcgtcttg agtccaaccc    840
ggtaagacac gacttatcgc cactggcagc agccactggt aacaggatta gcagagcgag    900
gtatgtaggc ggtgctacag agttcttgaa gtggtggcct aactacggct acactagaag    960
aacagtattt ggtatctgcg ctctgctgaa gccagttacc ttcggaaaaa gagttggtag   1020
ctcttgatcc ggcaaacaaa ccaccgctgg tagcggtggt ttttttgttt gcaagcagca   1080
gattacgcgc agaaaaaaag gatctcaaga agatcctttg atcttttcta cggggtctga   1140
cgctcagtgg aacgaaaact cacgttaagg gattttggtc atgagattat caaaaaggat   1200
cttcacctag atcctttaa attaaaaatg aagttttaaa tcaatctaaa gtatatgta    1260
gtaaacttgg tctgacagtt accaatgctt aatcagtgag gcacctatct cagcgatctg   1320
tctatttcgt tcatccatag ttgcctgact ccccgtcgtg tagataacta cgatacggga   1380
gggcttacca tctggcccca gtgctgcaat gataccgcga gcccacgct caccggctcc    1440
agatttatca gcaataaacc agccagccgg aagggccgag cgcagaagtg gtcctgcaac   1500
tttatccgcc tccatccagt ctattaattg ttgccgggaa gctagagtaa gtagttcgcc   1560
agttaatagt ttgcgcaacg ttgttgccat tgctacaggc atcgtggtgt cacgctcgtc   1620
gtttggtatg gcttcattca gctccggttc ccaacgatca aggcgagtta catgatcccc   1680
catgttgtgc aaaaaagcgg ttagctcctt cggtcctccg atcgttgtca gaagtaagtt   1740
ggccgcagtg ttatcactca tggttatggc agcactgcat aattctctta ctgtcatgcc   1800
atccgtaaga tgcttttctg tgactggtga gtactcaacc aagtcattct gagaatagtg   1860
tatgcggcga ccgagttgct cttgcccggc gtcaatacgg gataataccg cgccacatag   1920
cagaacttta aaagtgctca tcattggaaa acgttcttcg gggcgaaaac tctcaaggat   1980
cttaccgctg ttgagatcca gttcgatgta acccactcgt gcacccaact gatcttcagc   2040
atcttttact ttcaccagcg tttctgggtg agcaaaaaca ggaaggcaaa atgccgcaaa   2100
aaagggaata agggcgacac ggaaatgttg aatactcata ctcttccttt ttcaatatta   2160
ttgaagcatt tatcagggtt attgtctcat gagcggatac atatttgaat gtatttagaa   2220
aaataaacaa ataggggttc cgcgcacatt tccccgaaaa gtgccacctg atgcggtgtg   2280
aaataccgca cagatgcgta aggagaaaat accgcatcag gaaattgtaa gcgttaatat   2340
tttgttaaaa ttcgcgttaa atttttgtta aatcagctca ttttttaacc aataggccga   2400
aatcggcaaa atcccttata aatcaaaaga atagaccgag atagggttga gtgttgttcc   2460
agtttggaac aagagtccac tattaaagaa cgtggactcc aacgtcaaag ggcgaaaaac   2520
cgtctatcag ggcgatggcc cactacgtga accatcaccc taatcaagtt ttttggggtc   2580
gaggtgccgt aaagcactaa atcggaaccc taaagggagc ccccgattta gagcttgacg   2640
gggaaagccg gcgaacgtgg cgagaaagga agggaagaaa gcgaaaggag cgggcgctag   2700
ggcgctggca agtgtagcgg tcacgctgcg cgtaaccacc acacccgccg cgcttaatgc   2760
gccgctacag ggcgcgtcca ttcgccattc aggctgcgca actgttggga agggcgatcg   2820
gtgcgggcct cttcgctatt acgccagctg gcgaaagggg gatgtgctgc aaggcgatta   2880
agttgggtaa cgccagggtt ttcccagtca cgacgttgta aaacgacggc cagtgaattg   2940
taatacgact cactataggg cgaattgggc ccgacgtcgc atgctcccgg ccgccatggc   3000
```

| | |
|---|---|
| ggccgcggga attcgatctg cagctacaag attcttgctc tcggtcgtcg ccatggtcac | 3060 |
| cggagatttg agctgttgtt ctggagatac ggaagtgatt gaataattgg agaaagatcg | 3120 |
| tttgagaggg agatgtcgcg tcaaaccaaa tctcatgctc aaaagcacat cgtgaaggct | 3180 |
| agaacccggt gatgtaacga tcgagattcg aggaagaaga gacacaacaa cgcggccgcg | 3240 |
| aattc | 3245 |

<210> SEQ ID NO 80
<211> LENGTH: 3154
<212> TYPE: DNA
<213> ORGANISM: artificial sequence
<220> FEATURE:
<223> OTHER INFORMATION: plasmid

<400> SEQUENCE: 80

| | |
|---|---|
| gatcccccgg gctgcaggaa ttcgatatca agcttatcga taccgtcgac ctcgaggggg | 60 |
| ggcccggtac ccagcttttg ttcccttag tgagggttaa tttcgagctt ggcgtaatca | 120 |
| tggtcatagc tgtttcctgt gtgaaattgt tatccgctca caattccaca acatacga | 180 |
| gccggaagca taaagtgtaa agcctggggt gcctaatgag tgagctaact cacattaatt | 240 |
| gcgttgcgct cactgcccgc tttccagtcg ggaaacctgt cgtgccagct gcattaatga | 300 |
| atcggccaac gcgcgggag aggcggtttg cgtattgggc gctcttccgc ttcctcgctc | 360 |
| actgactcgc tgcgctcggt cgttcggctg cggcgagcgg tatcagctca ctcaaaggcg | 420 |
| gtaatacggt tatccacaga atcaggggat aacgcaggaa agaacatgtg agcaaaaggc | 480 |
| cagcaaaagg ccaggaaccg taaaaaggcc gcgttgctgg cgtttttcca taggctccgc | 540 |
| ccccctgacg agcatcacaa aaatcgacgc tcaagtcaga ggtggcgaaa cccgacagga | 600 |
| ctataaagat accaggcgtt tcccctgga agctccctcg tgcgctctcc tgttccgacc | 660 |
| ctgccgctta ccggatacct gtccgccttt ctcccttcgg aagcgtggc gctttctcat | 720 |
| agctcacgct gtaggtatct cagttcggtg taggtcgttc gctccaagct gggctgtgtg | 780 |
| cacgaacccc ccgttcagcc cgaccgctgc gccttatccg gtaactatcg tcttgagtcc | 840 |
| aacccggtaa gacacgactt atcgccactg gcagcagcca ctggtaacag gattagcaga | 900 |
| gcgaggtatg taggcggtgc tacagagttc ttgaagtggt ggcctaacta cggctacact | 960 |
| agaaggacag tatttggtat ctgcgctctg ctgaagccag ttaccttcgg aaaaagagtt | 1020 |
| ggtagctctt gatccggcaa acaaaccacc gctggtagcg tggtttttt tgtttgcaag | 1080 |
| cagcagatta cgcgcagaaa aaaggatct caagaagatc ctttgatctt ttctacgggg | 1140 |
| tctgacgctc agtggaacga aaactcacgt taagggattt tggtcatgag attatcaaaa | 1200 |
| aggatcttca cctagatcct tttaaattaa aaatgaagtt ttaaatcaat ctaaagtata | 1260 |
| tatgagtaaa cttggtctga cagttaccaa tgcttaatca gtgaggcacc tatctcagcg | 1320 |
| atctgtctat ttcgttcatc catagttgcc tgactcccg tcgtgtagat aactacgata | 1380 |
| cgggagggct taccatctgg ccccagtgct gcaatgatac cgcgagaccc acgctcaccg | 1440 |
| gctccagatt tatcagcaat aaaccagcca gccggaaggg ccgagcgcag aagtggtcct | 1500 |
| gcaactttat ccgcctccat ccagtctatt aattgttgcc gggaagctag agtaagtagt | 1560 |
| tcgccagtta atagtttgcg caacgttgtt gccattgcta caggcatcgt ggtgtcacgc | 1620 |
| tcgtcgtttg gtatggcttc attcagctcc ggttcccaac gatcaaggcg agttacatga | 1680 |
| tcccccatgt tgtgcaaaaa agcggttagc tccttcggtc ctccgatcgt tgtcagaagt | 1740 |
| aagttggccg cagtgttatc actcatggtt atggcagcac tgcataattc tcttactgtc | 1800 |

```
atgccatccg taagatgctt ttctgtgact ggtgagtact caaccaagtc attctgagaa    1860
tagtgtatgc ggcgaccgag ttgctcttgc ccggcgtcaa tacgggataa taccgcgcca    1920
catagcagaa ctttaaaagt gctcatcatt ggaaaacgtt cttcggggcg aaaactctca    1980
aggatcttac cgctgttgag atccagttcg atgtaaccca ctcgtgcacc caactgatct    2040
tcagcatctt ttactttcac cagcgtttct gggtgagcaa aacaggaag gcaaaatgcc    2100 gcaaaaaagg gaataagggc gacacggaaa tgttgaatac tcatactctt ccttttcaa    2160 tattattgaa gcatttatca gggttattgt ctcatgagcg gatacatatt tgaatgtatt    2220
tagaaaaata acaaatagg ggttccgcgc acatttcccc gaaaagtgcc acctaaattg    2280
taagcgttaa tattttgtta aaattcgcgt taaattttg ttaaatcagc tcatttttta    2340
accaataggc cgaaatcggc aaaatccctt ataaatcaaa agaatagacc gagataggt    2400 tgagtgttgt tccagtttgg aacaagagtc cactattaaa gaacgtggac tccaacgtca    2460
aagggcgaaa aaccgtctat cagggcgatg gcccactacg tgaaccatca ccctaatcaa    2520
gttttttggg gtcgaggtgc cgtaaagcac taaatcggaa ccctaaaggg agcccccgat    2580
ttagagcttg acggggaaag ccggcgaacg tggcgagaaa ggaagggaag aaagcgaaag    2640
gagcgggcgc tagggcgctg gcaagtgtag cggtcacgct gcgcgtaacc accacccg    2700 ccgcgcttaa tgccgcgcta cagggcgcgt cccattcgcc attcaggctg cgcaactgtt    2760
gggaagggcg atcggtgcgg gcctcttcgc tattacgcca gctggcgaaa ggggatgtg    2820 ctgcaaggcg attaagttgg gtaacgccag ggtttcccca gtcacgacgt tgtaaaacga    2880
cggccagtga attgtaatac gactcactat agggcgaatt ggagctccac cgcggtggcg    2940
gccgcgttgt tgtgtctctt cttcctcgaa tctcgatcgt tacatcaccg ggttctagcc    3000
ttcacgatgt gcttttgagc atgagatttg gtttgacgcg acatctccct ctcaaacgat    3060
ctttctccaa ttattcaatc acttccgtat ctccagaaca acagctcaaa tctccggtga    3120
ccatggcgac gaccgagagc aagaatcttg tagg                                3154
```

<210> SEQ ID NO 81
<211> LENGTH: 3331
<212> TYPE: DNA
<213> ORGANISM: artificial sequence
<220> FEATURE:
<223> OTHER INFORMATION: plasmid

<400> SEQUENCE: 81

```
ggaattcgat atcaagctta tcgataccgt cgacctcgag ggggggcccg gtacccagct      60
tttgttccct ttagtgaggg ttaatttcga gcttggcgta atcatggtca tagctgtttc     120
ctgtgtgaaa ttgttatccg ctcacaattc cacacaacat acgagccgga agcataaagt     180
gtaaagcctg gggtgcctaa tgagtgagct aactcacatt aattgcgttg cgctcactgc     240
ccgctttcca gtcgggaaac ctgtcgtgcc agctgcatta atgaatcggc caacgcgcgg     300
ggagaggcgg tttgcgtatt gggcgctctt ccgcttcctc gctcactgac tcgctgcgct     360
cggtcgttcg gctgcggcga gcggtatcag ctcactcaaa ggcggtaata cggttatcca     420
cagaatcagg ggataacgca ggaaagaaca tgtgagcaaa aggccagcaa aaggccagga     480
accgtaaaaa ggccgcgttg ctggcgtttt tccataggct ccgcccccct gacgagcatc     540
acaaaaatcg acgctcaagt cagaggtggc gaaacccgac aggactataa agataccagg     600
cgtttccccc tggaagctcc ctcgtgcgct ctcctgttcc gaccctgccg cttaccggat     660
```

```
acctgtccgc ctttctccct tcgggaagcg tggcgctttc tcatagctca cgctgtaggt    720
atctcagttc ggtgtaggtc gttcgctcca agctgggctg tgtgcacgaa ccccccgttc    780
agcccgaccg ctgcgcctta tccggtaact atcgtcttga gtccaacccg gtaagacacg    840
acttatcgcc actggcagca gccactggta acaggattag cagagcgagg tatgtaggcg    900
gtgctacaga gttcttgaag tggtggccta actacggcta cactagaagg acagtatttg    960
gtatctgcgc tctgctgaag ccagttacct tcggaaaaag agttggtagc tcttgatccg   1020
gcaaacaaac caccgctggt agcggtggtt tttttgtttg caagcagcag attacgcgca   1080 gaaaaaagg atctcaagaa gatcctttga tcttttctac ggggtctgac gctcagtgga   1140
acgaaaactc acgttaaggg attttggtca tgagattatc aaaaaggatc ttcacctaga   1200 tcctttaaa ttaaaatga agttttaaat caatctaaag tatatatgag taaacttggt   1260
ctgacagtta ccaatgctta atcagtgagg cacctatctc agcgatctgt ctatttcgtt   1320
catccatagt tgcctgactc cccgtcgtgt agataactac gatacgggag gcttaccat   1380 ctggccccag tgctgcaatg ataccgcgag acccacgctc accggctcca gatttatcag   1440
caataaacca gccagccgga agggccgagc gcagaagtgg tcctgcaact ttatccgcct   1500
ccatccagtc tattaattgt tgccgggaag ctagagtaag tagttcgcca gttaatagtt   1560
tgcgcaacgt tgttgccatt gctacaggca tcgtggtgtc acgctcgtcg tttggtatgg   1620
cttcattcag ctccggttcc caacgatcaa ggcgagttac atgatccccc atgttgtgca   1680
aaaaagcggt tagctccttc ggtcctccga tcgttgtcag aagtaagttg gccgcagtgt   1740
tatcactcat ggttatggca gcactgcata attctcttac tgtcatgcca tccgtaagat   1800
gcttttctgt gactggtgag tactcaacca agtcattctg agaatagtgt atgcggcgac   1860
cgagttgctc ttgcccggcg tcaatacggg ataataccgc gccacatagc agaactttaa   1920
aagtgctcat cattggaaaa cgttcttcgg ggcgaaaact ctcaaggatc ttaccgctgt   1980
tgagatccag ttcgatgtaa cccactcgtg cacccaactg atcttcagca tcttttactt   2040
tcaccagcgt ttctgggtga gcaaaaacag gaaggcaaaa tgccgcaaaa aagggaataa   2100
gggcgacacg gaaatgttga atactcatac tcttcctttt tcaatattat tgaagcattt   2160
atcagggtta ttgtctcatg agcggataca tatttgaatg tatttagaaa aataaacaaa   2220
taggggttcc gcgcacattt ccccgaaaag tgccacctaa attgtaagcg ttaatatttt   2280
gttaaaattc gcgttaaatt tttgttaaat cagctcattt tttaaccaat aggccgaaat   2340
cggcaaaatc ccttataaat caaaagaata gaccgagata gggttgagtg ttgttccagt   2400
ttggaacaag agtccactat taaagaacgt ggactccaac gtcaaagggc gaaaaaccgt   2460
ctatcagggc gatggcccac tacgtgaacc atcaccctaa tcaagttttt tggggtcgag   2520
gtgccgtaaa gcactaaatc ggaaccctaa agggagcccc cgatttagag cttgacgggg   2580
aaagccggcg aacgtggcga gaaaggaagg gaagaaagcg aaaggagcgg cgctagggc   2640 gctggcaagt gtagcggtca cgctgcgcgt aaccaccaca cccgccgcgc ttaatgcgcc   2700
gctacagggc gcgtcccatt cgccattcag gctgcgcaac tgttgggaag ggcgatcggt   2760
gcgggcctct tcgctattac gccagctggc gaaagggga tgtgctgcaa ggcgattaag   2820
ttgggtaacg ccagggtttt cccagtcacg acgttgtaaa acgacggcca gtgaattgta   2880
atacgactca ctatagggcg aattggagct ccaccgcggt ggcggccgcg ttgttgtgtc   2940
tcttcttcct cgaatctcga tcgttacatc accgggttct agccttcacg atgtgctttt   3000
gagcatgaga tttggtttga cgcgacatct ccctctcaaa cgatctttct ccaattattc   3060
```

```
aatcacttcc gtatctccag aacaacagct caaatctccg gtgaccatgg cgacgaccga    3120
gagcaagaat cttgtaggga tccttccaag gaggagacaa acaagaagga dacagaagat    3180
aagaaggagg tgggagtttc ggttcctcca ccgccagaga accagagcc tggcgattgt     3240 tgcggtagcg gttgcgtccg atgcgtttgg gatgtttatt acgatgagct cgaagattac    3300
aacaagcagc tttctggaga aactaactgc a                                   3331
```

<210> SEQ ID NO 82
<211> LENGTH: 3547
<212> TYPE: DNA
<213> ORGANISM: artificial sequence
<220> FEATURE:
<223> OTHER INFORMATION: plasmid

<400> SEQUENCE: 82

```
aattcgatat caagcttatc gataccgtcg acctcgaggg ggggcccggt acccagcttt      60
tgttcccttt agtgagggtt aatttcgagc ttggcgtaat catggtcata gctgtttcct     120
gtgtgaaatt gttatccgct cacaattcca cacaacatac gagccggaag cataaagtgt     180
aaagcctggg gtgcctaatg agtgagctaa ctcacattaa ttgcgttgcg ctcactgccc     240
gctttccagt cgggaaacct gtcgtgccag ctgcattaat gaatcggcca acgcgcgggg    300
agaggcggtt tgcgtattgg gcgctcttcc gcttcctcgc tcactgactc gctgcgctcg    360
gtcgttcggc tgcggcgagc ggtatcagct cactcaaagg cggtaatacg gttatccaca    420
gaatcagggg ataacgcagg aaagaacatg tgagcaaaag gccagcaaaa ggccaggaac    480
cgtaaaaagg ccgcgttgct ggcgtttttc cataggctcc gcccccctga cgagcatcac    540
aaaaatcgac gctcaagtca gaggtggcga aacccgacag gactataaag ataccaggcg    600
tttccccctg gaagctccct cgtgcgctct cctgttccga ccctgccgct taccggatac    660
ctgtccgcct ttctcccttc gggaagcgtg gcgctttctc atagctcacg ctgtaggtat    720
ctcagttcgg tgtaggtcgt tcgctccaag ctgggctgtg tgcacgaacc ccccgttcag    780
cccgaccgct gcgccttatc cggtaactat cgtcttgagt ccaacccggt aagacacgac    840
ttatcgccac tggcagcagc cactggtaac aggattagca gagcgaggta tgtaggcggt    900
gctacagagt tcttgaagtg gtggcctaac tacggctaca ctagaaggac agtatttggt    960
atctgcgctc tgctgaagcc agttaccttc ggaaaaagag ttggtagctc ttgatccggc   1020
aaacaaacca ccgctggtag cggtggtttt tttgtttgca agcagcagat tacgcgcaga   1080
aaaaaaggat ctcaagaaga tcctttgatc ttttctacgg ggtctgacgc tcagtggaac   1140
gaaaactcac gttaagggat tttggtcatg agattatcaa aaaggatctt cacctagatc   1200
cttttaaatt aaaaatgaag ttttaaatca atctaaagta tatatgagta aacttggtct   1260
gacagttacc aatgcttaat cagtgaggca cctatctcag cgatctgtct atttcgttca   1320
tccatagttg cctgactccc cgtcgtgtag ataactacga tacggagggg cttaccatct   1380
ggccccagtg ctgcaatgat accgcgagac ccacgctcac cggctccaga tttatcagca   1440
ataaaccagc cagccggaag ggccgagcgc agaagtggtc ctgcaacttt atccgcctcc   1500
atccagtcta ttaattgttg ccgggaagct agagtaagta gttcgccagt taatagtttg   1560
cgcaacgttg ttgccattgc tacaggcatc gtggtgtcac gctcgtcgtt tggtatggct   1620
tcattcagct ccggttccca acgatcaagg cgagttacat gatcccccat gttgtgcaaa   1680
aaagcggtta gctccttcgg tcctccgatc gttgtcagaa gtaagttggc cgcagtgtta   1740
```

```
tcactcatgg ttatggcagc actgcataat tctcttactg tcatgccatc cgtaagatgc    1800
ttttctgtga ctggtgagta ctcaaccaag tcattctgag aatagtgtat gcggcgaccg    1860
agttgctctt gcccggcgtc aatacgggat aataccgcgc cacatagcag aactttaaaa    1920
gtgctcatca ttggaaaacg ttcttcgggg cgaaaactct caaggatctt accgctgttg    1980
agatccagtt cgatgtaacc cactcgtgca cccaactgat cttcagcatc ttttactttc    2040
accagcgttt ctgggtgagc aaaaacagga aggcaaaatg ccgcaaaaaa gggaataagg    2100
gcgacacgga aatgttgaat actcatactc ttcctttttc aatattattg aagcatttat    2160
cagggttatt gtctcatgag cggatacata tttgaatgta tttagaaaaa taaacaaata    2220
ggggttccgc gcacatttcc ccgaaaagtg ccacctaaat tgtaagcgtt aatattttgt    2280
taaaattcgc gttaaatttt tgttaaatca gctcattttt taaccaatag gccgaaatcg    2340
gcaaaatccc ttataaatca aagaataga ccgagatagg gttgagtgtt gttccagttt    2400
ggaacaagag tccactatta agaacgtgg actccaacgt caagggcga aaaccgtct     2460
atcagggcga tggcccacta cgtgaaccat caccctaatc aagttttttg gggtcgaggt    2520
gccgtaaagc actaaatcgg aaccctaaag ggagccccg atttagagct tgacggggaa    2580
agccggcgaa cgtggcgaga aaggaaggga agaaagcgaa aggagcgggc gctagggcgc    2640
tggcaagtgt agcggtcacg ctgcgcgtaa ccaccacacc cgccgcgctt aatgcgccgc    2700
tacagggcgc gtcccattcg ccattcaggc tgcgcaactg ttgggaaggg cgatcggtgc    2760
gggcctcttc gctattacgc cagctggcga aggggatg tgctgcaagg cgattaagtt    2820
gggtaacgcc agggttttcc cagtcacgac gttgtaaaac gacggccagt gaattgtaat    2880
acgactcact atagggcgaa ttggagctcc accgcggtgg cggccgcgtt gttgtgtctc    2940
ttcttcctcg aatctcgatc gttacatcac cgggttctag ccttcacgat gtgcttttga    3000
gcatgagatt tggtttgacg cgacatctcc ctctcaaacg atctttctcc aattattcaa    3060
tcacttccgt atctccagaa caacagctca aatctccggt gaccatggcg acgaccgaga    3120
gcaagaatct tgtagggatc cttccaagga ggagacaaac aagaaggaga cagaagataa    3180
gaaggaggtg ggagtttcgg ttcctccacc gccagagaaa ccagagcctg gcgattgttg    3240
cggtagcggt tgcgtccgat gcgtttggga tgtttattac gatgagctcg aagattacaa    3300
caagcagctt tctggagaaa ctaactgcag ctacaagatt cttgctctcg gtcgtcgcca    3360
tggtcaccgg agatttgagc tgttgttctg gagatacgga agtgattgaa taattggaga    3420
aagatcgttt gagagggaga tgtcgcgtca aaccaaatct catgctcaaa gcacatcgt    3480
gaaggctaga acccggtgat gtaacgatcg agattcgagg aagaagagac acaacaacgc    3540
ggccgcg                                                              3547
```

<210> SEQ ID NO 83
<211> LENGTH: 3453
<212> TYPE: DNA
<213> ORGANISM: artificial sequence
<220> FEATURE:
<223> OTHER INFORMATION: plasmid

<400> SEQUENCE: 83

```
tcttccatag ccccccaagc ggccgcgaca caagtgtgag agtactaaat aaatgctttg     60
gttgtacgaa atcattacac taaataaaat aatcaaagct tatatatgcc ttccgctaag    120
gccgaatgca aagaaattgg ttctttctcg ttatcttttg ccacttttac tagtacgtat    180
taattactac ttaatcatct tgtttacgg ctcattatat ccgtcgacgg cgcgcccgat    240
```

```
catccggata tagttcctcc tttcagcaaa aaacccctca agacccgttt agaggcccca    300
aggggttatg ctagttattg ctcagcggtg gcagcagcca actcagcttc ctttcgggct    360
ttgttagcag ccggatcgat ccaagctgta cctcactatt cctttgccct cggacgagtg    420
ctggggcgtc ggtttccact atcggcgagt acttctacac agccatcggt ccagacggcc    480
gcgcttctgc gggcgatttg tgtacgcccg acagtcccgg ctccggatcg gacgattgcg    540
tcgcatcgac cctgcgccca agctgcatca tcgaaattgc cgtcaaccaa gctctgatag    600
agttggtcaa gaccaatgcg gagcatatac gcccggagcc gcggcgatcc tgcaagctcc    660
ggatgcctcc gctcgaagta gcgcgtctgc tgctccatac aagccaacca cggcctccag    720
aagaagatgt tggcgacctc gtattgggaa tccccgaaca tcgcctcgct ccagtcaatg    780
accgctgtta tgcggccatt gtccgtcagg acattgttgg agccgaaatc cgcgtgcacg    840
aggtgccgga cttcggggca gtcctcggcc caaagcatca gctcatcgag agcctgcgcg    900
acggacgcac tgacggtgtc gtccatcaca gtttgccagt gatacacatg gggatcagca    960
atcgcgcata tgaaatcacg ccatgtagtg tattgaccga ttccttgcgg tccgaatggg   1020
ccgaacccgc tcgtctggct aagatcggcc gcagcgatcg catccatagc ctccgcgacc   1080
ggctgcagaa cagcgggcag ttcggtttca ggcaggtctt gcaacgtgac accctgtgca   1140
cggcgggaga tgcaataggt caggctctcg ctgaattccc caatgtcaag cacttccgga   1200
atcgggagcg cggccgatgc aaagtgccga taaacataac gatctttgta gaaaccatcg   1260
gcgcagctat ttacccgcag gacatatcca cgccctccta catcgaagct gaaagcacga   1320
gattcttcgc cctccgagag ctgcatcagg tcggagacgc tgtcgaactt ttcgatcaga   1380
aacttctcga cagacgtcgc ggtgagttca ggcttttcca tgggtatatc tccttcttaa   1440
agttaaacaa aattatttct agagggaaac cgttgtggtc tccctatagt gagtcgtatt   1500
aatttcgcgg gatcgagatc tgatcaacct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgttttttcca taggctccgc cccccctgacg agcatcacaa   1800
aaatcgacgc tcaagtcaga ggtggcgaaa cccgacagga ctataaagat accaggcgtt   1860
tccccctgga agctccctcg tgcgctctcc tgttccgacc ctgccgctta ccggatacct   1920
gtccgccttt ctcccttcgg gaagcgtggc gctttctcaa tgctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaaggacag tatttggtat   2220
ctgcgctctg ctgaagccag ttaccttcgg aaaaagagtt ggtagctctt gatccggcaa   2280
acaaaccacc gctggtagcg gtggtttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgac attaacctat aaaaataggc gtatcacgag   2460
gccctttcgt ctcgcgcgtt tcggtgatga cggtgaaaac ctctgacaca tgcagctccc   2520
ggagacggtc acagcttgtc tgtaagcgga tgccgggagc agacaagccc gtcagggcgc   2580
```

```
gtcagcgggt gttggcgggt gtcggggctg gcttaactat gcggcatcag agcagattgt   2640
actgagagtg caccatatgg acatattgtc gttagaacgc ggctacaatt aatacataac   2700
cttatgtatc atacacatac gatttaggtg acactataga acggcgcgcc aagcttggat   2760
cctagcctaa gtacgtactc aaaatgccaa caaataaaaa aaagttgct ttaataatgc    2820 caaaacaaat taataaaaca cttacaacac cggattttttt ttaattaaaa tgtgccattt   2880
aggataaata gttaatattt ttaataatta tttaaaaagc cgtatctact aaaatgattt    2940
ttatttggtt gaaaatatta atatgtttaa atcaacacaa tctatcaaaa ttaaactaaa    3000
aaaaaaataa gtgtacgtgg ttaacattag tacagtaata taagaggaaa atgagaaatt   3060
aagaaattga aagcgagtct aatttttaaa ttatgaacct gcatatataa aaggaaagaa   3120
agaatccagg aagaaaagaa atgaaaccat gcatggtccc ctcgtcatca cgagtttctg   3180
ccatttgcaa tagaaacact gaaacacctt tctctttgtc acttaattga gatgccgaag   3240
ccacctcaca ccatgaactt catgaggtgt agcacccaag gcttccatag ccatgcatac   3300
tgaagaatgt ctcaagctca gcaccctact tctgtgacgt gtccctcatt caccttcctc   3360
tcttccctat aaataaccac gcctcaggtt ctccgcttca caactcaaac attctctcca   3420
ttggtcctta aacactcatc agtcatcacc atg                                3453

<210> SEQ ID NO 84
<211> LENGTH: 4072
<212> TYPE: DNA
<213> ORGANISM: artificial sequence
<220> FEATURE:
<223> OTHER INFORMATION: plasmid

<400> SEQUENCE: 84
ggccgcgaca caagtgtgag agtactaaat aaatgctttg gttgtacgaa atcattacac     60
taaataaaat aatcaaagct tatatatgcc ttccgctaag gccgaatgca agaaaattgg    120
ttctttctcg ttatcttttg ccacttttac tagtacgtat taattactac ttaatcatct   180
ttgtttacgg ctcattatat ccgtcgacgg cgcgcccgat catccggata tagttcctcc   240
tttcagcaaa aaacccctca agacccgttt agaggcccca aggggttatg ctagttattg    300
ctcagcggtg gcagcagcca actcagcttc cttttcgggct ttgttagcag ccggatcgat    360
ccaagctgta cctcactatt cctttgccct cggacgagtg ctggggcgtc ggtttccact    420
atcggcgagt acttctacac agccatcggt ccagacggcc gcgcttctgc gggcgatttg    480
tgtacgcccg acagtcccgg ctccggatcg acgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tcggccatt     780 gtccgtcagg acattgttgg agccgaaatc gcgtgcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct   1020
aagatcggcc gcagcgatcg catccatagc ctccgcgacc ggctgcagaa cagcgggcag   1080
ttcggtttca ggcaggtctt gcaacgtgac acctgtgca cggcgggaga tgcaataggt    1140
caggctctcg ctgaattccc caatgtcaag cacttccgga atcgggagcg cggccgatgc   1200
```

```
aaagtgccga taaacataac gatctttgta gaaaccatcg gcgcagctat ttacccgcag    1260
gacatatcca cgccctccta catcgaagct gaaagcacga gattcttcgc cctccgagag    1320
ctgcatcagg tcggagacgc tgtcgaactt ttcgatcaga aacttctcga cagacgtcgc    1380
ggtgagttca ggcttttcca tgggtatatc tccttcttaa agttaaacaa aattatttct    1440
agagggaaac cgttgtggtc tccctatagt gagtcgtatt aatttcgcgg gatcgagatc    1500
tgatcaacct gcattaatga atcggccaac gcgcggggag aggcggtttg cgtattgggc    1560
gctcttccgc ttcctcgctc actgactcgc tgcgctcggt cgttcggctg cggcgagcgg    1620
tatcagctca ctcaaaggcg gtaatacggt tatccacaga atcaggggat aacgcaggaa    1680
agaacatgtg agcaaaaggc cagcaaaagg ccaggaaccg taaaaaggcc gcgttgctgg    1740
cgttttccca taggctccgc cccctgacg agcatcacaa aaatcgacgc tcaagtcaga    1800
ggtggcgaaa cccgacagga ctataaagat accaggcgtt tcccctgga agctccctcg    1860 tgcgctctcc tgttccgacc ctgccgctta ccggatacct gtccgccttt ctcccttcgg    1920
gaagcgtggc gctttctcaa tgctcacgct gtaggtatct cagttcggtg taggtcgttc    1980
gctccaagct gggctgtgtg cacgaacccc ccgttcagcc cgaccgctgc gccttatccg    2040
gtaactatcg tcttgagtcc aacccggtaa gacacgactt atcgccactg gcagcagcca    2100
ctggtaacag gattagcaga gcgaggtatg taggcggtgc tacagagttc ttgaagtggt    2160
ggcctaacta cggctacact agaaggacag tatttggtat ctgcgctctg ctgaagccag    2220
ttaccttcgg aaaaagagtt ggtagctctt gatccggcaa acaaaccacc gctggtagcg    2280
gtggtttttt tgtttgcaag cagcagatta cgcgcagaaa aaaaggatct caagaagatc    2340
ctttgatctt ttctacgggg tctgacgctc agtggaacga aaactcacgt taagggattt    2400
tggtcatgac attaacctat aaaaataggc gtatcacgag gccctttcgt ctcgcgcgtt    2460
tcggtgatga cggtgaaaac ctctgacaca tgcagctccc ggagacggtc acagcttgtc    2520
tgtaagcgga tgccgggagc agacaagccc gtcagggcgc gtcagcgggt gttggcgggt    2580
gtcggggctg gcttaactat gcggcatcag agcagattgt actgagagtg caccatatgg    2640
acatattgtc gttagaacgc ggctacaatt aatacataac cttatgtatc atacacatac    2700
gatttaggtg acactataga acggcgcgcc aagcttggat cctagcctaa gtacgtactc    2760
aaaatgccaa caaataaaaa aaagttgct ttaataatgc aaaacaaat taataaaaca    2820 cttacaacac cggatttttt ttaattaaaa tgtgccattt aggataaata gttaatattt    2880
ttaataatta tttaaaaagc cgtatctact aaaatgattt ttatttggtt gaaaatatta    2940
atatgtttaa atcaacacaa tctatcaaaa ttaaactaaa aaaaaaataa gtgtacgtgg    3000
ttaacattag tacagtaata taagaggaaa atgagaaatt aagaaattga aagcgagtct    3060 aattttaaa ttatgaacct gcatatataa aaggaaagaa agaatccagg aagaaaagaa    3120
atgaaaccat gcatggtccc ctcgtcatca cgagtttctg ccatttgcaa tagaaacact    3180
gaaacacctt tctctttgtc acttaattga gatgccgaag ccacctcaca ccatgaactt    3240
catgaggtgt agcacccaag gcttccatag ccatgcatac tgaagaatgt ctcaagctca    3300
gcaccctact tctgtgacgt gtccctcatt caccttcctc tcttccctat aaataaccac    3360
gcctcaggtt ctccgcttca caactcaaac attctctcca ttggtcctta aacactcatc    3420
agtcatcacc atgtcttcca tagccccca agcggccgcg ttgttgtgtc tcttcttcct    3480
cgaatctcga tcgttacatc accgggttct agccttcacg atgtgctttt gagcatgaga    3540
```

```
tttggtttga cgcgacatct ccctctcaaa cgatctttct ccaattattc aatcacttcc    3600
gtatctccag aacaacagct caaatctccg gtgaccatgg cgacgaccga gagcaagaat    3660
cttgtaggga tccttccaag gaggagacaa acaagaagga gacagaagat aagaaggagg    3720
tgggagtttc ggttcctcca ccgccagaga aaccagagcc tggcgattgt tgcggtagcg    3780
gttgcgtccg atgcgtttgg gatgtttatt acgatgagct cgaagattac aacaagcagc    3840
tttctggaga aactaactgc agctacaaga ttcttgctct cggtcgtcgc catggtcacc    3900
ggagatttga gctgttgttc tggagatacg gaagtgattg aataattgga gaaagatcgt    3960
ttgagaggga gatgtcgcgt caaaccaaat ctcatgctca aaagcacatc gtgaaggcta    4020
gaacccggtg atgtaacgat cgagattcga ggaagaagag acacaacaac gc            4072

<210> SEQ ID NO 85
<211> LENGTH: 14827
<212> TYPE: DNA
<213> ORGANISM: artificial sequence
<220> FEATURE:
<223> OTHER INFORMATION: plasmid

<400> SEQUENCE: 85
cgcgcctcga gtgggcggat cccccgggct gcaggaattc actggccgtc gttttacaac      60
gtcgtgactg ggaaaaccct ggcgttaccc aacttaatcg ccttgcagca catcccccctt    120
tcgccagctg gcgtaatagc gaagaggccc gcaccgatcg cccttcccaa cagttgcgca    180
gcctgaatgg cgaatggatc gatccatcgc gatgtacctt tgttagtca gcctctcgat     240
tgctcatcgt cattacacag taccgaagtt tgatcgatct agtaacatag atgacaccgc    300
gcgcgataat ttatcctagt ttgcgcgcta tattttgttt tctatcgcgt attaaatgta    360
taattgcggg actctaatca taaaaaccca tctcataaat aacgtcatgc attacatgtt    420
aattattaca tgcttaacgt aattcaacag aaattatatg ataatcatcg caagaccggc    480
aacaggattc aatcttaaga aactttattg ccaaatgttt gaacgatctg cttcgacgca    540
ctccttcttt actccaccat ctcgtcctta ttgaaaacgt gggtagcacc aaaacgaatc    600
aagtcgctgg aactgaagtt accaatcacg ctggatgatt tgccagttgg attaatcttg    660
cctttccccg catgaataat attgatgaat gcatgcgtga ggggtagttc gatgttggca    720
atagctgcaa ttgccgcgac atcctccaac gagcataatt cttcagaaaa atagcgatgt    780
tccatgttgt cagggcatgc atgatgcacg ttatgaggtg acggtgctag gcagtattcc    840
ctcaaagttt catagtcagt atcatattca tcattgcatt cctgcaagag agaattgaga    900
cgcaatccac acgctgcggc aaccttccgg cgttcgtggt ctatttgctc ttggacgttg    960
caaacgtaag tgttggatcg atccggggtg ggcgaagaac tccagcatga tccccgcg    1020
ctggaggatc atccagccgg cgtcccggaa aacgattccg aagcccaacc tttcatagaa    1080
ggcggcggtg gaatcgaaat ctcgtgatgg caggttgggc gtcgcttggt cggtcatttc    1140
gaaccccaga gtcccgctca agaagaactcg tcaagaaggc gatagaaggc gatgcgctgc    1200
gaatcgggag cggcgatacc gtaaagcacg aggaagcggt cagcccattc gccgccaagc    1260
tcttcagcaa tatcacgggt agccaacgct atgtcctgat agcggtccgc cacacccagc    1320
cggccacagt cgatgaatcc agaaaagcgg ccatttttcca ccatgatatt cggcaagcag    1380
gcatcgccat gggtcacgac gagatcctcg ccgtcgggca tgcgcgcctt gagcctggcg    1440
aacagttcgg ctggcgcgag cccctgatgc tcttcgtcca gatcatcctg atcgacaaga    1500
ccggcttcca tccgagtacg tgctcgctcg atgcgatgtt tcgcttggtg gtcgaatggg    1560
```

```
caggtagccg gatcaagcgt atgcagccgc cgcattgcat cagccatgat ggatactttc    1620
tcggcaggag caaggtgaga tgacaggaga tcctgccccg gcacttcgcc caatagcagc    1680
cagtcccttc ccgcttcagt gacaacgtcg agcacagctg cgcaaggaac gcccgtcgtg    1740
gccagccacg atagccgcgc tgcctcgtcc tgcagttcat tcagggcacc ggacaggtcg    1800
gtcttgacaa aaagaaccgg gcgcccctgc gctgacagcc ggaacacggc ggcatcagag    1860
cagccgattg tctgttgtgc ccagtcatag ccgaatagcc tctccaccca agcggccgga    1920
gaacctgcgt gcaatccatc ttgttcaatc atgcgaaacg atccccgcaa gcttggagac    1980
tggtgatttc agcgtgtcct ctccaaatga aatgaacttc cttatataga ggaagggtct    2040
tgcgaaggat agtgggattg tgcgtcatcc cttacgtcag tggagatatc acatcaatcc    2100
acttgctttg aagacgtggt tggaacgtct tcttttttcca cgatgctcct cgtgggtggg    2160
ggtccatctt tgggaccact gtcggcagag gcatcttcaa cgatggcctt tcctttatcg    2220
caatgatggc atttgtagga gccaccttcc ttttccacta tcttcacaat aaagtgacag    2280
atagctgggc aatggaatcc gaggaggttt ccggatatta cccttgttg aaaagtctca     2340 attgcccttt ggtcttctga gactgtatct ttgatatttt tggagtagac aagcgtgtcg    2400
tgctccacca tgttgacgaa gattttcttc ttgtcattga gtcgtaagag actctgtatg    2460
aactgttcgc cagtctttac ggcgagttct gttaggtcct ctatttgaat ctttgactcc    2520
atggcctttg attcagtggg aactacccttt ttagagactc caatctctat tacttgcctt    2580
ggtttgtgaa gcaagcctttg aatcgtccat actggaatag tacttctgat cttgagaaat   2640
atatctttct ctgtgttctt gatgcagtta gtcctgaatc ttttgactgc atctttaacc    2700
ttcttgggaa ggtatttgat ctcctggaga ttattgctcg ggtagatcgt cttgatgaga    2760
cctgctgcgt aagcctctct aaccatctgt gggttagcat tctttctgaa attgaaaagg    2820
ctaatcttct cattatcagt ggtgaacatg gtatcgtcac cttctccgtc gaacttcctg    2880
actagatcgt agagatagag gaagtcgtcc attgtgatct ctggggcaaa ggagatctga    2940
attaattcga tatggtggat ttatcacaaa tgggacccgc cgccgacaga ggtgtgatgt    3000
taggccagga ctttgaaaat ttgcgcaact atcgtatagt ggccgacaaa ttgacgccga    3060
gttgacagac tgcctagcat ttgagtgaat tatgtgaggt aatgggctac actgaattgg    3120
tagctcaaac tgtcagtatt tatgtatatg agtgtatatt ttcgcataat ctcagaccaa    3180
tctgaagatg aaatgggtat ctgggaatgg cgaaatcaag gcatcgatcg tgaagtttct    3240
catctaagcc cccatttgga cgtgaatgta gacacgtcga aataaagatt tccgaattag    3300
aataatttgt ttattgcttt cgcctataaa tacgacggat cgtaatttgt cgttttatca    3360
aaatgtactt tcatttttata ataacgctgc ggacatctac attttgaat tgaaaaaaaa    3420 ttggtaatta ctcttctctt ttctccatat tgaccatcat actcattgct gatccatgta    3480 gatttccccgg acatgaagcc atttacaatt gaatatatcc tgccgccgct gccgctttgc    3540
acccggtgga gcttgcatgt tggtttctac gcagaactga gccggttagg cagataattt    3600
ccattgagaa ctgagccatg tgcaccttcc ccccaacacg gtgagcgacg gggcaacgga    3660
gtgatccaca tgggactttt aaacatcatc cgtcggatgg cgttgcgaga gaagcagtcg    3720
atccgtgaga tcagccgacg caccgggcag gcgcgcaaca cgatcgcaaa gtatttgaac    3780
gcaggtacaa tcgagccgac gttcacgcgg aacgaccaag caagctagct ttaatgcggt    3840
agtttatcac agttaaattg ctaacgcagt caggcaccgt gtatgaaatc taacaatgcg    3900
```

```
ctcatcgtca tcctcggcac cgtcaccctg gatgctgtag gcataggctt ggttatgccg    3960
gtactgccgg gcctcttgcg ggatatcgtc cattccgaca gcatcgccag tcactatggc    4020
gtgctgctag cgctatatgc gttgatgcaa tttctatgcg cacccgttct cggagcactg    4080
tccgaccgct ttggccgccg cccagtcctg ctcgcttcgc tacttggagc cactatcgac    4140
tacgcgatca tggcgaccac acccgtcctg tggtccaacc cctccgctgc tatagtgcag    4200
tcggcttctg acgttcagtg cagccgtctt ctgaaaacga catgtcgcac aagtcctaag    4260
ttacgcgaca ggctgccgcc ctgcccttt t cctggcgttt tcttgtcgcg tgttttagtc    4320
gcataaagta gaatacttgc gactagaacc ggagacatta cgccatgaac aagagcgccg    4380
ccgctggcct gctgggctat gcccgcgtca gcaccgacga ccaggacttg accaaccaac    4440
gggccgaact gcacgcggcc ggctgcacca agctgttttc cgagaagatc accggcacca    4500
ggcgcgaccg cccggagctg gccaggatgc ttgaccacct acgccctggc gacgttgtga    4560
cagtgaccag gctagaccgc ctggcccgca gcacccgcga cctactggac attgccgagc    4620
gcatccagga ggccggcgcg ggcctgcgta gcctggcaga gccgtgggcc gacaccacca    4680
cgccggccgg ccgcatggtg ttgaccgtgt tcgccggcat tgccgagttc gagcgttccc    4740
taatcatcga ccgcacccgg agcgggcgcg aggccgccaa ggcccgaggc gtgaagtttg    4800
gcccccgccc taccctcacc ccggcacaga tcgcgcacgc ccgcgagctg atcgaccagg    4860
aaggccgcac cgtgaaagag gcggctgcac tgcttggcgt gcatcgctcg accctgtacc    4920
gcgcacttga gcgcagcgag gaagtgacgc ccaccgaggc caggcggcgc ggtgccttcc    4980
gtgaggacgc attgaccgag gccgacgccc tggcggccgc cgagaatgaa cgccaagagg    5040
aacaagcatg aaaccgcacc aggacggcca ggacgaaccg ttttt catta ccgaagagat    5100
cgaggcggag atgatcgcgg ccgggtacgt gttcgagccg cccgcgcacg tctcaaccgt    5160
gcggctgcat gaaatcctgg ccggtttgtc tgatgccaag ctggcggcct ggccggccag    5220
cttggccgct gaagaaaccg agcgccgccg tctaaaaagg tgatgtgtat ttgagtaaaa    5280
cagcttgcgt catgcggtcg ctgcgtatat gatgcgatga gtaaataaac aaatacgcaa    5340
gggaacgcat gaagttatcg ctgtacttaa ccagaaaggc gggtcaggca agacgaccat    5400
cgcaacccat ctagcccgcg ccctgcaact cgccggggcc gatgttctgt tagtcgattc    5460
cgatccccag ggcagtgccc gcgattgggc ggccgtgcgg gaagatcaac gctaaccgt    5520
tgtcggcatc gaccgcccga cgattgaccg cgacgtgaag gccatcggcc ggcgcgactt    5580
cgtagtgatc gacggagcgc cccaggcggc ggacttggct gtgtccgcga tcaaggcagc    5640
cgacttcgtg ctgattccgg tgcagccaag cccttacgac atatgggcca ccgccgacct    5700
ggtggagctg gttaagcagc gcattgaggt cacggatgga aggctacaag cggcctttgt    5760
cgtgtcgcgg gcgatcaaag gcacgcgcat cggcggtgag gttgccgagg cgctggccgg    5820
gtacgagctg cccattcttg agtcccgtat cacgcagcgc gtgagctacc caggcactgc    5880
cgccgccggc acaaccgttc ttgaatcaga acccgagggc gacgctgccc gcgaggtcca    5940
ggcgctggcc gctgaaatta aatcaaaact catttgagtt aatgaggtaa agagaaaatg    6000
agcaaaagca caaacacgct aagtgccggc cgtccgagcg cacgcagcag caaggctgca    6060
acgttggcca gcctggcaga cacgccagcc atgaagcggg tcaactttca gttgccggcg    6120
gaggatcaca ccaagctgaa gatgtacgcg gtacgccaag gcaagaccat taccgagctg    6180
ctatctgaat acatcgcgca gctaccagag taaatgagca aatgaataaa tgagtagatg    6240
aattttagcg gctaaaggag gcggcatgga aaatcaagaa caaccaggca ccgacgccgt    6300
```

```
ggaatgcccc atgtgtggag aacgggcgg ttggccaggc gtaagcggct gggttgtctg   6360
ccggccctgc aatggcactg aaccccccaa gcccgaggaa tcggcgtgag cggtcgcaaa   6420
ccatccggcc cggtacaaat cggcgcggcg ctgggtgatg acctggtgga aagttgaag   6480 gccgcgcagg ccgcccagcg gcaacgcatc gaggcagaag cacgcccgg tgaatcgtgg   6540 caagcggccg ctgatcgaat ccgcaaagaa tcccggcaac cgccggcagc cggtgcgccg   6600
tcgattagga agccgcccaa gggcgacgag caaccagatt ttttcgttcc gatgctctat   6660
gacgtgggca cccgcgatag tcgcagcatc atggacgtgg ccgttttccg tctgtcgaag   6720
cgtgaccgac gagctggcga ggtgatccgc tacgagcttc cagacgggca cgtagaggtt   6780
tccgcagggc cggccggcat ggccagtgtg tgggattacg acctggtact gatggcggtt   6840
tcccatctaa ccgaatccat gaaccgatac cgggaaggga agggagacaa gcccggccgc   6900
gtgttccgtc cacacgttgc ggacgtactc aagttctgcc ggcgagccga tggcggaaag   6960
cagaaagacg acctggtaga aacctgcatt cggttaaaca ccacgcacgt tgccatgcag   7020
cgtacgaaga aggccaagaa cggccgcctg gtgacggtat ccgagggtga agccttgatt   7080
agccgctaca agatcgtaaa gagcgaaacc gggcggccgg agtacatcga gatcgagcta   7140
gctgattgga tgtaccgcga gatcacagaa ggcaagaacc cggacgtgct gacggttcac   7200
cccgattact ttttgatcga tcccggcatc ggccgttttc tctaccgcct ggcacgccgc   7260
gccgcaggca aggcagaagc cagatggttg ttcaagacga tctacgaacg cagtggcagc   7320 gccgagagt tcaagaagtt ctgttttcacc gtgcgcaagc tgatcgggtc aaatgacctg   7380
ccggagtacg atttgaagga ggaggcgggg caggctggcc cgatcctagt catgcgctac   7440
cgcaacctga tcgagggcga agcatccgcc ggttcctaat gtacgagca gatgctaggg   7500 caaattgccc tagcagggga aaaggtcga aaggtctct ttcctgtgga tagcacgtac   7560
attgggaacc caaagccgta cattgggaac cggaaccccgt acattgggaa cccaaagccg   7620
tacattggga accggtcaca catgtaagtg actgatataa aagagaaaaa aggcgatttt   7680
tccgcctaaa actctttaaa acttattaaa actcttaaaa cccgcctggc ctgtgcataa   7740
ctgtctggcc agcgcacagc cgaagagctg caaaaagcgc ctaccttcg gtcgctgcgc   7800 tccctacgcc ccgccgcttc gcgtcggcct atcgcggccg ctggccgctc aaaaatggct   7860
ggcctacggc caggcaatct accagggcgc ggacaagccg cgccgtcgcc actcgaccgc   7920
cggcgcccac atcaaggcac cctgcctcgc gcgtttcggt gatgacggtg aaaacctctg   7980
acacatgcag ctcccggaga cggtcacagc ttgtctgtaa gcggatgccg ggagcagaca   8040
agcccgtcag ggcgcgtcag cgggtgttgg cgggtgtcgg ggcgcagcca tgacccagtc   8100
acgtagcgat agcggagtgt atactggctt aactatgcgg catcagagca gattgtactg   8160
agagtgcacc atatgcggtg tgaaataccg cacagatgcg taaggagaaa ataccgcatc   8220
aggcgctctt ccgcttcctc gctcactgac tcgctgcgct cggtcgttcg gctgcggcga   8280
gcggtatcag ctcactcaaa ggcggtaata cggttatcca cagaatcagg ggataacgca   8340
ggaaagaaca tgtgagcaaa aggccagcaa aaggccagga accgtaaaaa ggccgcgttg   8400
ctggcgtttt tccataggct ccgcccccct gacgagcatc acaaaaatcg acgctcaagt   8460
cagaggtggc gaaacccgac aggactataa agataccagg cgtttccccc tggaagctcc   8520
ctcgtgcgct ctcctgttcc gaccctgccg cttaccggat acctgtccgc ctttctccct   8580
tcgggaagcg tggcgctttc tcatagctca cgctgtaggt atctcagttc ggtgtaggtc   8640
```

```
gttcgctcca agctgggctg tgtgcacgaa ccccccgttc agcccgaccg ctgcgcctta    8700
tccggtaact atcgtcttga gtccaacccg gtaagacacg acttatcgcc actggcagca    8760
gccactggta acaggattag cagagcgagg tatgtaggcg gtgctacaga gttcttgaag    8820
tggtggccta actacggcta cactagaagg acagtatttg gtatctgcgc tctgctgaag    8880
ccagttacct tcggaaaaag agttggtagc tcttgatccg gcaaacaaac caccgctggt    8940
agcggtggtt ttttgtttg caagcagcag attacgcgca gaaaaaaagg atctcaagaa    9000
gatcctttga tcttttctac ggggtctgac gctcagtgga acgaaaactc acgttaaggg    9060
attttggtca tgagattatc aaaaaggatc ttcacctaga tccttttaaa ttaaaaatga    9120
agttttaaat caatctaaag tatatatgag taaacttggt ctgacagtta ccaatgctta    9180
atcagtgagg cacctatctc agcgatctgt ctatttcgtt catccatagt tgcctgactc    9240
cccgtcgtgt agataactac gatacgggag ggcttaccat ctggccccag tgctgcaatg    9300
ataccgcgag acccacgctc accggctcca gatttatcag caataaacca gccagccgga    9360
agggccgagc gcagaagtgg tcctgcaact ttatccgcct ccatccagtc tattaattgt    9420
tgccgggaag ctagagtaag tagttcgcca gttaatagtt tgcgcaacgt tgttgccatt    9480
gctacaggca tcgtggtgtc acgctcgtcg tttggtatgg cttcattcag ctccggttcc    9540
caacgatcaa ggcgagttac atgatccccc atgttgtgca aaaaagcggt tagctccttc    9600
ggtcctccga tcgttgtcag aagtaagttg gccgcagtgt tatcactcat ggttatggca    9660
gcactgcata attctcttac tgtcatgcca tccgtaagat gcttttctgt gactggtgag    9720
tactcaacca agtcattctg agaatagtgt atgcggcgac cgagttgctc ttgcccggcg    9780
tcaacacggg ataataccgc gccacatagc agaactttaa aagtgctcat cattggaaaa    9840
gacctgcagg gggggggggg cgctgaggtc tgcctcgtga agaaggtgtt gctgactcat    9900
accaggcctg aatcgcccca tcatccagcc agaaagtgag ggagccacgg ttgatgagag    9960
ctttgttgta ggtggaccag ttggtgattt tgaacttttg ctttgccacg gaacggtctg    10020
cgttgtcggg aagatgcgtg atctgatcct tcaactcagc aaaagttcga tttattcaac    10080
aaagccgccg tcccgtcaag tcagcgtaat gctctgccag tgttacaacc aattaaccaa    10140
ttctgattag aaaaactcat cgagcatcaa atgaaactgc aatttattca tatcaggatt    10200
atcaatacca tatttttgaa aaagccgttt ctgtaatgaa ggagaaaact caccgaggca    10260
gttccatagg atggcaagat cctggtatcg gtctgcgatt ccgactcgtc aacatcaat     10320 acaacctatt aatttcccct cgtcaaaaat aaggttatca agtgagaaat caccatgagt    10380
gacgactgaa tccggtgaga atggcaaaag cttatgcatt tctttccaga cttgttcaac    10440
aggccagcca ttacgctcgt catcaaaatc actcgcatca accaaaccgt tattcattcg    10500
tgattgcgcc tgagcgagac gaaatacgcg atcgctgtta aaaggacaat acaaacagg     10560 aatcgaatgc aaccggcgca ggaacactgc cagcgcatca acaatatttt cacctgaatc    10620
aggatattct tctaatacct ggaatgctgt ttttcccgggg atcgcagtgg tgagtaacca    10680
tgcatcatca ggagtacgga taaaatgctt gatggtcgga agaggcataa attccgtcag    10740
ccagtttagt ctgaccatct catctgtaac atcattggca acgctacctt tgccatgttt    10800
cagaaacaac tctggcgcat cgggcttccc atacaatcga tagattgtcg cacctgattg    10860
cccgacatta tcgcgagccc atttataccc atataaatca gcatccatgt tggaatttaa    10920
tcgcggcctc gagcaagacg tttcccgttg aatatggctc ataacacccc ttgtattact    10980
gtttatgtaa gcagacagtt ttattgttca tgatgatata ttttatctt gtgcaatgta     11040
```

```
acatcagaga ttttgagaca caacgtggct ttccccccc cccctgcagg tcaattcggt   11100
cgatatggct attacgaaga aggctcgtgc gcggagtccc gtgaactttc ccacgcaaca   11160
agtgaaccgc accgggtttg ccggaggcca tttcgttaaa atgcgcagcc atggctgctt   11220
cgtccagcat ggcgtaatac tgatcctcgt cttcggctgg cggtatattg ccgatgggct   11280
tcaaaagccg ccgtggttga accagtctat ccattccaag gtagcgaact cgaccgcttc   11340
gaagctcctc catggtccac gccgatgaat gacctcggcc ttgtaaagac cgttgatcgc   11400
ttctgcgagg gcgttgtcgt gctgtcgccg acgcttccga tagatggctc gatacctgct   11460
tctgccaacc gctcggaata gcgaaaggac acgtattgaa caccgcgatc cgagtgatgc   11520
actaggccgc catgagcggg acgccgatca tgatgagcct cctcgagggc atcgaggaca   11580
aagcctgcat gtgctgtccg gctcgcccgc catccgacaa tgcgacgggc gaagacgtcg   11640
atcacgaagg ccacgtagac gaagccctcc caagtggcga cataagtacg acatgcgca   11700 aaggctttcc cggtttgtcg ctgatggtgc aagagacgct gaagcgcgat ccgatgcgca   11760
ggcatctgtt cgtcttccgc ggtcgtggcg gtggcctgat caaggtcact cgccgaagag   11820
ctgcatgatt ggctcgaaac cgagcggggg aaattgtcgc gcagttctcc cgtcgccgag   11880
gcgataaatt acatgctcaa gcgatgggat ggcattacgt cattcctcga tgacggcccg   11940
atttgcctga cgaacaatgc tgccgaacga acgctcagag gctatgtact cggcaggaag   12000
tcatggctgt ttgccggatc ggatcgttgt gctgaacgtg cggcgttcat ggcgacactg   12060
atcatgagcg ccaagctcaa taacatcgat ccgcaggcct ggcttgccga cgtccgcgcc   12120
gaccttgcgg acgctccgat cagcaggctt gagcaacagc tgccgtggaa ctggacatcc   12180
aagacactga gtgctcaggc ggcctgacct gcggccttca ccggatactt accccattat   12240
cgcagattgc gatgaagcat cagcgtcatt cagcaatctt gccaaagtat gcaggctcgc   12300
gagaatcgac gtgcgaaacc ggctggttgc gccaaagatc cgcttgcgga gcggtcgaac   12360
attcatgctg ggacttcaag aggtcgagta gaggaagaac cggaaaggtt gcaccggaaa   12420
atatgcgttc cttttggagag cgcctcatgg acgtgaacaa atcgcccgga ccaaggatgc   12480
cacggataca aaagctcgcg aagctcggtc ccgtgggtgt tctgtcgtct cgttgtacaa   12540
cgaaatccat tcccattccg cgctcaagat ggcttcccct cggcagttca tcagggctaa   12600
atcaatctag ccgacttgtc cggtgaaatg ggctgcactc caacagaaac aatcaaacaa   12660
acatacacag cgacttattc acacgagctc aaattacaac ggtatatatc ctgccagtca   12720
gcatcatcac accaaaagtt aggcccgaat agtttgaaat tagaaagctc gcaattgagg   12780
tctacaggcc aaattcgctc ttagccgtac aatattactc accggtgcga tgcccccat    12840 cgtaggtgaa ggtggaaatt aatgatccat cttgagacca caggcccaca acagctacca   12900
gtttcctcaa gggtccacca aaaacgtaag cgcttacgta catggtcgat aagaaaaggc   12960
aatttgtaga tgttaacatc caacgtcgct ttcaggggatc gatccaatac gcaaaccgcc   13020
tctccccgcg cgttggccga ttcattaatg cagctggcac gacaggtttc ccgactggaa   13080
agcgggcagt gagcgcaacg caattaatgt gagttagctc actcattagg caccccaggc   13140
tttacacttt atgcttccgg ctcgtatgtt gtgtggaatt gtgagcggat aacaatttca   13200
cacaggaaac agctatgacc atgattacgc caagcttgca tgcctgcagg tcgactctag   13260
aggatctggc gcgccaagct tggatcctag cctaagtacg tactcaaaat gccaacaaat   13320
aaaaaaaaag ttgctttaat aatgccaaaa caaattaata aaacacttac aacaccggat   13380
```

```
tttttttaat taaaatgtgc catttaggat aaatagttaa tatttttaat aattatttaa    13440
aaagccgtat ctactaaaat gatttttatt tggttgaaaa tattaatatg tttaaatcaa    13500
cacaatctat caaaattaaa ctaaaaaaaa aataagtgta cgtggttaac attagtacag    13560
taatataaga ggaaaatgag aaattaagaa attgaaagcg agtctaattt ttaaattatg    13620
aacctgcata tataaaagga aagaaagaat ccaggaagaa aagaaatgaa accatgcatg    13680
gtcccctcgt catcacgagt ttctgccatt tgcaatagaa acactgaaac acctttctct    13740
ttgtcactta attgagatgc cgaagccacc tcacaccatg aacttcatga ggtgtagcac    13800
ccaaggcttc catagccatg catactgaag aatgtctcaa gctcagcacc ctacttctgt    13860
gacgtgtccc tcattcacct tcctctcttc cctataaata accacgcctc aggttctccg    13920
cttcacaact caaacattct ctccattggt ccttaaacac tcatcagtca tcaccatgtc    13980
ttccatagcc ccccaagcgg ccgcgttgtt gtgtctcttc ttcctcgaat ctcgatcgtt    14040
acatcaccgg gttctagcct tcacgatgtg cttttgagca tgagatttgg tttgacgcga    14100
catctccctc tcaaacgatc tttctccaat tattcaatca cttccgtatc tccagaacaa    14160
cagctcaaat ctccggtgac catggcgacg accgagagca agaatcttgt agggatcctt    14220
ccaaggagga gacaaacaag aaggagacag aagataagaa ggaggtggga gtttcggttc    14280
ctccaccgcc agagaaacca gagcctggcg attgttgcgg tagcggttgc gtccgatgcg    14340
tttgggatgt ttattacgat gagctcgaag attacaacaa gcagctttct ggagaaacta    14400
actgcagcta caagattctt gctctcggtc gtcgccatgg tcaccggaga tttgagctgt    14460
tgttctggag atacggaagt gattgaataa ttggagaaag atcgtttgag agggagatgt    14520
cgcgtcaaac caaatctcat gctcaaaagc acatcgtgaa ggctagaacc cggtgatgta    14580
acgatcgaga ttcgaggaag aagagacaca acaacgcggc cgcgacacaa gtgtgagagt    14640
actaaataaa tgctttggtt gtacgaaatc attacactaa ataaaataat caaagcttat    14700
atatgccttc cgctaaggcc gaatgcaaag aaattggttc tttctcgtta tcttttgcca    14760
ctttactag tacgtattaa ttactactta atcatctttg tttacggctc attatatccg    14820
tcgacgg                                                               14827
```

<210> SEQ ID NO 86
<211> LENGTH: 21
<212> TYPE: DNA
<213> ORGANISM: artificial sequence
<220> FEATURE:
<223> OTHER INFORMATION: amiRNA

<400> SEQUENCE: 86
taacccaaca atcatcgacc c                                               21

<210> SEQ ID NO 87
<211> LENGTH: 21
<212> TYPE: DNA
<213> ORGANISM: artificial sequence
<220> FEATURE:
<223> OTHER INFORMATION: amiRNA

<400> SEQUENCE: 87
ttggagaaaa tagggtaggg t                                               21

<210> SEQ ID NO 88
<211> LENGTH: 21
<212> TYPE: DNA
<213> ORGANISM: artificial sequence

```
<220> FEATURE:
<223> OTHER INFORMATION: amiRNA

<400> SEQUENCE: 88
gggacgatga ttgttgggtt a                                              21

<210> SEQ ID NO 89
<211> LENGTH: 21
<212> TYPE: DNA
<213> ORGANISM: artificial sequence
<220> FEATURE:
<223> OTHER INFORMATION: amiRNA

<400> SEQUENCE: 89
accctaccct acattctcca t                                              21

<210> SEQ ID NO 90
<211> LENGTH: 590
<212> TYPE: DNA
<213> ORGANISM: artificial sequence
<220> FEATURE:
<223> OTHER INFORMATION: microRNA percursor
<220> FEATURE:
<221> NAME/KEY: misc_feature
<222> LOCATION: (539)..(541)
<223> OTHER INFORMATION: n is a, c, g, or t

<400> SEQUENCE: 90
gcggccgcgc gagaaacttt gtatgggcat ggttatttct cacttctcac cctcctttac    60
tttcttatgc taaatcctcc ttcccctata tctccaccct caaccccttt ttctcattat   120
aacttttggt gcctagatgg tgtgtgtgtg tgcgcgcgag agatctgagc tcaattttcc   180
tctctcaagt cctggtcatg cttttccaca gctttcttga acttcttatg catcttatat   240
ctctccacct ccaggatttt aagccctaga agctcaagaa agctgtggga gaatatggca   300
attcaggctt ttaattgctt tcatttggta ccatcacttg caagatttca gagtacaagg   360
tgaacacaca catcttcctc ttcatcaatt ctctagtttc atccttatct tttcattcac   420
ggtaactctc actaccctct ttcatcttat aagttatacc gggggtgtga tgttgatgag   480
tgtaaattaa atatatgtga tctctttctc tggaaaaatt ttcagtgtga tatacatann   540
natctcttaa tctagagatt ttatggcttt gttatatata aggcggccgc                590

<210> SEQ ID NO 91
<211> LENGTH: 605
<212> TYPE: DNA
<213> ORGANISM: artificial sequence
<220> FEATURE:
<223> OTHER INFORMATION: microRNA precursor
<220> FEATURE:
<221> NAME/KEY: misc_feature
<222> LOCATION: (548)..(550)
<223> OTHER INFORMATION: n is a, c, g, or t

<400> SEQUENCE: 91
gcggccgcgc gagaaacttt gtatgggcat ggttatttct cacttctcac cctcctttac    60
tttcttatgc taaatcctcc ttcccctata tctccaccct caaccccttt ttctcattat   120
aacttttggt gcctagatgg tgtgtgtgtg tgcgcgcgag agatctgagc tcaattttcc   180
tctctcaagt cctggtcatg ctgtttaaac cacagctttc ttgaacttct tatgcatctt   240
atatctctcc acctccagga ttttaagccc tagaagctca agaaagctgt gggagtttaa   300
actatggcaa ttcaggcttt taattgcttt catttggtac catcacttgc aagatttcag   360
```

| agtacaaggt gaacacacac atcttcctct tcatcaattc tctagtttca tccttatctt | 420 |
| ttcattcacg gtaactctca ctaccctctt tcatctttata agttataccg ggggtgtgat | 480 |
| gttgatgagt gtaaattaaa tatatgtgat ctctttctct ggaaaaattt tcagtgtgat | 540 |
| atacatannn atctcttaat ctagagattt tatggctttg ttatatataa ggaattcgcg | 600 |
| gccgc | 605 |

<210> SEQ ID NO 92
<211> LENGTH: 59
<212> TYPE: DNA
<213> ORGANISM: artificial sequence
<220> FEATURE:
<223> OTHER INFORMATION: primer

<400> SEQUENCE: 92

| tctcaagtcc tggtcatgct taacccaac aatcatcgac cccttatgca tcttatatc | 59 |

<210> SEQ ID NO 93
<211> LENGTH: 59
<212> TYPE: DNA
<213> ORGANISM: artificial sequence
<220> FEATURE:
<223> OTHER INFORMATION: primer

<400> SEQUENCE: 93

| cctgaattgc catattctaa cccaacaatc atcgtcccct agggcttaaa atcctggag | 59 |

<210> SEQ ID NO 94
<211> LENGTH: 4536
<212> TYPE: DNA
<213> ORGANISM: artificial sequence
<220> FEATURE:
<223> OTHER INFORMATION: plasmid
<220> FEATURE:
<221> NAME/KEY: misc_feature
<222> LOCATION: (4479)..(4481)
<223> OTHER INFORMATION: n is a, c, g, or t

<400> SEQUENCE: 94

| aagggcgaat tctgcagata tccatcacac tggcggccgc tcgagcatgc atctagaggg | 60 |
| cccaattcgc cctatagtga gtcgtattac aattcactgg ccgtcgtttt acaacgtcgt | 120 |
| gactgggaaa accctggcgt tacccaactt aatcgccttg cagcacatcc ccctttcgcc | 180 |
| agctggcgta atagcgaaga ggcccgcacc gatcgccctt cccaacagtt gcgcagcctg | 240 |
| aatggcgaat ggacgcgccc tgtagcggcg cattaagcgc ggcgggtgtg gtggttacgc | 300 |
| gcagcgtgac cgctacactt gccagcgccc tagcgcccgc tcctttcgct ttcttccctt | 360 |
| cctttctcgc cacgttcgcc ggctttcccc gtcaagctct aaatcggggg ctccctttag | 420 |
| ggttccgatt tagtgcttta cggcacctcg accccaaaaa acttgattag ggtgatggtt | 480 |
| cacgtagtgg gccatcgccc tgatagacgg ttttcgccc tttgacgttg gagtccacgt | 540 |
| tctttaatag tggactcttg ttccaaactg gaacaacact caaccctatc tcggtctatt | 600 |
| cttttgattt ataagggatt ttgccgattt cggcctattg gttaaaaaat gagctgattt | 660 |
| aacaaaaatt taacgcgaat tttaacaaaa ttcaggcgc aagggctgct aaaggaagcg | 720 |
| gaacacgtag aaagccagtc cgcagaaacg gtgctgaccc cggatgaatg tcagctactg | 780 |
| ggctatctgg acaagggaaa acgcaagcgc aaagagaaag caggtagctt gcagtgggct | 840 |
| tacatggcga tagctagact gggcggtttt atggacagca agcgaaccgg aattgccagc | 900 |
| tggggcgccc tctggtaagg ttgggaagcc ctgcaaagta aactggatgg ctttcttgcc | 960 |

-continued

```
gccaaggatc tgatggcgca ggggatcaag atctgatcaa gagacaggat gaggatcgtt    1020
tcgcatgatt gaacaagatg gattgcacgc aggttctccg gccgcttggg tggagaggct    1080
attcggctat gactgggcac aacagacaat cggctgctct gatgccgccg tgttccggct    1140
gtcagcgcag gggcgcccgg ttcttttttgt caagaccgac ctgtccggtg ccctgaatga    1200
actgcaggac gaggcagcgc ggctatcgtg gctggccacg acgggcgttc cttgcgcagc    1260
tgtgctcgac gttgtcactg aagcgggaag ggactggctg ctattgggcg aagtgccggg    1320
gcaggatctc ctgtcatccc accttgctcc tgccgagaaa gtatccatca tggctgatgc    1380
aatgcggcgc ctgcatacgc ttgatccggc tacctgccca ttcgaccacc aagcgaaaca    1440
tcgcatcgag cgagcacgta ctcggatgga agccggtctt gtcgatcagg atgatctgga    1500
cgaagagcat caggggctcg cgccagccga actgttcgcc aggctcaagg cgcgcatgcc    1560
cgacggcgag gatctcgtcg tgacccatgg cgatgcctgc ttgccgaata tcatggtgga    1620
aaatggccgc ttttctggat tcatcgactg tggccggctg ggtgtggcgg accgctatca    1680
ggacatagcg ttggctaccc gtgatattgc tgaagagctt ggcggcgaat gggctgaccg    1740
cttcctcgtg ctttacggta tcgccgctcc cgattcgcag cgcatcgcct tctatcgcct    1800
tcttgacgag ttcttctgaa ttgaaaaagg aagagtatga gtattcaaca tttccgtgtc    1860
gcccttattc cctttttgc ggcatttttgc cttcctgttt ttgctcaccc agaaacgctg    1920
gtgaaagtaa aagatgctga agatcagttg ggtgcacgag tgggttacat cgaactggat    1980
ctcaacagcg gtaagatcct tgagagtttt cgccccgaag aacgttttcc aatgatgagc    2040
acttttaaag ttctgctatg tggcgcggta ttatcccgta ttgacgccgg caagagcaa    2100 ctcggtcgcc gcatacacta ttctcagaat gacttggttg agtactcacc agtcacagaa    2160
aagcatctta cggatggcat gacagtaaga gaattatgca gtgctgccat aaccatgagt    2220
gataacactg cggccaactt acttctgaca acgatcggag gaccgaagga gctaaccgct    2280
tttttgcaca acatggggga tcatgtaact cgccttgatc gttgggaacc ggagctgaat    2340
gaagccatac caaacgacga gcgtgacacc acgatgcctg tagcaatggc aacaacgttg    2400
cgcaaactat taactggcga actacttact ctagcttccc ggcaacaatt aatagactgg    2460
atggaggcgg ataaagttgc aggaccactt ctgcgctcgg cccttccggc tggctggttt    2520
attgctgata atctggagc cggtgagcgt gggtctcgcg gtatcattgc agcactgggg    2580
ccagatggta agccctcccg tatcgtagtt atctacacga cggggagtca ggcaactatg    2640
gatgaacgaa atagacagat cgctgagata ggtgcctcac tgattaagca ttggtaactg    2700
tcagaccaag tttactcata tatactttag attgatttaa aacttcattt ttaatttaaa    2760
aggatctagg tgaagatcct ttttgataat ctcatgacca aaatcccta acgtgagttt    2820 tcgttccact gagcgtcaga ccccgtagaa aagatcaaag gatcttcttg agatccttt    2880 tttctgcgcg taatctgctg cttgcaaaca aaaaaaccac cgctaccagc ggtggtttgt    2940
ttgccggatc aagagctacc aactctttt ccgaaggtaa ctggcttcag cagagcgcag    3000
ataccaaata ctgttcttct agtgtagccg tagttaggcc accacttcaa gaactctgta    3060
gcaccgccta catacctcgc tctgctaatc ctgttaccag tggctgctgc cagtggcgat    3120
aagtcgtgtc ttaccgggtt ggactcaaga cgatagttac cggataaggc gcagcggtcg    3180
ggctgaacgg ggggttcgtg cacacagccc agcttggagc gaacgaccta caccgaactg    3240
agatacctac agcgtgagct atgagaaagc gccacgcttc ccgaagggag aaaggcggac    3300
```

| | |
|---|---|
| aggtatccgg taagcggcag ggtcggaaca ggagagcgca cgagggagct tccagggga | 3360 |
| aacgcctggt atctttatag tcctgtcggg tttcgccacc tctgacttga gcgtcgattt | 3420 |
| ttgtgatgct cgtcagggggg gcggagccta tggaaaaacg ccagcaacgc ggccttttta | 3480 |
| cggttcctgg cctttttgctg cctttttgct cacatgttct ttcctgcgtt atccctgat | 3540 |
| tctgtggata accgtattac cgcctttgag tgagctgata ccgctcgccg cagccgaacg | 3600 |
| accgagcgca gcgagtcagt gagcgaggaa gcggaagagc gcccaatacg caaaccgcct | 3660 |
| ctccccgcgc gttggccgat tcattaatgc agctggcacg acaggtttcc cgactggaaa | 3720 |
| gcgggcagtg agcgcaacgc aattaatgtg agttagctca ctcattaggc accccaggct | 3780 |
| ttacacttta tgcttccggc tcgtatgttg tgtggaattg tgagcggata acaatttcac | 3840 |
| acaggaaaca gctatgacca tgattacgcc aagcttggta ccgagctcgg atccactagt | 3900 |
| aacggccgcc agtgtgctgg aattcgccct tgcggccgcg cgagaaactt tgtatgggca | 3960 |
| tggttatttc tcacttctca ccctcctta ctttcttatg ctaaatcctc cttccctat | 4020 |
| atctccaccc tcaacccctt tttctcatta aacttttgg tgcctagatg gtgtgtgtgt | 4080 |
| gtgcgcgcga gagatctgag ctcaattttc ctctctcaag tcctggtcat gctgtttaaa | 4140 |
| ccacagcttt cttgaacttc ttatgcatct tatatctctc cacctccagg attttaagcc | 4200 |
| ctagaagctc aagaaagctg tgggagttta actatggca attcaggctt taaattgctt | 4260 |
| tcatttggta ccatcacttg caagatttca gagtacaagg tgaacacaca catcttcctc | 4320 |
| ttcatcaatt ctctagtttc atccttatct tttcattcac ggtaactctc actaccctct | 4380 |
| ttcatcttat aagttatacc ggggtgtga tgttgatgag tgtaaattaa atatatgtga | 4440 |
| tctctttctc tggaaaaatt ttcagtgtga tatacatann natctcttaa tctagagatt | 4500 |
| ttatggcttt gttatatata aggaattcgc ggccgc | 4536 |

<210> SEQ ID NO 95
<211> LENGTH: 974
<212> TYPE: DNA
<213> ORGANISM: artificial sequence
<220> FEATURE:
<223> OTHER INFORMATION: microRNA precursor

<400> SEQUENCE: 95

| | |
|---|---|
| gcggccgctt ctagctagct agggtttggg tagtgagtgt aataaagttg caaagttttt | 60 |
| ggttaggtta cgttttgacc ttattattat agttcaaagg gaaacattaa ttaaagggga | 120 |
| ttatgaagtg gagctccttg aagtccaatt gaggatctta ctgggtgaat tgagctgctt | 180 |
| agctatggat cccacagttc tacccatcaa taagtgcttt tgtggtagtc ttgtggcttc | 240 |
| catatctggg gagcttcatt tgcctttata gtattaacct tctttggatt gaagggagct | 300 |
| ctacacccct ctcttctttt ctctcataat aatttaaatt tgttatagac tctaaacttt | 360 |
| aaatgttttt tttgaagttt ttccgttttt ctcttttgcc atgatcccgt tcttgctgtg | 420 |
| gagtaacctt gtccgaggta tgtgcatgat tagatccata cttaatttgt gtgcatcacg | 480 |
| aaggtgaggt tgaaatgaac tttgcttttt tgaccttta ggaaagttct tttgttgcag | 540 |
| taatcaattt taattagttt taattgacac tattactttt attgtcatct tgttagtttt | 600 |
| tattgttgaa ttgagtgcat atttcctagg aaattctctt acctaacatt ttttatacag | 660 |
| atctatgctc ttggctcttg cccttactct tggccttgtg ttggttattt gtctacatat | 720 |
| ttattgactg gtcgatgaga catgtcacaa ttccttgggct tatttgttgg tctaataaaa | 780 |
| ggagtgctta ttgaaagatc aagacggaga ttcggtttta tataaataaa ctaaagatga | 840 |

```
catattagtg tgttgatgtc tcttcaggat aattttttgtt tgaaataata tggtaatgtc    900
ttgtctaaat ttgtgtacat aattcttact gattttttgg attgttggat ttttataaac    960
aaatctgcgg ccgc                                                      974

<210> SEQ ID NO 96
<211> LENGTH: 990
<212> TYPE: DNA
<213> ORGANISM: artificial sequence
<220> FEATURE:
<223> OTHER INFORMATION: in-fusion ready microRNA 159 precursor

<400> SEQUENCE: 96
gcggccgctt ctagctagct agggtttggg tagtgagtgt aataaagttg caaagttttt     60
ggttaggtta cgttttgacc ttattattat agttcaaagg gaaacattaa ttaaagggga    120
ttatgaagtg tttaaacgga gctccttgaa gtccaattga ggatcttact gggtgaattg    180
agctgcttag ctatggatcc cacagttcta cccatcaata agtgcttttg tggtagtctt    240
gtggcttcca tatctgggga gcttcatttg cctttatagt attaaccttc tttggattga    300
agggagctct agtttaaacc acccttctct tcttttctct cataataatt taaatttgtt    360
atagactcta aactttaaat gttttttttg aagttttttcc gttttttctct tttgccatga    420 tcccgttctt gctgtggagt aaccttgtcc gaggtatgtg catgattaga tccatactta    480
atttgtgtgc atcacgaagg tgaggttgaa atgaactttg cttttttgac cttttaggaa    540
agttcttttg ttgcagtaat caatttaat tagttttaat tgacactatt acttttattg      600
tcatctttgt tagttttatt gttgaattga gtgcatattt cctaggaaat tctcttacct    660
aacatttttt atacagatct atgctcttgg ctcttgccct tactcttggc cttgtgttgg    720
ttatttgtct acatatttat tgactggtcg atgagacatg tcacaattct tgggcttatt    780
tgttggtcta ataaaaggag tgcttattga aagatcaaga cggagattcg gttttatata    840
aataaactaa agatgacata ttagtgtgtt gatgtctctt caggataatt tttgtttgaa    900
ataatatggt aatgtcttgt ctaaatttgt gtacataatt cttactgatt ttttggattg    960
ttggattttt ataaacaaat ctgcggccgc                                     990

<210> SEQ ID NO 97
<211> LENGTH: 54
<212> TYPE: DNA
<213> ORGANISM: artificial sequence
<220> FEATURE:
<223> OTHER INFORMATION: primer

<400> SEQUENCE: 97
attaaggggg attatgaaga ccctacccta cattctccat tgaggatctt actg           54

<210> SEQ ID NO 98
<211> LENGTH: 53
<212> TYPE: DNA
<213> ORGANISM: artificial sequence
<220> FEATURE:
<223> OTHER INFORMATION: primer

<400> SEQUENCE: 98
agaaaagaag agaagggtga ccctacccta ttttctccaa gaaggttaat act             53

<210> SEQ ID NO 99
<211> LENGTH: 4911
<212> TYPE: DNA
```

<213> ORGANISM: artificial
<220> FEATURE:
<223> OTHER INFORMATION: plasmid

<400> SEQUENCE: 99

```
ggccgcgaat tcttctagct agctagggtt tgggtagtga gtgtaataaa gttgcaaagt      60
ttttggttag gttacgtttt gaccttatta ttatagttca aagggaaaca ttaattaaag     120
gggattatga agaccctacc ctacattctc cattgaggat cttactgggt gaattgagct     180
gcttagctat ggatcccaca gttctaccca tcaataagtg cttttgtggt agtcttgtgg     240
cttccatatc tggggagctt catttgcctt tatagtatta accttcttgg agaaaatagg     300
gtagggtcac ccttctcttc ttttctctca taataattta aatttgttat agactctaaa     360
ctttaaatgt ttttttgaa gttttccgt ttttctcttt tgccatgatc ccgttcttgc      420
tgtggagtaa ccttgtccga ggtatgtgca tgattagatc catacttaat ttgtgtgcat     480
cacgaaggtg aggttgaaat gaactttgct tttttgacct tttaggaaag ttcttttgtt     540
gcagtaatca atttaatta gttttaattg acactattac ttttattgtc atctttgtta     600
gttttattgt tgaattgagt gcatatttcc taggaaattc tcttacctaa catttttat      660
acagatctat gctcttggct cttgccctta ctcttggcct tgtgttggtt atttgtctac     720
atatttattg actggtcgat gagacatgtc acaattcttg gcttatttg ttggtctaat     780
aaaaggagtg cttattgaaa gatcaagacg gagattcggt tttatataaa taaactaaag     840
atgacatatt agtgtgttga tgtctcttca ggataatttt tgtttgaaat aatatggtaa     900
tgtcttgtct aaatttgtgt acataattct tactgatttt ttggattgtt ggattttat      960
aaacaaatct gcggccgcaa gggcgaattc tgcagatatc catcacactg gcggccgctc    1020
gagcatgcat ctagagggcc caattcgccc tatagtgagt cgtattacaa ttcactggcc    1080
gtcgttttac aacgtcgtga ctgggaaaac cctggcgtta cccaacttaa tcgccttgca    1140
gcacatcccc ctttcgccag ctggcgtaat agcgaagagg cccgcaccga tcgcccttcc    1200
caacagttgc gcagcctgaa tggcgaatgg acgcgccctg tagcggcgca ttaagcgcgg    1260
cgggtgtggt ggttacgcgc agcgtgaccg ctacacttgc cagcgcccta gcgcccgctc    1320
ctttcgcttt cttccttcc tttctcgcca cgttcgccgg ctttccccgt caagctctaa    1380
atcgggggct ccctttaggg ttccgattta gtgctttacg gcacctcgac cccaaaaaac    1440
ttgattaggg tgatggttca cgtagtgggc catcgccctg atagacggtt tttcgccctt    1500
tgacgttgga gtccacgttc tttaatagtg gactcttgtt ccaaactgga acaacactca    1560
accctatctc ggtctattct tttgatttat aagggatttt gccgatttcg gcctattggt    1620
taaaaaatga gctgatttaa caaaaattta acgcgaattt taacaaaatt cagggcgcaa    1680
gggctgctaa aggaagcgga acacgtagaa agccagtccg cagaaacggt gctgaccccg    1740
gatgaatgtc agctactggg ctatctggac aagggaaaac gcaagcgcaa agagaaagca    1800
ggtagcttgc agtgggctta catggcgata gctagactgg gcggttttat ggacagcaag    1860
cgaaccggaa ttgccagctg gggcgccctc tggtaaggtt gggaagccct gcaaagtaaa    1920
ctggatggct tcttgccgc caaggatctg atggcgcagg gatcaagat ctgatcaaga     1980
gacaggatga ggatcgtttc gcatgattga acaagatgga ttgcacgcag ttctccggc     2040
cgcttgggtg gagaggctat tcggctatga ctgggcacaa cagacaatcg gctgctctga    2100
tgccgccgtg ttccggctgt cagcgcaggg gcgcccggtt cttttttgtca agaccgacct    2160
gtccggtgcc ctgaatgaac tgcaggacga ggcagcgcgg ctatcgtggc tggccacgac    2220
```

```
gggcgttcct tgcgcagctg tgctcgacgt tgtcactgaa gcgggaaggg actggctgct    2280
attgggcgaa gtgccggggc aggatctcct gtcatcccac cttgctcctg ccagaaaagt    2340
atccatcatg gctgatgcaa tgcggcggct gcatacgctt gatccggcta cctgcccatt    2400
cgaccaccaa gcgaaacatc gcatcgagcg agcacgtact cggatggaag ccggtcttgt    2460
cgatcaggat gatctggacg aagagcatca ggggctcgcg ccagccgaac tgttcgccag    2520
gctcaaggcg cgcatgcccg acggcgagga tctcgtcgtg acccatggcg atgcctgctt    2580
gccgaatatc atggtggaaa atggccgctt ttctggattc atcgactgtg gccggctggg    2640
tgtggcggac cgctatcagg acatagcgtt ggctacccgt gatattgctg aagagcttgg    2700
cggcgaatgg gctgaccgct tcctcgtgct ttacggtatc gccgctcccg attcgcagcg    2760
catcgccttc tatcgccttc ttgacgagtt cttctgaatt gaaaaaggaa gagtatgagt    2820
attcaacatt tccgtgtcgc ccttattccc ttttttgcgg cattttgcct tcctgttttt    2880
gctcacccag aaacgctggt gaaagtaaaa gatgctgaag atcagttggg tgcacgagtg    2940
ggttacatcg aactggatct caacagcggt aagatccttg agagttttcg ccccgaagaa    3000
cgttttccaa tgatgagcac ttttaaagtt ctgctatgtg gcgcggtatt atcccgtatt    3060
gacgccgggc aagagcaact cggtcgccgc atacactatt ctcagaatga cttggttgag    3120
tactcaccag tcacagaaaa gcatcttacg gatggcatga cagtaagaga attatgcagt    3180
gctgccataa ccatgagtga taacactgcg gccaacttac ttctgacaac gatcggagga    3240
ccgaaggagc taaccgcttt tttgcacaac atgggggatc atgtaactcg ccttgatcgt    3300
tgggaaccgg agctgaatga agccatacca aacgacgagc gtgacaccac gatgcctgta    3360
gcaatggcaa caacgttgcg caaactatta actggcgaac tacttactct agcttcccgg    3420
caacaattaa tagactggat ggaggcggat aaagttgcag gaccacttct gcgctcggcc    3480
cttccggctg gctggtttat tgctgataaa tctggagccg gtgagcgtgg gtctcgcggt    3540
atcattgcag cactggggcc agatggtaag ccctcccgta tcgtagttat ctacacgacg    3600
gggagtcagg caactatgga tgaacgaaat agacagatcg ctgagatagg tgcctcactg    3660
attaagcatt ggtaactgtc agaccaagtt tactcatata ctttagat tgatttaaaa    3720
cttcattttt aatttaaaag gatctaggtg aagatccttt ttgataatct catgaccaaa    3780
atcccttaac gtgagttttc gttccactga gcgtcagacc ccgtagaaaa gatcaaagga    3840
tcttcttgag atcctttttt tctgcgcgta atctgctgct tgcaaacaaa aaaaccaccg    3900
ctaccagcgg tggtttgttt gccggatcaa gagctaccaa ctcttttttcc gaaggtaact    3960
ggcttcagca gagcgcagat accaaatact gttcttctag tgtagccgta gttaggccac    4020
cacttcaaga actctgtagc accgcctaca tacctcgctc tgctaatcct gttaccagtg    4080
gctgctgcca gtggcgataa gtcgtgtctt accgggttgg actcaagacg atagttaccg    4140
gataaggcgc agcggtcggg ctgaacgggg gttcgtgca cacagcccag cttggagcga    4200
acgacctaca ccgaactgag atacctacag cgtgagctat gagaaagcgc cacgcttccc    4260
gaagggagaa aggcggacag gtatccggta agcggcaggg tcggaacagg agagcgcacg    4320
agggagcttc caggggaaa cgcctggtat ctttatagtc ctgtcgggtt cgccacctc    4380
tgacttgagc gtcgattttt gtgatgctcg tcagggggc ggagcctatg gaaaaacgcc    4440
agcaacgcgg cctttttacg gttcctggcc ttttgctggc cttttgctca catgttcttt    4500
cctgcgttat cccctgattc tgtggataac cgtattaccg cctttgagtg agctgatacc    4560
```

```
gctcgccgca gccgaacgac cgagcgcagc gagtcagtga gcgaggaagc ggaagagcgc    4620
ccaatacgca aaccgcctct ccccgcgcgt tggccgattc attaatgcag ctggcacgac    4680
aggtttcccg actggaaagc gggcagtgag cgcaacgcaa ttaatgtgag ttagctcact    4740
cattaggcac cccaggcttt acactttatg cttccggctc gtatgttgtg tggaattgtg    4800
agcggataac aatttcacac aggaaacagc tatgaccatg attacgccaa gcttggtacc    4860
gagctcggat ccactagtaa cggccgccag tgtgctggaa ttcgcccttg c             4911

<210> SEQ ID NO 100
<211> LENGTH: 9130
<212> TYPE: DNA
<213> ORGANISM: artificial sequence
<220> FEATURE:
<223> OTHER INFORMATION: plasmid
<220> FEATURE:
<221> NAME/KEY: misc_feature
<222> LOCATION: (6642)..(6642)
<223> OTHER INFORMATION: n is a, c, g, or t

<400> SEQUENCE: 100
ggccgcgaca caagtgtgag agtactaaat aaatgctttg gttgtacgaa atcattacac      60
taaataaaat aatcaaagct tatatatgcc ttccgctaag gccgaatgca aagaaattgg     120
ttctttctcg ttatcttttg ccacttttac tagtacgtat taattactac ttaatcatct     180
ttgtttacgg ctcattatat ccgtcgacgg cgcgcccgat catccggata tagttcctcc     240
tttcagcaaa aaacccctca agacccgttt agaggcccca aggggttatg ctagttattg     300
ctcagcggtg gcagcagcca actcagcttc ctttcgggct ttgttagcag ccggatcgat     360
ccaagctgta cctcactatt cctttgccct cggacgagtg ctgggcgtc ggtttccact     420 atcggcgagt acttctacac agccatcggt ccagacggcc gcgcttctgc gggcgatttg     480
tgtacgcccg acagtcccgg ctccggatcg gacgattgcg tcgcatcgac cctgcgccca     540
agctgcatca tcgaaattgc cgtcaaccaa gctctgatag agttggtcaa gaccaatgcg     600
gagcatatac gcccggagcc gcggcgatcc tgcaagctcc ggatgcctcc gctcgaagta     660
gcgcgtctgc tgctccatac aagccaacca cggcctccag aagaagatgt tggcgacctc     720
gtattgggaa tccccgaaca tcgcctcgct ccagtcaatg accgctgtta tgcggccatt     780
gtccgtcagg acattgttgg agccgaaatc cgcgtgcacg aggtgccgga cttcggggca     840
gtcctcggcc caaagcatca gctcatcgag agcctgcgcg acggacgcac tgacggtgtc     900
gtccatcaca gtttgccagt gatacacatg gggatcagca atcgcgcata tgaaatcacg     960
ccatgtagtg tattgaccga ttccttgcgg tccgaatggg ccgaacccgc tcgtctggct    1020
aagatcggcc gcagcgatcg catccatagc ctccgcgacc ggctgcagaa cagcgggcag    1080
ttcggtttca ggcaggtctt gcaacgtgac accctgtgca cggcgggaga tgcaataggt    1140
caggctctcg ctgaattccc caatgtcaag cacttccgga atcgggagcg cggccgatgc    1200
aaagtgccga taaacataac gatctttgta gaaaccatcg cgcagctat ttacccgcag    1260 gacatatcca cgccctccta catcgaagct gaaagcacga gattcttcgc cctccgagag    1320
ctgcatcagg tcggagacgc tgtcgaactt ttcgatcaga aacttctcga cagacgtcgc    1380
ggtgagttca ggcttttcca tgggtatatc tccttcttaa agttaaacaa aattatttct    1440
agagggaaac cgttgtggtc tccctatagt gagtcgtatt aatttcgcgg gatcgagatc    1500
gatccaattc caatcccaca aaaatctgag cttaacagca cagttgctcc tctcagagca    1560
gaatcgggta ttcaacaccc tcatatcaac tactacgttg tgtataacgg tccacatgcc    1620
```

-continued

```
ggtatatacg atgactgggg ttgtacaaag gcggcaacaa acggcgttcc cggagttgca    1680
cacaagaaat ttgccactat tacagaggca agagcagcag ctgacgcgta cacaacaagt    1740
cagcaaacag acaggttgaa cttcatcccc aaaggagaag ctcaactcaa gcccaagagc    1800
tttgctaagg ccctaacaag cccaccaaag caaaaagccc actggctcac gctaggaacc    1860
aaaaggccca gcagtgatcc agccccaaaa gagatctcct ttgccccgga gattacaatg    1920
gacgatttcc tctatcttta cgatctagga aggaagttcg aaggtgaagg tgacgacact    1980
atgttcacca ctgataatga aaggttagc ctcttcaatt tcagaaagaa tgctgaccca     2040
cagatggtta gagaggccta cgcagcaggt ctcatcaaga cgatctaccc gagtaacaat    2100
ctccaggaga tcaaatacct tcccaagaag gttaaagatg cagtcaaaag attcaggact    2160
aattgcatca agaacacaga gaaagacata tttctcaaga tcagaagtac tattccagta    2220
tggacgattc aaggcttgct tcataaacca aggcaagtaa tagagattgg agtctctaaa    2280
aaggtagttc ctactgaatc taaggccatg catggagtct aagattcaaa tcgaggatct    2340
aacagaactc gccgtgaaga ctggcgaaca gttcatacag agtcttttac gactcaatga    2400
caagaagaaa atcttcgtca acatggtgga gcacgacact ctggtctact ccaaaaatgt    2460
caaagataca gtctcagaag accaaagggc tattgagact tttcaacaaa ggataatttc    2520
gggaaacctc ctcggattcc attgcccagc tatctgtcac ttcatcgaaa ggacagtaga    2580
aaaggaaggt ggctcctaca aatgccatca ttgcgataaa ggaaaggcta tcattcaaga    2640
tgcctctgcc gacagtggtc ccaaagatgg acccccaccc acgaggagca tcgtggaaaa    2700
agaagacgtt ccaaccacgt cttcaaagca agtggattga tgtgacatct ccactgacgt    2760
aagggatgac gcacaatccc actatccttc gcaagaccct tcctctatat aaggaagttc    2820
atttcatttg gagaggacac gctcgagctc atttctctat tacttcagcc ataacaaaag    2880
aactcttttc tcttcttatt aaaccatgaa aaagcctgaa ctcaccgcga cgtctgtcga    2940
gaagtttctg atcgaaaagt tcgacagcgt ctccgacctg atgcagctct cggagggcga    3000
agaatctcgt gctttcagct tcgatgtagg agggcgtgga tatgtcctgc gggtaaatag    3060
ctgcgccgat ggtttctaca aagatcgtta tgtttatcgg cactttgcat cggccgcgct    3120
cccgattccg gaagtgcttg acattgggga attcagcgag agcctgacct attgcatctc    3180
ccgccgtgca cagggtgtca cgttgcaaga cctgcctgaa accgaactgc ccgctgttct    3240
gcagccggtc gcggaggcca tggatgcgat cgctgcggcc gatcttagcc agacgagcgg    3300
gttcggccca ttcggaccgc aaggaatcgg tcaatacact acatggcgtg atttcatatg    3360
cgcgattgct gatccccatg tgtatcactg gcaaactgtg atggacgaca ccgtcagtgc    3420
gtccgtcgcg caggctctcg atgagctgat gctttgggcc gaggactgcc ccgaagtccg    3480
gcacctcgtg cacgcggatt tcggctccaa caatgtcctg acggacaatg gccgcataac    3540
agcggtcatt gactggagcg aggcgatgtt cggggattcc caatacgagg tcgccaacat    3600
cttcttctgg aggccgtggt tggcttgtat ggagcagcag acgcgctact tcgagcggag    3660
gcatccggag cttgcaggat cgccgcggct ccgggcgtat atgctccgca ttggtcttga    3720
ccaactctat cagagcttgg ttgacggcaa tttcgatgat gcagcttggg cgcagggtcg    3780
atgcgacgca atcgtccgat ccggagccgg gactgtcggg cgtacacaaa tcgcccgcag    3840
aagcgcggcc gtctggaccg atggctgtgt agaagtactc gccgatagtg gaaaccgacg    3900
ccccagcact cgtccgaggg caaaggaata gtgaggtacc taaagaagga gtgcgtcgaa    3960
```

-continued

```
gcagatcgtt caaacatttg gcaataaagt ttcttaagat tgaatcctgt tgccggtctt    4020
gcgatgatta tcatataatt tctgttgaat tacgttaagc atgtaataat taacatgtaa    4080
tgcatgacgt tatttatgag atgggttttt atgattagag tcccgcaatt atacatttaa    4140
tacgcgatag aaaacaaaat atagcgcgca aactaggata aattatcgcg cgcggtgtca    4200
tctatgttac tagatcgatg tcgaatctga tcaacctgca ttaatgaatc ggccaacgcg    4260
cggggagagg cggtttgcgt attgggcgct cttccgcttc ctcgctcact gactcgctgc    4320
gctcggtcgt tcggctgcgg cgagcggtat cagctcactc aaaggcggta atacggttat    4380
ccacagaatc aggggataac gcaggaaaga acatgtgagc aaaaggccag caaaaggcca    4440
ggaaccgtaa aaaggccgcg ttgctggcgt ttttccatag gctccgcccc cctgacgagc    4500
atcacaaaaa tcgacgctca agtcagaggt ggcgaaaccc gacaggacta taaagatacc    4560
aggcgtttcc ccctggaagc tccctcgtgc gctctcctgt tccgaccctg ccgcttaccg    4620
gatacctgtc cgcctttctc ccttcgggaa gcgtggcgct ttctcaatgc tcacgctgta    4680
ggtatctcag ttcggtgtag gtcgttcgct ccaagctggg ctgtgtgcac gaaccccccg    4740
ttcagcccga ccgctgcgcc ttatccggta actatcgtct tgagtccaac ccggtaagac    4800
acgacttatc gccactggca gcagccactg gtaacaggat tagcagagcg aggtatgtag    4860
gcggtgctac agagttcttg aagtggtggc ctaactacgg ctacactaga aggacagtat    4920
ttggtatctg cgctctgctg aagccagtta ccttcggaaa aagagttggt agctcttgat    4980
ccggcaaaca aaccaccgct ggtagcggtg gtttttttgt ttgcaagcag cagattacgc    5040
gcagaaaaaa aggatctcaa gaagatcctt tgatcttttc tacggggtct gacgctcagt    5100
ggaacgaaaa ctcacgttaa gggattttgg tcatgacatt aacctataaa aataggcgta    5160
tcacgaggcc ctttcgtctc gcgcgtttcg gtgatgacgg tgaaaacctc tgacacatgc    5220
agctcccgga gacggtcaca gcttgtctgt aagcggatgc cgggagcaga caagcccgtc    5280
agggcgcgtc agcgggtgtt ggcgggtgtc ggggctggct taactatgcg gcatcagagc    5340
agattgtact gagagtgcac catatggaca tattgtcgtt agaacgcggc tacaattaat    5400
acataacctt atgtatcata cacatacgat ttaggtgaca ctatagaacg gcgcgccaag    5460
cttggatcct cgaagagaag ggttaataac acactttttt aacattttta acacaaattt    5520
tagttattta aaaatttatt aaaaaattta aaataagaag aggaactctt taaataaatc    5580
taacttacaa aatttatgat ttttaataag ttttcaccaa taaaaaatgt cataaaaata    5640
tgttaaaaag tatattatca atattctctt tatgataaat aaaaagaaaa aaaaaataaa    5700
agttaagtga aaatgagatt gaagtgactt taggtgtgta taaatatatc aaccccgcca    5760
acaatttatt taatccaaat atattgaagt atattattcc atagccttta tttatttata    5820
tatttattat ataaaagctt tatttgttct aggttgttca tgaaatattt ttttggtttt    5880
atctccgttg taagaaaatc atgtgctttg tgtcgccact cactattgca gcttttcat     5940 gcattggtca gattgacggt tgattgtatt tttgtttttt atggttttgt gttatgactt    6000
aagtcttcat ctctttatct cttcatcagg tttgatggtt acctaatatg gtccatgggt    6060
acatgcatgg ttaaattagg tggccaactt tgttgtgaac gatagaattt ttttatatt    6120 aagtaaacta ttttatatt atgaaataat aataaaaaaa atatttatc attattaaca     6180 aaatcatatt agttaatttg ttaactctat aataaaagaa atactgtaac attcacatta    6240
catggtaaca tctttccacc ctttcatttg tttttttgttt gatgactttt ttcttgtttt   6300
aaatttattt cccttctttt aaatttggaa tacattatca tcatatataa actaaaatac    6360
```

```
taaaaacagg attacacaaa tgataaataa taacacaaat atttataaat ctagctgcaa    6420
tatatttaaa ctagctatat cgatattgta aaataaaact agctgcattg atactgataa    6480
aaaaatatca tgtgctttct ggactgatga tgcagtatac ttttgacatt gcctttattt    6540
tatttttcag aaaagctttc ttagttctgg gttcttcatt atttgtttcc catctccatt    6600
gtgaattgaa tcatttgctt cgtgtcacaa atacaattta gntaggtaca tgcattggtc    6660
agattcacgg tttattatgt catgacttaa gttcatggta gtacattacc tgccacgcat    6720
gcattatatt ggttagattt gataggcaaa tttggttgtc aacaatataa atataaataa    6780
tgtttttata ttacgaaata acagtgatca aaacaaacag ttttatcttt attaacaaga    6840
ttttgttttt gtttgatgac gttttttaat gtttacgctt tcccccttct tttgaattta    6900
gaacacttta tcatcataaa atcaaatact aaaaaaatta catatttcat aaataataac    6960
acaaatattt ttaaaaaatc tgaaataata atgaacaata ttacatatta tcacgaaaat    7020
tcattaataa aaatattata taaataaaat gtaatagtag ttatatgtag gaaaaaagta    7080
ctgcacgcat aatatataca aaaagattaa aatgaactat tataaataat aacactaaat    7140
taatggtgaa tcatatcaaa ataatgaaaa agtaaataaa atttgtaatt aacttctata    7200
tgtattacac acacaaataa taaataatag taaaaaaaat tatgataaat atttaccatc    7260
tcataagata tttaaaataa tgataaaaat atagattatt ttttatgcaa ctagctagcc    7320
aaaaagagaa cacgggtata tataaaaaga gtacctttaa attctactgt acttcccttta   7380 ttcctgacgt tttatatca agtggacata cgtgaagatt ttaattatca gtctaaaatat    7440 ttcattagca cttaatactt ttctgttttta ttcctatcct ataagtagtc ccgattctcc   7500
caacattgct tattcacaca actaactaag aaagtcttcc atagcccccc aagcggccgc    7560
gcgagaaact ttgtatgggc atggttattt ctcacttctc accctccttt actttcttat    7620
gctaaatcct ccttcccta tatctccacc ctcaacccct ttttctcatt ataacttttg     7680
gtgcctagat ggtgtgtgtg tgtgcgcgcg agagatctga gctcaatttt cctctctcaa    7740
gtcctggtca tgctttaacc caacaatcat cgaccccctta tgcatcttat atctctccac   7800
ctccaggatt ttaagcccta ggggacgatg attgttgggt tagaatatgg caattcaggc    7860
ttttaattgc tttcatttgg taccatcact tgcaagattt cagagtacaa ggtgaacaca    7920
cacatcttcc tcttcatcaa ttctctagtt tcatccttat cttttcattc acggtaactc    7980
tcactaccct ctttcatctt ataagttata ccggggtgt gatgttgatg agtgtaaatt      8040
aaatatatgt gatctctttc tctggaaaaa ttttcagtgt gatatacata ataatctctt     8100
aatctagaga ttttatggct ttgttatata taagcggcca attctgcaga tatccatcac    8160
actggaattc ttctagctag ctagggtttg ggtagtgagt gtaataaagt tgcaaagttt    8220
ttggttaggt tacgtttttga ccttattatt atagttcaaa gggaaacatt aattaaaggg   8280
gattatgaag acccctaccct acattctcca tgaggatct tactgggtga attgagctgc    8340
ttagctatgg atcccacagt tctacccatc aataagtgct tttgtggtag tcttgtggct    8400
tccatatctg gggagcttca tttgccttta tagtattaac cttcttggag aaaatagggt    8460
agggtcaccc ttctcttctt ttctctcata ataatttaaa tttgttatag actctaaaact  8520 ttaaatgttt tttttgaagt ttttccgttt ttctcttttg ccatgatccc gttcttgctg    8580
tggagtaacc ttgtccgagg tatgtgcatg attagatcca tacttaattt gtgtgcatca    8640
cgaaggtgag gttgaaatga actttgcttt tttgaccttt taggaaagtt cttttgttgc    8700
```

-continued

```
agtaatcaat tttaattagt tttaattgac actattactt ttattgtcat ctttgttagt    8760
tttattgttg aattgagtgc atatttccta ggaaattctc ttacctaaca ttttttatac    8820
agatctatgc tcttggctct tgcccttact cttggccttg tgttggttat ttgtctacat    8880
atttattgac tggtcgatga gacatgtcac aattcttggg cttatttgtt ggtctaataa    8940
aaggagtgct tattgaaaga tcaagacgga gattcggttt tatataaata aactaaagat    9000
gacatattag tgtgttgatg tctcttcagg ataattttg tttgaaataa tatggtaatg    9060
tcttgtctaa atttgtgtac ataattctta ctgattttt ggattgttgg attttataa    9120 acaaatctgc                                                           9130
```

<210> SEQ ID NO 101
<211> LENGTH: 607
<212> TYPE: DNA
<213> ORGANISM: Cyamopsis tetragonoloba

<400> SEQUENCE: 101

```
gcacgaggtt gcggctcaca gtcgttgtgc ttcccaatcc ccgatcccca aaagagagag     60
agagaatgag gtggtggcgg cgccggcgtt gaccatgaga ccagtagcaa ccgatttcac    120
ccaaaagctc ctcccttcca atctcattct ggccaccaac aatcgccttc aacgtacctc    180
tcccttcttt ctccatccat atcgcatggc cgacggcgca gcgacatcca atacacccgc    240
gccgcaccag atccaaccca aactggaccc aaacgccgag aagaaggaga atctaccgaa    300
ggagattcct ccgccgccgg agaagcccga gccggcgat tgttgcggca gcggatgcgt    360
ccgatgcgtt tgggatattt actatgagga gcttgaacaa tacaataagc tctacaaaca    420
cgacgattcc aaccccaaac cttaattagg atcattcttt tcccaatgta attcacaatt    480
caagggttaa aatgacatca tgattttgtc aatatctcca aagtttatcg ttaatggcaa    540
gctcagggtt caccttgcca aatttgacat tcaaggatgt gtagatctat actaagaaga    600
gcttgaa                                                              607
```

<210> SEQ ID NO 102
<211> LENGTH: 116
<212> TYPE: PRT
<213> ORGANISM: Cyamopsis tetragonoloba

<400> SEQUENCE: 102

```
Met Arg Pro Val Ala Thr Asp Phe Thr Gln Lys Leu Leu Pro Ser Asn
1               5                   10                  15

Leu Ile Leu Ala Thr Asn Asn Arg Leu Gln Arg Thr Ser Pro Phe Phe
            20                  25                  30

Leu His Pro Tyr Arg Met Ala Asp Gly Ala Ala Thr Ser Asn Thr Pro
        35                  40                  45

Ala Pro His Gln Ile Gln Pro Lys Leu Asp Pro Asn Ala Glu Lys Lys
    50                  55                  60

Glu Asn Leu Pro Lys Glu Ile Pro Pro Pro Glu Lys Pro Glu Pro
65                  70                  75                  80

Gly Asp Cys Cys Gly Ser Gly Cys Val Arg Cys Val Trp Asp Ile Tyr
                85                  90                  95

Tyr Glu Glu Leu Glu Gln Tyr Asn Lys Leu Tyr Lys His Asp Asp Ser
            100                 105                 110

Asn Pro Lys Pro
        115
```

<210> SEQ ID NO 103
<211> LENGTH: 608
<212> TYPE: DNA
<213> ORGANISM: Bahia

<400> SEQUENCE: 103

```
cgatggtgtc accaatcaca gcagcctccc cctcccttc cctttcggc ggcctgtatg      60
ctgggcgccg tcctccgcgt ctcggccccg atcccgtctc tcctccccgc gccgacgcgc    120
cctctcctac tccgccgccg cagccacagc ctccgcccg agacgcccat ggccgcggcc    180
gccccwcgcg acgccggcgc cacgaagccc gacgccgcgc cggcgccggc gccagtgccg    240
cagccacccg agaagccgct ccctggcgac tgctgcggga cggctgcgt ccgctgcgtc    300
tgggacatct attacgacga actcgacgcg tacgaaaagg ccctcgccgc ccacgcggcc    360
tccgccggcg gcaaggcctc ccctatcccg gctgacakca agcccagcga cggcgccaag    420
tcctgaagca cgtggggcgt catgcgtatc ccttcttctg ttcccaactg aaatagattt    480
tcagatatgc tgctagcaat tgttgacact gagacattac atatgtgtat gctagattga    540
gatgctttgt caattcaacc tcatcgttgt gcaagtgtgt aacaagagaa agttaatatg    600
attattaa                                                             608
```

<210> SEQ ID NO 104
<211> LENGTH: 122
<212> TYPE: PRT
<213> ORGANISM: Bahia
<220> FEATURE:
<221> NAME/KEY: misc_feature
<222> LOCATION: (114)..(114)
<223> OTHER INFORMATION: Xaa can be any naturally occurring amino acid

<400> SEQUENCE: 104

```
Met Leu Gly Ala Val Leu Arg Val Ser Ala Pro Ile Pro Ser Leu Leu
1               5                   10                  15

Pro Ala Pro Thr Arg Pro Leu Leu Arg Arg Arg Ser His Ser Leu
            20                  25                  30

Pro Pro Glu Thr Pro Met Ala Ala Ala Ala Pro Arg Asp Ala Gly Ala
        35                  40                  45

Thr Lys Pro Asp Ala Ala Pro Ala Pro Ala Pro Val Pro Gln Pro Pro
    50                  55                  60

Glu Lys Pro Leu Pro Gly Asp Cys Cys Gly Ser Gly Cys Val Arg Cys
65                  70                  75                  80

Val Trp Asp Ile Tyr Tyr Asp Glu Leu Asp Ala Tyr Glu Lys Ala Leu
                85                  90                  95

Ala Ala His Ala Ala Ser Ala Gly Gly Lys Ala Ser Pro Tyr Pro Ala
            100                 105                 110

Asp Xaa Lys Pro Ser Asp Gly Ala Lys Ser
        115                 120
```

<210> SEQ ID NO 105
<211> LENGTH: 133
<212> TYPE: PRT
<213> ORGANISM: Arabidopsis lyrata

<400> SEQUENCE: 105

```
Met Val Val Val Ser Leu His Arg Ile Ser Ile Thr Thr Ser Pro Gly
1               5                   10                  15

Ser Ser Leu His Asp Val Leu Leu Ser Met Arg Phe Gly Leu Thr Arg
            20                  25                  30
```

Arg His Leu Pro Leu Lys Arg Pro Phe Thr Asn Tyr Ser Ile Thr Ser
         35                  40                  45

Val Ser Pro Glu Gln Gln Leu Ile Ser Pro Val Thr Met Ala Thr Thr
 50                  55                  60

Glu Ser Gln Asn Leu Val Gln Ala Ser Lys Glu Thr Asn Lys Lys
 65                  70                  75                  80

Glu Val Glu Asp Thr Lys Glu Ile Leu Ala Pro Pro Pro Glu Lys
                 85                  90                  95

Pro Glu Pro Gly Asp Cys Cys Gly Ser Gly Cys Val Arg Cys Val Trp
             100                 105                 110

Asp Val Tyr Tyr Glu Glu Leu Glu Asp Tyr Asn Lys Lys Leu Ser Gly
             115                 120                 125

Glu Thr Lys Ser Val
        130

<210> SEQ ID NO 106
<211> LENGTH: 113
<212> TYPE: PRT
<213> ORGANISM: Picea sitchensis

<400> SEQUENCE: 106

Met Arg Ser Pro Phe Cys Ile Pro Ser Val Val Ser Ala Arg Thr Arg
 1               5                  10                  15

Val Cys Phe Arg Phe Thr Cys Phe Thr Met Ala Thr Val Ser Gly Gly
             20                  25                  30

Gly Val Glu Gly Lys Glu Asn Leu Glu Lys Ser Ile Glu Ala Lys Ala
         35                  40                  45

Lys Asp Glu Lys Lys Lys Ala Glu Glu Ile Glu Lys Ile Leu Met
 50                  55                  60

Glu Lys Ile Gly Pro Pro Pro Glu Lys Pro Leu Pro Gly Asp Cys Cys
 65                  70                  75                  80

Gly Ser Gly Cys Glu Ile Cys Val Trp Asp Thr Tyr Phe Asp Gln Leu
             85                  90                  95

Gln Glu Tyr Lys Lys Glu Lys Asp Ser Ile Leu Lys Ser Ile Ser Pro
             100                 105                 110

Pro

<210> SEQ ID NO 107
<211> LENGTH: 821
<212> TYPE: DNA
<213> ORGANISM: Hordeum vulgare

<400> SEQUENCE: 107
ctccgcggcc cgggctctcc gatcccgcct ctcttccccg cgccggggcg ccctctcatc     60
cacctatccc gccgcctccc tacggcgccc gccatggccg acgccaagaa gaccgacgcg    120
ccggcgaccc cggccccgga gccgcccgag aagccgctcc ccggcgactg ctgcggcagc    180
ggctgcgtcc gctgcgtctg ggacatctac tacgacgagc tccaggacta caaggaggcc    240
ctcgccgccc acgcggccgc ggccgatccc agcggcgaca ggcatgcgt cgacgagaag     300 aagaccgaat gatgagaccc gggaggaggc aggacccggg tgtgtatgct ggaactagta    360
ctgggaccaa ataggatgcg cggctcgagt gggatatggg agcatgactc atggaatggc    420
ggagcggcgt agctggcgtt gtggcgagaa aaaaaatac taccaacagg gggggcccga    480
gaccgagtga gtcctctaat tataatggaa gcaaaagcgt gaacgggtgt gtgcgcgggc    540
gtggtcttga agagctctgg tgaagctgtg ccgaggagca gatgtgtccg tgcgtccata    600
cgggtacaga gacgactagg aggtgttgta cgcggcttag tgagcgtggt taggcgggat 660
gaaggagaag gggaggggga aggcgtgaga tgatagaaga tgatgggttg acgagatatg 720
acgacggtgg agacgtagga ggcatgtgat aacagtaggc tgggctgagg tgggatgcgg 780
aaggaggaga gatatatgag gggagggtgc ggttatagac g 821

<210> SEQ ID NO 108
<211> LENGTH: 103
<212> TYPE: PRT
<213> ORGANISM: Hordeum vulgare

<400> SEQUENCE: 108

Leu Arg Gly Pro Gly Ser Pro Ile Pro Pro Leu Phe Pro Ala Pro Gly
1 5 10 15

Arg Pro Leu Ile His Leu Ser Arg Arg Leu Pro Thr Ala Pro Ala Met
20 25 30

Ala Asp Ala Lys Lys Thr Asp Ala Pro Ala Thr Pro Ala Pro Glu Pro
35 40 45

Pro Glu Lys Pro Leu Pro Gly Asp Cys Cys Gly Ser Gly Cys Val Arg
50 55 60

Cys Val Trp Asp Ile Tyr Tyr Asp Glu Leu Gln Asp Tyr Lys Glu Ala
65 70 75 80

Leu Ala Ala His Ala Ala Ala Ala Asp Pro Ser Gly Asp Lys Ala Cys
85 90 95

Val Asp Glu Lys Lys Thr Glu
100

<210> SEQ ID NO 109
<211> LENGTH: 547
<212> TYPE: DNA
<213> ORGANISM: Raphanus sativus

<400> SEQUENCE: 109
gggcatggtt tcgttgcatc atatccatcc tcgattctcg accgccgcat cgtcggaata 60
caatcgtcgc cggaaaagct tccacgatgt gcttctgagc atgagatttg gatttacgcg 120
agatctctct ctgaaacggt ccttggtcaa ctactattcc ttatctcgac aacaacgaca 180
cctcaagtcg cccatcacca tggccaccaa gagcgagaag acttccacgg aggagaagga 240
taagaaggag gaggtttcac tccctccgcc tccgccgccg gagaaaccag agcctggcga 300
ctgctgcggt agcggatgcg tgcgatgcgt ttgggatgtg tattacgaag agctccaaga 360
atacaacaag ctttctacat cccttcctgg acaaactaaa tccaattgaa tgctaaattt 420
ttgtgtgcaa atgtactcgt cttcgagttt gagaagtcga agatgatgtt atgtttgaac 480
attattggat cattatcgtt actacttatc tacaaagttt actaaaagaa aaaaaaaaaa 540
aaaaaaa 547

<210> SEQ ID NO 110
<211> LENGTH: 134
<212> TYPE: PRT
<213> ORGANISM: Raphanus sativus

<400> SEQUENCE: 110

Met Val Ser Leu His His Ile His Pro Arg Phe Ser Thr Ala Ala Ser
1 5 10 15

Ser Glu Tyr Asn Arg Arg Arg Lys Ser Phe His Asp Val Leu Leu Ser
20 25 30

```
Met Arg Phe Gly Phe Thr Arg Asp Leu Ser Leu Lys Arg Ser Leu Val
            35                  40                  45

Asn Tyr Tyr Ser Leu Ser Arg Gln Gln Arg His Leu Lys Ser Pro Ile
 50                  55                  60

Thr Met Ala Thr Lys Ser Glu Lys Thr Ser Thr Glu Glu Lys Asp Lys
 65                  70                  75                  80

Lys Glu Glu Val Ser Leu Pro Pro Pro Pro Pro Glu Lys Pro Glu
                 85                  90                  95

Pro Gly Asp Cys Cys Gly Ser Gly Cys Val Arg Cys Val Trp Asp Val
            100                 105                 110

Tyr Tyr Glu Glu Leu Gln Glu Tyr Asn Lys Leu Ser Thr Ser Leu Pro
            115                 120                 125

Gly Gln Thr Lys Ser Asn
    130
```

<210> SEQ ID NO 111
<211> LENGTH: 800
<212> TYPE: DNA
<213> ORGANISM: Dennstaedtia punctilobula

<400> SEQUENCE: 111

```
ggcccctaca atatcccaaa atttcatccg accaaagaaa ttttgggctg ctgtaacgct     60
ggtgaaggta atgaaggtag ctttcttgaa ctattcattg attccttcct tcttctcgcc    120
ctcacctgta ctacaacgag ggttagggtt tcgcgagact acaagggcgg caatgtccgg    180
taacagggag cctgatcccg atcttgtgct agaaagtact cctcccaagc agaagcagca    240
gaatcacaag aaagaagtag atggagaaga aagaaagaa gaagatgatg cagagatttt    300
gaggaagcag cttggcgagc ccctgagaa gcctttgcct ggagactgtt gcggcagtgg    360
atgtgtccga tgtgtctggg acatttattt tgacgagctc gagctttata actcccgcaa    420
ggatgtcctt gatgcccgcc gtgcttcgtg atagtaccaa ctcgggatgc ctactattca    480
tagctgaaga tttgcaagga ggcccacact catctctgca gcagctcaac tcatcaattt    540
tctgtgtgac ttgttttcaag gttccccgt gaccttgcac aatattttc attgatctgt    600
attctttacc atcataaaca ttggaattgg gggttcctga aaggactaaa tccctgtttt    660
tttttcaaggt aaccctgcca tttatgggtt aatctgtatt gttttccttcc atgtacatttt   720
gcctagattc taccatatac atcagaaggc cagaaataaa tccagggctt caattggctg    780
tccagatgct tcgttttggg                                                800
```

<210> SEQ ID NO 112
<211> LENGTH: 381
<212> TYPE: DNA
<213> ORGANISM: Dennstaedtia punctilobula

<400> SEQUENCE: 112

```
atgaaggtag ctttcttgaa ctattcattg attccttcct tcttctcgcc ctcacctgta     60
ctacaacgag ggttagggtt tcgcgagact acaagggcgg caatgtccgg taacagggag    120
cctgatcccg atcttgtgct agaaagtact cctcccaagc agaagcagca gaatcacaag    180
aaagaagtag atggagaaga agaaaagaa gaagatgatg cagagatttt gaggaagcag    240
cttggcgagc ccctgagaa gcctttgcct ggagactgtt gcggcagtgg atgtgtccga    300
tgtgtctggg acatttattt tgacgagctc gagctttata actcccgcaa ggatgtcctt    360
gatgcccgcc gtgcttcgtg a                                              381
```

<210> SEQ ID NO 113
<211> LENGTH: 126
<212> TYPE: PRT
<213> ORGANISM: Dennstaedtia punctilobula

<400> SEQUENCE: 113

```
Met Lys Val Ala Phe Leu Asn Tyr Ser Leu Ile Pro Ser Phe Phe Ser
1               5                   10                  15

Pro Ser Pro Val Leu Gln Arg Gly Leu Gly Phe Arg Glu Thr Thr Arg
            20                  25                  30

Ala Ala Met Ser Gly Asn Arg Glu Pro Asp Pro Asp Leu Val Leu Glu
        35                  40                  45

Ser Thr Pro Pro Lys Gln Lys Gln Gln Asn His Lys Lys Glu Val Asp
    50                  55                  60

Gly Glu Glu Lys Lys Glu Glu Asp Asp Ala Glu Ile Leu Arg Lys Gln
65                  70                  75                  80

Leu Gly Glu Pro Pro Glu Lys Pro Leu Pro Gly Asp Cys Cys Gly Ser
                85                  90                  95

Gly Cys Val Arg Cys Val Trp Asp Ile Tyr Phe Asp Glu Leu Glu Leu
            100                 105                 110

Tyr Asn Ser Arg Lys Asp Val Leu Asp Ala Arg Arg Ala Ser
        115                 120                 125
```

<210> SEQ ID NO 114
<211> LENGTH: 777
<212> TYPE: DNA
<213> ORGANISM: Osmunda cinnamomea

<400> SEQUENCE: 114

```
acaatgagat agcatgaggt tgggtatcct gccctgcccc ttcatcaggc ctctgcttcc      60
ctcgccatcc atcgcccctc cctcctccag cctcctaacc ttccgcgctt cgccacgagc     120
catggacaaa cagcaggttc tccatcccaa gcccgcggat ctccccaaga atgactccaa     180
acagaacgac ctaacgctgc ctgcggatca ggaggaatcg cagctcggtc ctccaccgga     240
aaagccgctc ccaggtgatt gctgtggcag cggttgcgtg cggtgtgtct gggataccta     300
tttcgaggag ctggatagtt acaacgagcg caaagaggcg tttgaatccc gcctgaagaa     360
gtcgcctcct ctgtaatttt ctacattggc ggtaggaaaa gggagtaaaa atttacgag     420
gaagaatgtg caatgttttt gtgaggatga agtatcaggt ggtggggata gttcagaagg     480
ctaagaactc caaagatctt tcaagttgat ggtttgaaac ttattgaatg gactctcatg     540
aagtcaagac tgcactctct ttattgttac agactttcca ttgatatatt ttttcgccat     600
attagcggac atgcagatgt cacttgagat cttcgtccaa gttgtggcca gctgattctt     660
tctatctgca gtggtgcatt tgcccaacca gctaccttct ctaagcattt tgatcagagc     720
ttctaaaaga gcaggctgaa gtgatgatat atggtttctt tacatcaatc atggctg       777
```

<210> SEQ ID NO 115
<211> LENGTH: 363
<212> TYPE: DNA
<213> ORGANISM: Osmunda cinnamomea

<400> SEQUENCE: 115

```
atgaggttgg gtatcctgcc ctgcccctta tcaggcctc tgcttccctc gccatccatc       60
gcccctccct cctccagcct cctaaccttc cgcgcttcgc cacgagccat ggacaaacag     120
```

```
caggttctcc atcccaagcc cgcggatctc cccaagaatg actccaaaca gaacgaccta    180
acgctgcctg cggatcagga ggaatcgcag ctcggtcctc caccggaaaa gccgctccca    240
ggtgattgct gtggcagcgg ttgcgtgcgg tgtgtctggg atacctattt cgaggagctg    300
gatagttaca acgagcgcaa agaggcgttt gaatcccgcc tgaagaagtc gcctcctctg    360
taa                                                                   363
```

```
<210> SEQ ID NO 116
<211> LENGTH: 120
<212> TYPE: PRT
<213> ORGANISM: Osmunda cinnamomea

<400> SEQUENCE: 116
```

Met Arg Leu Gly Ile Leu Pro Cys Pro Phe Ile Arg Pro Leu Leu Pro
1               5                   10                  15

Ser Pro Ser Ile Ala Pro Pro Ser Ser Ser Leu Leu Thr Phe Arg Ala
            20                  25                  30

Ser Pro Arg Ala Met Asp Lys Gln Gln Val Leu His Pro Lys Pro Ala
        35                  40                  45

Asp Leu Pro Lys Asn Asp Ser Lys Gln Asn Asp Leu Thr Leu Pro Ala
    50                  55                  60

Asp Gln Glu Glu Ser Gln Leu Gly Pro Pro Glu Lys Pro Leu Pro
65                  70                  75                  80

Gly Asp Cys Cys Gly Ser Gly Cys Val Arg Cys Val Trp Asp Thr Tyr
                85                  90                  95

Phe Glu Glu Leu Asp Ser Tyr Asn Glu Arg Lys Glu Ala Phe Glu Ser
            100                 105                 110

Arg Leu Lys Lys Ser Pro Pro Leu
        115                 120

```
<210> SEQ ID NO 117
<211> LENGTH: 25
<212> TYPE: PRT
<213> ORGANISM: Artificial sequence
<220> FEATURE:
<223> OTHER INFORMATION: misc_feature
<220> FEATURE:
<221> NAME/KEY: misc_feature
<222> LOCATION: (4)..(4)
<223> OTHER INFORMATION: X=EorL
<220> FEATURE:
<221> NAME/KEY: misc_feature
<222> LOCATION: (5)..(5)
<223> OTHER INFORMATION: X=A or P
<220> FEATURE:
<221> NAME/KEY: misc_feature
<222> LOCATION: (14)..(14)
<223> OTHER INFORMATION: X=V or E
<220> FEATURE:
<221> NAME/KEY: misc_feature
<222> LOCATION: (15)..(15)
<223> OTHER INFORMATION: X=R or I
<220> FEATURE:
<221> NAME/KEY: misc_feature
<222> LOCATION: (20)..(20)
<223> OTHER INFORMATION: X=V or I or T
<220> FEATURE:
<221> NAME/KEY: misc_feature
<222> LOCATION: (22)..(22)
<223> OTHER INFORMATION: X=Y or F
<220> FEATURE:
<221> NAME/KEY: misc_feature
```

```
<222> LOCATION: (23)..(23)
<223> OTHER INFORMATION: X=D or E
<220> FEATURE:
<221> NAME/KEY: misc_feature
<222> LOCATION: (24)..(24)
<223> OTHER INFORMATION: X=E or Q

<400> SEQUENCE: 117
```

Glu Lys Pro Xaa Xaa Gly Asp Cys Cys Gly Ser Gly Cys Xaa Xaa
1               5                   10                  15

Cys Val Trp Asp Xaa Tyr Xaa Xaa Xaa Leu
            20              25

```
<210> SEQ ID NO 118
<211> LENGTH: 117
<212> TYPE: PRT
<213> ORGANISM: Glycine max

<400> SEQUENCE: 118
```

Met Arg Thr Thr Ala Pro Ser Asp Phe Ile Phe Thr Gln Lys Leu His
1               5                   10                  15

Pro Phe Asn Ile Thr Ser Thr Lys Thr Ser Leu Gln Arg Thr Leu Pro
                20                  25                  30

Tyr Phe Leu Gln Leu Asn Arg Met Ala Glu Ala Ala Arg Thr Ala His
            35                  40                  45

Lys Pro Ala Pro His Pro Ile Gln Pro Lys Pro Asp Asp Lys Thr Pro
        50                  55                  60

Asn Pro Ala Lys Glu Ile Pro Pro Pro Glu Lys Pro Glu Pro Gly
65                  70                  75                  80

Asp Cys Cys Gly Ser Gly Cys Val Arg Cys Val Trp Asp Val Tyr Tyr
                85                  90                  95

Asp Glu Leu Glu Glu Tyr Asn Lys Arg Tyr Lys Gln Val Asp Pro Ser
                100                 105                 110

Pro Lys Pro Ser Ser
            115

```
<210> SEQ ID NO 119
<211> LENGTH: 132
<212> TYPE: PRT
<213> ORGANISM: Sorghum bicolor

<400> SEQUENCE: 119
```

Met Leu Gly Ala Val Val Arg Val Pro Ala Pro Ile Leu Leu Pro Leu
1               5                   10                  15

Leu Pro Gly Pro Thr Arg Pro Leu Leu Arg Arg Arg His Cys
                20                  25                  30

Leu Pro Pro Glu Ala Pro Met Ala Ser Ala Thr Pro Ser Asp Gly Gly
            35                  40                  45

Ala Ala Lys Pro Asp Ala Ala Pro Ala Pro Val Pro Val Pro Ala Pro
        50                  55                  60

Ala Pro Thr Pro Leu Pro Leu Pro Pro Glu Lys Pro Leu Pro Gly Asp
65                  70                  75                  80

Cys Cys Gly Ser Gly Cys Val Arg Cys Val Trp Asp Ile Tyr Phe Asp
                85                  90                  95

```
Glu Leu Asp Ala Tyr Asp Lys Ala Leu Ala Ala His Ala Ala Ala Ser
            100                 105                 110

Ser Gly Ser Gly Ala Lys Asp Ser Ala Asp Thr Lys Pro Ser Asp
        115                 120                 125

Gly Ala Lys Ser
        130

<210> SEQ ID NO 120
<211> LENGTH: 135
<212> TYPE: PRT
<213> ORGANISM: Arabidopsis thaliana

<400> SEQUENCE: 120

Met Val Val Ser Leu Leu Pro Arg Ile Ser Ile Val Thr Ser Pro
1               5                   10                  15

Gly Ser Ser Leu His Asp Val Leu Leu Ser Met Arg Phe Gly Leu Thr
                20                  25                  30

Arg His Leu Pro Leu Lys Arg Ser Phe Ser Asn Tyr Ser Ile Thr Ser
            35                  40                  45

Val Ser Pro Glu Gln Gln Leu Lys Ser Pro Val Thr Met Ala Thr Thr
50                  55                  60

Glu Ser Lys Asn Leu Val Glu Ala Ser Lys Glu Glu Thr Asn Lys Lys
65                  70                  75                  80

Glu Thr Glu Asp Lys Lys Glu Val Gly Val Ser Val Pro Pro Pro
                85                  90                  95

Glu Lys Pro Glu Pro Gly Asp Cys Cys Gly Ser Gly Cys Val Arg Cys
            100                 105                 110

Val Trp Asp Val Tyr Tyr Asp Glu Leu Glu Asp Tyr Asn Lys Gln Leu
            115                 120                 125

Ser Gly Glu Thr Lys Ser Ile
        130                 135

<210> SEQ ID NO 121
<211> LENGTH: 115
<212> TYPE: PRT
<213> ORGANISM: Oryza sativa

<400> SEQUENCE: 121

Met Leu Val Ala Ala Leu Arg Val Pro Ala Pro Ile Pro Ser Ser Leu
1               5                   10                  15

Pro Ser Pro Ala Arg Pro Leu Leu Arg Arg Arg Ser Ser His Arg Leu
                20                  25                  30

Pro Pro Pro Pro Pro Ala Ala Ser Met Ala Asp Ala Gly Gly Ala
            35                  40                  45

Thr Thr Asn Lys Pro Ala Pro Ala Pro Glu Pro Pro Glu Lys
        50                  55                  60

Pro Leu Pro Gly Asp Cys Cys Gly Ser Gly Cys Val Arg Cys Val Trp
65                  70                  75                  80

Asp Val Tyr Tyr Asp Glu Leu Asp Ala Tyr Asn Lys Ala Leu Ala Ala
                85                  90                  95

His Ser Ser Ser Ala Ser Ser Gly Ser Lys Pro Ala Thr Ser Asp Gly
            100                 105                 110

Ala Lys Ser
        115
```

PLANT SEEDS WITH ALTERED STORAGE COMPOUND LEVELS, RELATED CONSTRUCTS AND METHODS INVOLVING GENES ENCODING OXIDOREDUCTASE MOTIF POLYPEPTIDES

This application is a Continuation of U.S. application Ser. No. 13/039,779, filed Mar. 3, 2011, now pending, which claims the benefit of U.S. Provisional Application No. 61/609,906, filed Mar. 3, 2010, the entire content which is hereby incorporated by reference.

FIELD OF THE INVENTION

This invention is in the field of plant molecular biology. More specifically, this invention pertains to isolated nucleic acid fragments encoding oxidoreductase motif proteins in plants and seeds and the use of such fragments to modulate expression of a gene encoding oxidoreductase activity.

BACKGROUND OF THE INVENTION

At maturity, about 40% of soybean seed dry weight is protein and 20% extractable oil. These constitute the economically valuable products of the soybean crop. Plant oils for example are the most energy-rich biomass available from plants; they have twice the energy content of carbohydrates. It also requires very little energy to extract plant oils and convert them to fuels. Of the remaining 40% of seed weight, about 10% is soluble carbohydrate. The soluble carbohydrate portion contributes little to the economic value of soybean seeds and the main component of the soluble carbohydrate fraction, raffinosaccharides, are deleterious both to processing and to the food value of soybean meal in monogastric animals (Coon et al., (1988) Proceedings Soybean Utilization Alternatives, Univ. of Minnesota, pp. 203-211).

As the pathways of storage compound biosynthesis in seeds are becoming better understood it is clear that it may be possible to modulate the size of the storage compound pools in plant cells by altering the catalytic activity of specific enzymes in the oil, starch and soluble carbohydrate biosynthetic pathways (Taiz L., et al. *Plant Physiology*; The Benjamin/Cummings Publishing Company: New York, 1991). For example, studies investigating the over-expression of LPAT and DAGAT showed that the final steps acylating the glycerol backbone exert significant control over flux to lipids in seeds. Seed oil content could also be increased in oil-seed rape by overexpression of a yeast glycerol-3-phosphate dehydrogenase, whereas over-expression of the individual genes involved in de novo fatty acid synthesis in the plastid, such as acetyl-CoA carboxylase and fatty acid synthase, did not substantially alter the amount of lipids accumulated (Vigeolas H., et al. *Plant Biotechnology J.* 5, 431-441 (2007). A low-seed-oil mutant, wrinkled 1, has been identified in *Arabidopsis*. The mutation apparently causes a deficiency in the seed-specific regulation of carbohydrate metabolism (Focks, Nicole et al., Plant Physiol. (1998), 118(1), 91-101. There is a continued interest in identifying the genes that encode proteins that can modulate the synthesis of storage compounds, such as oil, protein, starch and soluble carbohydrates, in plants.

The biochemical term oxidoreductase refers to enzymes involved in the transfer of electrons from one molecule (the reductant, also called the hydrogen or electron donor) to another (the oxidant, also called the hydrogen or electron acceptor). For some oxidoreductase proteins catalytic properties are known while other proteins are only identified based on the presence of a motif found also in known oxidoreductase enzymes. Small, proteins, 10-30 kDA in size with, with an oxidoreductase motif (ORM) and unknown catalytic properties are prevalent in eukaryotes ranging from unicellular yeast and algae to the animal and plant kingdom. Yoshikawa et al (FEMS Yeast Research (2009), 9(1), 32-44.) disclose that disruption of YPL107W of *Saccharomyces cerevisae* encoding a protein with oxidoreductase motif and mitochondrial localization is hypersensitive osmotic and ethanol stress. Although proteins with an oxidoreductase motif closely related to that of YPL107W have been identified in every plant that was subjected to in-depth genome or EST sequencing few studies have been conducted on the role of these proteins. In view of the ubiquitous nature of genes encoding ORM proteins in plants further investigation of their role in plant growth and development and specifically in the regulation of storage compound content in seed is of great interest.

SUMMARY OF THE INVENTION

In a first embodiment the present invention concerns a transgenic plant comprising a recombinant DNA construct comprising a polynucleotide operably linked to at least one regulatory element, wherein said polynucleotide encodes a polypeptide having an amino acid sequence of at least 70% sequence identity, based on the Clustal V method of alignment, when compared to SEQ ID NO: 26, 28, 30, 32, 40, 42, 44, 46, 48, 64, 65, 66, 67, 69, 70, 102, 104, 105, 106, 108, 110, 113, 116, or 117 and wherein seeds from said transgenic plant have an altered oil, protein, starch and/or soluble carbohydrate content when compared to seeds from a control plant not comprising said recombinant DNA construct.

In a second embodiment the present invention concerns transgenic seed comprising a recombinant DNA construct comprising a polynucleotide operably linked to at least one regulatory element, wherein said polynucleotide encodes a polypeptide having an amino acid sequence of at least 70% sequence identity, based on the Clustal V method of alignment, when compared to SEQ ID NO: 26, 28, 30, 32, 40, 42, 44, 46, 48, 64, 65, 66, 67, 69, 70, 102, 104, 105, 106, 108, 110, 113, 116, or 117 and wherein said transgenic seed has an altered oil, protein, starch and/or soluble carbohydrate content when compared to a control seed not comprising said recombinant DNA construct.

In a third embodiment the present invention concerns transgenic seed comprising: a recombinant DNA construct comprising: (a) a polynucleotide operably linked to at least one regulatory element, wherein said polynucleotide encodes a polypeptide having an amino acid sequence of at least 70% sequence identity, based on the Clustal V method of alignment, when compared to SEQ ID NO: 26, 28, 30, 32, 40, 42, 44, 46, 48, 64, 65, 66, 67, 69, 70, 102, 104, 105, 106, 108, 110, 113, 116, or 117, or (b) a suppression DNA construct comprising at least one regulatory element operably linked to: (i) all or part of: (A) a nucleic acid sequence encoding a polypeptide having an amino acid sequence of at least 70% sequence identity, based on the Clustal V method of alignment, when compared to SEQ ID NO:: 26, 28, 30, 32, 40, 42, 44, 46, 48, 64, 65, 66, 67, 69, 70, 102, 104, 105, 106, 108, 110, 113, 116, or 117, or (B) a full complement of the nucleic acid sequence of (b)(i)(A); or (ii) a region derived from all or part of a sense strand or antisense strand of a target gene of interest, said region having a nucleic acid sequence of at least 70% sequence identity, based on the Clustal V method of alignment, when compared to said all or part of a sense strand or antisense strand from which said region is derived, and wherein said target gene of interest encodes an ORM protein, and wherein said plant has an altered oil, protein, starch and/or soluble carbohydrate content when compared to a control plant not comprising said recombinant DNA construct.

In a fourth embodiment the invention concerns transgenic seed having an increased oil content of at least 2% on a dry-weight basis when compared to the oil content of a non-transgenic seed, wherein said transgenic seed comprises a recombinant DNA construct comprising: (a) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (b) the full-length complement of (a): wherein (a) or (b) is of sufficient length to inhibit expression of endogenous activity in a transgenic plant and further wherein said seed has an increase in oil content of at least 2% on a dry-weight basis, as compared to seed obtained from a non-transgenic plant.

In a fifth embodiment the invention concerns transgenic seed comprising a recombinant DNA construct comprising: (a) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (b) the full-length complement of (a): wherein (a) or (b) is of sufficient length to inhibit expression of endogenous ORM proteins activity in a transgenic plant and further wherein said seed has an increase in oil content of at least 2% on a dry-weight basis, as compared to seed obtained from a non-transgenic plant.

In a sixth embodiment the present invention concerns a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70% sequence identity, based on the Clustal V method of alignment, when compared to SEQ ID NO: 26, 28, 30, 32, 34, 36, 38, 40, 42, 44, 46, 48, 64, 65, 66, 67, 69, 70, 102, 104, 105, 106, 108, 110, 113, 116, or 117; and (b) regenerating a transgenic plant from the transformed plant cell of (a); and (c) selecting a transgenic plant that produces a transgenic seed having an altered oil, protein, starch and/or soluble carbohydrate content, as compared to a transgenic seed obtained from a non-transgenic plant.

In a seventh embodiment this invention concerns a method for producing transgenic seed, the method comprising: (a) transforming a plant cell with a recombinant DNA construct comprising: (i) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (ii) the full-length complement of (i); wherein (i) or (ii) is of sufficient length to inhibit expression of endogenous ORM protein activity in a transgenic plant;
(b) regenerating a transgenic plant from the transformed plant cell of (a); and
(c) selecting a transgenic plant that produces a transgenic seed having an altered oil, protein, starch and/or soluble carbohydrate content, as compared to a transgenic seed obtained from a non-transgenic plant.

In an eighth embodiment, the present invention concerns a method for producing transgenic seed, the method comprising: (a) transforming a plant cell with a recombinant DNA construct comprising: (i) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (ii) the full-length complement of (i); wherein (i) or (ii) is of sufficient length to inhibit expression of endogenous ORM protein activity in a transgenic plant; (b) regenerating a transgenic plant from the transformed plant cell of (a); and (c) selecting a transgenic plant that produces a transgenic seed having an increase in oil content of at least 2% on a dry-weight basis, as compared to a transgenic seed obtained from a non-transgenic plant.

In a ninth embodiment the invention concerns a transgenic seed comprising: a recombinant DNA construct comprising: (a) a polynucleotide operably linked to at least one regulatory element, wherein said polynucleotide encodes a polypeptide having an amino acid sequence of at least 70% sequence identity, based on the Clustal V method of alignment, when compared to SEQ ID NO: 26, 28, 30, 32, 40, 42, 44, 46, 48, 64, 65, 66, 67, 69, 70, 102, 104, 105, 106, 108, 110, 113, 116, or 117 or (b) a suppression DNA construct comprising at least one regulatory element operably linked to: (i) all or part of: (A) a nucleic acid sequence encoding a polypeptide having an amino acid sequence of at least 70% sequence identity, based on the Clustal V method of alignment, when compared to SEQ ID NO: 26, 28, 30, 32, 40, 42, 44, 46, 48, 64, 65, 66, 67, 69, 70, 102, 104, 105, 106, 108, 110, 113, 116, or 117, or (B) a full complement of the nucleic acid sequence of (b)(i)(A); or (ii) a region derived from all or part of a sense strand or antisense strand of a target gene of interest, said region having a nucleic acid sequence of at least 70% sequence identity, based on the Clustal V method of alignment, when compared to said all or part of a sense strand or antisense strand from which said region is derived, and wherein said target gene of interest encodes a ORM protein, and wherein said plant has an altered, increased or decreased oil, protein, starch and/or soluble carbohydrate content when compared to a control plant not comprising said recombinant DNA construct.

In a tenth embodiment, the present invention includes an isolated polynucleotide comprising: (a) a nucleotide sequence encoding a polypeptide required for altering i.e. increasing or decreasing oil, protein, starch and/or soluble carbohydrate content, wherein the polypeptide has an amino acid sequence of at least 70% sequence identity when compared to SEQ ID NO: 32, 102, 104; 113, or 116, or (b) a full complement of the nucleotide sequence, wherein the full complement and the nucleotide sequence consist of the same number of nucleotides and are 100% complementary. The polypeptide may comprise the amino acid sequence of SEQ ID NO: 32; 102, 104; 113, or 116. The nucleotide sequence may comprise the nucleotide sequence of SEQ ID NO:31, 101, 103, 112, or 115.

In another embodiment, the present invention concerns a recombinant DNA construct comprising any of the isolated polynucleotides of the present invention operably linked to at least one regulatory sequence, and a cell, a plant, and a seed comprising the recombinant DNA construct. The cell may be eukaryotic, e.g., a yeast, insect or plant cell, or prokaryotic, e.g., a bacterial cell.

Seeds obtained from monocot and dicot plants (such as for example maize and soybean, respectively) comprising the recombinant constructs of the invention are within the scope of the present invention. Also included are seed-specific or seed-preferred promoters driving the expression of the nucleic acid sequences of the invention. Embryo or endosperm specific promoters driving the expression of the nucleic acid sequences of the invention are also included. Furthermore, the methods of the present inventions are useful for obtaining transgenic seeds from monocot plants (such as maize and rice) and dicot plants (such as soybean and canola).

Also within the scope of the invention are product(s) and/or by-product(s) obtained from the transgenic seed obtained from monocot or dicot plants, such as maize and soybean, respectively.

In another embodiment, this invention relates to a method for suppressing in a plant the level of expression of a gene encoding a polypeptide having ORM protein activity, wherein the method comprises transforming a monocot or dicot plant with any of the nucleic acid fragments of the present invention.

BRIEF DESCRIPTION OF THE DRAWING AND SEQUENCE LISTING

The invention can be more fully understood from the following detailed description and the accompanying Drawing and Sequence Listing which form a part of this application.

FIG. 1A-1B shows an alignment of the amino acid sequences of ORM proteins encoded by the nucleotide sequences derived from the following: *Brassica rapa* (SEQ ID NO:26, 28, and 30); *Helianthus annuus* (SEQ ID NO:32); *Ricinus communis* (SEQ ID NO:34); *Glycine max* (SEQ ID NO:36, and 38), *Zea mays* (SEQ ID NO:40, 42, 44, and 66, which corresponds to NCBI GI NO:195615148); *Oryza sativa* (SEQ ID NO:46); *Sorghum bicolor* (SEQ ID NO:48; *Populus trichocarpa* (SEQ ID NO:64; NCBI GI NO.:118481427); SEQ ID NO:65 corresponding to SEQ ID NO:36271 from US Patent Application US20060123505; SEQ ID NO:67 corresponding to SEQ ID NO:233249 of US Patent Application US20040214272; and *Arabidopsis thaliana* (SEQ ID NO:69, At5G17280). For the alignment, amino acids which are conserved among all sequences at a given position, are indicated with an asterisk (*). Dashes are used by the program to maximize the alignment of the sequences. A conserved sequence motif is boxed in the alignment and corresponds to SEQ ID NO:70.

FIG. 2 shows a chart of the percent sequence identity for each pair of amino acid sequences displayed in FIGS. 1A-1B.

FIG. 3A-3C shows an alignment of the amino acid sequences of ORM proteins encoded by the nucleotide sequences derived from the following: *Brassica rapa* (SEQ ID NO:26, 28, and 30); *Helianthus annuus* (SEQ ID NO:32); *Ricinus communis* (SEQ ID NO:34); *Glycine max* (SEQ ID NO:36, and 38), *Zea mays* (SEQ ID NO:40, 42, 44, and 66, which corresponds to NCBI GI NO:195615148); *Oryza sativa* (SEQ ID NO:46); *Sorghum bicolor* (SEQ ID NO:48; *Populus trichocarpa* (SEQ ID NO:64; NCBI GI NO.:118481427); SEQ ID NO:65 corresponding to SEQ ID NO:36271 from US Patent Application US20060123505; SEQ ID NO:67 corresponding to SEQ ID NO:233249 of US Patent Application US20040214272; *Arabidopsis thaliana* (SEQ ID NO:69, At5G17280), Guar (SEQ ID NO:102, Ids2c.pk014.b22), Bahia (SEQ ID NO:104, contig), *Arabidopsis lyrata* (SEQ ID NO:105, NCBI GI NO:297807753), *Picea sitchensis* (SEQ ID NO:106, NCBI GI NO:116782186), *Hordeum vulgare* (SEQ ID NO:108), *Raphanus sativus* (SEQ ID NO:110), *Dennstaedtia punctiloba* (SEQ ID NO:113), *Osmunda cinnamomea* (SEQ ID NO:116). For the alignment, amino acids which are conserved among all sequences at a given position, are indicated with an asterisk (*). Dashes are used by the program to maximize the alignment of the sequences. A conserved sequence motif is boxed in the alignment and corresponds to SEQ ID NO:117.

Figure 4:
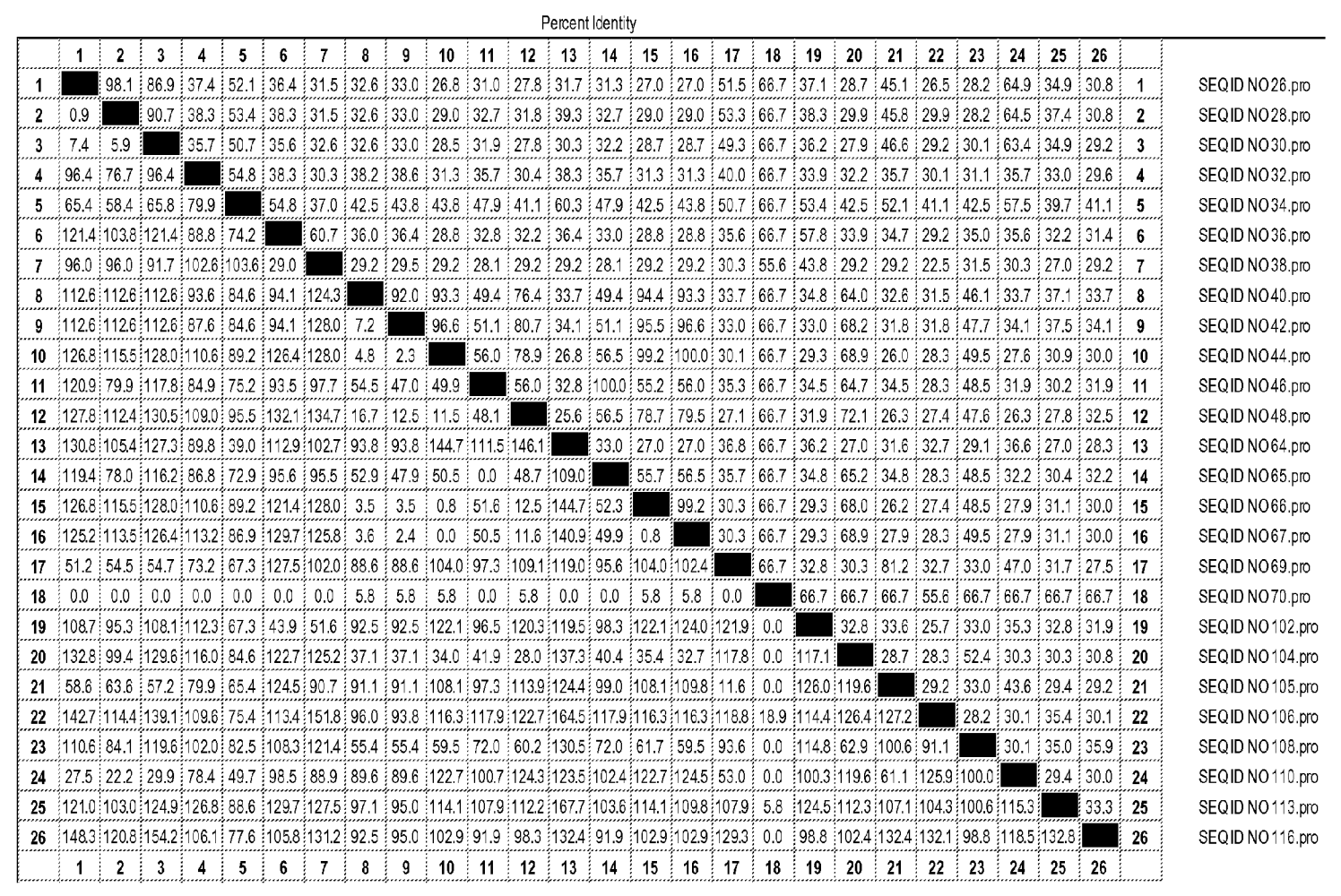

FIG. 4 shows a chart of the percent sequence identity for each pair of amino acid sequences displayed in FIGS. 3A-3C.

The sequence descriptions and Sequence Listing attached hereto comply with the rules governing nucleotide and/or amino acid sequence disclosures in patent applications as set forth in 37 C.F.R. §1.821-1.825.

SEQ ID NO:1 corresponds to the nucleotide sequence of vector PHSbarENDS2.
SEQ ID NO:2 corresponds to the nucleotide sequence of vector pUC9 and a polylinker.
SEQ ID NO:3 corresponds to the nucleotide sequence of vector pKR85.
SEQ ID NO:4 corresponds to the nucleotide sequence of vector pKR278.
SEQ ID NO:5 corresponds to the nucleotide sequence of vector pKR407.
SEQ ID NO:6 corresponds to the nucleotide sequence of vector pKR1468.
SEQ ID NO:7 corresponds to the nucleotide sequence of vector pKR1475.
SEQ ID NO:8 corresponds to the nucleotide sequence of vector pKR92.
SEQ ID NO:9 corresponds to the nucleotide sequence of vector pKR1478.
SEQ ID NO:10 corresponds to SAIFF and genomic DNA of Io17849.
SEQ ID NO:11 corresponds to the forward primer ORM ORF FWD.
SEQ ID NO:12 corresponds to the reverse primer ORM ORF REV.
SEQ ID NO:13 corresponds to the nucleotide sequence of vector pENTR comprising ORM.
SEQ ID NO:14 corresponds to the nucleotide sequence of vector pKR1478-ORM.
SEQ ID NO:15 corresponds to the nucleotide sequence of PKR1482.
SEQ ID NO:16 corresponds to the AthLcc In forward primer.
SEQ ID NO;17 corresponds to the AthLcc In reverse primer.
SEQ ID NO:18 corresponds to the PCR product with the laccase intron.
SEQ ID NO:19 corresponds to the nucleotide sequence of PSM1318.
SEQ ID NO:20 corresponds to the nucleotide sequence of pMBL18 ATTR12 INT.
SEQ ID NO:21 corresponds to the nucleotide sequence of PSM1789.
SEQ ID NO:22 corresponds to the nucleotide sequence of pMBL18 ATTR12 INT ATTR21.
SEQ ID NO:23 corresponds to the nucleotide sequence of vector pKR1480.
SEQ ID NO:24 corresponds to the nucleotide sequence of pKR1482-ORM.

Table 1 lists the polypeptides that are described herein, the designation of the clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire or functional protein derived from an FIS, a contig, an EST and PCR, or an FIS and PCR ("CGS").

TABLE 1

ORM Proteins

| Protein (Plant Source) | Clone Designation | Status | SEQ ID NO: (Nucleotide) | SEQ ID NO: (Amino Acid) |
|---|---|---|---|---|
| ORM (*Brassica rapa*) | TC44737 | CGS | 25 | 26 |
| ORM (*Brassica rapa*) | TC52165 | CGS | 27 | 28 |
| ORM (*Brassica rapa*) | TC52879 | CGS | 29 | 30 |
| ORM (*Helianthus annuus*) | hso1c.pk014.c16 | CGS | 31 | 32 |
| ORM (*Ricinus communis*) | XM_002533611 | CGS | 33 | 34 |
| ORM (*Glycine max*) | Glyma02g05870 | CGS | 35 | 36 |
| ORM (*Glycine max*) | Glyma16g24560 | CGS | 37 | 38 |
| ORM (*Zea mays*) | GRMZM2G1312101 | CGS | 39 | 40 |
| ORM (*Zea mays*) | pco642986 | CGS | 41 | 42 |
| ORM (*Zea mays*) | pco597536 | CGS | 43 | 44 |
| ORM (*Oryza sativa*) | Os09g36120 | CGS | 45 | 46 |
| ORM (*Sorghum bicolor*) | Sb02g030770 | CGS | 47 | 48 |

SEQ ID NO:49 is the nucleic acid sequence of the linker described in Example 19.
SEQ ID NO:50 is the nucleic acid sequence of vector pKS133 described in Example 18.
SEQ ID NO:51 corresponds to the single copy of ELVIS-LIVES.
SEQ ID NO:52 corresponds to two copies of ELVISLIVES.
SEQ ID NO:53 corresponds the primer described in Example 20.
SEQ ID NO:54 corresponds to the primer described in Example 20.
SEQ ID NO:55 corresponds to a synthetic PCR primer (SA195).
SEQ ID NO:56 corresponds to a synthetic PCR primer (SA196).
SEQ ID NO:57 corresponds to a synthetic PCR primer (SA200).
SEQ ID NO:58 corresponds to a synthetic PCR primer (SA201).
SEQ ID NO:59 corresponds to pGemTA.
SEQ ID NO:60 corresponds to pGemTB.
SEQ ID NO:61 corresponds to pGemT-ORM-HP.
SEQ ID NO:62 corresponds to pKS433.
SEQ ID NO:63 corresponds to pKS120.
SEQ ID NO:64 corresponds to NCBI GI NO: 118481427 (*Populus trichocarpa*)
SEQ ID NO:65 corresponds to SEQ ID NO:36271 from US Patent Application, US20060123505.
SEQ ID NO:66 corresponds to NCBI Gi NO: 195615148 (*Zea mays*).
SEQ ID NO:67 corresponds to SEQ ID NO:233249 of US20040214272.
SEQ ID NO:68 corresponds to the nucleotide sequence of At5G17280.
SEQ ID NO:69 corresponds to the amino acid sequence encoded by SEQ ID NO:68.
SEQ ID NO:70 is a conserved sequence motif associated with sequences included in the present invention as shown in FIGS. 1A and 1B.
SEQ ID NO:71 corresponds to the SA3 11 primer.
SEQ ID NO:72 corresponds to the SA3 12 primer.
SEQ ID NO:73 corresponds to the SA3 13 primer.
SEQ ID NO:74 corresponds to the SA3 14 primer.
SEQ ID NO:75 corresponds to the SA3 15 primer.
SEQ ID NO:76 corresponds to the SA3 16 primer.
SEQ ID NO:77 corresponds to the nucleotide sequence of pGEM T Easy-C.
SEQ ID NO:78 corresponds to the nucleotide sequence of pGEM T Easy-D.
SEQ ID NO:79 corresponds to the nucleotide sequence of pGEM T Easy-E.
SEQ ID NO:80 corresponds to the nucleotide sequence of pBluescript SK+-C.
SEQ ID NO:81 corresponds to the nucleotide sequence of pBluescript SK+-CD.
SEQ ID NO:82 corresponds to the nucleotide sequence of pBluescript SK+-CDE.
SEQ ID NO:83 corresponds to the nucleotide sequence of KS442.
SEQ ID NO:84 corresponds to the nucleotide sequence of KS442-CDE.
SEQ ID NO:85 corresponds to the nucleotide sequence of Io127
SEQ ID NO:86 corresponds to the sequence of artificial microRNA, OX16.
SEQ ID NO:87 corresponds to the sequence of artificial microRNA, OX2.
SEQ ID NO:88 corresponds to the sequence of artificial microRNA, OX16.
SEQ ID NO:89 corresponds to the sequence of artificial microRNA, OX2.
SEQ ID NO:90 corresponds to the microRNA 396 precursor.
SEQ ID NO:91 corresponds to the microRNA 396 precursor v3.
SEQ ID NO:92 corresponds to OX16 primer A.
SEQ ID NO:93 corresponds to OX16 primer B.
SEQ ID NO:94 corresponds to the nucleotide sequence of plasmid OX16.
SEQ ID NO:95 corresponds to the microRNA 159 precursor.
SEQ ID NO:96 corresponds to the in-fusion ready microRNA 159 precursor.
SEQ ID NO:97 corresponds to the 159 OX2 primer A.
SEQ ID NO:98 corresponds to the 159 OX2 primer B.
SEQ ID NO:99 corresponds to the nucleotide sequence of plasmid 159-OX2.
SEQ ID NO:100 corresponds to the nucleotide sequence of plasmid KS434.

SEQ ID NO:101 corresponds to the nucleotide sequence of a *Guar* ORM (Ids2c.pk014.b22).
SEQ ID NO:102 corresponds to the amino acid sequence of the *Guar* ORM encoded by Nucleotides of SEQ ID NO:101.
SEQ ID NO:103 corresponds to the nucleotide sequence of a contig of a *Bahia* ORM.
SEQ ID NO:104 corresponds to the amino acid sequence encoded by nucleotides of SEQ ID NO:103.
SEQ ID NO:105 corresponds to NCBI GI NO: 297807753 (*Arabidopsis lyrata*).
SEQ ID NO:106 corresponds to NCBI GI NO: 116782186 (*Picea sitchensis*).
SEQ ID NO:107 corresponds to a *Hordeum vulgare* ORM sequence, obtained a from a *Hordeum vulgare* seedling shoot EST library.
SEQ ID NO:108 corresponds to the partial amino acid sequence encoded by SEQ ID NO: 107.
SEQ ID NO:109 corresponds to a partial ORM nucleotide sequence obtained from *Raphanus sativus*.
SEQ ID NO:110 corresponds to the amino acid sequence encoded by SEQ ID NO:109.
SEQ ID NO:111 corresponds to the ORM nucleotide sequence from *Dennstaedtia punctiloba*.
SEQ ID NO:112 corresponds to the nucleotide sequence of the ORM-ORF of SEQ ID NO:111.
SEQ ID NO:113 corresponds to the amino acids sequence encoded by SEQ ID NO:112.
SEQ ID NO:114 corresponds to the ORM nucleotide sequence from *Osmunda cinnamomea*.
SEQ ID NO:115 corresponds to the nucleotide sequence of the ORM-ORF of SEQ ID NO:114.
SEQ ID NO:116 corresponds to the amino acid sequence encoded by SEQ ID NO:115.
SEQ ID NO:117: corresponds to a conserved sequence motif associated with sequences included in the present invention as shown in FIG. 3A-3C.
SEQ ID NO:118 corresponds to the amino acid sequence from *Glycine max* in US Patent US2004031072-A1-14947.
SEQ ID NO:119 corresponds to the amino acid sequence from *Sorghum bicolor* (NCBI GI: 8062081).
SEQ ID NO:120 corresponds to the amino acid sequence form *Arabidopsis thaliana* (BAB10515).
SEQ ID NO:121 corresponds to the amino acid sequence form *Oryza sativa* (NCBI GI: 5207721).
The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

All patents, patent applications, and publications cited throughout the application are hereby incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure a number of terms and abbreviations are used. The following definitions are provided.

"Open reading frame" is abbreviated ORF.
"Polymerase chain reaction" is abbreviated PCR.
"Triacylglycerols" are abbreviated TAGs.
"Co-enzyme A" is abbreviated CoA.
"Pyrophosphatase" is abbreviated PPiase.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated fatty acids and longer chain saturated fatty acids. Thus, "oil biosynthesis" generically refers to the synthesis of TAGs in the cell.

The term "modulation" or "alteration" in the context of the present invention refers to increases or decreases of ORM protein expression, protein level or enzyme activity, as well as to an increase or decrease in the storage compound levels, such as oil, protein, starch or soluble carbohydrates.

The term "plant" includes reference to whole plants, plant parts or organs (e.g., leaves, stems, roots, etc.), plant cells, seeds and progeny of same. Plant cell, as used herein includes, without limitation, cells obtained from or found in the following: seeds, suspension cultures, embryos, meristematic regions, callus tissue, leaves, roots, shoots, gametophytes, sporophytes, pollen and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants.

Examples of monocots include, but are not limited to (corn) maize, wheat, rice, *sorghum*, millet, barley, palm, lily, *Alstroemeria*, rye, and oat.

Examples of dicots include, but are not limited to, soybean, rape, sunflower, canola, grape, guayule, columbine, cotton, tobacco, peas, beans, flax, safflower, and alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue.

The term "plant organ" refers to plant tissue or group of tissues that constitute a morphologically and functionally distinct part of a plant.

The term "genome" refers to the following: 1. The entire complement of genetic material (genes and non-coding sequences) is present in each cell of an organism, or virus or organelle. 2. A complete set of chromosomes inherited as a (haploid) unit from one parent. The term "stably integrated" refers to the transfer of a nucleic acid fragment into the genome of a host organism or cell resulting in genetically stable inheritance.

The terms "polynucleotide", "polynucleotide sequence", "nucleic acid", nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" refers to materials, such as "isolated nucleic acid fragments" and/or "isolated polypeptides", which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "isolated nucleic acid fragment" is used interchangeably with "isolated polynucleotide" and is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of recombinant DNA constructs to produce the desired phenotype in a transformed plant. Recombinant DNA constructs can be designed for use in co-suppression or antisense by linking a nucleic acid fragment or subfragment thereof, whether or not it encodes an active enzyme, in the appropriate orientation relative to a plant promoter sequence.

"Cosuppression" refers to the production of sense RNA transcripts capable of suppressing the expression of identical or substantially similar native genes (U.S. Pat. No. 5,231,020). Cosuppression technology constitutes the subject matter of U.S. Pat. No. 5,231,020, which issued to Jorgensen et al. on Jul. 27, 1999. The phenomenon observed by Napoli et al. in petunia was referred to as "cosuppression" since expression of both the endogenous gene and the introduced transgene were suppressed (for reviews see Vaucheret et al., *Plant J.* 16:651-659 (1998); and Gura, *Nature* 404:804-808 (2000)).

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) *Plant Cell* 10:1747-1757).

In addition to cosuppression, antisense technology has also been used to block the function of specific genes in cells. Antisense RNA is complementary to the normally expressed RNA, and presumably inhibits gene expression by interacting with the normal RNA strand. The mechanisms by which the expression of a specific gene are inhibited by either antisense or sense RNA are on their way to being understood. However, the frequencies of obtaining the desired phenotype in a transgenic plant may vary with the design of the construct, the gene, the strength and specificity of its promoter, the method of transformation and the complexity of transgene insertion events (Baulcombe, *Curr. Biol.* 12(3):R82-84 (2002); Tang et al., *Genes Dev.* 17(1): 49-63 (2003); Yu et al., *Plant Cell. Rep.* 22(3):167-174 (2003)). Cosuppression and antisense inhibition are also referred to as "gene silencing", "post-transcriptional gene silencing" (PTGS), RNA interference or RNAi. See for example U.S. Pat. No. 6,506,559.

MicroRNAs (miRNA) are small regulatory RNSs that control gene expression. miRNAs bind to regions of target RNAs and inhibit their translation and, thus, interfere with production of the polypeptide encoded by the target RNA. miRNAs can be designed to be complementary to any region of the target sequence RNA including the 3' untranslated region, coding region, etc. miRNAs are processed from highly structured RNA precursors that are processed by the action of a ribonuclease III termed DICER. While the exact mechanism of action of miRNAs is unknown, it appears that they function to regulate expression of the target gene. See, e.g., U.S. Patent Publication No. 2004/0268441 A1 which was published on Dec. 30, 2004.

The term "expression", as used herein, refers to the production of a functional end-product, be it mRNA or translation of mRNA into a polypeptide. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Overexpression" refers to the production of a functional end-product in transgenic organisms that exceeds levels of production when compared to expression of that functional end-product in a normal, wild type or non-transformed organism.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is using particle-accelerated or "gene gun" transformation technology (Klein et al. (1987) *Nature* (*London*) 327:70-73; U.S. Pat. No. 4,945,050), or an *Agrobacterium*-mediated method (Ishida Y. et al. (1996) *Nature Biotech.* 14:745-750). The term "transformation" as used herein refers to both stable transformation and transient transformation.

"Antisense inhibition" refers to the production of antisense RNA transcripts capable of suppressing the expression of the target protein.

As stated herein, "suppression" refers to the reduction of the level of enzyme activity or protein functionality detectable in a transgenic plant when compared to the level of enzyme activity or protein functionality detectable in a plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to the decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in the desired cell.

"Gene silencing," as used herein, is a general term that refers to decreasing mRNA levels as compared to wild-type plants, does not specify mechanism and is inclusive, and not limited to, anti-sense, cosuppression, viral-suppression, hairpin suppression and stem-loop suppression.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. For example, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes that result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 1×SSC, 0.1% SDS, 60° C.) with the sequences exemplified herein, or to any portion of the nucleotide sequences reported herein and which are functionally equivalent to the gene or the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Unless stated otherwise, multiple alignment of the sequences provided herein were performed using the Clustal method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain a "percent identity" by viewing the "sequence distances" table on the same program.

Unless otherwise stated, "BLAST" sequence identity/similarity values provided herein refer to the value obtained using the BLAST 2.0 suite of programs using default parameters (Altschul et al., *Nucleic Acids Res.* 25:3389-3402 (1997)). Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=$^-$4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

"Sequence identity" or "identity" in the context of nucleic acid or polypeptide sequences refers to the nucleic acid bases or amino acid residues in the two sequences that are the same when aligned for maximum correspondence over a specified comparison window.

Thus, "Percentage of sequence identity" refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 55% to 100%. These identities can be determined using any of the programs described herein.

Sequence alignments and percent identity or similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal V method of alignment (Higgins, D. G. and Sharp, P. M. (1989) *Comput. Appl. Biosci.* 5:151-153; Higgins, D. G. et al. (1992) *Comput. Appl. Biosci.* 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other plant species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 55% to 100%. Indeed, any integer amino acid identity from 50%-100% may be useful in describing the present invention. Also, of interest is any full or partial complement of this isolated nucleotide fragment.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The terms "synthetic nucleic acid" or "synthetic genes" refer to nucleic acid molecules assembled either in whole or in part from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that is capable of directing expression a specific protein or functional RNA.

"Native gene" refers to a gene as found in nature with its own regulatory sequences.

"Chimeric gene" or "recombinant DNA construct" are used interchangeably herein, and refers to any gene that is not a native gene, comprising regulatory and coding sequences that are not found together in nature, or to an isolated native gene optionally modified and reintroduced into a host cell.

A chimeric gene may comprise regulatory sequences and coding sequences that are derived from different sources, or regulatory sequences and coding sequences derived from the same source, but arranged in a manner different than that found in nature. In one embodiment, a regulatory region and a coding sequence region are assembled from two different sources. In another embodiment, a regulatory region and a coding sequence region are derived from the same source but arranged in a manner different than that found in nature. In another embodiment, the coding sequence region is assembled from at least two different sources. In another embodiment, the coding region is assembled from the same source but in a manner not found in nature.

The term "endogenous gene" refers to a native gene in its natural location in the genome of an organism.

The term "foreign gene" refers to a gene not normally found in the host organism that is introduced into the host organism by gene transfer.

The term "transgene" refers to a gene that has been introduced into a host cell by a transformation procedure. Transgenes may become physically inserted into a genome of the host cell (e.g., through recombination) or may be maintained outside of a genome of the host cell (e.g., on an extrachromasomal array).

An "allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The term "coding sequence" refers to a DNA fragment that codes for a polypeptide having a specific amino acid sequence, or a structural RNA. The boundaries of a protein coding sequence are generally determined by a ribosome binding site (prokaryotes) or by an ATG start codon (eukaryotes) located at the 5' end of the mRNA and a transcription terminator sequence located just downstream of the open reading frame at the 3' end of the mRNA. A coding sequence can include, but is not limited to, DNA, cDNA, and recombinant nucleic acid sequences.

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be and are not limited to intracellular localization signals.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Sense" RNA refers to RNA transcript that includes the mRNA and can be translated into protein within a cell or in vitro.

"Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence.

"Functional RNA" refers to antisense RNA, ribozyme RNA, or other RNA that may not be translated, yet has an effect on cellular processes. The terms "complement" and "reverse complement" are used interchangeably herein with respect to mRNA transcripts, and are meant to define the antisense RNA of the message.

The term "recombinant DNA construct" refers to a DNA construct assembled from nucleic acid fragments obtained from different sources. The types and origins of the nucleic acid fragments may be very diverse.

A "recombinant expression construct" contains a nucleic acid fragment operably linked to at least one regulatory element, that is capable of effecting expression of the nucleic acid fragment. The recombinant expression construct may also affect expression of a homologous sequence in a host cell.

In one embodiment the choice of recombinant expression construct is dependent upon the method that will be used to transform host cells. The skilled artisan is well aware of the genetic elements that must be present on the recombinant expression construct in order to successfully transform, select and propagate host cells. The skilled artisan will also recognize that different independent transformation events may be screened to obtain lines displaying the desired expression level and pattern. Such screening may be accomplished by, but is not limited to, Southern analysis of DNA, Northern analysis of mRNA expression, Western analysis of protein expression, or phenotypic analysis.

The term "operably linked" refers to the association of nucleic acid fragments on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

"Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters which cause an isolated nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) Biochemistry of Plants 15:1-82. It is further recognized that since in most cases the exact boundaries of regulatory sequences have not been completely defined, DNA fragments of some variation may have identical promoter activity.

Specific examples of promoters that may be useful in expressing the nucleic acid fragments of the invention include, but are not limited to, the oleosin promoter (PCT Publication WO99/65479, published Dec. 12, 1999), the maize 27 kD zein promoter (Ueda et al (1994) Mol. Cell. Biol. 14:4350-4359), the ubiquitin promoter (Christensen et al (1992) Plant Mol. Biol. 18:675-680), the SAM synthetase promoter (PCT Publication WO00/37662, published Jun. 29, 2000), the CaMV 35S (Odell et al (1985) Nature 313:810-812), and the promoter described in PCT Publication WO02/099063 published Dec. 12, 2002.

The "translation leader sequence" refers to a polynucleotide fragment located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Mol. Biotechnol. 3:225-236).

An "intron" is an intervening sequence in a gene that does not encode a portion of the protein sequence. Thus, such sequences are transcribed into RNA but are then excised and are not translated. The term is also used for the excised RNA sequences.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989. Transformation methods are well known to those skilled in the art and are described below.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an inter-mediate temperature. One set of these three consecutive steps is referred to as a cycle.

"Stable transformation" refers to the transfer of a nucleic acid fragment into a genome of a host organism, including nuclear and organellar genomes, resulting in genetically stable inheritance.

In contrast, "transient transformation" refers to the transfer of a nucleic acid fragment into the nucleus, or DNA-containing organelle, of a host organism resulting in gene expression without integration or stable inheritance.

Host organisms comprising the transformed nucleic acid fragments are referred to as "transgenic" organisms.

The term "amplified" means the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "chromosomal location" includes reference to a length of a chromosome which may be measured by reference to the linear segment of DNA which it comprises. The chromosomal location can be defined by reference to two unique DNA sequences, i.e., markers.

The term "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

The present invention includes, inter alia, compositions and methods for altering or modulating (i.e., increasing or decreasing) the level of ORM polypeptides described herein in plants. The size of the oil, protein, starch and soluble carbohydrate pools in soybean seeds can be modulated or altered (i.e. increased or decreased) by altering the expression of a specific gene, encoding ORM protein.

In one embodiment, the present invention concerns a transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117 and wherein seed obtained from said transgenic plant has an altered oil, protein, starch and/or soluble carbohydrate content when compared to seed obtained from a control plant not comprising said recombinant DNA construct.

In a second embodiment the present invention concerns a transgenic seed obtained from the transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117 and wherein said transgenic seed has an altered oil, protein, starch and/or soluble carbohydrate content when compared to a control plant not comprising said recombinant DNA construct.

In a third embodiment the present invention concerns a transgenic seed obtained from the transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117 and wherein said transgenic seed has an increased starch content of at least 0.5%, 1%, 1.5%, 2%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11%, 11.5%, 12.0% 12.5%, 13.0, 13.5%. 14.0%, 14.5%, 15.0%, 15.5%, 15.0%, 16.5%, 17.0%, 17.5% 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29%, 29.5%, 30.0%, 30.5%, 31.0%, 31.5%, 32.0%, 32.5%, 33.0%, 33.5%, 34.0%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, or 50.0% on a dry weight basis when compared to a control seed not comprising said recombinant DNA construct.

In another embodiment, the present invention relates to a recombinant DNA construct comprising any of the isolated polynucleotides of the present invention operably linked to at least one regulatory sequence.

In another embodiment of the present invention, a recombinant construct of the present invention further comprises an enhancer.

In another embodiment, the present invention relates to a vector comprising any of the polynucleotides of the present invention.

In another embodiment, the present invention relates to an isolated polynucleotide fragment comprising a nucleotide sequence comprised by any of the polynucleotides of the present invention, wherein the nucleotide sequence contains at least 30, 40, 60, 100, 200, 300, 400, 500 or 600 nucleotides.

In another embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In yet another embodiment, the present invention relates to a method for transforming a cell, comprising transforming a cell with a polynucleotide of the present invention.

In another embodiment, the present invention relates to a method for producing a transgenic plant comprising transforming a plant cell with any of the isolated polynucleotides of the present invention and regenerating a transgenic plant from the transformed plant cell.

In another embodiment, a cell, plant, or seed comprising a recombinant DNA construct of the present invention.

In another embodiment, an isolated polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. Preferably the polypeptide is an ORM protein.

In another embodiment, an isolated polynucleotide comprising: (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 25, 27, 29, 31, 33, 35, 37, 39, 41, 43, 45, 47, 48, 68, 101, 103, 107, 109, 111, or 114; or (ii) a full complement of the nucleic acid sequence of (i). Any of the foregoing isolated polynucleotides may be utilized in any recombinant DNA constructs (including suppression DNA constructs) of the present invention. Preferably, the polypeptide is an ORM protein.

In one aspect, the present invention includes recombinant DNA constructs (including suppression DNA constructs).

In another embodiment, the present invention relates to a method of selecting an isolated polynucleotide that alters, i.e. increases or decreases, the level of expression of a ORM protein gene, protein or enzyme activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the ORM protein RNA, protein or enzyme activity in the host cell containing the isolated polynucleotide or recombinant DNA construct; (d) comparing the level of the PPiase RNA, protein or enzyme activity in the host cell containing the isolated polynucleotide or recombinant DNA construct with the level of the ORM protein RNA, protein or enzyme activity in a host cell that does not contain the isolated polynucleotide or recombinant DNA construct, and selecting the isolated polynucleotide or recombinant DNA construct that alters, i.e., increases or decreases, the level of expression of the ORM protein gene, protein or enzyme activity in the plant cell.

In another embodiment, this invention concerns a method for suppressing the level of expression of a gene encoding a ORM protein having ORM protein activity in a transgenic plant, wherein the method comprises: (a) transforming a plant cell with a fragment of the isolated polynucleotide of the invention; (b) regenerating a transgenic plant from the transformed plant cell of 9a); and (c) selecting a transgenic plant wherein the level of expression of a gene encoding a polypeptide having ORM protein activity has been suppressed.

Preferably, the gene encodes a polypeptide having ORM protein activity, and the plant is a soybean plant.

In another embodiment, the invention concerns a method for producing transgenic seed, the method comprising: a) transforming a plant cell with the recombinant DNA construct of (i) all or part of the nucleotide sequence set forth in SEQ ID NO: 25, 27, 29, 31, 33, 35, 37, 39, 41, 43, 45, 47, 48, 68, 101, 103, 107, 109, 111, or 114, or (ii) the complement of (i); wherein (i) or (ii) is useful in co-suppression or antisense suppression of endogenous ORM protein activity in a transgenic plant; (b) regenerating a transgenic plant from the transformed plant cell of (a); and (c) selecting a transgenic plant that produces transgenic seeds having an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% compared to seed obtained from a non-transgenic plant. Preferably, the seed is a soybean plant.

In another embodiment, a plant comprising in its genome a recombinant DNA construct comprising: (a) a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117 or (b) a suppression DNA construct comprising at least one regulatory element operably linked to: (i) all or part of: (A) a nucleic acid sequence encoding a polypeptide having an amino acid sequence of at least 70% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117, or (B) a full complement of the nucleic acid sequence of (b)(i)(A); or (ii) a region derived from all or part of a sense strand or antisense strand of a target gene of interest, said region having a nucleic acid sequence of at least 70% sequence identity, based on the Clustal V method of alignment, when compared to said all or part of a sense strand or antisense strand from which said region is derived, and wherein said target gene of interest encodes a ORM protein, and wherein said plant has an altered oil, protein, starch and/or soluble carbohydrate content, when compared to a control plant not comprising said recombinant DNA construct.

A transgenic seed having an increased oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% when compared to the oil content of a non-transgenic seed, wherein said transgenic seed comprises a recombinant DNA construct comprising: (a) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (b) the full-length complement of (a): wherein (a) or (b) is of sufficient length to inhibit expression of endogenous ORM protein activity in a transgenic plant and further wherein said seed has an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% on a dry-weight basis, as compared to seed obtained from a non-transgenic plant.

Yet another embodiment of the invention concerns a transgenic seed comprising a recombinant DNA construct comprising:

(a) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (b) the full-length complement of (a):

wherein (a) or (b) is of sufficient length to inhibit expression of endogenous ORM protein activity in a transgenic plant and further wherein said seed has an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% on a dry-weight basis, as compared to seed obtained from a non-transgenic plant.

In another embodiment, the invention concerns a method for producing a transgenic plant, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117; and (b) regenerating a plant from the transformed plant cell.

Another embodiment of the invention concerns, a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117; and (b) regenerating a transgenic plant from the transformed plant cell of (a); and (c) selecting a transgenic plant that produces a transgenic seed having an altered oil, protein, starch and/or soluble carbohydrate content, as compared to a transgenic seed obtained from a non-transgenic plant.

Another embodiment of the invention concerns, a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 26, 28, 30, 32, 34, 36, 38, 40, 42, 44, 46, 48, 64, 66, 67, 69, 70, 102, 104, 105, 106, 108, 110, 113, 116, or 117; and (b) regenerating a transgenic plant from the transformed plant cell of (a); and (c) selecting a transgenic plant that produces a transgenic seed having an increased starch content of at least 0.5%, 1%, 1.5%, 2%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11%, 11.5%, 12.0% 12.5%, 13.0, 13.5%. 14.0%, 14.5%, 15.0%, 15.5%, 15.0%, 16.5%, 17.0%, 17.5% 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29%, 29.5%, 30.0%, 30.5%, 31.0%, 31.5%, 32.0%, 32.5%, 33.0%, 33.5%, 34.0%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, or 50.0% on a dry weight basis as compared to a transgenic seed obtained from a non-transgenic plant.

In another embodiment, the invention concerns a method for producing transgenic seed, the method comprising: (a) transforming a plant cell with a recombinant DNA construct comprising: (i) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (ii) the full-length complement of (i); wherein (i) or (ii) is of sufficient length to inhibit expression of endogenous ORM protein activity in a transgenic plant; (b) regenerating a transgenic plant from the transformed plant cell of (a); and (c) selecting a transgenic plant that produces a transgenic seed having an altered oil, protein, starch and/or soluble carbohydrate content, as compared to a transgenic seed obtained from a non-transgenic plant.

A method for producing transgenic seed, the method comprising: (a) transforming a plant cell with a recombinant DNA construct comprising: (i) all or part of the nucleotide sequence set forth in SEQ ID NO: 25, 27, 29, 31, 33, 35, 37, 39, 41, 43, 45, 47, 48, 68, 101, 103, 107, 109, 111, or 114; or (ii) the full-length complement of (i);

wherein (i) or (ii) is of sufficient length to inhibit expression of endogenous ORM protein activity in a transgenic plant; (b) regenerating a transgenic plant from the transformed plant cell of (a); and (c) selecting a transgenic plant that produces a transgenic seed having an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, on a dry-weight basis, as compared to a transgenic seed obtained from a non-transgenic plant.

Soybeans can be processed into a number of products. For example, "soy protein products" can include, and are not limited to, those items listed in Table 2. "Soy protein products".

TABLE 2

Soy Protein Products Derived from Soybean Seeds[a]

Whole Soybean Products

Roasted Soybeans
Baked Soybeans
Soy Sprouts
Soy Milk
Specialty Soy Foods/Ingredients Soy Milk
Tofu
Tempeh
Miso
Soy Sauce
Hydrolyzed Vegetable Protein
Whipping Protein
Processed Soy Protein Products Full Fat and Defatted Flours
Soy Grits
Soy Hypocotyls TABLE 2-continued Soy Protein Products Derived from Soybean Seeds[a]

Soybean Meal
Soy Milk
Soy Protein Isolates
Soy Protein Concentrates
Textured Soy Proteins
Textured Flours and Concentrates
Textured Concentrates
Textured Isolates

[a]See Soy Protein Products: Characteristics, Nutritional Aspects and Utilization (1987). Soy Protein Council.

"Processing" refers to any physical and chemical methods used to obtain the products listed in Table A and includes, and is not limited to, heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991-1992).

"White" flakes refer to flaked, dehulled cotyledons that have been defatted and treated with controlled moist heat to have a PDI (AOCS: Ba10-65) of about 85 to 90. This term can also refer to a flour with a similar PDI that has been ground to pass through a No. 100 U.S. Standard Screen size.

"Grits" refer to defatted, dehulled cotyledons having a U.S. Standard screen size of between No. 10 and 80.

"Soy Protein Concentrates" refer to those products produced from dehulled, defatted soybeans by three basic processes: acid leaching (at about pH 4.5), extraction with alcohol (about 55-80%), and denaturing the protein with moist heat prior to extraction with water. Conditions typically used to prepare soy protein concentrates have been described by Pass ((1975) U.S. Pat. No. 3,897,574; Campbell et al., (1985) in New Protein Foods, ed. by Altschul and Wilcke, Academic Press, Vol. 5, Chapter 10, *Seed Storage Proteins*, pp 302-338).

"Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously (Atkinson (1970) U.S. Pat. No. 3,488,770, Horan (1985) In *New Protein Foods*, ed. by Altschul and Wilcke, Academic Press, Vol. 1A, Chapter 8, pp 367-414). Moreover, conditions used during extrusion processing of complex foodstuff mixtures that include soy protein products have been described previously (Rokey (1983) *Feed Manufacturing Technology III*, 222-237; McCulloch, U.S. Pat. No. 4,454,804).

TABLE 3

Generalized Steps for Soybean Oil and Byproduct Production

| Process Step | Process | Impurities Removed and/or By-Products Obtained |
|---|---|---|
| # 1 | soybean seed | |
| # 2 | oil extraction | meal |
| # 3 | Degumming | lecithin |
| # 4 | alkali or physical refining | gums, free fatty acids, pigments |
| # 5 | water washing | soap |
| # 6 | Bleaching | color, soap, metal |
| # 7 | (hydrogenation) | |
| # 8 | (winterization) | stearine |
| # 9 | Deodorization | free fatty acids, tocopherols, sterols, volatiles |
| # 10 | oil products | |

More specifically, soybean seeds are cleaned, tempered, dehulled, and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production, and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel, and cocoa butter.

For example, plant and microbial oils containing polyunsaturated fatty acids (PUFAs) that have been refined and/or purified can be hydrogenated, thereby resulting in fats with various melting properties and textures. Many processed fats (including spreads, confectionery fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, linoleic, and linolenic fatty acids, and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation, and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

In a another embodiment, the invention concerns a transgenic seed produced by any of the above methods. Preferably, the seed is a soybean seed.

The present invention concerns a transgenic soybean seed having increased total fatty acid content of at least 1%, 2%, 3%, 4%, 5%, 6%, 7%, 8%, 9%, 11%, 12%, 13%, 14%, 15%, 16%, 17%, 18%, 19%, 20%, 21%, 22%, 23%, 24%, 25%, 26%, 27%, 28%, 29%, or 30% when compared to the total fatty acid content of a non-transgenic, null segregant soybean seed. It is understood that any measurable increase in the total fatty acid content of a transgenic versus a non-transgenic, null segregant would be useful. Such increases in the total fatty acid content would include, but are not limited to, at least 1%, 2%, 3%, 4%, 5%, 6%, 7%, 8%, 9%, 11%, 12%, 13%, 14%, 15%, 16%, 17%, 18%, 19%, 20%, 21%, 22%, 23%, 24%, 25%, 26%, 27%, 28%, 29%, or 30%.

Regulatory sequences may include, and are not limited to, promoters, translation leader sequences, introns, and polyadenylation recognition sequences.

"Tissue-specific" promoters direct RNA production preferentially in particular types of cells or tissues. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

A number of promoters can be used to practice the present invention. The promoters can be selected based on the desired outcome. The nucleic acids can be combined with constitutive, tissue-specific (preferred), inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in particular cells/tissues of a plant. Any identifiable promoter may be used in the methods of the present invention which causes the desired temporal and spatial expression.

Promoters which are seed or embryo specific and may be useful in the invention include patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include Arabidopsis thaliana 2S seed storage protein gene promoter to express enkephalin peptides in Arabidopsis and Brassica napus seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J 6:3559-3564 (1987)).

A plethora of promoters is described in WO 00/18963, published on Apr. 6, 2000, the disclosure of which is hereby incorporated by reference. Examples of seed-specific promoters include, and are not limited to, the promoter for soybean Kunitz trypsin inhibitor (Kti3, Jofuku and Goldberg, *Plant Cell* 1:1079-1093 (1989)) β-conglycinin (Chen et al., *Dev. Genet.* 10:112-122 (1989)), the napin promoter, and the phaseolin promoter.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention includes compositions, and methods for making, heterologous promoters and/or enhancers operably linked to a native, endogenous (i.e., non-heterologous) form of a polynucleotide of the present invention.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994). A vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. in Enzymol.* 153:253-277 (1987).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

Preferred recombinant DNA constructs include the following combinations: a) a nucleic acid fragment corresponding to a promoter operably linked to at least one nucleic acid fragment encoding a selectable marker, followed by a nucleic acid fragment corresponding to a terminator, b) a nucleic acid fragment corresponding to a promoter operably linked to a nucleic acid fragment capable of producing a stem-loop structure, and followed by a nucleic acid fragment corresponding to a terminator, and c) any combination of a) and b) above. Preferably, in the stem-loop structure at least one nucleic acid fragment that is capable of suppressing expression of a native gene comprises the "loop" and is surrounded by nucleic acid fragments capable of producing a stem.

Preferred methods for transforming dicots and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al. (1996) *Plant Cell Rep.* 15:653-657, McKently et al. (1995) *Plant Cell Rep.* 14:699-703); papaya (Ling, K. et al. (1991) Bio/technology 9:752-758); and pea (Grant et al. (1995) *Plant Cell Rep.* 15:254-258). For a review of other commonly used methods of plant transformation see Newell, C. A. (2000) *Mol. Biotechnol.* 16:53-65. One of these methods of transformation uses *Agrobacterium rhizogenes* (Tepfler, M. and Casse-Delbart, F. (1987) *Microbiol. Sci.* 4:24-28). Transformation of soybeans using direct delivery of DNA has been published using PEG fusion (PCT publication WO 92/17598), electroporation (Chowrira, G. M. et al. (1995) *Mol. Biotechnol.* 3:17-23; Christou, P. et al. (1987) *Proc. Natl. Acad. Sci. U.S.A.* 84:3962-3966), microinjection, or particle bombardment (McCabe, D. E. et. Al. (1988) *Biol Technology* 6:923; Christou et al. (1988) *Plant Physiol.* 87:671-674).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants are well known in the art (Weissbach and Weissbach, (1988) In.: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants may be self-pollinated. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide(s) is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al. (1989) Molecular Cloning: A Laboratory Manual, Cold Spring Harbor Press; Maliga et al. (1995) Methods in Plant Molecular Biology, Cold Spring Harbor Press; Birren et al. (1998) Genome Analysis: Detecting Genes, 1, Cold Spring Harbor, New York; Birren et al. (1998) Genome Analysis: Analyzing DNA, 2, Cold Spring Harbor, New York; Plant Molecular Biology: A Laboratory Manual, eds. Clark, Springer, New York (1997)).

Assays to detect proteins may be performed by SDS-polyacrylamide gel electrophoresis or immunological assays. Assays to detect levels of substrates or products of enzymes may be performed using gas chromatography or liquid chromatography for separation and UV or visible spectrometry or mass spectrometry for detection, or the like. Determining the levels of mRNA of the enzyme of interest may be accomplished using northern-blotting or RT-PCR techniques. Once plants have been regenerated, and progeny plants homozygous for the transgene have been obtained, plants will have a stable phenotype that will be observed in similar seeds in later generations.

In another aspect, this invention includes a polynucleotide of this invention or a functionally equivalent subfragment thereof useful in antisense inhibition or cosuppression of expression of nucleic acid sequences encoding proteins having cytosolic pyrophosphatase activity, most preferably in antisense inhibition or cosuppression of an endogenous ORM protein gene.

Protocols for antisense inhibition or co-suppression are well known to those skilled in the art.

The sequences of the polynucleotide fragments used for suppression do not have to be 100% identical to the sequences of the polynucleotide fragment found in the gene to be suppressed. For example, suppression of all the subunits of the soybean seed storage protein β-conglycinin has been accomplished using a polynucleotide derived from a portion of the gene encoding the a subunit (U.S. Pat. No. 6,362,399). β-conglycinin is a heterogeneous glycoprotein composed of varying combinations of three highly negatively charged subunits identified as α, α' and β. The polynucleotide sequences encoding the α and α' subunits are 85% identical to each other while the polynucleotide sequences encoding the β subunit are 75 to 80% identical to the α and α' subunits, respectively. Thus, polynucleotides that are at least 75% identical to a region of the polynucleotide that is target for suppression have been shown to be effective in suppressing the desired target. The polynucleotide may be at least 80% identical, at least 90% identical, at least 95% identical, or about 100% identical to the desired target sequence.

The isolated nucleic acids and proteins and any embodiments of the present invention can be used over a broad range of plant types, particularly dicots such as the species of the genus Glycine.

It is believed that the nucleic acids and proteins and any embodiments of the present invention can be with monocots as well including, but not limited to, Graminiae including Sorghum bicolor and Zea mays.

The isolated nucleic acid and proteins of the present invention can also be used in species from the following dicot genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Antirrhinum, Pelargonium, Ranunculus, Senecio, Salpiglossis, Cucumis, Browallia, Glycine, Pisum, Phaseolus, and from the following monocot genera: Bromus, Asparagus, Hemerocallis, Panicum, Pennisetum, Lolium, Oryza, Avena, Hordeum, Secale, Triticum, Bambusa, Dendrocalamus, and Melocanna.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Examples

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Creation of an Arabidopsis Population with Activation-Tagged Genes

An 18.49-kb T-DNA based binary construct was created, pHSbarENDs2 (SEQ ID NO:1;), that contains four multimerized enhancer elements derived from the Cauliflower Mosaic Virus 35S promoter (corresponding to sequences −341 to −64, as defined by Odell et al., Nature 313:810-812 (1985)). The construct also contains vector sequences (pUC9) and a poly-linker (SEQ ID NO:2) to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

Arabidopsis activation-tagged populations were created by whole plant Agrobacterium transformation. The pHSbarENDs2 (SEQ ID NO:1) construct was transformed into Agrobacterium tumefaciens strain C58, grown in lysogeny broth medium at 25° C. to OD600~1.0. Cells were then pelleted by centrifugation and resuspended in an equal volume of 5% sucrose/0.05% Silwet L-77 (OSI Specialties, Inc). At early bolting, soil grown Arabidopsis thaliana ecotype Col-0 were top watered with the Agrobacterium suspension. A week later, the same plants were top watered again with the same Agrobacterium strain in sucrose/Silwet. The plants were then allowed to set seed as normal. The resulting T1 seed were sown on soil, and transgenic seedlings were selected by spraying with glufosinate (FINALE®; AgrEvo; Bayer Environmental Science). A total of 100,000 glufosinate resistant T1 seedlings were selected. T2 seed from each line was kept separate. Small aliquots of T2 seed from independently generated activation-tagged lines were pooled. The pooled seed were planted in soil and plants were grown to maturity producing T3 seed pools each comprised of seed derived from 96 activation-tagged lines.

Example 2

Identification and Characterization of Mutant Line Io17849

A method for screening *Arabidopsis* seed density was developed based on Focks and Benning (1998) with significant modifications. *Arabidopsis* seeds can be separated according to their density. Density layers were prepared by a mixture of 1.6 dibromohexane (d=1.6), 1-bromohexane (d=1.17) and mineral oil (d=0.84) at different ratios. From the bottom to the top of the tube, 6 layers of organic solvents each comprised of 2 mL were added sequentially. The ratios of 1.6 dibromohexane:1-bromohexane:mineral oil for each layer were 1:1:0, 1:2:0, 0:1:0, 0:5:1, 0:3:1, 0:0:1. About 600 mg of T3 seed of a given pool of 96 activation-tagged lines corresponding to about 30,000 seeds were loaded on to the surface layer of a 15 ml glass tube containing said step gradient. After centrifugation for 5 min at 2000×g, seeds were separated according to their density. The seeds in the lower two layers of the step gradient and from the bottom of the tube were collected. Organic solvents were removed by sequential washing with 100% and 80% ethanol and seeds were sterilized using a solution of 5% hydochloride (NaOCl) in water. Seed were rinsed in sterile water and plated on MS-1 media comprised of 0.5×MS salts, 1% (W/V) sucrose, 0.05 MES/KOH (pH 5.8), 200 µg/mL, 10 g/L agar and 15 mg $L^{-1}$ glufosinate ammonium (Basta; Sigma Aldrich, USA). A total of 520 T3 pools each derived from 96 T2 activation-tagged lines were screened in this manner. Seed pool 475 when subjected to density gradient centrifugation as described above produced about 25 seed with increased density. These seed were sterilized and plated on selective media containing Basta. Basta-resistant seedlings were transferred to soil and plants were grown in a controlled environment (22° C., 16 h light/8 h dark, 100-200 µE $m^{-2}s^{-1}$). to maturity for about 8-10 weeks alongside four untransformed wild type plants of the Columbia ecotype. Oil content of T4 seed and control seed was measured by NMR as follows.

NMR Based Analysis of Seed Oil Content:

Seed oil content was determined using a Maran Ultra NMR analyzer (Resonance Instruments Ltd, Whitney, Oxfordshire, UK). Samples (e.g., batches of *Arabidopsis* seed ranging in weight between 5 and 200 mg) were placed into pre-weighed 2 mL polypropylene tubes (Corning Inc, Corning N.Y., USA; Part no. 430917) previously labeled with unique bar code identifiers. Samples were then placed into 96 place carriers and processed through the following series of steps by an ADEPT COBRA 600™ SCARA robotic system:
1. pick up tube (the robotic arm was fitted with a vacuum pickup devise);
2. read bar code;
3. expose tube to antistatic device (ensured that *Arabidopsis* seed were not adhering to the tube walls);
4. weigh tube (containing the sample), to 0.0001 g precision;
5. take NMR reading; measured as the intensity of the proton spin echo 1 msec after a 22.95 MHz signal had been applied to the sample (data was collected for 32 NMR scans per sample);
6. return tube to rack; and
7. repeat process with next tube.

Bar codes, tubes weights and NMR readings were recorded by a computer connected to the system. Sample weight was determined by subtracting the polypropylene tube weight from the weight of the tube containing the sample.

Seed oil content of soybeans seed or soybean somatic embryos was calculated as follows:

$$\% \text{ oil (\% wt basis)} = \frac{(NMR \text{ signal}/\text{sample wt (g)}) - 70.58}{351.45}$$

Calibration parameters were determined by precisely weighing samples of soy oil (ranging from 0.0050 to 0.0700 g at approximately 0.0050 g intervals; weighed to a precision of 0.0001 g) into Corning tubes (see above) and subjecting them to NMR analysis. A calibration curve of oil content (% seed wt basis; assuming a standard seed weight of 0.1500 g) to NMR value was established.

The relationship between seed oil contents measured by NMR and absolute oil contents measured by classical analytical chemistry methods was determined as follows. Fifty soybean seed, chosen to have a range of oil contents, were dried at 40° C. in a forced air oven for 48 h. Individual seeds were subjected to NMR analysis, as described above, and were then ground to a fine powder in a GenoGrinder (SPEX Centriprep (Metuchen, N.J., U.S.A.); 1500 oscillations per minute, for 1 minute). Aliquots of between 70 and 100 mg were weighed (to 0.0001 g precision) into 13×100 mm glass tubes fitted with Teflon® lined screw caps; the remainder of the powder from each bean was used to determine moisture content, by weight difference after 18 h in a forced air oven at 105° C. Heptane (3 mL) was added to the powders in the tubes and after vortex mixing samples were extracted, on an end-over-end agitator, for 1 h at room temperature. The extracts were centrifuged, 1500×g for 10 min, the supernatant decanted into a clean tube and the pellets were extracted two more times (1 h each) with 1 mL heptane. The supernatants from the three extractions were combined and 50 µL internal standard (triheptadecanoic acid; 10 mg/mL toluene) was added prior to evaporation to dryness at room temperature under a stream of nitrogen gas; standards containing 0, 0.0050, 0.0100, 0.0150, 0.0200 and 0.0300 g soybean oil, in 5 mL heptane, were prepared in the same manner. Fats were converted to fatty acid methyl esters (FAMEs) by adding 1 mL 5% sulfuric acid (v:v. in anhydrous methanol) to the dried pellets and heating them at 80° C. for 30 min, with occasional vortex mixing. The samples were allowed to cool to room temperature and 1 mL 25% aqueous sodium chloride was added followed by 0.8 mL heptane. After vortex mixing the phases were allowed to separate and the upper organic phase was transferred to a sample vial and subjected to GC analysis.

Plotting NMR determined oil contents versus GC determined oil contents resulted in a linear relationship between 9.66 and 26.27% oil (GC values; % seed wt basis) with a slope of 1.0225 and an $R^2$ of 0.9744; based on a seed moisture content that averaged 2.6+/−0.8%.

Seed oil content (on a % seed weight basis) of *Arabidopsis* seed was calculated as follows:

mg oil=(NMR signal−2.1112)/37.514;

% oil=[(mg oil)/1000]/[g of seed sample weight]× 100.

Prior to establishing this formula, *Arabidopsis* seed oil was extracted as follows. Approximately 5 g of mature *Arabidopsis* seed (cv Columbia) were ground to a fine powder using a mortar and pestle. The powder was placed into a 33×94 mm paper thimble (Ahlstrom #7100-3394; Ahlstrom, Mount Holly Springs, Pa., USA) and the oil extracted during approximately 40 extraction cycles with petroleum ether (BP 39.9-51.7° C.) in a Soxhlet apparatus. The extract was allowed to cool and the crude oil was recovered by removing the solvent under vacuum in a rotary evaporator. Calibration parameters were determined by precisely weighing 11 standard samples of partially purified *Arabidopsis* oil (samples contained 3.6, 6.3, 7.9, 9.6, 12.8, 16.3, 20.3, 28.2, 32.1, 39.9 and 60 mg of partially purified *Arabidopsis* oil) weighed to a precision of 0.0001 g) into 2 mL polypropylene tubes (Corning Inc, Corning N.Y., USA; Part no. 430917) and subjecting them to NMR analysis. A calibration curve of oil content (% seed weight basis) to NMR value was established.

Table 4 shows that the seed oil content of T4 activation-tagged line with Bar code ID K17849 is only 86% of that of the average of four WT control plants grown in the same flat.

TABLE 4

Oil Content of T4 activation-tagged lines derived from T3 pool 256

| BARCODE | % Oil | T3 pool ID # | oil content % of WT |
|---|---|---|---|
| K17835 | 40.1 | 256 | 95.8 |
| K17836 | 43.0 | 256 | 102.7 |
| K17837 | 42.2 | 256 | 100.8 |
| K17838 | 42.6 | 256 | 101.8 |
| K17839 | 41.7 | 256 | 99.6 |
| K17840 | 42.4 | 256 | 101.3 |
| K17841 | 43.7 | 256 | 104.5 |
| K17842 | 40.9 | 256 | 97.6 |
| K17843 | 42.9 | 256 | 102.5 |
| K17844 | 43.3 | 256 | 103.5 |
| K17845 | 43.6 | 256 | 104.1 |
| K17846 | 41.5 | 256 | 99.1 |
| K17847 | 40.9 | 256 | 97.8 |
| K17848 | 41.7 | 256 | 99.7 |
| K17849 | 36.0 | 256 | 86.0 |
| K17851 | 43.3 | 256 | 103.5 |
| K17852 | 42.8 | 256 | 102.3 |
| K17853 | 43.0 | 256 | 102.8 |
| K17854 | 42.1 | 256 | 100.6 |
| K17855 | 42.8 | 256 | 102.2 |
| K17856 | 41.9 | wt |  |
| K17857 | 40.2 | wt |  |

K17849 was renamed Io17849. T4 seed were plated on selective media and nine glufosinate-resistant seedlings were planted in the same flat as six untransformed WT plants. Plants were grown to maturity and oil content was determined by NMR.

TABLE 5

Oil Content of T5 seed of activation-tagged line Io17849

| BARCODE | T5 activation-tagged line ID | % Oil | Average % oil | oil content % of WT | Average oil content % of WT |
|---|---|---|---|---|---|
| K24753 | lo17849 | 39.3 |  | 95.3 |  |
| K24747 | lo17849 | 38.9 |  | 94.2 |  |
| K24752 | lo17849 | 38.8 |  | 94.1 |  |
| K24746 | lo17849 | 38.4 |  | 93.2 |  |
| K24750 | lo17849 | 38.4 |  | 93.1 |  |
| K24751 | lo17849 | 38.2 |  | 92.7 |  |
| K24748 | lo17849 | 38.0 |  | 92.1 |  |
| K24754 | lo17849 | 37.8 |  | 91.5 |  |
| K24749 | lo17849 | 36.9 | 38.3 | 89.5 | 92.9 |
| K24760 | wt | 42.9 |  |  |  |
| K24755 | wt | 41.7 |  |  |  |
| K24757 | wt | 41.6 |  |  |  |
| K24756 | wt | 40.9 |  |  |  |
| K24759 | wt | 40.7 |  |  |  |
| K24758 | wt | 39.7 |  |  |  |

Table 5 shows that the seed oil content of T5 seed of activation-tagged line Io17849 is between 89.5 and 95.3% of that of WT control plants grown in the same flat. The average seed oil content of all T5 lines of Io17849 was 93% of the WT control plant average. Twenty-four Basta-resistant T5 seedlings of Io17849 were planted in the same flat alongside 12 untransformed WT control plants of the Columbia ecotype. Plants were grown to maturity and seed was bulk-harvested from all 24 Io17849 and 12 WT plants. Oil content of Io17849 and WT seed was measured by NMR (Table 6).

TABLE 6

Oil Content of T6 activation-tagged line lo17849

| Barcode | % Oil | Seed ID | oil content % of WT |
|---|---|---|---|
| K37207 | 39.7 | LO 17849 | 92.3 |
| K37208 | 43.0 | WT |  |

T6 seed of Io17849 and WT seed produced under identical conditions were subjected to compositional analysis as described below. Seed weight was measured by determining the weight of 100 seed. This analysis was performed in triplicate.

Tissue Preparation:

*Arabidopsis* seed (approximately 0.5 g in a ½×2" polycarbonate vial) was ground to a homogeneous paste in a GENOGRINDER® (3×30 sec at 1400 strokes per minute, with a 15 sec interval between each round of agitation). After the second round of agitation, the vials were removed and the *Arabidopsis* paste was scraped from the walls with a spatula prior to the last burst of agitation.

Determination of Protein Content:

Protein contents were estimated by combustion analysis on a Thermo FINNIGAN™ Flash 1112EA combustion analyzer running in the NCS mode (vanadium pentoxide was omitted) according to instructions of the manufacturer. Triplicate samples of the ground pastes, 4-8 mg, weighed to an accuracy of 0.001 mg on a METTLER-TOLEDO® MX5 micro balance, were used for analysis. Protein contents were calculated by multiplying % N, determined by the analyzer, by 6.25. Final protein contents were expressed on a % tissue weight basis.

Determination of Non-Structural Carbohydrate Content:

Sub-samples of the ground paste were weighed (to an accuracy of 0.1 mg) into 13×100 mm glass tubes; the tubes had TEFLON® lined screw-cap closures. Three replicates were prepared for each sample tested.

Lipid extraction was performed by adding 2 ml aliquots of heptane to each tube. The tubes were vortex mixed and placed into an ultrasonic bath (VWR Scientific Model 750D) filled with water heated to 60° C. The samples were sonicated at full-power (~360 W) for 15 min and were then centrifuged (5 min×1700 g). The supernatants were transferred to clean 13×100 mm glass tubes and the pellets were extracted 2 more times with heptane (2 ml, second extraction; 1 ml third extraction) with the supernatants from each extraction being pooled. After lipid extraction 1 ml acetone was added to the pellets and after vortex mixing, to fully disperse the material, they were taken to dryness in a Speedvac.

Non-Structural Carbohydrate Extraction and Analysis:

Two ml of 80% ethanol was added to the dried pellets from above. The samples were thoroughly vortex mixed until the plant material was fully dispersed in the solvent prior to sonication at 60° C. for 15 min. After centrifugation, 5 min×1700 g, the supernatants were decanted into clean 13×100 mm glass tubes. Two more extractions with 80% ethanol were performed and the supernatants from each were pooled. The extracted pellets were suspended in acetone and dried (as above). An internal standard β-phenyl glucopyranoside (100 μl of a 0.5000+/−0.0010 g/100 ml stock) was added to each extract prior to drying in a Speedvac. The extracts were maintained in a desiccator until further analysis.

The acetone dried powders from above were suspended in 0.9 ml MOPS (3-N[Morpholino]propane-sulfonic acid; 50 mM, 5 mM $CaCl_2$, pH 7.0) buffer containing 100 U of heat-stable α-amylase (from *Bacillus licheniformis*; Sigma A-4551). Samples were placed in a heat block (90° C.) for 75 min and were vortex mixed every 15 min. Samples were then allowed to cool to room temperature and 0.6 ml acetate buffer (285 mM, pH 4.5) containing 5 U amyloglucosidase (Roche 110 202 367 001) was added to each. Samples were incubated for 15-18 h at 55° C. in a water bath fitted with a reciprocating shaker; standards of soluble potato starch (Sigma S-2630) were included to ensure that starch digestion went to completion.

Post-digestion the released carbohydrates were extracted prior to analysis. Absolute ethanol (6 ml) was added to each tube and after vortex mixing the samples were sonicated for 15 min at 60° C. Samples were centrifuged (5 min×1700 g) and the supernatants were decanted into clean 13×100 mm glass tubes. The pellets were extracted 2 more times with 3 ml of 80% ethanol and the resulting supernatants were pooled. Internal standard (100 μl β-phenyl glucopyranoside, as above) was added to each sample prior to drying in a Speedvac.

Sample Preparation and Analysis:

The dried samples from the soluble and starch extractions described above were solubilized in anhydrous pyridine (Sigma-Aldrich P57506) containing 30 mg/ml of hydroxylamine HCl (Sigma-Aldrich 159417). Samples were placed on an orbital shaker (300 rpm) overnight and were then heated for 1 hr (75° C.) with vigorous vortex mixing applied every 15 min. After cooling to room temperature, 1 ml hexamethyldisilazane (Sigma-Aldrich H-4875) and 100 μl trifluoroacetic acid (Sigma-Aldrich T-6508) were added.

The samples were vortex mixed and the precipitates were allowed to settle prior to transferring the supernatants to GC sample vials.

Samples were analyzed on an Agilent 6890 gas chromatograph fitted with a DB-17MS capillary column (15 m×0.32 mm×0.25 um film). Inlet and detector temperatures were both 275° C. After injection (2 μl, 20:1 split) the initial column temperature (150° C.) was increased to 180° C. at a rate of 3° C./min and then at 25° C./min to a final temperature of 320° C. The final temperature was maintained for 10 min. The carrier gas was $H_2$ at a linear velocity of 51 cm/sec. Detection was by flame ionization. Data analysis was performed using Agilent ChemStation software. Each sugar was quantified relative to the internal standard and detector responses were applied for each individual carbohydrate (calculated from standards run with each set of samples). Final carbohydrate concentrations were expressed on a tissue weight basis.

Carbohydrates were identified by retention time matching with authentic samples of each sugar run in the same chromatographic set and by GC-MS with spectral matching to the NIST Mass Spectral Library Version 2a, build Jul. 1, 2002.

TABLE 7

Compositional Analysis of Io17849 and WT Control Seed

| Genotype | Barcode ID | Oil (%, NMR) | Protein % | Seed Weight (μg) | fructose (μg mg-1 seed) |
|---|---|---|---|---|---|
| Io17849 | K37207 | 39.7 | 16.95 | 24 | 0.66 |
| WT | K37208 | 43.0 | 15.49 | 23.67 | 0.57 |
| | Δ TG/WT % | −7.7 | 9.4 | 1.4 | 15.8 |

| Genotype | Barcode ID | glucose (μg mg-1 seed) | sucrose (μg mg-1 seed) | raffinose (μg mg-1 seed) | stachyose (μg mg-1 seed) |
|---|---|---|---|---|---|
| Io17849 | K37207 | 9.54 | 16.07 | 1.44 | 4.71 |
| WT | K37208 | 8.02 | 17.59 | 1.21 | 3.48 |
| | Δ TG/WT % | 19.0 | −8.6 | 19.0 | 35.3 |

Table 7 shows that no change of seed weight is associated with the seed oil reduction in Io17849. There is however a 10% increase in protein content in Io17849 compared to control seed. The soluble carbohydrate profile of Io17849 differs from that of WT seed. The former shows decrease a sucrose and increased levels of fructose, glucose, raffinose and stachyose.

In summary the Io17849 contains a genetic locus that confers glufosinate herbicide resistance. Presence of this transgene is associated with a low oil trait (reduction in oil content of 5-8% compared to WT) that is accompanied by unaltered seed size, increased protein content and a shift in the carbohydrate profile mature dry seed that consists of decreased sucrose levels and increased levels of fructose, glucose and raffinosaccharides.

Example 3

Identification of Activation-Tagged Genes

Genes flanking the T-DNA insert in the Io17849 lines were identified using one, or both, of the following two standard procedures: (1) thermal asymmetric interlaced (TAIL) PCR (Liu et al., *Plant J.* 8:457-63 (1995)); and (2) SAIFF PCR (Siebert et al., *Nucleic Acids Res.* 23:1087-1088 (1995)). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence. Once a tag of genomic sequence flanking a T-DNA insert is obtained, candidate genes are identified by alignment to publicly available *Arabidopsis* genome sequence. Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged Genes in Io17849

Construction of pKR1478 for Seed Specific Overexpression of Genes in *Arabidopsis*

Plasmid pKR85 (SEQ ID NO:3; described in US Patent Application Publication US 2007/0118929 published on May 24, 2007) was digested with HindIII and the fragment containing the hygromycin selectable marker was re-ligated together to produce pKR278 (SEQ ID NO:4).

Plasmid pKR407 (SEQ ID NO:5; described in PCT Int. Appl. WO 2008/124048 published on Oct. 16, 2008) was digested with BamHI/HindIII and the fragment containing the Gy1 promoter/NotI/LegA2 terminator cassette was effectively cloned into the BamHI/HindIII fragment of pKR278 (SEQ ID NO:4) to produce pKR1468 (SEQ ID NO:6).

Plasmid pKR1468 (SEQ ID NO:6) was digested with NotI and the resulting DNA ends were filled using Klenow. After filling to form blunt ends, the DNA fragments were treated with calf intestinal alkaline phosphatase and separated using agarose gel electrophoresis. The purified fragment was ligated with cassette frmA containing a chloramphenicol resistance and ccdB genes flanked by attR1 and attR2 sites, using the Gateway® Vector Conversion System (Cat. No. 11823-029, Invitrogen Corporation) following the manufacturer's protocol to pKR1475 (SEQ ID NO:7).

Plasmid pKR1475 (SEQ ID NO:7) was digested with AscI and the fragment containing the Gy1 promoter/NotI/LegA2 terminator Gateway® L/R cloning cassette was cloned into the AscI fragment of binary vector pKR92 (SEQ ID NO:8; described in US Patent Application Publication US 2007/0118929 published on May 24, 2007) to produce pKR1478 (SEQ ID NO:9).

In this way, genes flanked by attL1 and attL2 sites could be cloned into pKR1478 (SEQ ID NO:9) using Gateway® technology (Invitrogen Corporation) and the gene could be expressed in *Arabidopsis* from the strong, seed-specific soybean Gy1 promoter in soy.

The activation tagged-line (Io17849) showing reduced oil content was further analyzed. DNA from the line was extracted, and genes flanking the T-DNA insert in the mutant line were identified using ligation-mediated PCR (Siebert et al., *Nucleic Acids Res.* 23:1087-1088 (1995)). A single amplified fragment was identified that contained a T-DNA border sequence and *Arabidopsis* genomic sequence. The sequence of this PCR product which contains part of the left border of the inserted T-DNA is set forth as SEQ ID NO:10. Once a tag of genomic sequence flanking a T-DNA insert was obtained, a candidate gene was identified by alignment of SEQ ID NO:10 to the completed *Arabidopsis* genome (NCBI). Specifically, the SAIFF PCR product generated with PCR primers corresponding to the left border sequence of the T-DNA present in pHSbarENDs2 aligns with sequence of the *Arabidopsis* genome that is located in the second intron of *Arabidopsis* gene At5g17270 and 5949 bp upstream of the inferred start codon of At5g17280.

Validation of Candidate *Arabidopsis* Gene (At5g17280) Via Transformation into *Arabidopsis*

The gene At5g17280, specifically its inferred start codon is 5.5 kb downstream of the SAIFF sequence corresponding to sequence adjacent to the left T-DNA border in Io17849. This gene is annotated as encoding a protein with an oxidoreductase motif (ORM). Primers ORM ORF FWD (SEQ ID NO:11) and ORM ORF REV (SEQ ID NO:12) were used to amplify the At5g17280 ORF from genomic DNA of *Arabidopsis* plants of the Columbia ecotype. The PCR product was cloned into pENTR (Invitrogen, USA) to give pENTR-ORM (SEQ ID NO:13). The At5g17280 ORF was inserted in the sense orientation downstream of the GY1 promoter in binary plant transformation vector pKR1478 using Gateway LR recombinase (Invitrogen, USA) using manufacturer instructions. The sequence of the resulting plasmid pKR1478-ORM is set forth as SEQ ID NO:14.

pKR1478-ORM (SEQ ID NO:14) was introduced into *Agrobacterium tumefaciens* NTL4 (Luo et al, *Molecular Plant-Microbe Interactions* (2001) 14(1):98-103) by electroporation. Briefly, 1 µg plasmid DNA was mixed with 100 µL of electro-competent cells on ice. The cell suspension was transferred to a 100 µL electroporation cuvette (1 mm gap width) and electroporated using a BIORAD electroporator set to 1 kV, 400Ω and 25 µF. Cells were transferred to 1 mL LB medium and incubated for 2 h at 30° C. Cells were plated onto LB medium containing 50 µg/mL kanamycin. Plates were incubated at 30° C. for 60 h. Recombinant *Agrobacterium* cultures (500 mL LB, 50 µg/mL kanamycin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 cm² pot in METRO-MIX® 360 soil mixture for 4 weeks (22° C., 16 h light/8 h dark, 100 µE $m^{-2}s^{-1}$). Plants were repeatedly dipped into the *Agrobacterium* suspension harboring the binary vector pKR1478-ORM and kept in a dark, high humidity environment for 24 h. Post dipping, plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20×20 cm) containing 150 mL of sterile plant growth medium comprised of 0.5×MS salts, 0.53% (W/V) sorbitol, 0.05 MES/KOH (pH 5.8), 200 µg/mL TIMENTIN®, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. T1 Plants are grown to maturity alongside wt control plants and T2 seeds were harvested. A total of six wt plant were grown alongside the T1 plants and two bulk samples were generated by combining seed from three wt plants. Oil content was measured by NMR and is shown in Table 8

TABLE 8

Seed oil content of T1 plants generated with binary vector pKR1478-ORM for seed-specific over-expression of At5g17280

| Construct | BARCODE | % oil | oil content % of WT | avg. oil content % of WT |
|---|---|---|---|---|
| pKR1478-ORM | K42329 | 42.4 | 104.7 | |
| pKR1478-ORM | K42319 | 41.6 | 102.8 | |
| pKR1478-ORM | K42320 | 41.0 | 101.4 | |
| pKR1478-ORM | K42326 | 40.6 | 100.5 | |
| pKR1478-ORM | K42330 | 40.1 | 99.1 | |
| pKR1478-ORM | K42324 | 40.0 | 98.8 | |
| pKR1478-ORM | K42333 | 39.8 | 98.4 | |
| pKR1478-ORM | K42323 | 39.7 | 98.1 | |
| pKR1478-ORM | K42321 | 39.3 | 97.3 | |
| pKR1478-ORM | K42332 | 38.3 | 94.8 | |
| pKR1478-ORM | K42328 | 38.1 | 94.1 | |
| pKR1478-ORM | K42322 | 37.8 | 93.6 | |
| pKR1478-ORM | K42327 | 37.1 | 91.6 | |
| pKR1478-ORM | K42325 | 35.6 | 88.0 | |
| pKR1478-ORM | K42334 | 34.1 | 84.2 | |
| pKR1478-ORM | K42331 | 34.0 | 84.1 | 95.7 |
| wt | K42335 | 40.4 | | |

T2 seed of events K42334 and K42331 were plated on selective media and planted alongside untransformed wt control plants. Plants were gown to maturity. Seeds were harvested and oil content was measured by NMR (Table 9)

TABLE 9

Seed oil content of T2 plants generated with binary vector pKR1478-PAE for seed-specific over-expression of At5g17280

| Event ID | Construct | BARCODE | % oil | oil content % of WT | avg. oil content % of WT |
|---|---|---|---|---|---|
| K42334 | pKR1478-ORM | K44550 | 40.5 | 102.0 | |
| | pKR1478-ORM | K44537 | 39.2 | 98.9 | |
| | pKR1478-ORM | K44543 | 39.2 | 98.7 | |
| | pKR1478-ORM | K44553 | 39.0 | 98.2 | |
| | pKR1478-ORM | K44535 | 38.1 | 96.0 | |
| | pKR1478-ORM | K44545 | 37.9 | 95.5 | |
| | pKR1478-ORM | K44546 | 37.5 | 94.5 | |
| | pKR1478-ORM | K44551 | 37.2 | 93.8 | |
| | pKR1478-ORM | K44542 | 36.9 | 92.9 | |
| | pKR1478-ORM | K44549 | 36.6 | 92.1 | |
| | pKR1478-ORM | K44538 | 36.4 | 91.7 | |
| | pKR1478-ORM | K44547 | 36.2 | 91.1 | |
| | pKR1478-ORM | K44552 | 36.1 | 91.1 | |
| | pKR1478-ORM | K44540 | 35.6 | 89.8 | |
| | pKR1478-ORM | K44539 | 35.4 | 89.3 | |
| | pKR1478-ORM | K44544 | 35.0 | 88.1 | |
| | pKR1478-ORM | K44534 | 34.7 | 87.4 | |
| | pKR1478-ORM | K44536 | 34.4 | 86.7 | |
| | pKR1478-ORM | K44548 | 33.0 | 83.2 | |
| | pKR1478-ORM | K44541 | 30.3 | 76.2 | 91.9 |
| | wt | K44563 | 42.9 | | |
| | wt | K44555 | 42.6 | | |
| | wt | K44558 | 41.4 | | |
| | wt | K44559 | 40.6 | | |
| | wt | K44554 | 39.7 | | |
| | wt | K44557 | 39.3 | | |
| | wt | K44564 | 39.3 | | |
| | wt | K44561 | 38.8 | | |
| | wt | K44556 | 38.6 | | |
| | wt | K44562 | 38.2 | | |
| | wt | K44565 | 37.8 | | |
| | wt | K44560 | 37.1 | | |
| K42331 | pKR1478-ORM | K46263 | 40.3 | 94.0 | |
| | pKR1478-ORM | K46264 | 39.7 | 92.6 | |
| | pKR1478-ORM | K46266 | 39.7 | 92.5 | |
| | pKR1478-ORM | K46268 | 38.8 | 90.4 | |
| | pKR1478-ORM | K46262 | 38.7 | 90.3 | |
| | pKR1478-ORM | K46248 | 38.7 | 90.3 | |
| | pKR1478-ORM | K46251 | 38.4 | 89.6 | |
| | pKR1478-ORM | K46269 | 38.4 | 89.5 | |
| | pKR1478-ORM | K46249 | 38.3 | 89.4 | |
| | pKR1478-ORM | K46250 | 38.3 | 89.2 | |

TABLE 9-continued

Seed oil content of T2 plants generated with binary vector pKR1478-PAE for seed-specific over-expression of At5g17280

| Event ID | Construct | BARCODE | % oil | oil content % of WT | avg. oil content % of WT |
|---|---|---|---|---|---|
| | pKR1478-ORM | K46258 | 38.3 | 89.2 | |
| | pKR1478-ORM | K46261 | 38.1 | 88.8 | |
| | pKR1478-ORM | K46254 | 38.0 | 88.7 | |
| | pKR1478-ORM | K46255 | 38.0 | 88.7 | |
| | pKR1478-ORM | K46267 | 37.9 | 88.3 | |
| | pKR1478-ORM | K46256 | 37.8 | 88.1 | |
| | pKR1478-ORM | K46253 | 37.6 | 87.6 | |
| | pKR1478-ORM | K46265 | 37.3 | 87.1 | |
| | pKR1478-ORM | K46257 | 37.2 | 86.7 | |
| | pKR1478-ORM | K46259 | 37.1 | 86.5 | |
| | pKR1478-ORM | K46260 | 36.9 | 86.0 | |
| | pKR1478-ORM | K46252 | 35.8 | 83.6 | 89.0 |
| | wt | K46275 | 44.7 | | |
| | wt | K46270 | 43.6 | | |
| | wt | K46272 | 43.4 | | |
| | wt | K46280 | 43.4 | | |
| | wt | K46281 | 43.3 | | |
| | wt | K46277 | 43.2 | | |
| | wt | K46271 | 43.0 | | |
| | wt | K46273 | 42.8 | | |
| | wt | K46278 | 42.7 | | |
| | wt | K46279 | 42.6 | | |
| | wt | K46276 | 42.2 | | |
| | wt | K46274 | 39.8 | | |

T3 seed of lines K44584 and K44581 derived from event K42334 were plated on selective media and planted alongside untransformed wt control plants. Plants were gown to maturity. Seeds were harvested and oil content was measured by NMR (Table 10)

TABLE 10

Seed oil content of T3 plants generated with binary vector pKR1478-PAE for seed-specific over-expression of At5g17280

| Event ID | Construct | BARCODE | % oil | oil content % of WT | avg. oil content % of WT |
|---|---|---|---|---|---|
| K42334/K44548 | pKR1478-ORM | K49194 | 39.3 | 92.9 | |
| | pKR1478-ORM | K49193 | 39.0 | 92.1 | |
| | pKR1478-ORM | K49204 | 38.9 | 92.1 | |
| | pKR1478-ORM | K49206 | 38.7 | 91.5 | |
| | pKR1478-ORM | K49197 | 38.7 | 91.5 | |
| | pKR1478-ORM | K49208 | 38.7 | 91.5 | |
| | pKR1478-ORM | K49199 | 38.2 | 90.3 | |
| | pKR1478-ORM | K49207 | 37.8 | 89.4 | |
| | pKR1478-ORM | K49214 | 37.7 | 89.0 | |
| | pKR1478-ORM | K49196 | 37.6 | 88.9 | |
| | pKR1478-ORM | K49191 | 37.5 | 88.8 | |
| | pKR1478-ORM | K49192 | 37.3 | 88.2 | |
| | pKR1478-ORM | K49205 | 37.2 | 87.8 | |
| | pKR1478-ORM | K49209 | 36.5 | 86.3 | |
| | pKR1478-ORM | K49211 | 36.5 | 86.2 | |
| | pKR1478-ORM | K49212 | 36.4 | 86.0 | |
| | pKR1478-ORM | K49200 | 36.3 | 85.9 | 89.3 |
| | wt | K49223 | 43.0 | | |
| | wt | K49219 | 42.8 | | |
| | wt | K49221 | 42.7 | | |
| | wt | K49222 | 42.4 | | |
| | wt | K49220 | 42.1 | | |
| | wt | K49216 | 42.0 | | |
| | wt | K49218 | 41.8 | | |
| | wt | K49217 | 41.7 | | |
| K42334/K44541 | pKR1478-ORM | K49174 | 38.8 | 93.0 | |
| | pKR1478-ORM | K49152 | 38.1 | 91.3 | |
| | pKR1478-ORM | K49173 | 38.1 | 91.3 | |
| | pKR1478-ORM | K49177 | 37.7 | 90.2 | |
| | pKR1478-ORM | K49162 | 37.6 | 90.1 | |
| | pKR1478-ORM | K49176 | 36.9 | 88.2 | |
| | pKR1478-ORM | K49167 | 36.8 | 88.2 | |
| | pKR1478-ORM | K49157 | 36.8 | 88.2 | |
| | pKR1478-ORM | K49163 | 36.8 | 88.1 | |
| | pKR1478-ORM | K49170 | 36.7 | 87.9 | |
| | pKR1478-ORM | K49171 | 36.7 | 87.8 | |
| | pKR1478-ORM | K49178 | 36.6 | 87.7 | |
| | pKR1478-ORM | K49154 | 36.5 | 87.3 | |
| | pKR1478-ORM | K49156 | 35.7 | 85.5 | |
| | pKR1478-ORM | K49165 | 35.0 | 83.7 | |
| | pKR1478-ORM | K49161 | 33.8 | 80.9 | |
| | pKR1478-ORM | K49179 | 33.6 | 80.5 | 87.6 |
| | wt | K49185 | 43.1 | | |
| | wt | K49186 | 42.5 | | |
| | wt | K49187 | 42.3 | | |
| | wt | K49181 | 42.2 | | |
| | wt | K49182 | 42.0 | | |
| | wt | K49184 | 41.5 | | |
| | wt | K49180 | 40.8 | | |
| | wt | K49183 | 39.8 | | |

Tables 8-10 demonstrate that seed specific over-expression of At5g17280 leads to a decrease in oil content of 10%. The decrease in oil content associated with the transgene is heritable. This finding suggests that the low seed oil phenotype in Io17849 in related to increased expression of At5g17280 resulting from the nearby insertion of quadruple 35S enhancer sequence present in the pHSbarENDs2-derived T-DNA.

Example 5

Seed-Specific RNAi of At5g17280. Generation and Phenotypic Characterization of Transgenic Lines A binary plant transformation vector pKR1482 (SEQ ID NO:15) for generation of hairpin constructs facilitating seed-specific RNAi under control of the GY1 promoter derived from the soy gene Glyma03g32030.1 was constructed. The RNAi-related expression cassette that can be used for cloning of a given DNA fragment flanked by ATTL sites in antisense and sense orientation downstream of the seed-specific promoter. The two gene fragments are interrupted by a spliceable intron sequence derived from the *Arabidopsis* gene At2g38080.

An intron of an *Arabidopsis laccase* gene (At2g38080) was amplified from genomic *Arabidopsis* DNA of ecotype Columbia using primers AthLcc IN FWD (SEQ ID NO:16) and AthLcc IN REV (SEQ ID NO:17). PCR products were cloned into pGEM T EASY (Promega, USA) according to manufacturer instructions and sequenced. The DNA sequence of the PCR product containing the laccase intron is set forth as SEQ ID NO:18. The PCR primers introduce an HpaI restriction site at the 5' end of the intron and restriction sites for NruI and SpeI at the 3' end of the intron. A three-way ligation of DNA fragments was performed as follows. XbaI digested, dephosphorylated DNA of pMBL18 (Nakano, Yoshio; Yoshida, Yasuo; Yamashita, Yoshihisa; Koga, Toshihiko. Construction of a series of pACYC-derived plasmid vectors. Gene (1995), 162(1), 157-8.) was ligated to the XbaI, EcoRV DNA fragment of PSM1318 (SEQ ID NO:19) containing ATTR12 sites a DNA Gyrase inhibitor gene (ccdB), a chloramphenicol acetyltransferase gene, an HpaI/SpeI restriction fragment excised from pGEM T EASY Lacc INT (SEQ ID NO:18) containing intron 1 of At2g38080. Ligation products were transformed into the DB 3.1 strain of *E. coli* (Invitrogen, USA). Recombinant clones were characterized by restriction digests and sequenced. The DNA sequence of the resulting plasmid pMBL18 ATTR12 INT is set forth as SEQ ID NO:20. DNA of pMBL18 ATTR12 INT was linearized with NruI, dephosphorylated and ligated to the XbaI, EcoRV DNA fragment of PSM1789 (SEQ ID NO: 21) containing ATTR12 sites and a DNA Gyrase inhibitor gene (ccdB). Prior to ligation ends of the PSM1789 restriction fragment had been filled in with T4 DNA polymerase (Promega, USA). Ligation products were transformed into the DB 3.1 strain of *E. coli* (Invitrogen, USA). Recombinant clones were characterized by restriction digests and sequenced. The DNA sequence of the resulting plasmid pMBL18 ATTR12 INT ATTR21 is set forth as SEQ ID NO:22.

Plasmid pMBL18 ATTR12 INT ATTR21 (SEQ ID NO:22) was digested with XbaI and after filling to blunt the XbaI site generated, the resulting DNA was digested with EcI13611 and the fragment containing the attR cassettes was cloned into the NotI/BsiWI (where the NotI site was completely filled in) fragment of pKR1468 (SEQ ID NO:6), containing the Gy1 promoter, to produce pKR1480 (SEQ ID NO:23).

pKR1480 (SEQ ID NO:23) was digested with AscI and the fragment containing the Gy1 promoter/attR cassettes was cloned into the AscI fragment of binary vector pKR92 (SEQ ID NO:8) to produce pKR1482 (SEQ ID NO:15).

5 µg of plasmid DNA of pENTR-ORM (SEQ ID NO:13). was digested with EcoRV/HpaI. A restriction fragment of 0.7 kb (derived from pENTR-ORM) was excised from an agarose gel. The purified DNA fragment was inserted into vector pKR1482 using LR clonase (Invitrogen) according to the manufacturers instructions, to give pKR1482-ORM (SEQ ID NO:24)

pKR1482-ORM (SEQ ID NO:24) was introduced into *Agrobacterium tumefaciens* NTL4 (Luo et al, *Molecular Plant-Microbe Interactions* (2001) 14(1):98-103) by electroporation. Briefly, 1 µg plasmid DNA was mixed with 100 µL of electro-competent cells on ice. The cell suspension was transferred to a 100 µL electroporation cuvette (1 mm gap width) and electroporated using a BIORAD electroporator set to 1 kV, 400Ω and 25 µF. Cells were transferred to 1 mL LB medium and incubated for 2 h at 30° C. Cells were plated onto LB medium containing 50 µg/mL kanamycin. Plates were incubated at 30° C. for 60 h. Recombinant *Agrobacterium* cultures (500 mL LB, 50 µg/mL kanamycin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 cm$^2$ pot in METRO-MIX® 360 soil mixture for 4 weeks (22° C., 16 h light/8 h dark, 100 µE m$^{-2}$s$^{-1}$). Plants were repeatedly dipped into the *Agrobacterium* suspension harboring the binary vector pKR1482-ORM (SEQ ID NO:24) and kept in a dark, high humidity environment for 24 h. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20×20 cm) containing 150 mL of sterile plant growth medium comprised of 0.5×MS salts, 0.53% (W/V) sorbitol, 0.05 MES/KOH (pH 5.8), 200 µg/mL TIMENTIN®, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. Plants were grown to maturity and T2 seeds were harvested. A total of 15 events were generated with pKR1482-ORM (SEQ ID NO:24). Six wild-type (WT) control plants were grown in the same flat. WT seeds were bulk harvested thus generating two batches of wt control seed derived form three plants. T2 seed of individual transgenic lines were harvested. Oil content was measured by NMR as described above.

TABLE 11

Seed oil content of T1 plants generated with binary vector pKR1482-ORM for seed specific gene suppression of At5g17280 (Experiment 1)

| Construct | BARCODE | % oil | oil content % of WT | avg. oil content % of WT |
|---|---|---|---|---|
| pKR1482-ORM | K42351 | 41.4 | 111.5 | |
| pKR1482-ORM | K42355 | 41.0 | 110.4 | |
| pKR1482-ORM | K42361 | 40.8 | 109.8 | |
| pKR1482-ORM | K42360 | 40.5 | 109.0 | |
| pKR1482-ORM | K42359 | 40.2 | 108.2 | |
| pKR1482-ORM | K42350 | 40.1 | 107.8 | |
| pKR1482-ORM | K42362 | 39.5 | 106.2 | |
| pKR1482-ORM | K42353 | 38.6 | 103.8 | |
| pKR1482-ORM | K42352 | 38.5 | 103.7 | |
| pKR1482-ORM | K42354 | 38.3 | 103.0 | |
| pKR1482-ORM | K42356 | 38.3 | 102.9 | |
| pKR1482-ORM | K42358 | 37.8 | 101.8 | |
| pKR1482-ORM | K42349 | 36.7 | 98.9 | |
| pKR1482-ORM | K42357 | 36.2 | 97.5 | |
| pKR1482-ORM | K42348 | 36.0 | 96.8 | 104.7 |
| wt | K42363 | 38.4 | | |
| wt | K42364 | 35.9 | | |

Table 11 shows that seed-specific down regulation of At5g17280 leads to increased oil content in *Arabidopsis* seed.

T2 seeds of event K42355 that carries transgene pKR1482-ORM (SEQ ID NO: 24) were plated on plant growth media containing kanamycin. Plants were grown to maturity alongside WT plants of the Columbia ecotype grown in the same flats. Oil content of T3 seed is depicted in Table 12.

TABLE 12

Seed oil content of T2 plants generated with binary vector pKR1482-ORM for seed specific gene suppression of At5g17280 (Experiment 1)

| Event ID | Construct | BARCODE | % oil | oil content % of WT | avg. oil content % of WT |
|---|---|---|---|---|---|
| K42335 | pKR1482-ORM | K44642 | 43.3 | 107.8 | |
| | pKR1482-ORM | K44650 | 43.1 | 107.3 | |
| | pKR1482-ORM | K44643 | 42.8 | 106.5 | |
| | pKR1482-ORM | K44637 | 42.6 | 106.0 | |
| | pKR1482-ORM | K44641 | 42.2 | 105.1 | |
| | pKR1482-ORM | K44647 | 41.6 | 103.5 | |
| | pKR1482-ORM | K44652 | 41.3 | 102.8 | |
| | pKR1482-ORM | K44636 | 41.3 | 102.7 | |
| | pKR1482-ORM | K44639 | 41.0 | 102.1 | |
| | pKR1482-ORM | K44646 | 41.0 | 102.0 | |
| | pKR1482-ORM | K44653 | 40.9 | 101.7 | |
| | pKR1482-ORM | K44649 | 40.4 | 100.5 | |
| | pKR1482-ORM | K44644 | 40.3 | 100.2 | |
| | pKR1482-ORM | K44657 | 39.9 | 99.2 | |
| | pKR1482-ORM | K44654 | 39.5 | 98.3 | |
| | pKR1482-ORM | K44656 | 39.0 | 97.1 | |
| | pKR1482-ORM | K44651 | 38.4 | 95.6 | 102.0 |
| wt | | K44658 | 41.7 | | |
| wt | | K44661 | 41.3 | | |
| wt | | K44663 | 41.2 | | |
| wt | | K44664 | 41.1 | | |
| wt | | K44666 | 40.7 | | |
| wt | | K44662 | 40.1 | | |
| wt | | K44665 | 38.8 | | |
| wt | | K44668 | 38.4 | | |
| wt | | K44667 | 38.3 | | |

T3 seeds of lines K44650 and K44637 derived from event K42355 that carries transgene pKR1482-ORM were plated on plant growth media containing kanamycin. Plants were grown to maturity alongside WT plants of the Columbia ecotype grown in the same flats. Oil content of T3 seed is depicted in Table 13.

TABLE 13

Seed oil content of T3 plants generated with binary vector pKR1482-ORM for seed specific gene suppression of At5g17280 (Experiment 1)

| Event ID | Construct | BARCODE | % oil | oil content % of WT | avg. oil content % of WT |
|---|---|---|---|---|---|
| K42335/ K44650 | pKR1482-ORM | K49241 | 43.5 | 105.7 | |
| | pKR1482-ORM | K49231 | 43.3 | 105.3 | |
| | pKR1482-ORM | K49236 | 42.9 | 104.1 | |
| | pKR1482-ORM | K49227 | 42.8 | 104.0 | |
| | pKR1482-ORM | K49239 | 42.7 | 103.9 | |
| | pKR1482-ORM | K49234 | 42.7 | 103.8 | |
| | pKR1482-ORM | K49226 | 42.7 | 103.8 | |
| | pKR1482-ORM | K49249 | 42.6 | 103.6 | |
| | pKR1482-ORM | K49237 | 42.6 | 103.5 | |
| | pKR1482-ORM | K49233 | 42.6 | 103.4 | |
| | pKR1482-ORM | K49225 | 42.4 | 103.1 | |
| | pKR1482-ORM | K49228 | 42.4 | 103.0 | |
| | pKR1482-ORM | K49230 | 42.2 | 102.5 | |

TABLE 13-continued

Seed oil content of T3 plants generated with binary vector pKR1482-ORM for seed specific gene suppression of At5g17280 (Experiment 1)

| Event ID | Construct | BARCODE | % oil | oil content % of WT | avg. oil content % of WT |
|---|---|---|---|---|---|
| | pKR1482-ORM | K49244 | 42.1 | 102.3 | |
| | pKR1482-ORM | K49242 | 42.1 | 102.2 | |
| | pKR1482-ORM | K49232 | 42.0 | 102.1 | |
| | pKR1482-ORM | K49224 | 42.0 | 102.0 | |
| | pKR1482-ORM | K49248 | 41.8 | 101.6 | |
| | pKR1482-ORM | K49246 | 41.7 | 101.3 | |
| | pKR1482-ORM | K49238 | 41.6 | 101.0 | |
| | pKR1482-ORM | K49247 | 41.5 | 100.8 | |
| | pKR1482-ORM | K49245 | 41.5 | 100.7 | |
| | pKR1482-ORM | K49240 | 41.4 | 100.7 | |
| | pKR1482-ORM | K49250 | 41.3 | 100.4 | |
| | pKR1482-ORM | K49235 | 41.1 | 99.9 | |
| | pKR1482-ORM | K49229 | 41.1 | 99.8 | |
| | pKR1482-ORM | K49243 | 41.0 | 99.6 | 102.4 |
| | wt | K49255 | 42.2 | | |
| | wt | K49257 | 41.8 | | |
| | wt | K49252 | 41.7 | | |
| | wt | K49256 | 41.5 | | |
| | wt | K49251 | 40.9 | | |
| | wt | K49253 | 40.3 | | |
| | wt | K49254 | 39.6 | | |
| K42335/ K44637 | pKR1482-ORM | K49600 | 42.3 | 116.5 | |
| | pKR1482-ORM | K49595 | 42.0 | 115.6 | |
| | pKR1482-ORM | K49596 | 41.9 | 115.2 | |
| | pKR1482-ORM | K49582 | 41.7 | 114.8 | |
| | pKR1482-ORM | K49598 | 41.5 | 114.2 | |
| | pKR1482-ORM | K49594 | 41.5 | 114.1 | |
| | pKR1482-ORM | K49591 | 41.4 | 113.9 | |
| | pKR1482-ORM | K49583 | 41.3 | 113.6 | |
| | pKR1482-ORM | K49592 | 41.1 | 113.2 | |
| | pKR1482-ORM | K49601 | 40.8 | 112.4 | |
| | pKR1482-ORM | K49576 | 40.8 | 112.2 | |
| | pKR1482-ORM | K49587 | 40.7 | 111.9 | |
| | pKR1482-ORM | K49599 | 40.5 | 111.4 | |
| | pKR1482-ORM | K49597 | 40.4 | 111.4 | |
| | pKR1482-ORM | K49579 | 40.4 | 111.2 | |
| | pKR1482-ORM | K49580 | 40.2 | 110.6 | |
| | pKR1482-ORM | K49578 | 40.1 | 110.4 | |
| | pKR1482-ORM | K49585 | 40.1 | 110.3 | |
| | pKR1482-ORM | K49586 | 40.0 | 110.3 | |
| | pKR1482-ORM | K49590 | 40.0 | 110.0 | |
| | pKR1482-ORM | K49588 | 39.6 | 109.1 | |
| | pKR1482-ORM | K49581 | 39.6 | 109.0 | |
| | pKR1482-ORM | K49584 | 39.3 | 108.3 | |
| | pKR1482-ORM | K49574 | 39.2 | 107.9 | |
| | pKR1482-ORM | K49593 | 39.2 | 107.8 | |
| | pKR1482-ORM | K49589 | 39.1 | 107.7 | |
| | pKR1482-ORM | K49577 | 39.0 | 107.3 | |
| | pKR1482-ORM | K49575 | 35.8 | 98.5 | 111.0 |
| | wt | K49604 | 39.1 | | |
| | wt | K49603 | 37.7 | | |
| | wt | K49606 | 36.7 | | |
| | wt | K49602 | 34.1 | | |
| | wt | K49605 | 33.9 | | |

Additional events were generated with pKR1482-ORM in a second experiment henceforth referred to as Experiment 2. Oil content of T1 and T2 plants of pKR1482-ORM events derived from Experiment 2 is shown in Tables 14 and 15.

TABLE 14

Seed oil content of T1 plants generated with binary vector pKR1482-ORM for seed specific gene suppression of At5g17280 (Experiment 2)

| Construct | BARCODE | % oil | oil content % of WT |
|---|---|---|---|
| pKR1482-ORM | K47030 | 41.8 | 104.9 |
| pKR1482-ORM | K47021 | 41.2 | 103.4 |
| pKR1482-ORM | K47018 | 41.1 | 103.2 |
| pKR1482-ORM | K47017 | 41.0 | 103.0 |
| pKR1482-ORM | K47013 | 40.3 | 101.1 |
| pKR1482-ORM | K47028 | 40.2 | 101.0 |
| pKR1482-ORM | K47015 | 40.2 | 100.8 |
| pKR1482-ORM | K47007 | 40.0 | 100.2 |
| pKR1482-ORM | K47025 | 39.6 | 99.3 |
| pKR1482-ORM | K47029 | 39.5 | 99.0 |
| pKR1482-ORM | K47008 | 39.3 | 98.7 |
| pKR1482-ORM | K47022 | 38.8 | 97.5 |
| pKR1482-ORM | K47020 | 38.8 | 97.3 |
| pKR1482-ORM | K47014 | 38.5 | 96.6 |
| pKR1482-ORM | K47026 | 38.4 | 96.2 |

TABLE 14-continued

Seed oil content of T1 plants generated with binary vector pKR1482-ORM for seed specific gene suppression of At5g17280 (Experiment 2)

| Construct | BARCODE | % oil | oil content % of WT |
|---|---|---|---|
| pKR1482-ORM | K47012 | 38.2 | 95.8 |
| pKR1482-ORM | K47023 | 38.0 | 95.4 |
| pKR1482-ORM | K47010 | 37.9 | 95.1 |
| pKR1482-ORM | K47019 | 37.3 | 93.5 |
| pKR1482-ORM | K47011 | 37.2 | 93.4 |
| pKR1482-ORM | K47027 | 37.2 | 93.3 |
| pKR1482-ORM | K47009 | 35.6 | 89.4 |
| pKR1482-ORM | K47024 | 35.5 | 89.1 |
| pKR1482-ORM | K47016 | 32.3 | 81.1 |
| wt | K47308 | 40.9 | |
| wt | K47312 | 40.4 | |
| wt | K47306 | 40.3 | |
| wt | K47307 | 40.2 | |
| wt | K47302 | 40.1 | |
| wt | K47301 | 39.9 | |
| wt | K47310 | 39.7 | |
| wt | K47305 | 39.6 | |
| wt | K47309 | 39.5 | |
| wt | K47311 | 39.3 | |
| wt | K47304 | 39.2 | |
| wt | K47303 | 39.1 | |

TABLE 15

Seed oil content of T2 plants generated with binary vector pKR1482-ORM for seed specific gene suppression of At5g17280 (Experiment 2)

| Event ID | Construct | BARCODE | % oil | oil content % of WT | avg. oil content % of WT |
|---|---|---|---|---|---|
| K47021 | pKR1482-ORM | K50089 | 44.5 | 107.6 | |
| | pKR1482-ORM | K50087 | 44.3 | 107.3 | |
| | pKR1482-ORM | K50093 | 44.3 | 107.3 | |
| | pKR1482-ORM | K50085 | 44.1 | 106.7 | |
| | pKR1482-ORM | K50086 | 43.9 | 106.3 | |
| | pKR1482-ORM | K50088 | 43.8 | 106.0 | |
| | pKR1482-ORM | K50091 | 43.6 | 105.6 | |
| | pKR1482-ORM | K50090 | 43.3 | 104.9 | |
| | pKR1482-ORM | K50094 | 43.0 | 104.2 | |
| | pKR1482-ORM | K50084 | 42.7 | 103.3 | |
| | pKR1482-ORM | K50092 | 42.5 | 102.8 | 105.6 |
| | wt | K50097 | 42.2 | | |
| | wt | K50099 | 42.2 | | |
| | wt | K50100 | 41.8 | | |
| | wt | K50095 | 41.6 | | |
| | wt | K50098 | 40.2 | | |
| | wt | K50096 | 39.7 | | |
| K47018 | pKR1482-ORM | K50105 | 44.9 | 108.7 | |
| | pKR1482-ORM | K50102 | 44.7 | 108.2 | |
| | pKR1482-ORM | K50122 | 44.2 | 107.1 | |
| | pKR1482-ORM | K50109 | 44.2 | 107.0 | |
| | pKR1482-ORM | K50104 | 44.0 | 106.6 | |
| | pKR1482-ORM | K50114 | 44.0 | 106.5 | |
| | pKR1482-ORM | K50112 | 43.8 | 106.0 | |
| | pKR1482-ORM | K50111 | 43.7 | 105.9 | |
| | pKR1482-ORM | K50121 | 43.7 | 105.8 | |
| | pKR1482-ORM | K50115 | 43.6 | 105.7 | |
| | pKR1482-ORM | K50101 | 43.6 | 105.6 | |
| | pKR1482-ORM | K50106 | 43.6 | 105.6 | |
| | pKR1482-ORM | K50120 | 43.5 | 105.3 | |
| | pKR1482-ORM | K50123 | 43.4 | 105.2 | |
| | pKR1482-ORM | K50103 | 43.2 | 104.6 | |
| | pKR1482-ORM | K50110 | 43.1 | 104.4 | |
| | pKR1482-ORM | K50117 | 43.1 | 104.4 | |
| | pKR1482-ORM | K50108 | 43.0 | 104.1 | |
| | pKR1482-ORM | K50118 | 42.8 | 103.7 | |
| | pKR1482-ORM | K50119 | 42.5 | 103.0 | |
| | pKR1482-ORM | K50113 | 42.2 | 102.2 | |
| | pKR1482-ORM | K50107 | 42.1 | 101.9 | |
| | pKR1482-ORM | K50116 | 40.3 | 97.6 | 105.0 |
| | wt | K50129 | 42.8 | | |
| | wt | K50132 | 42.7 | | |
| | wt | K50130 | 42.7 | | |
| | wt | K50133 | 42.5 | | |
| | wt | K50134 | 42.3 | | |
| | wt | K50124 | 42.2 | | |
| | wt | K50127 | 41.7 | | |
| | wt | K50128 | 41.3 | | |
| | wt | K50125 | 39.7 | | |
| | wt | K50126 | 39.2 | | |
| | wt | K50131 | 37.1 | | |

Tables 11, 12, 13, 14 and 15 demonstrate that an oil increase of about 2-11% is associated with seed-specific down regulation of At5g17280. The oil increase is observed in multiple events and is heritable.

Example 6

Identification of cDNA Clones cDNA clones encoding an ORM motif protein can be identified by conducting BLAST (Basic Local Alignment Search Tool; Altschul et al. (1993) *J. Mol. Biol.* 215:403-

410; see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States (1993) Nat. Genet. 3:266-272) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST are reported herein as "p Log" values, which represent the negative of the logarithm of the reported P-value or E-value. Accordingly, the greater the p Log value, the greater the likelihood that the cDNA-encoded sequence and the BLAST "hit" represent homologous proteins.

ESTs sequences can be compared to the Genbank database as described above. ESTs that contain sequences more 5- or 3-prime can be found by using the BLASTN algorithm (Altschul et al (1997) Nucleic Acids Res. 25:3389-3402.) against the DUPONT™ proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above. Homologous genes belonging to different species can be found by comparing the amino acid sequence of a known gene (from either a proprietary source or a public database) against an EST database using the TBLASTN algorithm. The TBLASTN algorithm searches an amino acid query against a nucleotide database that is translated in all 6 reading frames. This search allows for differences in nucleotide codon usage between different species, and for codon degeneracy.

Example 7

Characterization of cDNA Clones Encoding ORM Protein Polypeptides

A cDNA library representing mRNAs from sunflower was prepared and cDNA clones encoding ORM polypeptides were identified. Clone hso1c.pk014.c16 was obtained from a cDNA library prepared from transgenic sunflower plants.

Example 8

Identification of Genes of Brassica napus Closely-Related to At5g17280

Public DNA sequences (NCBI and Brassica napus EST assembly (N) Brassica napus EST assembly version 3.0 (Jul. 30, 2007) from the Gene Index Project at Dana-Farber Cancer Institute were searched using the predicted amino acid sequence of At5g17280 and tBLASTn. The assembly encompasses about 558465 public ESTs and has a total of 90310 sequences (47591 assemblies and 42719 singletons). There are three genes encoding proteins with homology to At5g17280. These genes, their % identity to At5g17280 and SEQ ID NOs are listed in Table 16.

TABLE 16

Brassica rapa gene closely related to At5g17280

| Gene name | % AA sequence identity to At5g17280 | SEQ ID NO: NT | SEQ ID NO: AA |
|---|---|---|---|
| TC44737 | 51.8 | 25 | 26 |
| TC52165 | 53.3 | 27 | 28 |
| TC52879 | 48.2 | 29 | 30 |

Example 9

Identification of Genes of Sunflower Genes Closely-Related to At5g17280

Applicants Sunflower EST libraries were searched using the predicted amino acid sequence of were searched using the predicted amino acid sequence of At5g17280 and tBLASTn. and tBLASTn. There is one EST encoding a protein that shares 47.2 sequence identity to At5g17280. The gene, its % identity to At5g17280 and SEQ ID NOs are listed in Table 17. Clone hso1c.pk014.c16 shares 38.3% sequence identity with the public sequence from Populus trichocarpa (NCBI GI:118481427, SEQ ID NO:64) and 35.7% sequence identity with SEQ ID NO: 36271 of US20060123505 (SEQ ID NO:65).

TABLE 17

Sunflower (Helianthus annuus) gene closely related to At5g17280

| Gene name | % AA sequence identity to At5g17280 | SEQ ID NO: AA | SEQ ID NO: NT |
|---|---|---|---|
| hso1c.pk014.c16 | 39.1 | 31 | 32 |

Example 10

Identification of Genes of Castor Genes Closely-Related to At5g17280

The Non-redundant protein data set from NCBI including non-redundant GenBank CDS translations+PDB+SwissProt+PIR+PRF protein sequences was searched using the predicted amino acid sequence of At5g17280 and tBLASTn. There is one gene XM_002533611 which shares 50.7% amino acid sequence identity to At5g17280. This gene, its % identity to At5g17280 and SEQ ID NOs are listed in Table 18.

TABLE 18

Castor (*Ricinus communis*) gene closely related to At5g17280

| Gene name | % AA sequence identity to At5g17280 | SEQ ID NO: NT | SEQ ID NO: AA |
|---|---|---|---|
| XM_002533611 | 50.7 | 33 | 34 |

Example 11

Identification of Genes of Soybean (*Glycine Max*) Closely-Related to At5g17280

Public DNA sequences (Soybean cDNAs Glyma1.01 (JGI) (N) Predicted cDNAs from Soybean JGI Glyma1.01 genomic sequence, FGENESH predictions, and EST PASA analysis.) were searched using the predicted amino acid sequence of At5g17280 and tBLASTn. There are two genes that encode protein which share between 38.2 and 30.3% amino acid sequence identity with the predicted protein At5g17280. These genes, its properties and SEQ ID NO are listed in Table 19

TABLE 19

Soybean genes closely related to At5g17280

| Gene name | % AA sequence identity to At5g17280 | SEQ ID NO: NT | SEQ ID NO: AA |
|---|---|---|---|
| Glyma02g05870 | 38.2 | 35 | 36 |
| Glyma16g24560 | 30.3 | 37 | 38 |

Example 12

Identification of Genes of Maize (*Zea Mays*) Closely-Related to At5g17280

The filtered Gene Set cDNAs of the maize genome sequence in the public maize database was searched using the predicted amino acid sequence of At5g17280 and tBLASTn. In addition applicant's maize EST data base was searched in a similar fashion. These genes, its properties and SEQ ID NO are listed in Table 20. Maize GRMZM2G132101 shares 94.4% sequence identity with the public sequence from maize, NCBI Gi NO: 195615148 (SEQ ID NO: 66) and 93.3 sequence identity with SEQ ID NO:233249 of US20040214272 (SEQ ID NO:67). Maize cDNA pco642986 shares 95.5% sequence identity with the public sequence from maize, NCBI Gi NO: 195615148 (SEQ ID NO: 66) and 96.6% sequence identity with SEQ ID NO:233249 of US20040214272 (SEQ ID NO:67). Maize cDNA pco597536 shares 99.2% sequence identity with the public sequence from maize, NCBI Gi NO: 195615148 (SEQ ID NO:66) and 100% sequence identity with SEQ ID NO:233249 of US20040214272 (SEQ ID NO:67).

TABLE 20

Maize genes closely related to At5g17280

| Gene name | % AA sequence identity to At5g17280 | SEQ ID NO: NT | SEQ ID NO: AA |
|---|---|---|---|
| GRMZM2G132101 | 33.7 | 39 | 40 |
| pco642986 | 33.0 | 41 | 42 |
| pco597536 | 30.9 | 43 | 44 |

Example 13

Identification of Genes of Rice (*Oryza sativa*) Closely-Related to At5g17280

A public database of transcripts from rice gene models (*Oryza sativa* (*japonica* cultivar-group) MSU Rice Genome Annotation Project Osa1 release 6 (January 2009)) which includes untranslated regions (UTR) but no introns was searched using the predicted amino acid sequence of At5g17280 and tBLASTn. There is one gene which shares 34.5% amino acid sequence identity to At5g17280. This gene, its % identity to At5g17280 and SEQ ID NOs are listed in Table 21.

TABLE 21

Rice gene closely related to At5g17280

| Gene name | % AA sequence identity to At5g17280 | SEQ ID NO: NT | SEQ ID NO: AA |
|---|---|---|---|
| Os09g36120 | 34.5 | 45 | 46 |

Example 14

Identification of Genes of Sorghum (*Sorghum bicolor*) Closely-Related to At5g17280

The predicted coding sequences (mRNA) from the *Sorghum* JGI genomic sequence, version 1.4 were searched using the predicted amino acid sequence of At5g17280 and tBLASTn. There is one gene which shares 30.9% amino acid sequence identity to At5g17280. This gene, its % identity to At5g17280 and SEQ ID NOs are listed in Table 22.

TABLE 22

*Sorghum* gene closely related to At5g17280

| Gene name | % AA sequence identity to At5g17280 | SEQ ID NO: NT | SEQ ID NO: AA |
|---|---|---|---|
| Sb02g030770 | 30.9 | 47 | 48 |

Example 15

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferate from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810-812) and the 3' region of the nopaline synthase gene from the T-DNA of the Ti plasmid of Agrobacterium tumefaciens.

The particle bombardment method (Klein et al. (1987) Nature 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi. Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833-839).

Example 16

Expression of Chimeric Genes in Dicot Cells

A seed-specific construct composed of the promoter and transcription terminator from the gene encoding the β subunit of the seed storage protein phaseolin from the bean Phaseolus vulgaris (Doyle et al. (1986) J. Biol. Chem. 261:9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872 can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below. Soybean embryogenic suspension cultures can be maintained in 35 mL of liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810-812), the hygromycin phosphotransferase gene from plasmid pJR225 (from E. coli; Gritz et al. (1983) Gene 25:179-188) and the 3' region of the nopaline synthase gene from the T-DNA of the Ti plasmid of Agrobacterium tumefaciens. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene. To 50 µL of a 60 mg/mL 1 µm gold particle suspension is added (in order): 5 µL DNA (1 µg/µL), 20 µL spermidine (0.1 M), and 50 µL CaCl$_2$ (2.5M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk. Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 17

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis. For high level expression, a plasmid clone with the cDNA insert in the correct orientation relative to the T7 promoter can be transformed into E. coli strain BL21(DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 18

Transformation of Somatic Soybean Embryo Cultures

Generic Stable Soybean Transformation Protocol:

Soybean embryogenic suspension cultures are maintained in 35 ml liquid media (SB55 or SBP6) on a rotary shaker, 150 rpm, at 28° C. with mixed fluorescent and incandescent lights on a 16:8 h day/night schedule. Cultures are subcultured every four weeks by inoculating approximately 35 mg of tissue into 35 ml of liquid medium.

TABLE 23

| Stock Solutions (g/L): | |
|---|---|
| MS Sulfate 100X Stock | |
| $MgSO_4\ 7H_2O$ | 37.0 |
| $MnSO_4\ H_2O$ | 1.69 |
| $ZnSO_4\ 7H_2O$ | 0.86 |
| $CuSO_4\ 5H_2O$ | 0.0025 |
| MS Halides 100X Stock | |
| $CaCl_2\ 2H_2O$ | 44.0 |
| KI | 0.083 |
| $CoCl_2\ 6H_2O$ | 0.00125 |
| $KH_2PO_4$ | 17.0 |
| $H_3BO_3$ | 0.62 |
| $Na_2MoO_4\ 2H_2O$ | 0.025 |
| MS FeEDTA 100X Stock | |
| $Na_2EDTA$ | 3.724 |
| $FeSO_4\ 7H_2O$ | 2.784 |
| B5 Vitamin Stock | |
| 10 g m-inositol | |
| 100 mg nicotinic acid | |
| 100 mg pyridoxine HCl | |
| 1 g thiamine | |
| SB55 (per Liter, pH 5.7) | |
| 10 ml each MS stocks | |
| 1 ml B5 Vitamin stock | |
| 0.8 g $NH_4NO_3$ | |
| 3.033 g $KNO_3$ | |
| 1 ml 2,4-D (10 mg/mL stock) | |
| 60 g sucrose | |
| 0.667 g asparagine | |
| SBP6 same as SB55 except 0.5 ml 2,4-D | |
| SB103 (per Liter, pH 5.7) | |
| 1X MS Salts | |
| 6% maltose | |
| 750 mg $MgCl_2$ | |
| 0.2% Gelrite | |
| SB71-1 (per Liter, pH 5.7) | |
| 1X B5 salts | |
| 1 ml B5 vitamin stock | |
| 3% sucrose | |
| 750 mg $MgCl_2$ | |
| 0.2% Gelrite | |

Soybean embryogenic suspension cultures are transformed with plasmid DNA by the method of particle gun bombardment (Klein et al (1987) *Nature* 327:70). A DuPont Biolistic PDS1 000/HE instrument (helium retrofit) is used for these transformations.

To 50 ml of a 60 mg/ml 1 μm gold particle suspension is added (in order); 5 μL DNA (1 μg/μl), 20 μl spermidine (0.1 M), and 50 μl $CaCl_2$ (2.5 M). The particle preparation is agitated for 3 min, spun in a microfuge for 10 sec and the supernatant removed. The DNA-coated particles are then washed once in 400 μl 70% ethanol and re suspended in 40 μl of anhydrous ethanol. The DNA/particle suspension is sonicated three times for 1 sec each. Five μl of the DNA-coated gold particles are then loaded on each macro carrier disk. For selection, a plasmid conferring resistance to hygromycin phosphotransferase (HPT) may be co-bombarded with the silencing construct of interest.

Approximately 300-400 mg of a four week old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1000 psi and the chamber is evacuated to a vacuum of 28 inches of mercury. The tissue is placed approximately 3.5 inches away from the retaining screen and bombarded three times. Following bombardment, the tissue is placed back into liquid and cultured as described above.

Eleven days post bombardment, the liquid media is exchanged with fresh SB55 containing 50 mg/ml hygromycin. The selective media is refreshed weekly. Seven weeks post bombardment, green, transformed tissue is observed growing from untransformed, necrotic embryogenic clusters. Isolated green tissue is removed and inoculated into individual flasks to generate new, clonally propagated, transformed embryogenic suspension cultures. Thus each new line is treated as an independent transformation event. These suspensions can then be maintained as suspensions of embryos maintained in an immature developmental stage or regenerated into whole plants by maturation and germination of individual somatic embryos.

Independent lines of transformed embryogenic clusters are removed from liquid culture and placed on a solid agar media (SB103) containing no hormones or antibiotics. Embryos are cultured for four weeks at 26° C. with mixed fluorescent and incandescent lights on a 16:8 h day/night schedule. During this period, individual embryos are removed from the clusters and screened for alterations in gene expression.

It should be noted that any detectable phenotype, resulting from the altered expression of a target gene, can be screened at this stage. This would include, but not be limited to, alterations in oil content, protein content, carbohydrate content, growth rate, viability, or the ability to develop normally into a soybean plant.

Example 19

Plasmid DNAs for "Complementary Region" Co-Suppression

The plasmids in the following experiments are made using standard cloning methods well known to those skilled in the art (Sambrook et al (1989) *Molecular Cloning*, CSHL Press, New York). A starting plasmid pKS18HH (U.S. Pat. No. 5,846,784 the contents of which are hereby incorporated by reference) contains a hygromycin B phosphotransferase (HPT) obtained from *E. coli* strain W677 under the control of a T7 promoter and the 35S cauliflower mosaic virus promoter. Plasmid pKS18HH thus contains the T7 promoter/HPT/T7 terminator cassette for expression of the HPT enzyme in certain strains of *E. coli*, such as NovaBlue (DE3) [from Novagen], that are lysogenic for lambda DE3 (which carries the T7 RNA Polymerase gene under lacV5 control).

Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restriction endonuclease sites suitable for the cloning other chimeric genes into this vector. Plasmid ZBL100 (PCT Application No. WO 00/11176 published on Mar. 2, 2000) is a derivative of pKS18HH with a reduced NOS 3' terminator. Plasmid pKS67 is a ZBL100 derivative with the insertion of a beta-conglycinin promoter, in front of a NotI cloning site, followed by a phaseolin 3' terminator (described in PCT Application No. WO 94/11516, published on May 26, 1994).

The 2.5 kb plasmid pKS17 contains pSP72 (obtained from Promega Biosystems) and the T7 promoter/HPT/T7 3' terminator region, and is the original vector into which the 3.2 kb BamHI-SalI fragment containing the 35S/HPT/NOS cassette was cloned to form pKS18HH. The plasmid pKS102 is a pKS17 derivative that is digested with XhoI and SalI, treated with mung-bean nuclease to generate blunt ends, and ligated to insert the linker described in SEQ ID NO:49:

The plasmid pKS83 has the 2.3 kb BamHI fragment of ML70 containing the Kti3 promoter/NotI/Kti3 3' terminator region (described in PCT Application No. WO 94/11516, published on May 26, 1994) ligated into the BamHI site of pKS17. Additional methods for suppression of endogenous genes are well know in the art and have been described in the detailed description of the instant invention and can be used to reduce the expression of endogenous ORM protein or enzyme activity in a plant cell.

Example 20

Suppression by ELVISLIVES Complementary Region

Constructs can be made which have "synthetic complementary regions" (SCR). In this example the target sequence is placed between complementary sequences that are not known to be part of any biologically derived gene or genome (i.e. sequences that are "synthetic" or conjured up from the mind of the inventor). The target DNA would therefore be in the sense or antisense orientation and the complementary RNA would be unrelated to any known nucleic acid sequence. It is possible to design a standard "suppression vector" into which pieces of any target gene for suppression could be dropped. The plasmids pKS106, pKS124, and pKS133 (SEQ ID NO:50) exemplify this. One skilled in the art will appreciate that all of the plasmid vectors contain antibiotic selection genes such as, but not limited to, hygromycin phosphotransferase with promoters such as the T7 inducible promoter.

pKS106 uses the beta-conglycinin promoter while the pKS124 and pKS133 plasmids use the Kti promoter, both of these promoters exhibit strong tissue specific expression in the seeds of soybean. pKS106 uses a 3' termination region from the phaseolin gene, and pKS124 and pKS133 use a Kti 3' termination region. pKS106 and pKS124 have single copies of the 36 nucleotide EagI-ELVISLIVES sequence surrounding a NotI site (the amino acids given in parentheses are back-translated from the complementary strand): SEQ ID NO:51

```
EagI E L V I S L I V E S NotI
CGGCCG GAG CTG GTC ATC TCG CTC ATC GTC GAG TCG GCGGCCGC (S) (E) (V) (I) (L) (S) (I) (V) (L) (E) EagI
CGA CTC GAC GAT GAG CGA GAT GAC CAG CTC CGGCCG
``` pKS133 has 2× copies of ELVISLIVES surrounding the NotI site: SEQ ID NO:52

```
EagI E L V I S L I V E S EagI E L V I S
cggccggagctggtcatctcgctcatcgtcgagtcg gcggccg gagctggtcatctcg L I V E S NotI (S)(E (V)(I)(L)(S)(I)(V)(L)(E) EagI
ctcatcgtcgagtcg gcggccgc cgactcgacgatgagcgagatgaccagctc cggccgc (S)(E)(V)(I)(L)(S)(I)(V)(L)(E) EagI
cgactcgacgatgagcgagatgaccagctc cggccg
```

The idea is that the single EL linker (SCR) can be duplicated to increase stem lengths in increments of approximately 40 nucleotides. A series of vectors will cover the SCR lengths between 40 bp and the 300 bp. Various target gene lengths can also be evaluated. It is believed that certain combinations of target lengths and complementary region lengths will give optimum suppression of the target, however, it is expected that the suppression phenomenon works well over a wide range of sizes and sequences. It is also believed that the lengths and ratios providing optimum suppression may vary somewhat given different target sequences and/or complementary regions.

The plasmid pKS106 is made by putting the EagI fragment of ELVISLIVES (SEQ ID NO:51) into the NotI site of pKS67. The ELVISLIVES fragment is made by PCR using two primers (SEQ ID NO:53 and SEQ ID NO:54) and no other DNA.

The product of the PCR reaction is digested with EagI (5'-CGGCCG-3') and then ligated into NotI digested pKS67. The term "ELVISLIVES" and "EL" are used interchangeably herein.

Additional plasmids can be used to test this example and any synthetic sequence, or naturally occurring sequence, can be used in an analogous manner.

Example 21

Screening of Transgenic Lines for Alterations in Oil, Protein, Starch and Soluble Carbohydrate Content Transgenic lines can be selected from soybean transformed with a suppression plasmid, such as those described in Example 19 and Example 20. Transgenic lines can be screened for down regulation of plastidic HpaII aldolase in soybean, by measuring alteration in oil, starch, protein, soluble carbohydrate and/or seed weight. Compositional analysis including measurements of seed compositional parameters such as protein content and content of soluble carbohydrates of soybean seed derived from transgenic events that show seed-specific down-regulation of ORM genes is performed as follows:

Oil content of mature soybean seed or lyophilized soybean somatic embryos can be measured by NMR as described in Example 2.

Non-Structural Carbohydrate and Protein Analysis.

Dry soybean seed are ground to a fine powder in a GenoGrinder and subsamples are weighed (to an accuracy of 0.0001 g) into 13×100 mm glass tubes; the tubes have Teflon® lined screw-cap closures. Three replicates are prepared for each sample tested. Tissue dry weights are calculated by weighing sub-samples before and after drying in a forced air oven for 18 h at 105 C.

Lipid extraction is performed by adding 2 ml aliquots of heptane to each tube. The tubes are vortex mixed and placed into an ultrasonic bath (VWR Scientific Model 750D) filled with water heated to 60 C. The samples are sonicated at full-power (~360W) for 15 min and were then centrifuged (5 min×1700 g). The supernatants are transferred to clean 13×100 mm glass tubes and the pellets are extracted 2 more times with heptane (2 ml, second extraction, 1 ml third extraction) with the supernatants from each extraction being pooled. After lipid extraction 1 ml acetone is added to the pellets and after vortex mixing, to fully disperse the material, they are taken to dryness in a Speedvac.

Non-Structural Carbohydrate Extraction and Analysis.

Two ml of 80% ethanol is added to the acetone dried pellets from above. The samples are thoroughly vortex mixed until the plant material was fully dispersed in the solvent prior to sonication at 60 C for 15 min. After centrifugation, 5 min×1700 g, the supernatants are decanted into clean 13×100 mm glass tubes. Two more extractions with 80% ethanol are performed and the supernatants from each are pooled. The extracted pellets are suspended in acetone and dried (as above). An internal standard β-phenyl glucopyranoside (100 ul of a 0.5000+/−0.0010 g/100 ml stock) is added to each extract prior to drying in a Speedvac. The extracts are maintained in a desiccator until further analysis.

The acetone dried powders from above were suspended in 0.9 ml MOPS (3-N[Morpholino]propane-sulfonic acid; 50 mM, 5 mM $CaCl_2$, pH 7.0) buffer containing 1000 of heat stable α-amylase (from *Bacillus licheniformis*; Sigma A-4551). Samples are placed in a heat block (90 C) for 75 min and were vortex mixed every 15 min. Samples are then allowed to cool to room temperature and 0.6 ml acetate buffer (285 mM, pH 4.5) containing 5U amyloglucosidase (Roche 110 202 367 001) is added to each. Samples are incubated for 15-18 h at 55 C in a water bath fitted with a reciprocating shaker; standards of soluble potato starch (Sigma S-2630) are included to ensure that starch digestion went to completion.

Post-digestion the released carbohydrates are extracted prior to analysis. Absolute ethanol (6 ml) is added to each tube and after vortex mixing the samples were sonicated for 15 min at 60 C. Samples were centrifuged (5 min×1700 g) and the supernatants were decanted into clean 13×100 mm glass tubes. The pellets are extracted 2 more times with 3 ml of 80% ethanol and the resulting supernatants are pooled. Internal standard (100 ul β-phenyl glucopyranoside, as above) is added to each sample prior to drying in a Speedvac.

Sample Preparation and Analysis

The dried samples from the soluble and starch extractions described above are solubilized in anhydrous pyridine (Sigma-Aldrich P57506) containing 30 mg/ml of hydroxylamine HCl (Sigma-Aldrich 159417). Samples are placed on an orbital shaker (300 rpm) overnight and are then heated for 1 hr (75 C) with vigorous vortex mixing applied every 15 min. After cooling to room temperature 1 ml hexamethyldisilazane (Sigma-Aldrich H-4875) and 100 ul trifluoroacetic acid (Sigma-Aldrich T-6508) are added. The samples are vortex mixed and the precipitates are allowed to settle prior to transferring the supernatants to GC sample vials. Samples are analyzed on an Agilent 6890 gas chromatograph fitted with a DB-17MS capillary column (15 m×0.32 mm×0.25 um film). Inlet and detector temperatures are both 275 C. After injection (2 ul, 20:1 split) the initial column temperature (150 C) is increased to 180 C at a rate 3 C/min and then at 25 C/min to a final temperature of 320 C. The final temperature is maintained for 10 min. The carrier gas is $H_2$ at a linear velocity of 51 cm/sec. Detection is by flame ionization. Data analysis is performed using Agilent ChemStation software. Each sugar is quantified relative to the internal standard and detector responses were applied for each individual carbohydrate (calculated from standards run with each set of samples). Final carbohydrate concentrations are expressed on a tissue dry weight basis.

Protein Analysis

Protein contents are estimated by combustion analysis on a Thermo Finnigan Flash 1112EA combustion analyzer. Samples, 4-8 mg, weighed to an accuracy of 0.001 mg on a Mettler-Toledo MX5 micro balance are used for analysis. Protein contents were calculated by multiplying % N, determined by the analyzer, by 6.25. Final protein contents are expressed on a % tissue dry weight basis. Additionally, the composition of intact single seed and bulk quantities of seed or powders derived from them, may be measured by near-infrared analysis. Measurements of moisture, protein and oil content in soy and moisture, protein, oil and starch content in corn can be measured when combined with the appropriate calibrations.

Example 22

Screening of Transgenic Maize Lines for Alterations in Oil, Protein, Starch and Soluble Carbohydrate Content Transgenic maize lines prepared by the method described in Example 15 can be screened essentially as described in Example 21. Embryo-specific downregulation of ORM gene expression is expected to lead to an increase in seed oil content. In contrast overexpression of ORM genes in the endosperm-specific is expected to lead to an increase in seed starch and/or protein content.

Example 23

Seed-Specific RNAi of ORM Genes in Soybean

A plasmid vector (pKS433) for generation of transgenic soybean events that show seed specific down-regulation of the soy ORM genes corresponding to Glyma02g05870 and Glyma16g24560 genes was constructed.

Briefly plasmid DNA of applicants EST clone sl1.pk0142.e6 corresponding to Glyma02g05870 (SEQ ID NO:35) was used in a PCR reactions with Primers SA195 (SEQ ID NO:55) and SA196 (SEQ ID NO:56) and SA200 (SEQ ID NO:57) and SA201 (SEQ ID NO:58). A PCR product of 0.39 kb was generated with SA195 (SEQ ID NO:55) and SA196 (SEQ ID NO:56). It was gel purified and is henceforth known as product A. A PCR product of 0.19 kb was generated with SA200 (SEQ ID NO:57) and SA201 (SEQ ID NO:58). It was gel purified and is henceforth known as product B. PCR products A and B were cloned into pGEM T to give pGEM TA (SEQ ID NO:59) and pGEM TB (SEQ ID NO:60), respectively. pGEM TA (SEQ ID NO:59) was digested with HhaI. The digested DNA was treated with Klenow polymerase (NEB, Ipswich, Mass., USA), specifically the 3'-5' exonuclease activity of said enzyme was used to create blunt ends. A 0.58 kb DNA fragment was gel-purified. pGEM TB (SEQ ID NO:60), was linearized by digestion with BamHI. Overhanging ends were filled-in with Klenow polymerase activity and 3' ends were dephosphorylated using calf intestinal phosphatase (NEB, Ipswich, Mass., USA). The 0.58 kb HhaI fragment was ligated to BamHI-linearized pGEM TB to give rise to pGEM T-ORM-HP (SEQ ID NO:61).

pGEM T-ORM-HP (SEQ ID NO:61) was digested with NotI. A 0.56 kb was gel-purified. The gel purified product was ligated using T4 ligase and thereby cloned in the sense orientation behind the Kti promoter of soybean expression vector KS126 (PCT Publication No. WO 04/071467) that had previously been linearized with the restriction enzyme NotI to give pKS433 (SEQ ID NO:62).

Plasmid DNA of pKS433 can be used to generate transgenic somatic embryos or seed of soybean using hygromycin selection as described in Example 14. Composition of transgenic somatic embryos or soybean seed generated with pKS433 can be determined as described in Example 19.

The plasmid vector pKS123 is described in PCT Application No. WO 02/08269. Plasmid pKS120 (SEQ ID NO: 63) is identical to pKS123 (supra) with the exception that the HindIII fragment containing Bcon/NotI/Phas3' cassette was removed.

Generation of Transgenic Somatic Embryos:

Soybean somatic embryos soybean tissue was co-bombarded as described below with a plasmid DNA of pKS120 or pKS433

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 h day/night photoperiod at light intensity of 60-85 µE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., Nature 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time, secondary embryos were cut and placed into SB196 liquid media for 7 days.

Preparation of DNA for Bombardment:

Plasmid DNA of pKS120 or pKS433 were used for bombardment.

A 50 µL aliquot of sterile distilled water containing 1 mg of gold particles was added to 5 µL of a 1 µg/µL plasmid DNA solution 50 µL 2.5M $CaCl_2$ and 20 µL of 0.1 M spermidine. The mixture was pulsed 5 times on level 4 of a vortex shaker and spun for 5 sec in a bench microfuge. After a wash with 150 µL of 100% ethanol, the pellet was suspended by sonication in 85 µL of 100% ethanol. Five µL of DNA suspension was dispensed to each flying disk of the Biolistic PDS1 000/HE instrument disk. Each 5 µL aliquot contained approximately 0.058 mg gold particles per bombardment (i.e., per disk).

Tissue Preparation and Bombardment with DNA:

Approximately 100-150 mg of 7 day old embryonic suspension cultures were placed in an empty, sterile 60×15 mm petri dish and the dish was placed inside of an empty 150×25 mm Petri dish. Tissue was bombarded 1 shot per plate with membrane rupture pressure set at 650 PSI and the chamber was evacuated to a vacuum of 27-28 inches of mercury. Tissue was placed approximately 2.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six to eight days post-bombardment, the SB196 is exchanged with fresh SB196 containing 30 mg/L hygromycin. The selection media was refreshed weekly. Four to six weeks post-selection, green, transformed tissue was observed growing from untransformed, necrotic embryogenic clusters. Isolated, green tissue was removed and inoculated into multi-well plates to generate new, clonally propagated, transformed embryogenic suspension cultures.

Embryo Maturation:

Transformed embryogenic clusters were cultured for one-three weeks at 26° C. in SB196 under cool white fluorescent (Phillips cool white Econowatt F40/CW/RS/EW) and Agro (Phillips F40 Agro) bulbs (40 watt) on a 16:8 hrphotoperiod with light intensity of 90-120 µE/$m^2$s. After this time embryo clusters were removed to a solid agar media, SB166, for 1 week. Then subcultured to medium SB103 for 3 weeks. Alternatively, embryo clusters were removed to SB228 (SHaM) liquid media, 35 mL in 250 mL Erlenmeyer flask, for 2-3 weeks. Tissue cultured in SB228 was maintained on a rotary shaker, 130 rpm, 26° C. with cool white fluorescent lights on 16:8 h day/night photoperiod at light intensity of 60-85 μE/m2/s. During this period, individual embryos were removed from the clusters and screened for alterations in their fatty acid compositions as described supra.

Media Recipes:

| SB 196 - FN Lite Liquid Proliferation Medium (per liter) | |
| --- | --- |
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| Asparagine | 1.0 gm |
| Sucrose (1%) | 10 gm |
| pH 5.8 | |

FN Lite Stock Solutions

| Stock Number | | 1000 mL | 500 mL |
| --- | --- | --- | --- |
| 1 | MS Fe EDTA 100x Stock | | |
| | $Na_2$ EDTA* | 3.724 g | 1.862 g |
| | $FeSO_4 - 7H_2O$ | 2.784 g | 1.392 g |
| 2 | MS Sulfate 100x stock | | |
| | $MgSO_4 - 7H_2O$ | 37.0 g | 18.5 g |
| | $MnSO_4 - H_2O$ | 1.69 g | 0.845 g |
| | $ZnSO_4 - 7H_2O$ | 0.86 g | 0.43 g |
| | $CuSO_4 - 5H_2O$ | 0.0025 g | 0.00125 g |
| 3 | FN Lite Halides 100x Stock | | |
| | $CaCl_2 - 2H_2O$ | 30.0 g | 15.0 g |
| | KI | 0.083 g | 0.0715 g |
| | $CoCl_2 - 6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4 - 2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g Glucose
2 mL 2,4-D (20 mg/L final concentration)
pH 5.7
8 g TC agar SB199 Solid Medium (Per Liter)

1 package MS salts (Gibco/BRL—Cat. No. 11117-066)
1 mL B5 vitamins 1000× stock
30 g Sucrose
4 ml 2,4-D (40 mg/L final concentration)
pH 7.0
2 gm Gelrite SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g Activated charcoal
pH 5.7
2 g Gelrite SB 103 Solid Medium (Per Liter)

1 package MS salts (Gibco/BRL—Cat. No. 11117-066)
1 mL B5 vitamins 1000× stock
60 g maltose
750 mg MgCl2 hexahydrate
pH 5.7
2 g Gelrite SB 71-4 Solid Medium (Per Liter)

1 bottle Gamborg's B5 salts w/ sucrose (Gibco/BRL—Cat. No. 21153-036)
pH 5.7
5 g TC agar 2,4-D Stock Obtain premade from Phytotech Cat. No. D 295—concentration 1 mg/mL B5 Vitamins Stock (Per 100 mL)

Store aliquots at −20° C.
10 g Myo-inositol
100 mg Nicotinic acid
100 mg Pyridoxine HCl
1 g Thiamine
If the solution does not dissolve quickly enough, apply a low level of heat via the hot stir plate.

SB 228

Soybean Histodifferentiation & Maturation (SHaM)
(Per Liter)

| | |
| --- | --- |
| DDI H2O | 600 ml |
| FN-Lite Macro Salts for SHaM 10X | 100 ml |
| MS Micro Salts 1000x | 1 ml |
| MS FeEDTA 100x | 10 ml |
| CaCl 100x | 6.82 ml |
| B5 Vitamins 1000x | 1 ml |
| L-Methionine | 0.149 g |
| Sucrose | 30 g |
| Sorbitol | 30 g |
| Adjust volume to 900 mL | |
| pH 5.8 | |
| Autoclave | |
| Add to cooled media (≤30 C): | |
| *Glutamine (Final conc. 30 mM) 4% | 110 mL |

*Note: Final volume will be 1010 mL after glutamine addition.

Because glutamine degrades relatively rapidly, it may be preferable to add immediately prior to using media. Expiration 2 weeks after glutamine is added; base media can be kept longer w/o glutamine.

FN-Lite Macro for SHAM 10×

Stock #1 (Per Liter)

| | |
|---|---|
| (NH₄)2SO₄ (Ammonium Sulfate) | 4.63 g |
| KNO₃ (Potassium Nitrate) | 28.3 g |
| MgSO₄*7H₂O (Magnesium Sulfate Heptahydrate) | 3.7 g |
| KH₂PO₄ (Potassium Phosphate, Monobasic) | 1.85 g |

Bring to volume
Autoclave

MS Micro 1000×

Stock #2 (Per 1 Liter)

| | |
|---|---|
| H₃BO₃ (Boric Acid) | 6.2 g |
| MnSO₄*H₂O (Manganese Sulfate Monohydrate) | 16.9 g |
| ZnSO4*7H2O (Zinc Sulfate Heptahydrate) | 8.6 g |
| Na₂MoO₄*2H2O (Sodium Molybdate Dihydrate) | 0.25 g |
| CuSO₄*5H₂O (Copper Sulfate Pentahydrate) | 0.025 g |
| CoCl₂*6H₂O (Cobalt Chloride Hexahydrate) | 0.025 g |
| KI (Potassium Iodide) | 0.8300 g |

Bring to volume
Autoclave

FeEDTA 100×

Stock #3 (Per Liter)

| | |
|---|---|
| Na₂EDTA* (Sodium EDTA) | 3.73 g |
| FeSO₄*7H₂O (Iron Sulfate Heptahydrate) | 2.78 g |

*EDTA must be completely dissolved before adding iron.
Bring to Volume
Solution is photosensitive. Bottle(s) should be wrapped in foil to omit light.
Autoclave

Ca 100×

Stock #4 (Per Liter)

| | |
|---|---|
| CaCl₂*2H₂O (Calcium Chloride Dihydrate) | 44 g |

Bring to Volume
Autoclave

B5 Vitamin 1000×

Stock #5 (Per Liter)

| | |
|---|---|
| Thiamine*HCl | 10 g |
| Nicotinic Acid | 1 g |
| Pyridoxine*HCl | 1 g |
| Myo-Inositol | 100 g |

Bring to Volume
Store frozen

4% Glutamine

Stock #6 (Per Liter)

| | |
|---|---|
| DDI water heated to 30° C. | 900 ml |
| L-Glutamine | 40 g |

Gradually add while stirring and applying low heat.
Do not exceed 35° C.
Bring to Volume
Filter Sterilize
Store frozen*
*Note: Warm thawed stock in 31° C. bath to fully dissolve crystals.

Oil Analysis:

Oil content of somatic embryos is measured using NMR. Briefly lyophilized soybean somatic embryo tissue is pulverized in genogrinder vial as described previously (Example 2). 20-200 mg of tissue powder were transferred to NMR tubes. Oil content of the somatic embryo tissue powder is calculated from the NMR signal as described in Example 2.

Example 24

Compositional Analysis of *Arabidopsis* Events Transformed with DNA Constructs for Seed-Preferred Silencing of ORM Genes The example describes seed composition of transgenic events gene generated with pKR1482-ORM (SEQ ID NO:24). It demonstrates that transformation with DNA constructs for silencing of genes encoding ORM genes leads to increased oil content that is accompanied by a reduction in seed storage protein and soluble carbohydrate content. T4 seed of event K42335 described in Table 13 of Example 5 and T3 seed of event K47021 and K47018 described in Table 15 of Example 5 were used to create three bulk seed samples. Three bulk seed sample of WT control plants grown alongside the T4 and T3 plants described in Tables 13 and 15 of Example 5 were also generated. Oil content of the six seed samples was measured by NMR as described in Example 2. The seed samples were subjected to compositional analysis of protein and soluble carbohydrate content of triplicate samples as described in Example 2. The results of this analysis are summarized in Table 24.

TABLE 24

Seed composition of arabidospis events transformed with DNA constructs for silencing of ORM genes

| Genotype | Event ID | Oil (%, NMR) | Protein % | fructose ($\mu g\ mg^{-1}$ seed) | glucose ($\mu g\ mg^{-1}$ seed) |
|---|---|---|---|---|---|
| pKR1482-ORM | K42335/ K44650 | 44.3 | 16.7 | 0.2 | 3.3 |
| | WT | 42.1 | 18.0 | 0.3 | 4.3 |
| | Δ TG/WT % | 5.2 | −7.2 | −29.7 | −23.2 |

| Genotype | Bar code ID | sucrose ($\mu g\ mg^{-1}$ seed) | raffinose ($\mu g\ mg^{-1}$ seed) | stachyose ($\mu g\ mg^{-1}$ seed) | total soluble CHO ($\mu g\ mg^{-1}$ seed) |
|---|---|---|---|---|---|
| pKR1482-ORM | K42335/ K44650 | 11.8 | 0.1 | 0.6 | 16.6 |
| | WT | 15.9 | 0.3 | 0.2 | 21.3 |
| | Δ TG/WT % | −25.9 | −57.2 | 167.9 | −21.9 |

TABLE 24-continued

Seed composition of arabidospis events transformed with
DNA constructs for silencing of ORM genes

| Genotype | Event ID | Oil (%, NMR) | Protein % | fructose (µg mg$^{-1}$ seed) | glucose (µg mg$^{-1}$ seed) |
|---|---|---|---|---|---|
| pKR1482-ORM | K47021 | 44.9 | 16.7 | 0.3 | 3.5 |
|  | WT | 42.5 | 17.9 | 0.2 | 4.0 |
|  | Δ TG/WT % | 5.6 | −6.7 | 16.1 | −12.5 |

| Genotype | Event ID | sucrose (µg mg$^{-1}$ seed) | raffinose (µg mg$^{-1}$ seed) | stachyose (µg mg$^{-1}$ seed) | total soluble CHO (µg mg$^{-1}$ seed) |
|---|---|---|---|---|---|
| pKR1482-ORM | K47021 | 14.6 | 0.3 | 0.3 | 19.2 |
|  | WT | 15.9 | 0.4 | 0.8 | 21.6 |
|  | Δ TG/WT % | −8.3 | −22.1 | −65.8 | −10.9 |

| Genotype | Event ID | Oil (%, NMR) | Protein % | fructose (µg mg$^{-1}$ seed) | glucose (µg mg$^{-1}$ seed) |
|---|---|---|---|---|---|
| pKR1482-ORM | K47018 | 44.8 | 15.7 | 0.2 | 2.7 |
|  | WT | 42.6 | 17.7 | 0.3 | 4.3 |
|  | Δ TG/WT % | 5.2 | −11.1 | −16.6 | −37.0 |

| Genotype | Event ID | sucrose (µg mg$^{-1}$ seed) | raffinose (µg mg$^{-1}$ seed) | stachyose (µg mg$^{-1}$ seed) | total soluble CHO (µg mg$^{-1}$ seed) |
|---|---|---|---|---|---|
| pKR1482-ORM | K47018 | 15.2 | 0.3 | 0.8 | 19.5 |
|  | WT | 16.1 | 0.4 | 1.2 | 22.5 |
|  | Δ TG/WT % | −5.7 | −13.4 | −32.2 | −13.1 |

Table 24 demonstrates that the oil increase associated with the presence of the pKR1482-ORM transgene (SEQ ID NO:24) is accompanied by a reduction in seed protein content and a reduction in soluble carbohydrate content. The latter was calculated by summarizing the content of pinitol, sorbitol, fructose, glucose, myo-Inositol, sucrose, raffinose and stachyose.

Example 25

Compositional Analysis of *Arabidopsis* Events Transformed with DNA Constructs for Seed-Preferred Over-Expression of ORM Genes The example describes seed composition of transgenic events gene generated with pKR1478-ORM (SEQ ID NO:14). It demonstrates that transformation with DNA constructs for seed-preferred overexpression genes encoding ORM genes leads to decreased oil content that is accompanied by increased seed storage protein and a small decrease in soluble carbohydrate content.

T4 seed of event K42334 described in Table 10 of Example 4 were used to create two bulk seed samples. Bulk seed sample of WT control plants grown alongside the T3 plants described in Table 10 of Example 4 were also generated. Oil content of the four seed samples was measured by NMR as described in Example 2. The seed samples were subjected to compositional analysis of protein and soluble carbohydrate content of triplicate samples as described in Example 2. The results of this analysis are summarized in Table 25.

TABLE 25

Seed composition of arabidospis events transformed with DNA
constructs for seed-preferred overexpression of ORM genes

| Genotype | Event ID | Oil (%, NMR) | Protein % | fructose (µg mg$^{-1}$ seed) | glucose (µg mg$^{-1}$ seed) |
|---|---|---|---|---|---|
| pKR1478-ORM | K42334/K44548 | 39.5 | 19.3 | 0.2 | 4.9 |
|  | WT | 42.3 | 17.2 | 0.3 | 3.4 |
|  | Δ TG/WT % | −6.6 | 12.5 | −11.9 | 41.1 |

| Genotype | Event ID | sucrose (µg mg$^{-1}$ seed) | raffinose (µg mg$^{-1}$ seed) | stachyose (µg mg$^{-1}$ seed) | total soluble CHO (µg mg$^{-1}$ seed) |
|---|---|---|---|---|---|
| pKR1478-ORM | K42334/K44548 | 12.8 | 0.4 | 1.6 | 20.1 |
|  | WT | 16.4 | 0.4 | 1.6 | 22.4 |
|  | Δ TG/WT % | −22.3 | −5.1 | 0.0 | −10.2 |

| Genotype | Event ID | Oil (%, NMR) | Protein % | fructose (µg mg$^{-1}$ seed) | glucose (µg mg$^{-1}$ seed) |
|---|---|---|---|---|---|
| pKR1478-ORM | K42334/K44541 | 37.0 | 19.8 | 0.3 | 6.2 |
|  | WT | 42.2 | 17.8 | 0.3 | 3.7 |
|  | Δ TG/WT % | −12.3 | 11.1 | 11.5 | 65.9 |

| Genotype | Event ID | sucrose (µg mg$^{-1}$ seed) | raffinose (µg mg$^{-1}$ seed) | stachyose (µg mg$^{-1}$ seed) | total soluble CHO (µg mg$^{-1}$ seed) |
|---|---|---|---|---|---|
| pKR1478-ORM | K42334/K44541 | 13.1 | 0.4 | 2.1 | 22.6 |
|  | WT | 16.6 | 0.4 | 1.8 | 23.2 |
|  | Δ TG/WT % | −21.2 | 0.5 | 17.4 | −2.6 |

Table 25 shows that the oil reduction associated with seed-specific over-expression of ORM genes such as At5g17280 is accompanied by an increase in seed storage protein and a small decrease in soluble carbohydrate content of the seed.

Example 25

Characterization of *Arabidopsis* Events Transformed with a DNA Construct that Contains an Intron-Less Inverted Repeat Construct Derived from Sequences of the At5g17280 (ORM) Gene A plasmid vector Io127 for generation of transgenic *arabidopsis* events that show seed specific down-regulation of the ORM gene corresponding to At5g17280 was constructed.

Briefly, plasmid DNA isolated from a pooled *Arabidopsis* cDNA library was used in two PCR reactions with either primers SA311 (SEQ ID NO:71) and SA 312 (SEQ ID NO:72) or SA313 (SEQ ID NO:73) and SA 314 (SEQ ID NO:74). A PCR product of 0.208 kb was generated with SA311 (SEQ ID NO:71) and SA 312 (SEQ ID NO:72). It was gel purified and is henceforth known as product C. A PCR product of 0.183 kb was generated with SA313 (SEQ ID NO:73) and SA 314 (SEQ ID NO:74). It was gel purified and is henceforth known as product D. In a similar fashion a PCR product of 0.208 kb was generated with SA316 (SEQ ID NO:75) and SA 315 (SEQ ID NO:76). It was gel purified and is henceforth known as product E. PCR products C, D and E were cloned into pGEM T easy using instructions of the manufacturer which generated plasmids pGEM T easy C (SEQ ID NO:77), pGEM T easy D (SEQ ID NO:78), pGEM T easy E (SEQ ID NO:79). A restriction fragment of 215 bp was excised form pGEM T easy C with NotI and BamHI and cloned into pBluesript SK+ (Stratagene, USA). The resulting plasmid pBluescript-C (SEQ ID NO:80) was linearized with BamHI and PstI and ligated to a 193 bp fragment excised from pGEM T easy D with BamHI and PstI. The resulting plasmid pBluescript-CD (SEQ ID NO:81) was linearized with PstI and EcoRI and ligated to a 218 bp fragment excised from pGEM T easy E with PstI, EcoRI to give pBluescript-CDE (SEQ ID NO:82). A fragment of 619 bp was excised from pBluescript-CDE with NotI and ligated to NotI linearized KS442 (SEQ ID NO:83) to give KS442-CDE (SEQ ID NO:84).

Prior to this KS442 was constructed as follows. KS121 (PCT Application No. WO 02/00904) was digested BamHI and XmnI and ligated to a fragment comprised of the soybean GYI promoter. The GYI promoter was obtained from KS349 (US 20080295204 A1, published Nov. 27, 2008). Briefly, KS349 was digested with NcoI, overhangs were filled in with Klenow DNA polymerase (NEB, USA) according to manufacturer instructions. The linearized KS349 plasmid was digested with BamHI thus releasing the GYI promoter used for construction of KS442.

KS442-CDE was digested with AscI and a DNA fragment of 1.558 kb was ligated to Asc-linearized pKR92 (SEQ ID NO:8) to give Io127 (SEQ ID NO:85).

Plasmid DNA of Io127 was used for agrobacterium-mediated transformation of arabidopsis as described in Example 4. A total of 54 events were generated with Io127. T1 plant of these events were grown to maturity alongside WT control plants. Seed were harvested and oil content was measured by NMR as described in Example 2. The results of this analysis are summarized in Table 26.

TABLE 26

Seed oil content of T1 plants generated with binary vector Io127 for seed-specific silencing of At5g17280

| construct/ genotype | event ID | % oil | oil content % of WT avg | |
|---|---|---|---|---|
| ARALO 127 | K61385 | 42.0 | 116.5 | |
| ARALO 127 | K61388 | 41.0 | 113.7 | |
| ARALO 127 | K61386 | 40.6 | 112.6 | |
| ARALO 127 | K61389 | 40.2 | 111.5 | |
| ARALO 127 | K61377 | 40.1 | 111.2 | |
| ARALO 127 | K61375 | 40.0 | 110.9 | |
| ARALO 127 | K61379 | 39.6 | 109.8 | |
| ARALO 127 | K61378 | 39.5 | 109.5 | |
| ARALO 127 | K61383 | 39.3 | 109.0 | |
| ARALO 127 | K61367 | 39.0 | 108.2 | |
| ARALO 127 | K61371 | 38.9 | 107.9 | |
| ARALO 127 | K61372 | 38.8 | 107.6 | |
| ARALO 127 | K61394 | 38.5 | 106.8 | |
| ARALO 127 | K61382 | 38.4 | 106.5 | |
| ARALO 127 | K61393 | 38.2 | 105.9 | |
| ARALO 127 | K61391 | 38.2 | 105.9 | |
| ARALO 127 | K61387 | 38.1 | 105.7 | |
| ARALO 127 | K61373 | 37.9 | 105.1 | |
| ARALO 127 | K61381 | 37.4 | 103.7 | |
| ARALO 127 | K61368 | 37.2 | 103.2 | |
| ARALO 127 | K61374 | 37.2 | 103.2 | |
| ARALO 127 | K61392 | 37.2 | 103.2 | |
| ARALO 127 | K61380 | 37.1 | 102.9 | |
| ARALO 127 | K61370 | 36.6 | 101.5 | |
| ARALO 127 | K61384 | 36.5 | 101.2 | |
| ARALO 127 | K61369 | 35.3 | 97.9 | |
| ARALO 127 | K61376 | 34.8 | 96.5 | avg oil content % of WT |

TABLE 26-continued

Seed oil content of T1 plants generated with binary vector Io127 for seed-specific silencing of At5g17280

| construct/ genotype | event ID | % oil | oil content % of WT avg | |
|---|---|---|---|---|
| ARALO 127 | K61390 | 34.8 | 96.5 | 106.2 |
| col | | 37.2 | | |
| col | | 36.9 | | |
| col | | 36.8 | | |
| col | | 35.5 | WT avg | |
| col | | 33.9 | 36.06 | |
| ARALO 127 | K61403 | 41.0 | 118.2 | |
| ARALO 127 | K61406 | 39.7 | 114.4 | |
| ARALO 127 | K61425 | 39.4 | 113.5 | |
| ARALO 127 | K61405 | 39.2 | 113.0 | |
| ARALO 127 | K61401 | 39.2 | 113.0 | |
| ARALO 127 | K61408 | 39.1 | 112.7 | |
| ARALO 127 | K61416 | 38.9 | 112.1 | |
| ARALO 127 | K61415 | 38.9 | 112.1 | |
| ARALO 127 | K61404 | 38.5 | 111.0 | |
| ARALO 127 | K61420 | 38.4 | 110.7 | |
| ARALO 127 | K61414 | 38.2 | 110.1 | |
| ARALO 127 | K61407 | 37.8 | 108.9 | |
| ARALO 127 | K61402 | 37.8 | 108.9 | |
| ARALO 127 | K61400 | 37.7 | 108.6 | |
| ARALO 127 | K61424 | 37.4 | 107.8 | |
| ARALO 127 | K61421 | 37.3 | 107.5 | |
| ARALO 127 | K61417 | 37.3 | 107.5 | |
| ARALO 127 | K61419 | 37.2 | 107.2 | |
| ARALO 127 | K61411 | 37.2 | 107.2 | |
| ARALO 127 | K61426 | 36.5 | 105.2 | |
| ARALO 127 | K61409 | 36.3 | 104.6 | |
| ARALO 127 | K61413 | 35.8 | 103.2 | |
| ARALO 127 | K61418 | 35.7 | 102.9 | |
| ARALO 127 | K61422 | 35.5 | 102.3 | |
| ARALO 127 | K61410 | 35.4 | 102.0 | avg oil content % of WT |
| ARALO 127 | K61412 | 35.3 | 101.7 | 108.7 |
| col | | 36.7 | | |
| col | | 36.5 | | |
| col | | 34.2 | WT avg | |
| col | | 31.4 | 34.7 | |

T2 seed of events K61385, K61388, K61386 and K61403 were germinated on selective plant growth media containing kanamycin, planted in soil alongside WT plants and grown to maturity. T3 seed oil content was measured by NMR. The results of this analysis are summarized in Table 27.

TABLE 27

Seed oil content of T2 plants generated with binary vector Io127 for seed preferred silencing of At5g17280

| event ID/ genotype | Line ID | % oil | oil content % of WT avg |
|---|---|---|---|
| K61385 | K62439 | 42.7 | 109.5 |
| | K62454 | 42.3 | 108.5 |
| | K62447 | 41.9 | 107.4 |
| | K63000 | 41.9 | 107.4 |
| | K63001 | 41.9 | 107.4 |
| | K62441 | 41.8 | 107.2 |
| | K62453 | 41.4 | 106.2 |
| | K62444 | 41.1 | 105.4 |
| | K62440 | 40.9 | 104.9 |
| | K62452 | 40.7 | 104.4 |
| | K62450 | 40.5 | 103.8 |
| | K62442 | 40.5 | 103.8 |
| | K62445 | 40.5 | 103.8 |
| | K62456 | 39.7 | 101.8 |
| | K62443 | 39.7 | 101.8 |
| | K62448 | 38.5 | 98.7 |

TABLE 27-continued

Seed oil content of T2 plants generated with binary vector lo127 for seed preferred silencing of At5g17280

| event ID/genotype | Line ID | % oil | oil content % of WT avg | avg oil content % of WT |
|---|---|---|---|---|
| | K62446 | 38.0 | 97.4 | |
| | K62455 | 37.8 | 96.9 | |
| | K62451 | 37.5 | 96.2 | avg oil content % of WT |
| | K62449 | 37.2 | 95.4 | 103.4 |
| col | | 42.5 | | |
| col | | 41.5 | | |
| col | | 40.8 | | |
| col | | 40.0 | | |
| col | | 39.9 | | |
| col | | 39.8 | | |
| col | | 39.0 | | |
| col | | 37.6 | | |
| col | | 36.3 | | |
| col | | 36.0 | WT avg | |
| col | | 35.6 | 39 | |
| K61388 | K62406 | 42.6 | 107.4 | |
| | K62414 | 42.5 | 107.2 | |
| | K62410 | 42.4 | 106.9 | |
| | K62411 | 42.2 | 106.4 | |
| | K62419 | 42.2 | 106.4 | |
| | K62413 | 42.0 | 105.9 | |
| | K62415 | 41.7 | 105.1 | |
| | K62408 | 41.3 | 104.1 | |
| | K62412 | 41.3 | 104.1 | |
| | K62422 | 41.2 | 103.9 | |
| | K62424 | 41.1 | 103.6 | |
| | K62404 | 41.1 | 103.6 | |
| | K62425 | 41.1 | 103.6 | |
| | K62417 | 40.9 | 103.1 | |
| | K62409 | 40.8 | 102.9 | |
| | K62423 | 40.7 | 102.6 | |
| | K62421 | 40.5 | 102.1 | |
| | K62416 | 40.0 | 100.8 | |
| | K62426 | 39.9 | 100.6 | |
| | K62418 | 39.8 | 100.3 | |
| | K62427 | 38.3 | 96.6 | |
| | K62407 | 38.0 | 95.8 | |
| | K62420 | 37.3 | 94.0 | avg oil content % of WT |
| | K62405 | 36.4 | 91.8 | 102.5 |
| col | | 41.2 | | |
| col | | 41.2 | | |
| col | | 41.0 | | |
| col | | 40.9 | | |
| col | | 40.6 | | |
| col | | 39.4 | | |
| col | | 38.9 | | |
| col | | 38.7 | | |
| col | | 38.7 | | |
| col | | 38.5 | WT avg | |
| col | | 37.2 | 39.7 | |
| K61386 | K63580 | 45.2 | 110.9 | |
| | K63587 | 45.1 | 110.6 | |
| | K63577 | 44.8 | 109.9 | |
| | K63575 | 44.8 | 109.9 | |
| | K63589 | 44.3 | 108.6 | |
| | K63585 | 43.7 | 107.2 | |
| | K63578 | 43.2 | 105.9 | |
| | K62744 | 43.2 | 105.9 | |
| | K63583 | 43.2 | 105.9 | |
| | K63576 | 43.1 | 105.7 | |
| | K63592 | 43.1 | 105.7 | |
| | K63579 | 43.0 | 105.5 | |
| | K63593 | 42.9 | 105.2 | |
| | K63591 | 42.7 | 104.7 | |
| | K63584 | 41.6 | 102.0 | |
| | K63586 | 41.6 | 102.0 | |
| | K63574 | 41.5 | 101.8 | |
| | K63590 | 41.2 | 101.0 | |
| | K63581 | 40.7 | 99.8 | |
| | K63582 | 40.1 | 98.3 | |
| | K63588 | 39.4 | 96.6 | |
| | K63595 | 37.4 | 91.7 | |
| | K63596 | 37.3 | 91.5 | avg oil content % of WT |
| | K63594 | 36.9 | 90.5 | 103.2 |
| col | K63601 | 44.6 | | |
| col | K63600 | 43.0 | | |
| col | K63598 | 42.4 | | |
| col | K63599 | 41.1 | | |
| col | K63604 | 41.1 | | |
| col | K63606 | 41.0 | | |
| col | K63605 | 40.9 | | |
| col | K63608 | 40.3 | | |
| col | K63597 | 39.9 | | |
| col | K63607 | 39.4 | | |
| col | K63602 | 38.9 | WT avg | |
| col | K63603 | 36.7 | 40.8 | |
| K61403 | K62316 | 43.1 | 111.5 | |
| | K62308 | 43.0 | 111.3 | |
| | K62321 | 43.0 | 111.3 | |
| | K62315 | 42.1 | 109.0 | |
| | K62306 | 41.8 | 108.2 | |
| | K62318 | 41.4 | 107.1 | |
| | K62312 | 41.4 | 107.1 | |
| | K62324 | 41.3 | 106.9 | |
| | K62305 | 41.0 | 106.1 | |
| | K62323 | 40.7 | 105.3 | |
| | K62313 | 40.3 | 104.3 | |
| | K62310 | 40.0 | 103.5 | |
| | K62314 | 39.6 | 102.5 | |
| | K62307 | 39.6 | 102.5 | |
| | K62322 | 38.8 | 100.4 | |
| | K62317 | 37.4 | 96.8 | |
| | K62309 | 37.1 | 96.0 | |
| | K62320 | 37.0 | 95.8 | |
| | K62319 | 36.7 | 95.0 | avg oil content % of WT |
| | K62311 | 28.7 | 74.3 | 102.7 |
| col | | 41.6 | | |
| col | | 40.7 | | |
| col | | 40.4 | | |
| col | | 40.0 | | |
| col | | 38.6 | | |
| col | | 38.3 | | |
| col | | 35.8 | WT avg | |
| col | | 33.7 | 38.6 | |

Table 23-25 show that silencing of ORM genes such as At5g17280 using hairpin constructs that contain an intronless inverted repeat lead to a heritable oil increase. In T3 lines that still segregate for the Io127 derived T-DNA insertion the average oil content was 2.5-3.4% higher than that of WT control plants.

Example 25

Seed-Preferred Silencing of ORM Genes in Soybean Using Artificial miRNAs

The example describes the construction of a plasmid vector for soybean transformation. The plasmid provides seed-preferred expression of two artificial microRNAs that target soybean ORM genes Glyma02g05870 and Glyma16g24560, respectively.

Vectors were made to silence ORM genes using an artificial microRNA largely as described in U.S. patent application Ser. No. 12/335,717, filed Dec. 16, 2008. The following briefly explains the procedure.

Design of Artificial MicroRNA Sequences

Artificial microRNAs (amiRNAs) that would have the ability to silence the desired target genes were designed largely according to rules described in Schwab R, et al. (2005) *Dev Cell* 8: 517-27. To summarize, microRNA sequences are 21 nucleotides in length, start at their 5'-end with a "U", display 5' instability relative to their star sequence which is achieved by including a C or G at position 19, and their 10th nucleotide is either an "A" or an "U". An additional requirement for artificial microRNA design was that the amiRNA have a high free delta-G as calculated using the ZipFold algorithm (Markham, N. R. & Zuker, M. (2005) *Nucleic Acids Res.* 33: W577-W581.) The DNA sequence corresponding to the amiRNA (OX16) that was used to silence Glyma16g24560 is set forth in SEQ ID NO:86. The DNA sequence corresponding to the amiRNA (OX2) that was used to silence the Glyma02g05870 gene is set forth in SEQ ID NO:87.

Design of an Artificial Star Sequences

"Star sequences" are those that base pair with the amiRNA sequences, in the precursor RNA, to form imperfect stem structures. To form a perfect stem structure the star sequence would be the exact reverse complement of the amiRNA. The soybean precursor sequence as described in "Novel and nodulation-regulated microRNAs in soybean roots" Subramanian S, Fu Y, Sunkar R, Barbazuk W B, Zhu J K, Yu O BMC Genomics. 9:160(2008) and accessed on mirBase (Conservation and divergence of microRNA families in plants" Dezulian T, Palatnik J F, Huson D H, Weigel D (2005) Genome Biology 6:P13) was folded using mfold (M. Zuker (2003) *Nucleic Acids Res.* 31: 3406-15; and D. H. Mathews, J. et al. (1999) *J. Mol. Biol.* 288: 911-940). The miRNA sequence was then replaced with the amiRNA sequence and the endogenous star sequence was replaced with the exact reverse complement of the amiRNA. Changes in the artificial star sequence were introduced so that the structure of the stem would remain the same as the endogenous structure. The altered sequence was then folded with mfold and the original and altered structures were compared by eye. If necessary, further alternations to the artificial star sequence were introduced to maintain the original structure. The first amiRNA star sequence (OX16 star) that was used to silence Glyma16g24560 is set forth as SEQ ID NO:88. The $2^{nd}$ amiRNA star sequence (OX2 star) that was used to silence Glyma02g05870 is set forth as SEQ ID NO:89.

Conversion of Genomic MicroRNA Precursors to Artificial MicroRNA Precursors

Genomic miRNA precursor genes as described in US Patent Publication No. 2009-0155910A1, published Jun. 18, 2009 can be converted to amiRNAs using overlapping PCR and the resulting DNAs are completely sequenced. These DNAs are then cloned downstream of an appropriate promoter in a vector capable of soybean transformation.

Alternatively, amiRNAs can be synthesized commercially, for example by Codon Devices, (Cambridge, Mass.), DNA 2.0 (Menlo Park, Calif.) or Genescript (Piscataway, N.J.). The synthesized DNA is then cloned downstream of an appropriate promoter in a vector capable of soybean transformation.

Alternatively, amiRNAs can be constructed using In-Fusion™ technology (Clontech, Mountain View, Calif.). Conversion of Genomic MicroRNA Precursors to Artificial MicroRNA Precursors Genomic miRNA precursor genes were converted to amiRNA precursors using In-Fusion™ as described above. In brief, the microRNA 396b precursor (SEQ ID NO: 90) was altered to include Pme I sites immediately flanking the star and microRNA sequences to form the in-fusion ready microRNA 396b precursorv3 (SEQ ID NO: 91).

The microRNA 396b precursor (Seq ID 90) was used as a PCR template with the primers shown in SEQ ID NO:92 and SEQ ID NO:93. The primers are designed according to the protocol provided by Clontech (USA) and do not leave any footprint of the Pme I sites after the In-Fusion recombination reaction. The amplified sequence is recombined into the in-fusion ready microRNA 396b (SEQ ID NO:91) cloned into pCR2.1 and digested with Pme I. This was done using protocols provided with the In-Fusion™ kit. The resulting plasmid 396b-OX16 is shown in SEQ ID 94.

To construct 159-OX2, the microRNA 159 precursor (SEQ ID No: 95) was altered to include Pme I sites immediately flanking the star and microRNA sequences to form the in-fusion ready microRNA 159 precursor (SEQ ID NO: 96).

The microRNA 159 precursor (SEQ ID NO: 95) was used as a PCR template with the primers shown in SEQ ID NO:97 and SEQ ID NO:98. The primers are designed according to the protocol provided by Clontech and do not leave any footprint of the Pme I sites after the In-Fusion recombination reaction. The amplified sequences is recombined into the in-fusion ready microRNA 159 (SEQ ID NO:96) cloned into pCR2.1 and digested with Pme I. This was done using protocols provided with the In-Fusion™ kit. The resulting plasmid 159-OX2 is shown in Table 3 (SEQ ID NO: 99). The 611 bp Not I-Eco RI fragment was removed from 396b-OX16 (SEQ ID NO:94) and a 965 bp EcoRI-Not I fragment was removed from 159-OX2 SEQ ID NO: 100 and cloned into the Not I site of KS126 (PCT Publication No. WO 04/071467) to form KS 434 (SEQ ID NO 100).

Example 26

Compositional Analysis of Soybean Somatic Embryos Transformed with Constructs for RNAi- or amiRNA-Mediated Suppression of ORM Gene Expression DNA of plasmids KS120, KS433 and KS434 were stably transformed into soybean suspension cultures and transgenic somatic embryos were generated as described in Example 23. Oil content was analyzed by NMR as described in Example 2.

TABLE 30

Oil content of somatic embryos generated with plasmids KS120, KS433 and KS434

| experiment name | plasmid | event id | % oil | average % oil |
|---|---|---|---|---|
| 2698 | KS120 | K57206 | 6.6 | |
| | | K57198 | 6.2 | |
| | | K57195 | 5.0 | |
| | | K57207 | 5.0 | |
| | | K57201 | 5.0 | |
| | | K57211 | 4.9 | |
| | | K57187 | 4.8 | |
| | | K57204 | 4.6 | |
| | | K57189 | 4.3 | |
| | | K57212 | 4.3 | |
| | | K57194 | 4.2 | |
| | | K57188 | 4.0 | |
| | | K57193 | 3.9 | |
| | | K57190 | 3.9 | |
| | | K57200 | 3.8 | |
| | | K57202 | 3.8 | |

TABLE 30-continued

Oil content of somatic embryos generated with plasmids KS120, KS433 and KS434

| experiment name | plasmid | event id | % oil | average % oil |
|---|---|---|---|---|
| | | K57191 | 3.7 | |
| | | K57210 | 3.6 | |
| | | K57205 | 3.5 | |
| | | K57209 | 3.5 | |
| | | K57208 | 3.4 | |
| | | K57199 | 3.1 | |
| | | K57197 | 3.1 | |
| | | K57192 | 3.0 | |
| | | K57203 | 2.6 | |
| | | K57196 | 2.4 | 4.1 |
| 2699 | KS433 | K57232 | 10.0 | |
| | | K57238 | 9.9 | |
| | | K57236 | 9.8 | |
| | | K57224 | 9.4 | |
| | | K57215 | 8.2 | |
| | | K57220 | 8.2 | |
| | | K57225 | 8.1 | |
| | | K57222 | 8.1 | |
| | | K57237 | 7.5 | |
| | | K57221 | 7.2 | |
| | | K57233 | 7.0 | |
| | | K57229 | 6.9 | |
| | | K57234 | 6.5 | |
| | | K57217 | 6.3 | |
| | | K57213 | 6.1 | |
| | | K57230 | 5.9 | |
| | | K57214 | 5.8 | |
| | | K57227 | 5.3 | |
| | | K57226 | 5.3 | |
| | | K57231 | 5.2 | |
| | | K57223 | 4.9 | |
| | | K57219 | 4.5 | |
| | | K57235 | 4.1 | |
| | | K57228 | 3.9 | |
| | | K57218 | 2.8 | |
| | | K57216 | 1.9 | 6.5 |
| 2700 | KS434 | K57239 | 7.6 | |
| | | K57247 | 7.1 | |
| | | K57261 | 6.5 | |
| | | K57242 | 6.3 | |
| | | K57243 | 6.0 | |
| | | K57252 | 5.8 | |
| | | K57256 | 5.7 | |
| | | K57260 | 5.6 | |
| | | K57264 | 5.5 | |
| | | K57251 | 5.2 | |
| | | K57255 | 5.2 | |
| | | K57263 | 5.2 | |
| | | K57245 | 4.7 | |
| | | K57249 | 4.7 | |
| | | K57265 | 4.7 | |
| | | K57266 | 4.6 | |
| | | K57246 | 4.6 | |
| | | K57250 | 4.5 | |
| | | K57240 | 4.4 | |
| | | K57257 | 4.3 | |
| | | K57248 | 4.1 | |
| | | K57269 | 3.6 | |
| | | K57259 | 3.4 | |
| | | K57267 | 3.2 | |
| | | K57254 | 3.1 | |
| | | K57268 | 2.9 | |
| | | K57262 | 2.9 | |
| | | K57253 | 2.9 | |
| | | K57258 | 2.6 | |
| | | K57244 | 2.6 | |
| | | K57241 | 2.5 | 4.6 |

Table 30 shows that silencing of the soybean ORM genes Glyma02g05870 and Glyma16g24560 (KS433) using RNAi- or amiRNA-mediated suppression led to an increase in oil compared to the control.

What is claimed is:

1. A method for producing a dicot plant, the method comprising:
   a) obtaining a modified plant cell comprising a polynucleotide operably linked to at least one regulatory sequence, wherein the polynucleotide encodes a polypeptide having an amino acid sequence of at least 95% sequence identity when compared to SEQ ID NO: 36 or 38; and
   b) regenerating a dicot plant from the plant cell of (a); wherein seed obtained from said plant exhibits an altered oil, protein, starch or soluble carbohydrate content when compared to a seed from a control plant not comprising said polynucleotide.

2. Seed obtained by the method of claim 1, wherein the seed is soybean seed, comprises the polynucleotide and exhibits an altered oil or protein content when compared to a seed from a control plant not comprising said polynucleotide.

3. The seed of claim 2, wherein the seed exhibits an increase in oil content when compared to a seed from a control plant not comprising said polynucleotide.

4. The method of claim 1, wherein the seed obtained from the plant regenerated in step (b) has increased oil content compared with the oil content of seed from the control plant.

5. The method of claim 4, wherein the plant regenerated in step (b) is a soybean plant.

6. A method for producing dicot seeds, the method comprising:
   (a) obtaining a modified plant cell comprising a polynucleotide operably linked to at least one regulatory sequence, wherein the polynucleotide encodes a polypeptide having an amino acid sequence of at least 95% sequence identity to SEQ ID NO: 36 or 38, and is expressed such that expression of endogenous oxidoreductase motif (ORM) protein in the plant cell is reduced;
   (b) regenerating a dicot plant from the plant cell of (a); and
   (c) selecting a plant that produces a seed having an altered oil, protein, starch or soluble carbohydrate content, as compared to a control seed obtained from a control plant not comprising said polynucleotide.

7. The method of claim 6, wherein the seed has increased oil content compared with the oil content of the control seed.

8. The method of claim 7, wherein the seed is a soybean seed.

9. Seed obtained by the method of claim 6, wherein the seed is soybean seed, comprises the modified polynucleotide and exhibits an altered oil or protein content when compared to a seed from a control plant not comprising said polynucleotide.

10. The seed of claim 9, wherein the seed exhibits an increase in oil content when compared to a seed from a control plant not comprising said polynucleotide.

11. The method of claim 6, wherein said seed has an increased oil content of at least 2% when compared to the oil content of the control seed.

12. A transformed dicot plant comprising
   a polynucleotide stably transformed in the genome of the plant, wherein the polynucleotide encodes a polypeptide having an amino acid sequence of at least 95% sequence identity when compared to SEQ ID NO: 36 or 38; and wherein seed obtained from said transformed dicot plant has altered oxidoreductase motif (ORM) protein activity and altered oil, protein, starch or soluble carbohydrate content when compared to a seed from a control plant not comprising said polynucleotide.

13. The transformed plant of claim 12, wherein the seed obtained from the transformed plant has increased oil content compared with the oil content of the control seed.

14. The transformed plant of claim 13, wherein the transformed plant is a soybean plant.

15. A transformed dicot seed comprising a polynucleotide operably linked to at least one regulatory element, wherein said polynucleotide encodes a polypeptide having an amino acid sequence of at least 95% sequence identity when compared to SEQ ID NO: 36 or 38, wherein said dicot seed has an altered oxidoreductase motif (ORM) protein activity and altered oil, protein, starch and/or soluble carbohydrate content when compared to a seed from a control plant not comprising said polynucleotide.

16. The transformed seed of claim 15, wherein said seed has an increased oil content of at least 2% when compared to the oil content of the control seed.

17. The seed of claim 15, wherein the seed is soybean seed.

18. The transformed seed of claim 15, wherein the transformed seed has increased oil content compared with the oil content of the control seed.

19. The transformed seed of claim 18, wherein the transformed seed is a soybean seed.

20. A method for producing transgenic dicot seeds, the method comprising:
   (a) transforming a plant cell with a recombinant DNA construct comprising (i) a polynucleotide operably linked to at least one regulatory sequence, wherein the polynucleotide encodes a polypeptide having an amino acid sequence of at least 95% sequence identity to SEQ ID NO: 36 or 38, or (ii) a full-length complement of the polynucleotide sufficient to reduce expression of endogenous oxidoreductase motif (ORM) protein in the plant cell;
   (b) regenerating a transgenic plant from the transformed plant cell of (a); and
   (c) selecting a transgenic dicot plant that produces a transgenic seed having an altered oil, protein, starch or soluble carbohydrate content as compared to a control seed obtained from a control plant not comprising said polynucleotide.

21. The method of any one of claim 1, 6, or 20, wherein the seed is soybean seed.

22. The method of claim 20, wherein the at least one regulatory element is a seed-specific or seed-preferred promoter.

23. Seed obtained by the method of claim 20, wherein the seed is soybean seed, comprises the recombinant construct and exhibits an altered oil or protein content when compared to a seed from a control plant not comprising said polynucleotide.

24. The seed of claim 23, wherein the seed exhibits an increase in oil content when compared to a seed from a control plant not comprising said polynucleotide.

* * * * *